United States Patent
Stengel et al.

(10) Patent No.: US 8,273,890 B2
(45) Date of Patent: Sep. 25, 2012

(54) THIOPHENE-IMIDAZOPYRIDINES

(75) Inventors: Thomas Stengel, Constance (DE); Mathias Schmidt, Constance (DE); Steffen Weinbrenner, Constance (DE); Alexander Weber, Biberach An Der Riss (DE); Petra Gimmnich, Constance (DE); Volker Gekeler, Constance (DE); Thomas Beckers, Freiburg (DE); Astrid Zimmermann, Muhltal (DE); Thomas Maier, Stockach (DE); Beate Schmidt, Allensbach (DE); Florian Dehmel, Aachen (DE)

(73) Assignee: 4SC AG, Planegg-Martinsried (DE)

(*) Notice: Subject to any disclaimer, the term of this patent is extended or adjusted under 35 U.S.C. 154(b) by 14 days.

(21) Appl. No.: 12/667,093

(22) PCT Filed: Jun. 26, 2008

(86) PCT No.: PCT/EP2008/058184
§ 371 (c)(1), (2), (4) Date: Jul. 13, 2010

(87) PCT Pub. No.: WO2009/003911
PCT Pub. Date: Jan. 8, 2009

(65) Prior Publication Data
US 2010/0278833 A1    Nov. 4, 2010

(30) Foreign Application Priority Data

Jun. 29, 2007 (EP) .................... 07111460
Mar. 7, 2008 (EP) .................... 08102383

(51) Int. Cl.
C07D 471/02 (2006.01)
C07D 491/02 (2006.01)
C07D 498/02 (2006.01)
C07D 513/02 (2006.01)
C07D 515/02 (2006.01)
A61K 31/44 (2006.01)

(52) U.S. Cl. .................... 546/118; 514/303
(58) Field of Classification Search .................... None
See application file for complete search history.

(56) References Cited

U.S. PATENT DOCUMENTS 8,030,327 B2 * 10/2011 Sato et al. .................... 514/300
2008/0103136 A1  5/2008 Sato et al.
2008/0214563 A1  9/2008 Cheung et al.

FOREIGN PATENT DOCUMENTS

| EP | 1 813 613 A1 | 8/2007 |
| WO | WO 2004014899 A1 * | 2/2004 |
| WO | WO 2006/049339 A1 * | 5/2006 |
| WO | WO 2006049339 A1 * | 5/2006 |
| WO | WO 2007/030359 A1 | 3/2007 |
| WO | WO 2007/030361 A2 * | 3/2007 |
| WO | WO 2007030361 A2 * | 3/2007 |

OTHER PUBLICATIONS

Lansing, TJ. et al. In vitro biological activity of a novel small-molecule inhibitor of polo-like kinase 1. Molecular Cancer Therapeutics. 2007, vol. 6, No. 2, p. 453, table 1.*
Freshney, RI. Culture of Animal Cells: A Manual of Basic Technique. John Wiley and Sons. 2005, 5th Ed., p. 8.*
Dermer, GB. Another Anniversary for the War on Cancer. Bio/Technology. 1994, vol. 12, p. 320.*
Cornelison, TL. Human papillomavirus genotype 16 vaccines for cervical cancer prophylaxis and treatment. Curr. Opin. Oncol. 2000, vol. 12(5), p. 466.*
International Search Report of PCT/EP2008/058184 (Sep. 22, 2008).
T. J. Lansing et al., "In Vitro Biological Activity of a Novel Small-Molecule Inhibitor of Polo-Like Kinase 1", Mol. Cancer Ther., vol. 6, No. 2 (Feb. 2007) pp. 450-459.

* cited by examiner

*Primary Examiner* — Rita Desai
*Assistant Examiner* — Ben S Michelson
(74) *Attorney, Agent, or Firm* — Millen, White, Zelano & Branigan, P.C.

(57) ABSTRACT

The invention relates to thiophene-imidazopyridine compounds according to formula (I), wherein the substituents and symbols are as defined in the description. The compounds are inhibitors of Plk1.

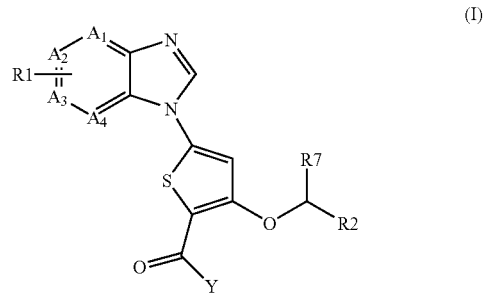

(I)

19 Claims, No Drawings

THIOPHENE-IMIDAZOPYRIDINES

FIELD OF APPLICATION OF THE INVENTION

The invention relates to thiophene-imidazopyridine compounds which can be used in the pharmaceutical industry for the manufacture of pharmaceutical compositions. The invention further relates to the contribution made to the art by the finding that said thiophene-imidazopyridine compounds are potent inhibitors of polo-like kinase 1 (Plk1). This activity is known to result in many cases in a cell cycle-dependent, anti-proliferative and apoptosis inducing activity.

The invention also relates to the use of these compounds for the therapy of hyperproliferative diseases, in particular human cancer.

KNOWN TECHNICAL BACKGROUND

Tumor cells are characterized by a partial or complete loss of control of the cell cycle. This loss of cell cycle control results in excessive cell division activity and, thus, in uncontrolled growth. It is known that Plk1, the human orthologue of polo kinase of *Drosophila*, is an essential regulator of the M-phase of the cell cycle. Targeted interference with Plk1 function in cancer cells such as antisense molecules, siRNA, or antibody microinjection is known to result in mitotic arrest of the cells followed by the onset of cell death. Moreover, it was found that Plk1 is overexpressed in a wide variety of human cancers including, but not limited to breast, prostate, stomach or ovaries.

Inhibitors of Plk1 are known from WO 03/93249, WO 2004/014899, WO 2004/043936, WO 2004/074244, WO 2004/087652, WO 2005/019193, WO 2005/037827, WO 2005/042505, WO 2005/075470, WO 2005/123736, WO 2006/008028, WO 2006/018185, WO 2006/018222, WO 2006/021544, WO 2006/021547, WO 2006/025567, WO 2006/049339, WO 2007/030359, WO 2007/030361 and WO 2007/030366.

Insufficient susceptibility to known medicines of many tumor types requires the development of novel compounds as chemotherapeutic agents such as, for example, Plk1 inhibiting compounds interfering with cancer cell cycle and/or proliferation. Thus, subject of the present invention are novel Plk1 inhibitors.

DESCRIPTION OF THE INVENTION

It has now been found that the thiophene-imidazopyridine compounds described in detail below are characterized by surprising and advantageous properties such as, among others, the selective inhibition of Plk1 enzyme. It can be expected that among these Plk1 inhibitors there will be compounds that selectively inhibit proliferation and induce cell death in proliferating cancer cells while being inactive on arrested cells. Moreover it was observed that many of the thiophene-imidazopyridine compounds arrest proliferating cancer cells in mitosis.

Accordingly, the invention relates to compounds of formula (I)

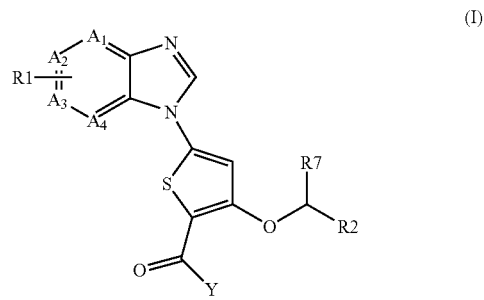

wherein
R1 is —H, —CH$_2$OH, —CH$_2$N(R3)R4, —C(O)N(R5)R6, —OCH$_3$, —F, —Cl, —Br, —CH$_2$SO$_2$CH$_3$, or —CH$_2$O-piperidyl, the piperidyl group optionally being N-substituted by C1-C4 alkyl,
and wherein R1 is attached to either A$_2$ or to A$_3$;
R2 is phenyl optionally having 1 to 3 substituents independently selected from —F, —Cl, —Br, —I, —CN, —OH, —NO$_2$, —SO$_2$CH$_3$, C1-C4 alkyl optionally being substituted with 1 to 3 F atoms, C1-C4 alkoxy optionally being substituted with 1 to 3 F atoms, C1-C4 alkylamino, and C1-C4 dialkylamino;
A$_1$, A$_2$, A$_3$ and A$_4$ independently are CR1, CH or N, wherein one of A$_1$, A$_2$, A$_3$ and A$_4$ is N, one of A$_2$ and A$_3$ is CR1, and all others are CH;
Y is —OH or —NH$_2$;
R3 is —H, —SO$_2$CH$_3$, C1-C4 alkyl, C2-C3 alkyl substituted with —OR8, C2-C3 alkyl substituted with —N(R8)R9, C3-C6 cycloalkyl, or saturated four- to six-membered heterocyclyl with at least one ring atom being N, the heterocyclyl group optionally being N-substituted with C1-C4 alkyl, phenyl, pyridyl, or pyrimidyl;
R4 is —H, —SO$_2$CH$_3$, C1-C4 alkyl, C2-C3 alkyl substituted with —OR8, C2-C3 alkyl substituted with —N(R8)R9, C3-C6 cycloalkyl, or saturated four- to six-membered heterocyclyl with at least one ring atom being N, the heterocyclyl group optionally being N-substituted with C1-C4 alkyl, phenyl, pyridyl, or pyrimidyl;
or
R3 and R4, together with the nitrogen atom they are bound to, form a saturated four- to seven-membered heterocycle, the heterocycle optionally containing one more heteroatom which is N, O or S, S optionally being oxidized to a —SO— group or a —SO$_2$— group,
and the heterocycle optionally being substituted by one or two substituents which independently are —OH, —F, amino, C1-C4 alkylamino, C1-C4 dialkylamino, C1-C4 alkyl optionally being substituted with 1 to 3 F atoms, C1-C4 acyl, benzoyl, phenoxy, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di(C1-C4 alkyl)aminoethyl, phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, N-methylpiperazinyl, N-methylpiperazinylcarbonyl, or oxo, or R3 and R4, together with the nitrogen atom they are bound to, form a bridged system which is 2,5-diazabicyclo[2.2.1]hept-2-yl or 5-methyl-2,5-diazabicyclo[2.2.1]hept-2-yl;

R5 is —H, methyl, C1-C4 alkoxyethyl, or four- to six-membered N-ethylheterocyclyl;

R6 is —H, methyl, C1-C4 alkoxyethyl, or four- to six-membered N-ethylheterocyclyl;

R7 is —H, methyl, ethyl, —CH$_2$OH or —CF$_3$;

R8 is —H or C1-C4 alkyl; and

R9 is —H or C1-C4 alkyl;

or

R8 and R9, together with the nitrogen atom they are bound to, form a saturated four- to six-membered heterocycle, the heterocycle optionally containing one more heteroatom which is N, O or S, S optionally being oxidized to a —SO— group or a —SO$_2$— group;

a salt of one of the compounds, a stereoisomer of one of the compounds, or a salt of a stereoisomer of one of the compounds.

In a preferred embodiment, the invention relates to compounds of formula (I), wherein R1 is —H, —CH$_2$OH, —CH$_2$N(R3)R4, —C(O)N(R5)R6, —OCH$_3$, —F, —Cl, —Br, —CH$_2$SO$_2$CH$_3$, or —CH$_2$O-piperidyl, the piperidyl group optionally being N-substituted by C1-C4 alkyl, and wherein R1 is attached to either A$_2$ or to A$_3$;

R2 is phenyl optionally having 1 to 3 substituents independently selected from —F, —Cl, —Br, I, —CN, —SO$_2$CH$_3$, C1-C4 alkyl optionally being substituted with 1 to 3 F atoms, C1-C4 alkoxy optionally being substituted with 1 to 3 F atoms, C1-C4 alkylamino, and C1-C4 dialkylamino;

A$_1$ and A$_4$ are C, one of A$_2$ and A$_3$ is CR1 and the other of A$_2$ and A$_3$ is N;

Y is —OH or —NH$_2$;

R3 is —H, —SO$_2$CH$_3$, C1-C4 alkyl, C2-C3 alkyl substituted with —OR8, C2-C3 alkyl substituted with —N(R8)R9, C3-C6 cycloalkyl, piperidine-4-yl optionally being N-substituted with C1-C4 alkyl, phenyl, pyridyl, or pyrimidyl, or piperidine-3-yl optionally being N-substituted with C1-C4 alkyl, phenyl, pyridyl, or pyrimidyl;

R4 is —H, —SO$_2$CH$_3$, C1-C4 alkyl, C2-C3 alkyl substituted with —OR8, C2-C3 alkyl substituted with —N(R8)R9, C3-C6 cycloalkyl, piperidine-4-yl optionally being N-substituted with C1-C4 alkyl, phenyl, pyridyl, or pyrimidyl, or piperidine-3-yl optionally being N-substituted with C1-C4 alkyl, phenyl, pyridyl, or pyrimidyl;

or

R3 and R4, together with the nitrogen atom they are bound to, form a saturated four- to seven-membered heterocycle, the heterocycle optionally containing one more heteroatom which is N, O or S, S optionally being oxidized to a —SO— group or a —SO$_2$— group, and the heterocycle optionally being substituted by one or two substituents which independently are —OH, —F, amino, C1-C4 alkylamino, C1-C4 dialkylamino, C1-C4 alkyl optionally being substituted with 1 to 3 F atoms, C1-C4 acyl, benzoyl, phenoxy, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di(C1-C4 alkyl)aminoethyl, phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, N-methylpiperazinyl, N-methylpiperazinylcarbonyl, or oxo, or R3 and R4, together with the nitrogen atom they are bound to, form a bridged system which is 2,5-diazabicyclo[2.2.1]hept-2-yl or 5-methyl-2,5-diazabicyclo[2.2.1]hept-2-yl;

R5 is —H, methyl, C1-C4 alkoxyethyl, or four- to six-membered N-ethylheterocyclyl;

R6 is —H, methyl, C1-C4 alkoxyethyl, or four- to six-membered N-ethylheterocyclyl;

R7 is —H, methyl, ethyl, —CH$_2$OH, or —CF$_3$;

R8 is —H or C1-C4 alkyl; and

R9 is —H or C1-C4 alkyl;

or

R8 and R9, together with the nitrogen atom they are bound to, form a saturated four- to six-membered heterocycle, the heterocycle optionally containing one more heteroatom which is N, O or S, S optionally being oxidized to a —SO— group or a —SO$_2$— group;

a salt of one of the compounds, a stereoisomer of one of the compounds, or a salt of a stereoisomer of one of the compounds.

In another preferred embodiment, the invention relates to compounds of formula (I), wherein R1 is —H, —CH$_2$N(R3)R4, —CH$_2$SO$_2$CH$_3$, or —CH$_2$O-piperidyl, the piperidyl group optionally being N-substituted by C1-C4 alkyl, and wherein R1 is attached to either A$_2$ or to A$_3$;

R2 is phenyl optionally having 1 to 3 substituents independently selected from —F, —Cl, —Br, I, —CN, —SO$_2$CH$_3$, C1-C4 alkyl optionally being substituted with 1 to 3 F atoms, C1-C4 alkoxy optionally being substituted with 1 to 3 F atoms, C1-C4 alkylamino, and C1-C4 dialkylamino;

A$_1$ and A$_4$ are C, one of A$_2$ and A$_3$ is CR1 and the other of A$_2$ and A$_3$ is N;

Y is —OH or —NH$_2$;

R3 is —H, C2-C3 alkyl substituted with —OR8, C2-C3 alkyl substituted with —N(R8)R9, C3-C6 cycloalkyl, piperidine-4-yl optionally being N-substituted with C1-C4 alkyl, phenyl, pyridyl, or pyrimidyl, or piperidine-3-yl optionally being N-substituted with C1-C4 alkyl, phenyl, pyridyl, or pyrimidyl;

R4 is —H, C2-C3 alkyl substituted with —OR8, C2-C3 alkyl substituted with —N(R8)R9, C3-C6 cycloalkyl, piperidine-4-yl optionally being N-substituted with C1-C4 alkyl, phenyl, pyridyl, or pyrimidyl, or piperidine-3-yl optionally being N-substituted with C1-C4 alkyl, phenyl, pyridyl, or pyrimidyl;

or

R3 and R4, together with the nitrogen atom they are bound to, form a saturated four- to seven-membered heterocycle, the heterocycle optionally containing one more heteroatom being N, O or S, S optionally being oxidized to a —SO— group or a —SO$_2$— group, and the heterocycle optionally being substituted by one or two substituents which independently are —OH, —F, amino, C1-C4 alkylamino, C1-C4 dialkylamino, C1-C4 alkyl optionally being substituted with 1 to 3 F atoms, C1-C4 acyl, benzoyl, phenoxy, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di(C1-C4 alkyl)aminoethyl, phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, N-methylpiperazinyl, N-methylpiperazinylcarbonyl, or oxo, or R3 and R4, together with the nitrogen atom they are bound to, form a bridged system which is 2,5-diazabicyclo[2.2.1]hept-2-yl or 5-methyl-2,5-diazabicyclo[2.2.1]hept-2-yl;

R7 is —H, methyl, ethyl, —CH$_2$OH, or —CF$_3$;

R8 is —H or C1-C4 alkyl; and

R9 is —H or C1-C4 alkyl;

or

R8 and R9, together with the nitrogen atom they are bound to, form a saturated four- to six-membered heterocycle optionally containing one more heteroatom being N, O or S, S optionally being oxidized to a —SO— group or a —SO$_2$— group;

a salt of one of the compounds, a stereoisomer of one of the compounds, or a salt of a stereoisomer of one of the compounds.

In another preferred embodiment, the invention relates to compounds of formula (I), wherein R1 is —CH$_2$N(R3)R4, —CH$_2$SO$_2$CH$_3$, or —CH$_2$O-piperidyl, the piperidyl group optionally being N-substituted by C1-C4 alkyl, and wherein R1 is attached to either A$_2$ or to A$_3$;

R2 is phenyl having a substituent in the 2-position and optionally up to two substituents in the remaining positions, the substituents being —F, —Cl, —Br, —I, —CN, —SO$_2$CH$_3$, C1-C4 alkyl optionally being substituted with 1 to 3 F atoms, C1-C4 alkoxy optionally being substituted with 1 to 3 F atoms, C1-C4 alkylamino, or C1-C4 dialkylamino;

A$_1$ and A$_4$ are C, one of A$_2$ and A$_3$ is CR1 and the other of A$_2$ and A$_3$ is N;

Y is —NH$_2$;

R3 is —H or piperidine-4-yl optionally being N-substituted with C1-C4 alkyl; and R4 is —H or piperidine-4-yl optionally being N-substituted with C1-C4 alkyl;

or

R3 and R4, together with the nitrogen atom they are bound to, form a piperazine ring or 1,4-diazepane ring, the piperazine or 1,4-diazepane optionally being substituted by one or two substituents independently being —F, C1-C4 alkyl, C1-C4 alkyl substituted with 1 to 3 F atoms, C1-C4 acyl, benzoyl, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di(C1-C4 alkyl)aminoethyl, phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, or oxo, or R3 and R4, together with the nitrogen atom they are bound to, form a bridged system which is 2,5-diazabicyclo[2.2.1]hept-2-yl or 5-methyl-2,5-diazabicyclo[2.2.1]hept-2-yl;

R7 is —H, methyl, —CH$_2$OH, or —CF$_3$;

a salt of one of the compounds, a stereoisomer of one of the compounds, or a salt of a stereoisomer of one of the compounds.

In another preferred embodiment, the invention relates to compounds of formula (I), wherein R1 is —CH$_2$N(R3)R4 and is attached to either A$_2$ or to A$_3$;

R2 is phenyl having a —F, —Cl, —Br, —I, trifluormethyl, difluormethoxy or trifluormethoxy substituent in the 2-position and optionally up to two substituents in the remaining positions, the up to two substituents independently being —F, —Cl, —Br, I, —CN, —SO$_2$CH$_3$, C1-C4 alkyl optionally being substituted with 1 to 3 F atoms, C1-C4 alkoxy optionally being substituted with 1 to 3 F atoms, C1-C4 alkylamino, or C1-C4 dialkylamino;

A$_1$ and A$_4$ are CH, one of A$_2$ and A$_3$ is CR1 and the other of A$_2$ and A$_3$ is N;

Y is —NH$_2$;

R3 and R4, together with the nitrogen atom they are bound to, form a piperazine ring or 1,4-diazepane ring, the piperazine or 1,4-diazepane optionally being substituted by one or two substituents independently being —F, C1-C4 alkyl optionally being substituted with 1 to 3 F atoms, C1-C4 acyl, benzoyl, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di(C$_1$-C$_4$ alkyl)aminoethyl; phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, or oxo;

R7 is —H, methyl, —CH$_2$OH, or —CF$_3$;

a salt of one of the compounds, a stereoisomer of one of the compounds, or a salt of a stereoisomer of one of the compounds.

In another preferred embodiment, the invention relates to compounds of formula (I), wherein R1 is —CH$_2$N(R3)R4 and is attached to either A$_2$ or to A$_3$;

A$_1$ and A$_4$ are CH;

one of A$_2$ and A$_3$ is CR1 and the other is N;

R2 is phenyl having a —Cl, —Br, trifluormethyl, difluormethoxy or trifluormethoxy group in 2-position and optionally up to two substituents in the remaining positions, the substituents being —F, —Cl, —Br, —CN, —SO$_2$Me, C1-C4 alkyl, C1-C4 alkyl substituted with 1 to 3 F atoms, C1-C4 alkoxy, C1-C4 alkoxy substituted with 1 to 3 F atoms, C1-C4 alkylamino, or C1-C4 dialkylamino;

Y is —NH$_2$;

R3 and R4, together with the nitrogen atom they are bound to, form a piperazine ring, the piperazine optionally being substituted by one substituent being C1-C4 alkyl, C1-C4 alkyl substituted with 1 to 3 F atoms, or cyclopropyl;

R7 is methyl —CH$_2$OH, or CF$_3$.

a salt of one of the compounds, a stereoisomer of one of the compounds, or a salt of a stereoisomer of one of the compounds.

In another preferred embodiment, the invention relates to compounds of formula (I), wherein R1 is —CH$_2$N(R3)R4 and is attached to A$_3$;

A$_1$ and A$_4$ are CH;

A$_2$ is N;

A$_3$ is CR1;

R2 is phenyl having a —Cl, —Br, trifluormethyl, difluormethoxy or trifluormethoxy group in 2-position;

Y is —NH$_2$;

R3 and R4, together with the nitrogen atom they are bound to, form a piperazine ring, the piperazine optionally being substituted by one substituent being C1-C4 alkyl, C1-C4 alkyl substituted with 1 to 3 F atoms, or cyclopropyl, R7 is methyl, —CH$_2$OH, or CF$_3$;

a salt of one of the compounds, a stereoisomer of one of the compounds, or a salt of a stereoisomer of one of the compounds.

In another preferred embodiment, the invention relates to compounds of formula (I), wherein R1 is —CH$_2$N(R3)R4 and is attached to A$_3$;

A$_1$ and A$_4$ are CH;

A$_2$ is N;

A$_3$ is CR1;

R2 is phenyl having trifluormethyl in 2-position;

Y is —NH$_2$;

R3 and R4, together with the nitrogen atom they are bound to, form a piperazine ring, the piperazine ring optionally being substituted by one or two substituents being C1-C4 alkyl, C1-C4 alkyl substituted with 1 to 3 F atoms, cyclopropyl, C1-C4 acyl, benzoyl, 1-carboxamidyl, 1-carboxamidyl substituted with C1-C4 alkyl, 1-carboxamidyl substituted with phenyl, 1-carboximidamidyl, sulfonyl, sulfonyl substituted with C1-C4 alkyl, sulfonyl substituted with phenyl, hydroxyethyl, 2-(C1-C4 alkoxy)ethyl, 2-aminoethyl, 2-N—(C1-C4 alkyl)aminoethyl, 2-N,N-di(C1-C4 alkyl)aminoethyl; phenyl, pyridyl, or oxo;

R7 is methyl;

a salt of one of the compounds, a stereoisomer of one of the compounds, or a salt of a stereoisomer of one of the compounds.

In another preferred embodiment, the invention relates to compounds of formula (I), wherein R1 is —CH$_2$O-piperidyl, the piperidyl group optionally being N-substituted by C1-C4 alkyl, and is attached to either A$_2$ or to A$_3$;

A$_1$ and A$_4$ are CH;

one of A$_2$ and A$_3$ is CR1 and the other is N;

R2 is phenyl having a —Cl, —Br, trifluormethyl, difluormethoxy or trifluormethoxy group in 2-position and optionally up to two substituents in the remaining positions, the substituents being —F, —Cl, —Br, —CN, —SO$_2$Me, C1-C4 alkyl, C1-C4 alkyl substituted with 1 to 3 F atoms, C1-C4 alkoxy, C1-C4 alkoxy substituted with 1 to 3 F atoms, C1-C4 alkylamino, or C1-C4 dialkylamino;

Y is —NH$_2$;

R7 is methyl, —CH$_2$OH, or CF$_3$;

a salt of one of the compounds, a stereoisomer of one of the compounds, or a salt of a stereoisomer of one of the compounds.

In another preferred embodiment, the invention relates to compounds of formula (I), wherein R1 is —CH$_2$O-piperidyl, the piperidyl group optionally being N-substituted by C1-C4 alkyl and is attached to A$_3$;

A$_1$ and A$_4$ are CH;

A$_2$ is N;

R2 is phenyl having a —Cl, —Br, trifluormethyl, difluormethoxy or trifluormethoxy group in 2-position;

Y is —NH$_2$;

R7 is methyl, —CH$_2$OH, or CF$_3$;

a salt of one of the compounds, a stereoisomer of one of the compounds, or a salt of a stereoisomer of one of the compounds.

In another preferred embodiment, the invention relates to compounds of formula (I), wherein R1 is —CH$_2$SO$_2$CH$_3$, and wherein R1 is attached to either A$_2$ or to A$_3$;

A$_1$ and A$_4$ are CH;

one of A$_2$ and A$_3$ is CR1 and the other is N;

R2 is phenyl having a —Cl, —Br, trifluormethyl, difluormethoxy or trifluormethoxy group in 2-position and optionally up to two substituents in the remaining positions, the substituents being —F, —Cl, —Br, —CN, —SO$_2$Me, C1-C4 alkyl, C1-C4 alkyl substituted with 1 to 3 F atoms, C1-C4 alkoxy, C1-C4 alkoxy substituted with 1 to 3 F atoms, C1-C4 alkylamino, or C1-C4 dialkylamino;

Y is —NH$_2$;

R7 is methyl, —CH$_2$OH, or CF$_3$;

a salt of one of the compounds, a stereoisomer of one of the compounds, or a salt of a stereoisomer of one of the compounds.

In another preferred embodiment, the invention relates to compounds of formula (I), wherein R1 is —CH$_2$SO$_2$CH$_3$ and is attached to A$_3$;

A$_1$ and A$_4$ are CH;

A$_2$ is N;

R2 is phenyl having a —Cl, —Br, trifluormethyl, difluormethoxy or trifluormethoxy group in 2-position;

Y is —NH$_2$;

R7 is methyl, —CH$_2$OH, or CF$_3$;

a salt of one of the compounds, a stereoisomer of one of the compounds, or a salt of a stereoisomer of one of the compounds.

In another preferred embodiment, the invention relates to compounds of formula (I), wherein R1 is —CH$_2$N(R3)R4 and wherein R1 is attached to either A$_2$ or to A$_3$;

A$_1$ and A$_4$ are CH;

one of A$_2$ and A$_3$ is CR1 and the other is N;

R3 is —H, piperidine-4-yl or piperidine-4-yl being N-substituted with C1-C4 alkyl;

R4 is —H, piperidine-4-yl or piperidine-4-yl being N-substituted with C1-C4 alkyl;

R2 is phenyl having a —Cl, —Br, trifluormethyl, difluormethoxy or trifluormethoxy group in 2-position and optionally up to two substituents in the remaining positions, the substituents being —F, —Cl, —Br, —CN, —SO$_2$Me, C1-C4 alkyl, C1-C4 alkyl substituted with 1 to 3 F atoms, C1-C4 alkoxy, C1-C4 alkoxy substituted with 1 to 3 F atoms, C1-C4 alkylamino, or C1-C4 dialkylamino;

Y is —NH$_2$;

R7 is methyl, —CH$_2$OH, or CF$_3$;

a salt of one of the compounds, a stereoisomer of one of the compounds, or a salt of a stereoisomer of one of the compounds.

In another preferred embodiment, the invention relates to compounds of formula (I), wherein R1 is —CH$_2$N(R3)R4 and is attached to A$_3$;

A$_1$ and A$_4$ are CH;

A$_2$ is N;

A$_3$ is CR1;

R3 is —H, piperidine-4-yl or piperidine-4-yl being N-substituted with C1-C4 alkyl;

R4 is —H, piperidine-4-yl or piperidine-4-yl being N-substituted with C1-C4 alkyl;

R2 is phenyl having a —Cl, —Br, trifluormethyl, difluormethoxy or trifluormethoxy group in 2-position;

Y is —NH$_2$;

R7 is methyl, —CH$_2$OH, or CF$_3$;

a salt of one of the compounds, a stereoisomer of one of the compounds, or a salt of a stereoisomer of one of the compounds.

In another preferred embodiment, the invention relates to compounds of formula (I), wherein R1 is N-methylpiperazine.

In another preferred embodiment, the invention relates to compounds of formula (I), wherein R1 is —CH$_2$N(R3)R4.

In another preferred embodiment, the invention relates to compounds of formula (I), wherein R1 is —CH$_2$N(R3)R4 and is attached to A$_3$.

In another preferred embodiment, the invention relates to compounds of formula (I), wherein R1 is —CH$_2$O-piperidyl, the piperidyl group optionally being N-substituted by C1-C4 alkyl, and is attached to either A$_2$ or to A$_3$.

In another preferred embodiment, the invention relates to compounds of formula (I), wherein R1 attached to A$_2$.

In another preferred embodiment, the invention relates to compounds of formula (I), wherein R1 is attached to A$_3$.

In another preferred embodiment, the invention relates to compounds of formula (I), wherein R1 is —CH$_2$SO$_2$CH$_3$.

In another preferred embodiment, the invention relates to compounds of formula (I), wherein R2 is phenyl having a substituent in the 2-position and optionally up to two substituents in the remaining positions, the substituents being —F, —Cl, —Br, —I, —CN, —SO$_2$CH$_3$, C1-C4 alkyl optionally being substituted with 1 to 3 F atoms, C1-C4 alkoxy optionally being substituted with 1 to 3 F atoms, C1-C4 alkylamino, or C1-C4 dialkylamino.

In another preferred embodiment, the invention relates to compounds of formula (I), wherein R2 is phenyl having a —Cl, —Br, trifluormethyl, difluormethoxy or trifluormethoxy group in 2-position.

In another preferred embodiment, the invention relates to compounds of formula (I), wherein R2 is 2-chlorphenyl.

In another preferred embodiment, the invention relates to compounds of formula (I), wherein R2 is 2-trifluoromethylphenyl.

In another preferred embodiment, the invention relates to compounds of formula (I), wherein Y is —NH$_2$.

In another preferred embodiment, the invention relates to compounds of formula (I), wherein R3 is piperidine-4-yl being N-substituted with C1-C4 alkyl and R4 is H.

In another preferred embodiment, the invention relates to compounds of formula (I), wherein R3 is piperidine-4-yl and R4 is H.

In another preferred embodiment, the invention relates to compounds of formula (I), wherein A$_2$ and A$_3$ are CR1 or N.

In another preferred embodiment, the invention relates to compounds of formula (I), wherein A$_2$ is CR1.

In another preferred embodiment, the invention relates to compounds of formula (I), wherein A$_3$ is CR1.

In another preferred embodiment, the invention relates to compounds of formula (I), wherein A$_2$ is N.

In another preferred embodiment, the invention relates to compounds of formula (I), wherein A$_3$ is N.

In another preferred embodiment, the invention relates to compounds of formula (I), wherein R3 is piperidine-4-yl being N-substituted with C1-C4 alkyl and R4 is H.

In another preferred embodiment, the invention relates to compounds of formula (I), wherein R3 is piperidine-4-yl and R4 is H.

In another preferred embodiment, the invention relates to compounds of formula (I), wherein R3 and R4, together with the nitrogen atom they are bound to, form a piperazine ring, the piperazine ring optionally being substituted by one or two substituents independently being —F, C1-C4 alkyl, C1-C4 alkyl substituted with 1 to 3 F atoms, C1-C4 acyl, benzoyl, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di(C1-C4 alkyl)aminoethyl, phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, or oxo.

In another preferred embodiment, the invention relates to compounds of formula (I), wherein R3 and R4, together with the nitrogen atom they are bound to, form a 1,4-diazepane ring, the 1,4-diazepane ring optionally being substituted by one or two substituents independently being —F, C1-C4 alkyl, C1-C4 alkyl substituted with 1 to 3 F atoms, C1-C4 acyl, benzoyl, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di (C1-C4 alkyl)aminoethyl, phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, or oxo.

In another preferred embodiment, the invention relates to compounds of formula (I), wherein R7 is —CH$_2$OH.

In another preferred embodiment, the invention relates to compounds of formula (I), wherein R7 is CF$_3$.

In another preferred embodiment, the invention relates to compounds of formula (I), wherein R7 is methyl.

CR1 represents a ring carbon atom to which substituent R1 is bound.

C1-C4 alkyl represents a straight-chain or branched alkyl group having 1 to 4 carbon atoms, including methyl, ethyl, propyl, isopropyl, butyl, isobutyl, sec-butyl, and tert-butyl.

C2-C3 alkyl presents a straight-chain or branched alkyl group having 2 or 3 carbon atoms, including ethyl, propyl, and isopropyl.

C1-C4 alkoxy represents groups which, in addition to the oxygen atom, contain a straight chain or branched C1-C4 alkyl group as outlined above. Accordingly, C1-C4 alkoxy includes methoxy, ethoxy, propoxy, isopropoxy, butoxy, isobutoxy, sec-butoxy, and tert-butoxy.

C1-C4 alkylamino represents groups in which the nitrogen atom is bound to a hydrogen atom and to straight chain or branched C1-C4 alkyl groups as outlined above. Accordingly, C1-C4 alkylamino includes methylamino, ethylamino, propylamino, isopropylamino, butylamino, isobutylamino, sec-butylamino and tert-butylamino.

C1-C4 dialkylamino represents groups in which the nitrogen atom is bound to two identical or non-identical straight chain or branched C1-C4 alkyl groups which include methyl, ethyl, propyl, isopropyl, butyl, isobutyl, sec-butyl, or tert-butyl.

Di(C1-C4 alkyl)aminoethyl represents groups in which the nitrogen atom is bound to two straight chain or branched C1-C4 alkyl groups which include methyl, ethyl, propyl, isopropyl, butyl, isobutyl, sec-butyl, or tert-butyl.

C3-C6 cycloalkyl represents the cyclopropyl, cyclobutyl, cyclopentyl, and cyclohexyl groups.

Four- to six-membered heterocyclyl represents a saturated carbocycle group with four to six carbon ring atoms, one of which is replaced by an N atom and another of which optionally is replaced by an N, O or S atom. Examples for saturated four- to six-membered heterocyclyl comprise without limitation azetidinyl, 1,3-oxazolidinyl, 1,3-thiazolidinyl, isoxazolidinyl, isothiazolidinyl, 1,2,4-triazolidinyl, 1,2,4-oxadiazolidinyl, 1,2,4-thiadiazolidinyl, pyrrolidinyl, piperazinyl, piperidinyl, morpholinyl, 1,1-dioxothiomorpholinyl, hexahydropyrimidinyl, 1,3-oxazinanyl, 1,3-thiazinanyl, hexahydropyridazinyl, 1,2-oxazinanyl, 1,2-thiazinanyl, 1,2,4-triazinanyl, 1,2,5-oxadiazinanyl, and 1,2,5-thiadiazinanyl.

Four- to six-membered N-ethylheterocyclyl represents a four- to six-membered heterocyclyl which is N-substituted by an ethyl group.

Saturated four- to seven-membered heterocycle represents a saturated carbocycle with four to seven carbon ring atoms, one of which is replaced by an N atom and another of which optionally is replaced by an N, O or S atom. Examples for saturated four- to six-membered heterocycle comprise without limitation azetidine, 1,3-oxazolidine, 1,3-thiazolidine, isoxazolidine, isothiazolidine, 1,2,4-triazolidine, 1,2,4-oxadiazolidine, 1,2,4-thiadiazolidine, pyrrolidine, piperazine, piperidine, morpholine, 1,1-dioxothiomorpholine, hexahydropyrimidine, 1,3-oxazinane, 1,3-thiazinane, hexahydropyridazine, 1,2-oxazinane, 1,2-thiazinane, 1,2,4-triazinane, 1,2,5-oxadiazinane, 1,2,5-thiadiazinane, azepane, 1,4-diazepane, 1,4-oxazepane, and 1,4-thiazepane.

C1-C4 acyl represents groups comprising a carbonyl group which is part of a straight or branched C1-C4 chain. Examples for C1-C4 acyl are formyl, acetyl, propionyl, butyryl and isobutyryl.

Oxo means an oxygen atom which is bound by a double bond to a carbon atom, giving rise to a carbonyl group.

It is to be understood that the invention covers all combinations of substituent groups referred to hereinabove. In particular, the invention covers all combinations of preferred groups described herein.

Salts of the compounds according to the invention and the stereoisomers of the salts include all inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxybenzoyl)benzoates, butyrates, sulfosalicylates, maleates, laurates, malates, lactates, fumarates, succinates, oxalates, tartrates, stearates, benzenesulfonates (besylates), toluenesulfonates (tosylates), methanesulfonates (mesylates), laurylsulfonates, 3-hydroxy-2-naphthoates, lactobionates, galactarates, embonates and ascorbates.

Examples of salts with bases include, but are not limited to, lithium, sodium, potassium, calcium, aluminum, magnesium, titanium, ammonium, meglumine and guanidinium salts.

The salts include water-insoluble (or practically insoluble) and, particularly, water-soluble salts.

The compounds according to the invention, the salts thereof and the stereoisomers of the compounds or the salts thereof may contain, e.g. when isolated in crystalline form, varying amounts of solvents. Included within the scope of the invention are, therefore, all solvates of the compounds of formula (I), the salts thereof, and the stereoisomers of the compounds and the salts thereof. Hydrates are a preferred example of said solvates.

The invention further relates to stereoisomers of formula (I). The invention also relates to mixtures of stereoisomers, including the racemates.

Some of the compounds, salts thereof, and stereoisomers of the compounds or the salts thereof may exist in different crystalline forms (polymorphs) as well as in amorphous forms, which are intended to be within the scope of the invention.

Furthermore, derivatives of the compounds of formula (I), the salts thereof, stereoisomers of the compounds or the salts thereof which are converted into compound (I), a salt thereof, or a stereoisomer of the compound or a salt thereof in a biological system (bioprecursors or prodrugs) are covered by the invention. Said biological system is e.g. a mammalian organism, particularly a human subject. The prodrug is, for example, converted into the compound of formula (I), a salt thereof, or a stereoisomer of the compound or a salt thereof by metabolic processes. For example, prodrugs may be esters of the compounds of formula (I) which can be readily hydrolyzed after uptake by a biological systems, e.g., by an esterase, to yield unmodified compound of formula (I).

The compounds according to the invention can be prepared as follows.

Reaction Scheme 1:

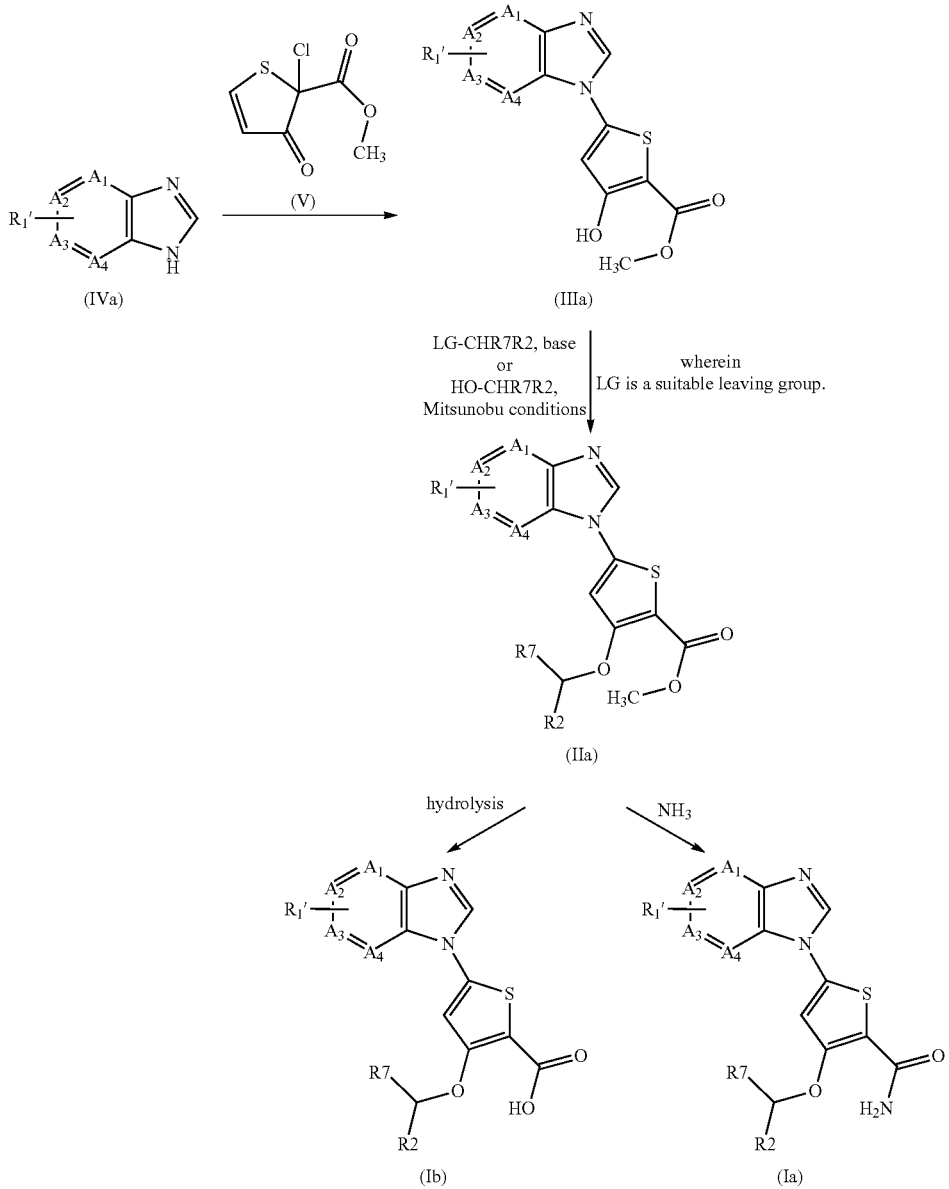

Compounds of formula (IVa), LG-CHR7R2 and HO—CHR7R2 (R2 and R7 having the same meaning as outlined above) are commercially available or can be obtained according to procedures known in the art or methods as described in reaction schemes 3-5. R1' includes, but is not limited to, —Cl, —OMe, —CH$_2$OPG, —C(O)N(R5)R6 (R5 and R6 having the same meaning as outlined above). Specific examples of a suitable protecting group (PG) include, but are not limited to, t-butyldimethylsilyl (TBDMS) and t-butyldiphenylsilyl (TBDPS). For the synthesis of compound (V), see Corral, C., Lissavetzky, J., *Synthesis* (1984), 847-850.

Specific examples of a suitable leaving group (LG) include, but are not limited to, bromide and chloride. An alternative leaving group might be —OSO2CH3.

Due to tautomerism of the imidazole moiety, the reaction between non-symmetrical compounds (IVa) and (V) usually yields compounds (IIIa) as a mixture of regioisomers. In certain cases the formation of one of the two possible isomers is strongly preferred. The reaction is carried out in an appropriate solvent, e.g. CHCl$_3$, CH$_2$Cl$_2$ or toluene, preferably at room temperature. In some cases the addition of a suitable amine base (e.g. 2,2,6,6-tetramethylpiperidine or N-methylimidazole) may improve the yields. It is also possible to separate the mixture of regioisomers at the stage of compounds (IIIa), (IIa), (Ia) and (If), e.g., by flash column chromatography or by preparative HPLC. Preferentially the separation of the regioisomeric mixture is accomplished at the stage of compounds (IIa).

Typically, compounds of formula (IIIa) are used for the next reaction step towards compounds (Ia) as crude material without further purification. The synthesis of compounds (IIa) can either be carried out with a compound of formula LG-CHR7R2 in the presence of a base or with a compound of formula HO—CHR7R2 under standard Mitsunobu conditions. Under Mitsunobu conditions typically a compound of formula (IIIa), an alcohol of the formula HO—CHR7R2, a triarylphosphine, and a dialkyl azodicarboxylate are reacted in an inert solvent at room temperature. Examples of suitable triarylphosphines include but are not limited to triphenylphosphine, tri-p-toluoylphosphine, and trimesitylphosphine. Examples of suitable dialkyl azodicarboxylates include, but are not limited to, diethyl azodicarboxylate, diisopropyl azodicarboxylate, and di-tert-butyl azodicarboxylate. Examples of suitable inert solvents for this reaction include, but are not limited to, tetrahydrofuran, dioxane, 1,2-dimethoxyethane, dichloromethane, and toluene. Further details can be found, e.g., in Hughes, D. L., *Organic Reactions* (1992), 42, 335-656; and in Mitsunobu, O., *Synthesis* (1981), 1-28.

In case of a chiral alcohol, under Mitsunobu conditions inversion of stereochemistry is observed.

Compounds of formula (Ia) can be obtained from (IIa). This reaction is typically performed at elevated temperatures in a sealed vessel (e.g., in the cavity of a microwave oven or in an autoclave) with an excess of ammonia. Typical temperatures, without being meant as a limitation, include the range from about 100 to 130° C. Suitable solvents for this reaction include, but are not limited to, methanol and ethanol.

Compounds of formula (Ib) can be obtained from (IIa) by acidic or basic hydrolysis, basic hydrolysis being preferred.

The structural assignment of the regioisomers (attachment of the thiophene ring at N-1 or N-3 of the imidazole) can be established by two-dimensional $^1$H NMR experiments (NOESY, COSY), which can be performed at the stage of compounds of the formula (Ia-f), (IIa) and (IIIa). Exemplarily, the analysis is shown for examples 16 and 17.

Optionally, the two dimensional 1H NMR experiments are performed for both or for only one of the two regioisomers.

Reaction scheme 2:

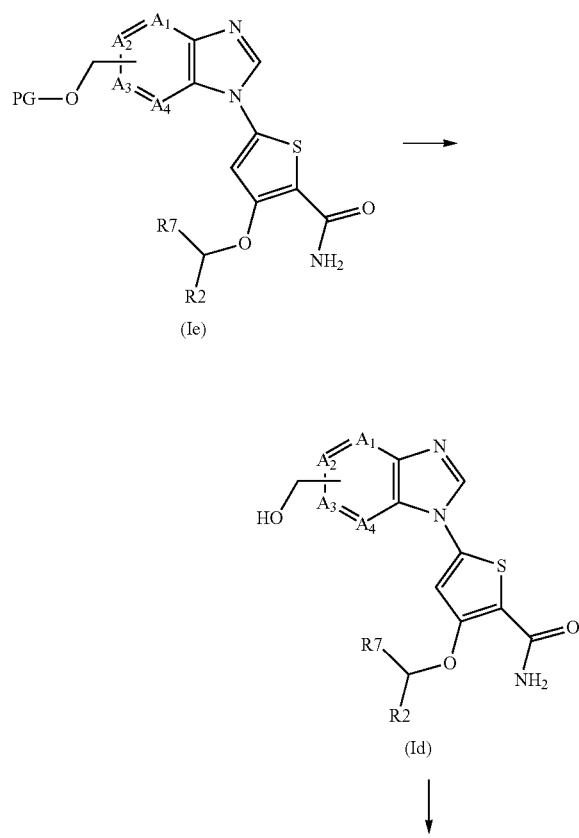

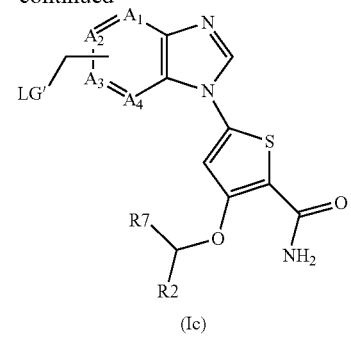

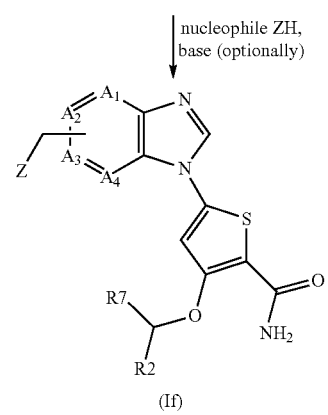

Compounds of formula (Ie) are a subtype of compounds of formula (Ia) and can be trans-formed to compounds of the formula (Id), (Ic) and (If) as outlined in scheme 2.

Specific examples of a suitable protecting group (PG) include, but are not limited to, t-butyldimethylsilyl (TBDMS) and t-butyldiphenylsilyl (TBDPS). Deprotection of a t-butyldimethylsilyl (TBDMS) or a t-butyldiphenylsilyl (TBDPS) group of compounds of formula (Ie) leading to compounds (Id) is carried out under standard conditions (e.g. tetra-n-butylammonium fluoride (TBAF) in THF). Details can be found in Kocienski, P. J., *Protecting Groups*, Georg Thieme Verlag, Stuttgart, 1994, p. 21-87, and in Greene, T. W., Wuts, P. G. M., *Protecting Groups in Organic Synthesis* ($3^{rd}$ *Edition*), J. Wiley & Sons, New York, 1999, p. 17-200.

Primary alcohols of formula (Id) can be converted to compounds (Ic) carrying a suitable leaving group (LG') by methods known in the art. A suitable leaving group, LG', includes, but is not limited to, —OSO$_2$CH$_3$. The introduction of this group can be accomplished, e.g., by reaction of compounds (Id) with (CH$_3$SO$_2$O)$_2$ or CH$_3$SO$_2$Cl in the presence of a base such as, e.g., triethylamine. Alternative leaving groups LG' might be chloride or bromide.

Reaction of compounds of formula (Ic) with certain nucleophiles (compounds of formula ZH), optionally in the presence of a base, yields compounds of formula (If).

Compounds of formula (ZH) include but are not limited to amines of the formula R3R4NH (R3 and R4 having the meaning as outlined above), N-substituted piperidin-4-ols, and magnesium or sodium methylsulfinate. Compounds of formula (ZH) are commercially available or can be obtained according to procedures known in the art.

Suitable bases include, but are not limited to, potassium carbonate, sodium hydride and triethylamine.

Reaction scheme 3:

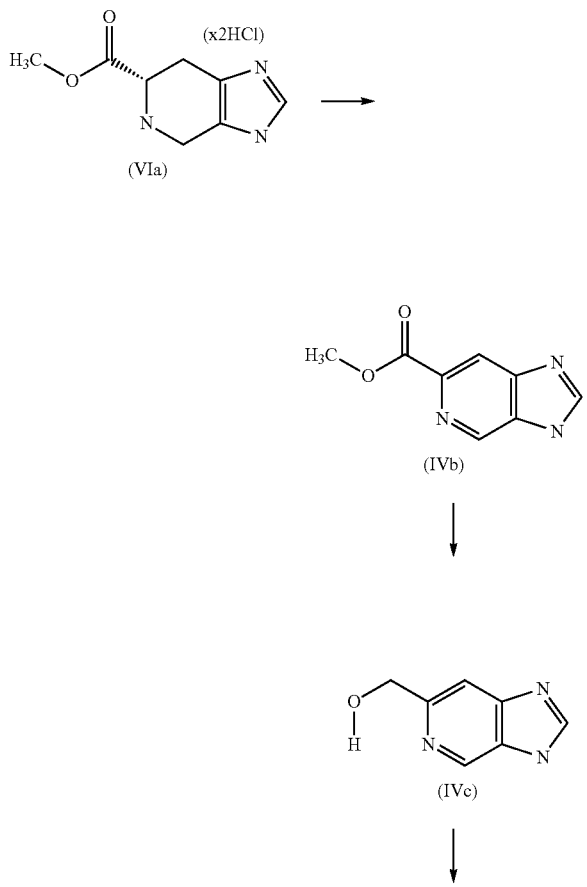

Reaction scheme 4:

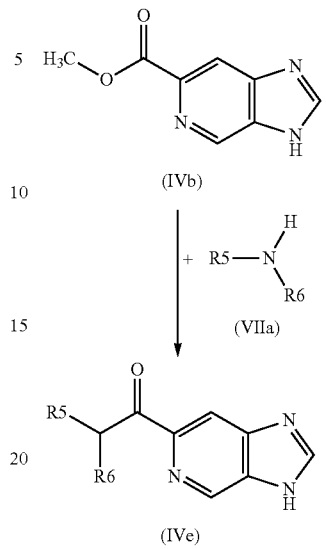

Compounds of formula (VIIa) are commercially available or can be obtained according to procedures known in the art.

Compounds of formula (IVe) are synthesized by reaction of compound (IVb) with an excess of the respective amines of the formula (VIIa) at elevated temperatures (e.g., about 140° C.) in a sealed vessel as described above. Suitable solvents for the reaction include, but are not limited to, methanol.

Compounds of formula (IVe) are a subtype of compounds of formula (IVa) and are subjected to subsequent reactions as outlined in scheme 1.

Reaction scheme 5:

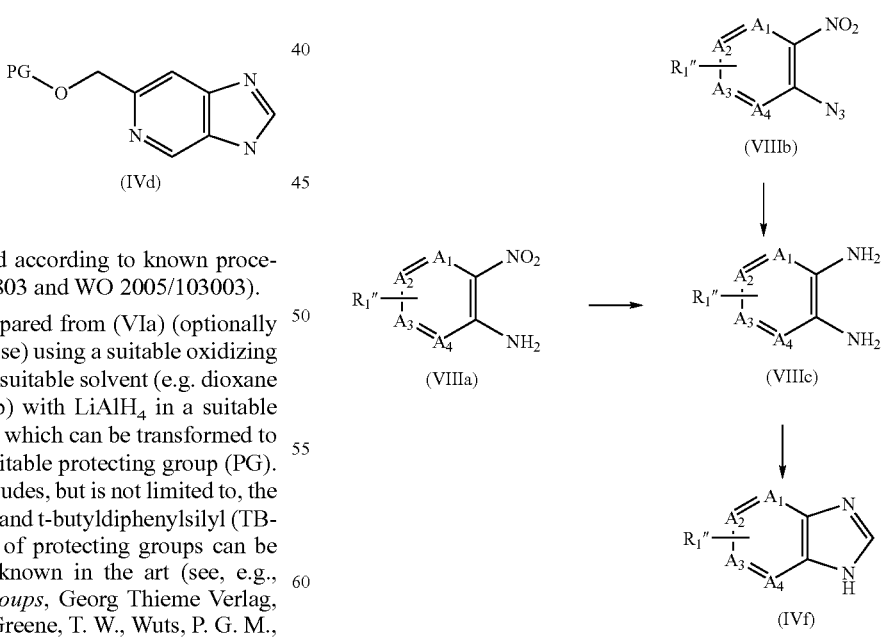

Compound (VIa) is prepared according to known procedures (see, e.g., WO 2004/039803 and WO 2005/103003).

Compound (IVb) can be prepared from (VIa) (optionally as dihydrochloride or as free base) using a suitable oxidizing agent (e.g. $SeO_2$ or $MnO_2$) in a suitable solvent (e.g. dioxane or toluene). Reduction of (IVb) with $LiAlH_4$ in a suitable solvent (e.g. THF) yields (IVc) which can be transformed to compound (IVd), carrying a suitable protecting group (PG). A suitable protecting group includes, but is not limited to, the t-butyldimethylsilyl (TBDMS) and t-butyldiphenylsilyl (TB-DPS) group. The introduction of protecting groups can be carried out under conditions known in the art (see, e.g., Kocienski, P. J. *Protecting Groups*, Georg Thieme Verlag, Stuttgart, 1994, p. 21-87, and Greene, T. W., Wuts, P. G. M., *Protecting Groups in Organic Synthesis* (3$^{rd}$ Edition), J. Wiley & Sons, New York, 1999, p. 17-200).

Compounds of formula (IVd) are a subtype of compounds of formula (IVa) and are subjected to subsequent reactions as outlined in scheme 1.

Compounds of formula (VIIIc) are commercially available or can be obtained according to procedures known in the art. Substituents R1" include, but are not limited to, —$OCH_3$ and —Cl.

The diamines (VIIIc) can be obtained, e.g., from compounds of formula (VIIIa) or (VIIIb) via reductive hydrogenation (e.g. with $H_2$/Pd), and may be used for the next step without purification. Compounds of formula (IVf) can be obtained by reaction of (VIIIc) with formic acid under reflux conditions. Compounds of formula (IVf) are a subtype of compounds of formula (IVa) and are subjected to subsequent reactions as outlined in scheme 1.

Compounds of formula (I) can be converted into different compounds of formula (I) by methods known in the art. For example, A compound of formula (I) wherein Y is —$CONH_2$ can be prepared from a compound of formula (I) wherein Y is —COOH by formation of the corresponding acid chloride (e.g., with $SOCl_2$) and subsequent reaction with $NH_4OH$.

A compound of formula (I) wherein R1 is —$CH_2OH$ can be converted into the corresponding aldehyde by oxidation, e.g., with the aid of a suitable oxidation reagent, and subsequently reacted with a suitable amine under reductive amination conditions (e.g., with $NaBH(OAc)_3$ as reducing agent), leading to the corresponding amine.

A compound of formula (I) wherein R1 is —$CH_2$-piperazinyl can be converted into the corresponding N-alkylated, N-acylated or N-carbamoylated piperazine by reaction with an appropriate alkyl halogenide, carboxylic acid chloride, or isocyanate.

It is known to the person skilled in the art that, if there are a number of reactive centers on a starting or intermediate compound, it may be necessary to block one or more reactive centers temporarily by protective groups in order to allow a reaction to proceed specifically at the desired reaction center.

The compounds according to the invention are isolated and purified in a manner known per se, e.g. by distilling off the solvent in vacuo and recrystallizing the residue obtained from a suitable solvent, or by subjecting it to one of the customary purification methods, such as column chromatography employing a suitable support material.

Salts according to the invention of the compounds of formula (I) and of the stereoisomers thereof can be obtained by dissolving the free compound in a suitable solvent (for example a ketone such as acetone, methylethylketone or methylisobutylketone, an ether such as diethyl ether, tetrahydrofurane or dioxane, a chlorinated hydrocarbon such as methylene chloride or chloroform, a low molecular weight aliphatic alcohol such as methanol, ethanol or isopropanol, a low molecular weight aliphatic ester such as ethyl acetate or isopropyl acetate, an amide such as dimethylformamide, a nitril such as acetonitril, or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or a ratio differing therefrom. The salts can be obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

In case R7 being methyl, ethyl, —$CH_2OH$ or $CF_3$, the compounds according to the invention (including the salts thereof) are characterized by one stereogenic center at the carbon atom to which the substituents R7 and R2 are attached. This stereogenic center may have the absolute configuration R or the absolute configuration S (according to the rules of Cahn, Ingold and Prelog). In the formula below, the position of this asymmetrically substituted carbon atom is indicated by an asterisk:

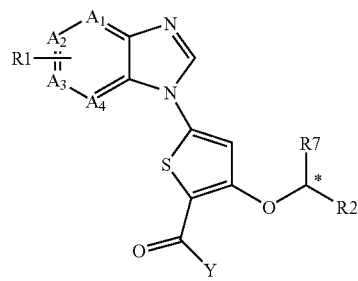

Accordingly, the invention further includes all mixtures of the stereoisomers mentioned above independent of the ratio of different stereoisomers to each other, including the racemates.

Accordingly, the invention further includes compounds of formula (I) wherein the carbon atom to which R2 and R7 are attached has the absolute configuration R.

Accordingly, the invention further includes compounds of formula (I) wherein the carbon atom to which R2 and R7 are attached has the absolute configuration S.

Pure diastereomers and pure enantiomers of the compounds of formula (I) and the salts thereof according to the invention can be obtained, e.g., by asymmetric synthesis, by using chiral starting compounds in synthesis and/or by splitting up enantiomeric and diastereomeric mixtures obtained in synthesis. Preferably, the pure diastereomeric and pure enantiomeric compounds of the invention are obtainable by asymmetric synthesis and/or by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

As will be appreciated by persons skilled in the art, the invention is not limited to the particular embodiments described herein, but covers all modifications of said embodiments that are within the spirit and scope of the invention as defined by the appended claims.

All patents, patent applications, publications, test methods and other materials cited herein are incorporated by reference in their entireties.

The following examples illustrate the invention in greater detail, without restricting it. Further compounds according to the invention, of which the preparation is not explicitly described, can be prepared in an analogous way.

The compounds which are mentioned in the examples, the salts thereof, and stereoisomers of the compounds and the salts thereof represent preferred embodiments of the invention.

EXAMPLES $^1$H-NMR spectra were recorded using either Bruker DPX200 or Bruker AV400 or Bruker AVII300 or Bruker AV600 spectrometer in CDCl$_3$ or D$_6$-DMSO. Two dimensional $^1$H NMR experiments (NOESY, COSY) were recorded using a Bruker DRX400. Chemical shifts are reported in parts per million (ppm) with tetramethylsilane (TMS) as an internal standard at zero ppm. Coupling constants (J) are given in Hertz and the abbreviations s, d, t, q, m, and br refer to singlet, doublet, triplet, quartet, multiplet, and broad, respectively. The mass determinations were carried out by LCQ (Thermofinnigan). LC-MS determinations were carried out with an Agilent 1100. Preparative HPLC purification were carried out with a Varian ProStar using either phenomenex Gemini C18 or phenomenex Synergi RP-polar columns or on a customary instrument from Gilson using a reversed phase column (C18, Phenomenex, Gemini, 75×30 mm, 5 µm) as stationary phase. Microwave reactions were carried out in an Emrys OptimizerEXP. Melting points were determined using a Buechi Melting Point B-545. Flash chromatography was conducted with Macherey-Nagel silica gel 60M (230-400 mesh), with Macherey-Nagel Alox N or with Biotage Isolute Flash NH2.

The following abbreviations are used: h: hour(s), ° C.: degrees centigrade, l: liter(s), ml: milliliter(s), DMSO: dimethyl sulfoxide, DMF: N,N-dimethylformamide, THF: tetrahydrofuran, DCM: dichloromethane, TBAF: tetra-n-butylammonium fluoride, mp.: melting point, MS: mass spectrometry, $^1$H NMR: $^1$H nuclear magnetic resonance spectroscopy. $^{13}$C NMR: $^{13}$C nuclear magnetic resonance spectroscopy, HPLC: High Performance Liquid Chromatography, NOESY: Nuclear Overhauser Effect Spectroscopy, NOE: Nuclear Overhauser Effect, COSY: Correlated Spectroscopy.

Final Compounds of Type (Ia) and (Ib)

1. 5-(6-Chloro-1H-imidazo[4,5-c]pyridin-1-yl)-3-{[2-(trifluoromethyl)benzyl]oxy}thiophene-2-carboxamide A mixture of 140 mg of methyl 5-(6-chloro-1H-imidazo[4,5-c]pyridin-1-yl)-3-{[2-(trifluoromethyl)benzyl]oxy}thiophene-2-carboxylate and 20 ml of a saturated solution of ammonia in methanol were stirred in a microwave vial at 120° C. for 4 h in the microwave cavity. The reaction mixture was concentrated to half of the volume. The solid that precipitated after standing was collected and recrystallized from acetonitrile to give the title compound.

$^1$H NMR (400 MHz, D$_6$-DMSO): δ=5.57 (s, 2H), 6.82 (bs, 1H), 7.75-7.69 (m, 1H), 7.73 (s, 1H), 7.76-7.87 (m, 4H), 7.90 (s, 1H), 8.84 (s, 1H), 8.93 (s, 1H).
MS (MH$^+$ found)=453.0
mp.: 248-249° C. (under decomposition)

2. 5-(1H-Imidazo[4,5-c]pyridin-1-yl)-3-{[2-(trifluoromethyl)benzyl]oxy}thio-phene-2-carboxamide In a similar manner as described for example 1, 195 mg of methyl 5-(1H-imidazo[4,5-c]pyridin-1-yl)-3-{[2-(trifluoromethyl)benzyl]oxy}thiophene-2-carboxylate (compound B1a) and 36 ml of a saturated solution of ammonia in methanol yield the title compound.

$^1$H NMR (200 MHz, D$_6$-DMSO): δ=5.55 (s, 2H), 6.80 (bs, 1H), 7.62-7.87 (m, 7H), 8.54 (d, J=5.8 Hz, 1H), 8.81 (s, 1H), 9.10 (s, 1H).
MS (MH$^+$ found)=419.1
mp.: 226-227° C. (under decomposition)

3. 5-(3H-Imidazo[4,5-c]pyridin-3-yl)-3-{[2-(trifluoromethyl)benzyl]oxy}thio-phene-2-carboxamide A mixture of 1.40 g of methyl 5-(3H-imidazo[4,5-c]pyridin-3-yl)-3-{[2-(trifluoromethyl)benzyl]oxy}thiophene-2-carboxylate (compound B1b) and 65 ml of a saturated solution of ammonia in methanol were stirred in an autoclave at 130° C. for 7 h. The mixture was allowed to cool down to room temperature and concentrated to about half of the volume. The precipitated solid was filtered, widely dissolved in 500 ml of methanol upon heating and filtered again. The filtrate was concentrated to about 25 ml upon which solid precipitated. It was filtered, dissolved in acetonitrile containing small amounts of water and finally the solution was lyophilized to give the title compound as a colorless powder.

The structural assignment of the regioisomer was unequivocally established by two-dimensional $^1$H NMR experiments (NOESY, COSY).

$^1$H NMR (400 MHz, D$_6$-DMSO): δ=5.57 (s, 2H), 6.81 (bs, 1H), 7.64-7.68 (m, 1H), 7.74 (bs, 1H), 7.77-7.87 (m, 5H), 8.52 (d, J=5.5 Hz, 1H), 8.87 (s, 1H), 9.18 (s, 1H).
MS (MH$^+$ found)=419.1

4. 1-(5-Carbamoyl-4-{[2-(trifluoromethyl)benzyl]oxy}-2-thienyl)-N-(2-methoxyethyl)-1H-imidazo[4,5-c]pyridine-6-carboxamide In a similar manner as described for example 1, 246 mg of methyl 5-{6-[(2-methoxyethyl)carbamoyl]-1H-imidazo[4,5-c]pyridin-1-yl}-3-{[2-(trifluoromethyl)benzyl]oxy}thiophene-2-carboxylate (compound B8) and 40 ml of a saturated solution of ammonia in methanol give the title compound.

The structural assignment of the regioisomer was unequivocally established by two-dimensional $^1$H NMR experiments (NOESY, COSY).

$^1$H NMR (600 MHz, D$_6$-DMSO): δ=3.30 (s, 3H), 3.52-3.54 (m, 4H), 5.56 (s, 2H), 6.83 (bs, 1H), 7.65-7.68 (m, 1H), 7.76 (s, 1H), 7.80-7.90 (m, 4H), 8.39 (s, 1H), 8.77-8.79 (m, 1H), 8.95 (s, 1H), 9.14 (s, 1H).
MS (MH$^+$ found)=520.0
mp.: 227-228° C. (under decomposition)

5. 1-(5-Carbamoyl-4-{[2-(trifluoromethyl)benzyl]oxy}-2-thienyl)-N-(2-morpholin-4-ylethyl)-1H-imidazo[4,5-c]pyridine-6-carboxamide A mixture of 150 mg of methyl 5-{6-[(2-morpholin-4-ylethyl)carbamoyl]-1H-imidazo[4,5-c]pyridin-1-yl}-3-{[2-(trifluoromethyl)benzyl]oxy}thiophene-2-carboxylate (compound B9) and 20 ml of a saturated solution of ammonia in methanol was stirred in a microwave vial at 125° C. for 4 h in the microwave cavity. The reaction mixture was concentrated to dryness, the resulting residue was dissolved in 5 ml of methanol and purified by preparative HPLC (water/acetonitrile, elution gradient 9/1 to 1/9 (v/v)). After lyophilization the title compound was obtained.

The structural assignment of the regioisomers was unequivocally established by two-dimensional $^1$H NMR experiments (NOESY, COSY).

$^1$H NMR (400 MHz, D$_6$-DMSO): δ=2.48 (m, 4H), 2.55-2.58 (m, 2H), 3.48-3.53 (m, 2H), 3.60 (t, J=4.5 Hz, 4H), 5.55 (s, 2H), 6.83 (bs, 1H), 7.64-7.68 (m, 1H), 7.77-7.90 (m, 5H), 8.39 (s, 1H), 8.83 (t, J=5.8 Hz, 1H), 8.95 (s, 1H), 9.14 (s, 1H).

MS (MH$^+$ found)=575.1

6. 5-{6-[(Diethylamino)methyl]-1H-imidazo[4,5-c]pyridin-1-yl}-3-{[2-(trifluoromethyl)benzyl]oxy}thiophene-2-carboxamide To a solution of 58 mg of [1-(5-carbamoyl-4-{[2-(trifluoromethyl)benzyl]oxy}-2-thienyl)-1H-imidazo[4,5-c]pyridin-6-yl]methyl methanesulfonate (compound A1) in 4 ml of dichloromethane were added 146 mg of diethylamine, and the reaction mixture was stirred at room temperature for 12 h. The mixture was concentrated to dryness under vacuum and the residue was dissolved in acetonitrile/water and purified by preparative HPLC (water/acetonitrile, elution gradient 9/1 to 1/9 (v/v)). After lyophilization the title compound was obtained.

$^1$H NMR (400 MHz, D$_6$-DMSO): δ=1.00 (t, J=7.1 Hz, 6H), 2.55 (q, J=7.1 Hz, 4H), 3.81 (s, 2H), 5.54 (s, 2H), 6.82 (bs, 1H), 7.64-7.67 (m, 1H), 7.72 (s, 1H), 7.77-7.86 (m, 5H), 8.76 (s, 1H), 8.97 (s, 1H).

MS (MH$^+$ found)=504.0

7. 5-{6-[(Cyclopropylamino)methyl]-1H-imidazo[4,5-c]pyridin-1-yl}-3-{[2-(trifluoromethyl)benzyl]oxy}thiophene-2-carboxamide In a similar manner as described for example 6, 58 mg of [1-(5-carbamoyl-4-{[2-(trifluoromethyl)benzyl]oxy}-2-thienyl)-1H-imidazo[4,5-c]pyridin-6-yl]methyl methanesulfonate (compound A1) and 228 mg of cyclopropylamine in 5 ml dichloromethane yield the title compound.

$^1$H NMR (400 MHz, D$_6$-DMSO): δ=0.40-0.46 (m, 4H), 2.21-2.26 (m, 1H), 4.09 (s, 2H), 5.54 (s, 2H), 6.81 (bs, 1H), 7.64-7.68 (m, 1H), 7.72-7.87 (m, 7H), 8.77 (s, 1H), 9.03 (s, 1H).

MS (MH$^+$ found)=487.9

8. 5-{6-[(4-Methylpiperazin-1-yl)methyl]1H-imidazo[4,5-c]pyridin-1-yl}-3-{[2-(trifluoromethyl)benzyl]oxy}thiophene-2-carboxamide In a similar manner as described for example 6, 58 mg of [1-(5-carbamoyl-4-{[2-(trifluoromethyl)benzyl]oxy}-2-thienyl)-1H-imidazo[4,5-c]pyridin-6-yl]methyl methanesulfonate (compound A1) and 200 mg of 1-methylpiperazine in 5 ml dichloromethane yield the title compound.

$^1$H NMR (400 MHz, D$_6$-DMSO): δ=2.14 (s, 3H), 2.33 (bs, 4H), 2.47 (bs, 4H), 3.73 (s, 2H), 5.54 (s, 2H), 6.81 (bs, 1H), 7.64-7.58 (m, 1H), 7.72-7.87 (m, 6H), 8.76 (s, 1H), 8.99 (s, 1H).

MS (MH$^+$ found)=531.0

9. 5-[6-(Hydroxymethyl)-1H-imidazo[4,5-c]pyridin-1-yl]-3-{[2-(trifluoromethyl)benzyl]oxy}thiophene-2-carboxamide A mixture of 3.15 g of methyl 5-[6-({[tert-butyl(dimethyl)silyl]oxy}methyl)-1H-imidazo[4,5-c]pyridin-1-yl]-3-{[2-(trifluoromethyl)benzyl]oxy}thiophene-2-carboxylate (compound B2b) and 218 ml of a saturated solution of ammonia in methanol was stirred in an autoclave at 120° C. for 3 h. The mixture was allowed to cool down to room temperature and concentrated to dryness to give the crude corresponding acid amide that was immediately used for the next step without further purification. The residue was dissolved in 180 ml tetrahydrofuran and to this solution is added 2.0 ml of tetra-n-butylammonium fluoride solution (~75% in H$_2$O) at 0° C. The reaction mixture was stirred at 0° C. for 12 h. The solvent was evaporated and the residue was treated with 250 ml dichloromethane and 60 ml saturated aqueous NaHCO$_3$ solution. The resulting precipitate was dissolved by addition of propan-2-ol, the organic layer was separated, washed with 60 ml saturated aqueous NaHCO$_3$ solution, dried with MgSO$_4$ and concentrated under vacuum. The residue was suspended in 40 ml dichloromethane and stirred for one hour. The suspension was filtered, the filter cake washed with 20 ml dichloromethane and dried under vacuum to yield the title compound.

The structural assignment of the regioisomers was unequivocally established by two-dimensional $^1$H NMR experiments (NOESY, COSY).

$^1$H NMR (300 MHz, D$_6$-DMSO): δ=4.72 (d, J=5.5 Hz, 2H), 5.54-5.56 (m, 3H), 6.80 (bs, 1H), 7.63-7.68 (m, 1H), 7.74-7.88 (m, 6H), 8.78 (s, 1H), 8.98 (d, J=0.9 Hz, 1H).

MS (MH$^+$ found)=449.0

10. 5-[6-(Hydroxymethyl)-3H-imidazo[4,5-c]pyridin-3-yl]-3-{[2-(trifluoromethyl)benzyl]oxy}thiophene-2-carboxamide In a similar manner as described for example 9, 94 mg 5-[6-({[tert-butyl(dimethyl)silyl]oxy}methyl)-3H-imidazo[4,5-c]pyridin-3-yl]-3-{[2-(trifluoromethyl)benzyl]oxy}thiophene-2-carboxamide (compound A2) and 53 mg of tetra-n-butylammonium fluoride solution (~75% in H$_2$O) in 6 ml tetrahydrofuran yield the title compound.

The structural assignment of the regioisomers was unequivocally established by two-dimensional $^1$H NMR experiments (NOESY, COSY).

$^1$H NMR (300 MHz, D$_6$-DMSO): δ=4.71 (d, J=5.8 Hz, 2H), 5.46 (t, J=5.8 Hz, 1H), 5.57 (s, 2H), 6.80 (bs, 1H), 7.63-7.87 (m, 7H), 8.84 (s, 1H), 9.06 (d, J=0.9 Hz, 1H).

MS (MH$^+$ found)=449.0

11. 1-(5-Carbamoyl-4-{[2-(trifluoromethyl)benzyl]oxy}-2-thienyl)-N-methyl-N-(2-morpholin-4-yl-ethyl)-1H-imidazo[4,5-c]pyridine-6-carboxamide To a suspension of 25 mg sodium hydride (60% dispersion in mineral oil) in 2 ml anhydrous N,N-dimethylformamide is added 236 mg methyl 5-{6-[(2-morpholin-4-ylethyl)carbamoyl]-1H-imidazo[4,5-c]pyridin-1-yl}-3-{[2-(trifluoromethyl)benzyl]oxy}-thiophene-2-carboxylate (compound B9) portionwise at 0° C. and the mixture was stirred for 30 minutes. 114 mg methyl iodide were added dropwise and after the addition the ice bath was removed and the reaction mixture was stirred at room temperature for 12 h. The solvent was evaporated and the residue was dissolved in 3 ml methanol and purified by preparative HPLC (water/acetonitrile, elution gradient 9/1 to 1/9 (v/v)) to give 5-[6-(methyl-(2-morpholin-4-yl-ethylcarbamoyl)-imidazo[4,5-c]pyridin-1-yl]-3-(2-trifluoromethyl benzyloxy)-thio-phene-2-carboxylic acid methylester as crude material which was used for the next step without further purification.

In a similar manner as described for example 5, 29 mg of the above-synthesized crude 5-[6-(methyl-(2-morpholin-4-yl-ethylcarbamoyl)-imidazo[4,5-c]pyridin-1-yl]-3-(2-trifluoromethyl benzyloxy)-thiophene-2-carboxylic acid methylester and 20 ml of a saturated solution of ammonia in methanol yield the title compound.

The structural assignment of the regioisomer was unequivocally established by two-dimensional $^1$H NMR experiments (NOESY, COSY).

$^1$H NMR (300 MHz, CDCl$_3$): δ=2.37 (bs, 2H), 2.62-2.74 (m, 4H), 3.18 (s, 3H), 3.58 (bs, 2H), 3.67-3.74 (m, 4H), 5.47 (s, 2H), 5.73 (bs, 1H), 6.93 (bs, 1H), 7.03 (s, 1H), 7.53-7.58 (m, 1H), 7.64-7.70 (m, 2H), 7.78 (d, J=7.7 Hz, 1H), 7.97-8.03 (m, 1H), 8.18 (s, 1H), 9.10 (d, J=10.2 Hz, 1H).

MS (MH$^+$ found)=589.0

12. 3-[1-(2-Chlorophenyl)ethoxy]-5-(3H-imidazo[4,5-c]pyridin-3-yl)thio-phene-2-carboxamide In a similar manner as described for example B3, 300 mg of an isomeric mixture of methyl 3-hydroxy-5-(1H-imidazo[4,5-c]pyridin-1-yl)thiophene-2-carboxylate and methyl 3-hydroxy-5-(3H-imidazo[4,5-c]pyridin-3-yl)thiophene-2-carboxylate (example C1) and 181 mg K$_2$CO$_3$ and 206 mg 1-chloro-2-(1-chloroethyl)benzene in 5 ml N,N-dimethylformamide yield methyl 3-[1-(2-chlorophenyl)ethoxy]-5-(1H-imidazo[4,5-c]pyridin-1-yl)thiophene-2-carboxylate and methyl 3-[1-(2-chlorophenyl)ethoxy]-5-(3H-imidazo[4,5-c]pyridin-3-yl)thiophene-2-carboxylate.

A mixture of 49 mg of the above-synthesized methyl 3-[1-(2-chlorophenyl)ethoxy]-5-(3H-imidazo[4,5-c]pyridin-3-yl)thiophene-2-carboxylate and 5 ml of a saturated solution of ammonia in methanol was stirred in a microwave vial at 125° C. for 4 h in the microwave cavity. The reaction mixture was allowed to cool down to room temperature, then another 5 ml of a saturated solution of ammonia in methanol were added and the procedure was repeated as described above. The solvent was removed under vacuum and the residue was purified by flash chromatography to yield the title compound.

The structural assignment of the regioisomer was unequivocally established by two-dimensional $^1$H NMR experiments (NOESY, COSY).

$^1$H NMR (400 MHz, D$_6$-DMSO): δ=1.75 (d, J=6.3 Hz, 3H), 6.03 (q, J=6.3 Hz, 1H), 7.13 (bs, 1H), 7.35 (s, 1H), 7.37-7.46 (m, 2H), 7.50 (dd, J=1.2 and 7.9 Hz, 1H), 7.70 (dd, J=1.5 and 7.7 Hz, 1H), 7.80-7.83 (m, 2H), 8.49 (d, J=5.5 Hz, 1H), 8.79 (s, 1H), 8.94 (s, 1H).

MS (MH$^+$ found)=399.9

13. 5-(3H-Imidazo[4,5-c]pyridin-3-yl)-3-{1-[2-(trifluoromethyl)phenyl]ethoxy}thiophene-2-carboxamide In a similar manner as described for example B3, 300 mg of an isomeric mixture of methyl 3-hydroxy-5-(1H-imidazo[4,5-c]pyridin-1-yl)thiophene-2-carboxylate and methyl 3-hydroxy-5-(3H-imidazo[4,5-c]pyridin-3-yl)thiophene-2-carboxylate (example C1) and 181 mg K$_2$CO$_3$ and 332 mg 1-(1-bromoethyl)-2-(trifluoromethyl)benzene in ml N,N-dimethylformamide yield methyl 5-(1H-imidazo[4,5-c]pyridin-1-yl)-3-{1-[2-(trifluoro-methyl)phenyl]ethoxy}thiophene-2-carboxylate and methyl 5-(3H-imidazo[4,5-c]pyridin-3-yl)-3-{1-[2-(trifluoromethyl)phenyl]ethoxy}thiophene-2-carboxylate.

A mixture of 92 mg of the above-synthesized methyl 5-(3H-imidazo[4,5-c]pyridin-3-yl)-3-{1-[2-(trifluoromethyl)phenyl]ethoxy}thiophene-2-carboxylate and 10 ml of a saturated solution of ammonia in methanol was stirred in a microwave vial at 125° C. for 4 h in the microwave cavity. The reaction mixture was allowed to come to room temperature, then another 10 ml of a saturated solution of ammonia in methanol were added and the procedure was repeated as described above. The solvent was removed under vacuum and the residue was purified by flash chromatography (n-hexane/ethyl acetate, elution gradient 10/0 to 3/7 (v/v)) to give the title compound.

The structural assignment of the regioisomer was unequivocally established by two-dimensional $^1$H NMR experiments (NOESY, COSY).

$^1$H NMR (400 MHz, D$_6$-DMSO): δ=1.76 (d, J=6.2 Hz, 3H), 6.00 (q, J=6.2 Hz, 1H), 7.14 (bs, 1H), 7.27 (s, 1H), 7.57 (t, J=7.7 Hz, 1H), 7.76-7.85 (m, 4H), 7.96 (d, J=7.7 Hz, 1H), 8.49 (d, J=5.5 Hz, 1H), 8.76 (s, 1H), 8.91 (s, 1H).

MS (MH$^+$ found)=433.0

14. 5-(1H-Imidazo[4,5-c]pyridin-1-yl)-3-{1-[2-(trifluoromethyl)phenyl]ethoxy}thiophene-2-carboxamide In a similar manner as described for example B3, 300 mg of an isomeric mixture of methyl 3-hydroxy-5-(1H-imidazo[4,5-c]pyridin-1-yl)thiophene-2-carboxylate and methyl 3-hydroxy-5-(3H-imidazo[4,5-c]pyridin-3-yl)thiophene-2-carboxylate (example C1) and 181 mg K$_2$CO$_3$ and 332 mg 1-(1-bromoethyl)-2-(trifluoromethyl)benzene in 5 ml N,N-dimethylformamide yield methyl 5-(1H-imidazo[4,5-c]pyridin-1-yl)-3-{1-[2-(trifluoromethyl)phenyl]ethoxy}thiophene-2-carboxylate and methyl 5-(3H-imidazo[4,5-c]pyridin-3-yl)-3-{1-[2-(trifluoromethyl)phenyl]ethoxy}thiophene-2-carboxylate.

A mixture of 86 mg of the above-synthesized methyl 5-(1H-imidazo[4,5-c]pyridin-1-yl)-3-{1-[2-(trifluoromethyl)phenyl]ethoxy}thiophene-2-carboxylate and 10 ml of a saturated solution of ammonia in methanol was stirred in a microwave vial at 125° C. for 4 h in the microwave cavity. The reaction mixture was allowed to cool down to room temperature, then another 10 ml of a saturated solution of ammonia in methanol were added and the procedure was repeated as described above. The solvent was removed under vacuum and the residue was purified by flash chromatography to give the title compound.

The structural assignment of the regioisomer was unequivocally established by two-dimensional $^1$H NMR experiments (NOESY, COSY).

$^1$H NMR (400 MHz, D$_6$-DMSO): δ=1.77 (d, J=6.2 Hz, 3H), 5.97 (q, J=6.0 Hz, 1H), 7.14 (bs, 1H), 7.22 (s, 1H), 7.55-7.59 (m, 2H), 7.76-7.81 (m, 2H), 7.85 (bs, 1H), 7.96 (d, J=7.8 Hz, 1H), 8.49 (d, J=5.6 Hz, 1H), 8.69 (s, 1H), 9.07 (s, 1H).

MS (MH$^+$ found)=432.9

15. 3-[1-(2-Chlorophenyl)ethoxy]-5-(1H-imidazo[4,5-c]pyridin-1-yl)thio-phene-2-carboxamide In a similar manner as described for example B3, 300 mg of an isomeric mixture of methyl 3-hydroxy-5-(1H-imidazo[4,5-c]pyridin-1-yl)thiophene-2-carboxylate and methyl 3-hydroxy-5-(3H-imidazo[4,5-c]pyridin-3-yl)thiophene-2-carboxylate (example C1) and 181 mg K$_2$CO$_3$ and 206 mg 1-chloro-2-(1-chloroethyl)benzene in 5 ml N,N-dimethylformamide yield methyl 3-[1-(2-chlorophenyl)ethoxy]-5-(1H-imidazo[4,5-c]pyridin-1-yl)thiophene-2-carboxylate and methyl 3-[1-(2-chlorophenyl)ethoxy]-5-(3H-imidazo[4,5-c]pyridin-3-yl)thiophene-2-carboxylate.

A mixture of 87 mg of the above-synthesized methyl 3-[1-(2-chlorophenyl)ethoxy]-5-(1H-imidazo[4,5-c]pyridin-1-yl)thiophene-2-carboxylate and 10 ml of a saturated solution of ammonia in methanol was stirred in a microwave vial at 125° C. for 4 h in the microwave cavity. The reaction mixture was allowed to cool down to room temperature, then another 10 ml of a saturated solution of ammonia in methanol were added and the procedure was repeated as described above. The solvent was removed under vacuum and the residue was purified by flash chromatography to yield the title compound.

The structural assignment of the regioisomer was unequivocally established by two-dimensional $^1$H NMR experiments (NOESY, COSY).

$^1$H NMR (400 MHz, D$_6$-DMSO): δ=1.75 (d, J=6.4 Hz, 3H), 6.00 (q, J=6.4 Hz, 1H), 7.13 (bs, 1H), 7.30 (s, 1H), 7.30-7.45 (m, 2H), 7.51 (dd, J=1.2 and 7.7 Hz, 1H), 7.59-7.61 (m, 1H), 7.70 (dd, J=1.6 and 7.7 Hz, 1H), 7.83 (bs, 1H), 8.49 (d, J=5.7 Hz, 1H), 8.72 (s, 1H), 9.07 (s, 1H).

MS (MH$^+$ found)=398.9

16. 5-(6-Methoxy-1H-imidazo[4,5-c]pyridin-1-yl)-3-{[2-(trifluoromethyl)benzyl]oxy}thiophene-2-carboxamide A suspension of 140 mg of an isomeric mixture of methyl 5-(6-methoxy-3H-imidazo[4,5-c]pyridin-3-yl)-3-{[2-(trifluoromethyl)benzyl]oxy}thiophene-2-carboxylate and methyl 5-(6-methoxy-1H-imidazo[4,5-c]pyridin-1-yl)-3-{[2-(trifluoromethyl)benzyl]oxy}thiophene-2-carboxylate (compounds B6a and B6b) in 20 ml of a saturated solution of ammonia in methanol was stirred in a microwave vial at 130° C. for 5 h in the microwave cavity. The reaction mixture was concentrated to dryness, the residue dissolved in 4 ml acetonitrile and 3 ml acidic buffer (KH$_2$PO$_4$, pH=2) and the isomers were separated and purified by preparative HPLC (acidic buffer/acetonitrile, 7/3 (v/v)). The acetonitrile was removed under vacuum and the aqueous solution was treated with NH$_4$OH until pH 8-9 was reached. The aqueous solution was extracted with dichloromethane three times and the combined organic layers were dried and concentrated to dryness under vacuum to yield the title compound.

The structural assignment of the regioisomer was unequivocally established by two-dimensional $^1$H NMR experiments (NOESY, COSY).

NOE-crosspeaks were detected between H-8 and H-7, H-7 and H-4', H-4' and H-2:

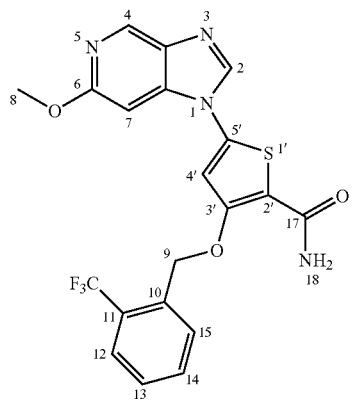

$^1$H NMR (400 MHz, D$_6$-DMSO): δ=3.94 (s, 3H, H-8), 5.56 (s, 2H, H-9), 6.79 (bs, 1H, H-18), 7.11 (s, 1H, H-7), 7.64-7.70 (m, 3H, including s, 1H, H-4' at 7.68; bs, 1H, H-18 and 1H out of H-12, H-13, H-14, H-15), 7.77-7.86 (m, 3H, three H's out of H-12, H-13, H-14, H-15), 8.64 (s, 1H, H-2), 8.69 (s, 1H, H-4).

MS (MH$^+$ found)=449.1

17. 5-(6-Methoxy-3H-imidazo[4,5-c]pyridin-3-yl)-3-{[2-(trifluoromethyl)benzyl]oxy}thiophene-2-carboxamide The title compound was obtained as described in example 16.

The structural assignment of the regioisomer was unequivocally established by two-dimensional $^1$H NMR experiments (NOESY, COSY).

NOE-crosspeaks were detected between H-4 and H-4', H-4' and H-2 as well as H-8 and H-7:

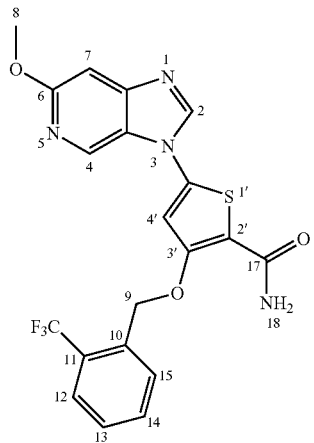

$^1$H NMR (400 MHz, D$_6$-DMSO): δ=3.92 (s, 3H, H-8), 5.56 (s, 2H, H-9), 6.77 (bs, 1H, H-18), 7.15 (s, 1H, H-7), 7.64-7.68 (m, 2H, H-18 and H-13 or H-14), 7.72 (s, 1H, H-4'), 7.79 (t, J=7.5 Hz, 1H, H-13 or H-14), 7.84-7.86 (m, 2H, H-12 and H-15), 8.80 (s, 1H, H-4), 8.81 (s, 1H, H-2).

MS (MH$^+$ found)=449.0

18. 5-(6-Methoxy-1H-imidazo[4,5-c]pyridin-1-yl)-3-{[2-(trifluoromethyl)benzyl]oxy}thiophene-2-carboxylic acid To a solution of 1.2 g of an isomeric mixture of methyl 5-(6-methoxy-3H-imidazo[4,5-c]pyridin-3-yl)-3-{[2-(trifluoromethyl)benzyl]oxy}thiophene-2-carboxylate and methyl 5-(6-methoxy-1H-imidazo[4,5-c]pyridin-1-yl)-3-{[2-(trifluoromethyl)benzyl]oxy}thiophene-2-carboxylate (compounds B6a and B6b) in 30 ml tetrahydrofuran were added dropwise 30 ml of a 1N solution of LiOH. The reaction mixture was stirred for 12 h at room temperature and poured into a mixture of 200 ml diethylether and 0.1 N NaOH (1:1). The organic and aqueous layers were separated and the aqueous layer was acidified with HCl until pH 2 was reached. The aqueous layer was extracted with ethyl acetate (2×50 ml). The combined organic layers were dried with MgSO$_4$ and concentrated to dryness under vacuum. The residue was purified by preparative HPLC to yield the title compound. The structural assignment of the title compound was unequivocally established by two-dimensional $^1$H NMR experiments (NOESY, COSY).

$^1$H NMR (400 MHz, D$_6$-DMSO): δ=3.94 (s, 3H), 5.49 (s, 2H), 7.13 (s, 1H), 7.61 (t, J=7.7 Hz, 1H), 7.66 (s, 1H), 7.76-7.82 (m, 2H), 7.96 (d, J=7.7 Hz, 1H), 8.68 (s, 1H), 8.69 (s, 1H), 12.83 (bs, 1H).

MS (MH$^+$ found)=450.1

19. 5-(3H-Imidazo[4,5-b]pyridin-3-yl)-3-{[2-(trifluoromethyl)benzyl]oxy}thio-phene-2-carboxamide In a similar manner as described for example 20, 4.41 g of methyl 5-(3H-imidazo[4,5-b]pyridin-3-yl)-3-{[2-(trifluoromethyl)benzyl]oxy}thiophene-2-carboxylate (compound B5b) and 400 ml of a saturated solution of ammonia in methanol yield the title compound.

$^1$H NMR (200 MHz, D$_6$-DMSO): δ=5.52 (s, 2H), 6.74 (bs, 1H), 7.46 (dd, J=4.9 and 8.1 Hz, 1H), 7.61-7.89 (m, 6H), 8.26 (dd, J=1.4 and 8.1 Hz, 1H), 8.53 (dd, J=1.4 and 4.8 Hz, 1H), 9.10 (s, 1H).

MS (MH$^+$ found)=419.0

20. 5-(1H-Imidazo[4,5-b]pyridin-1-yl)-3-{[2-(trifluoromethyl)benzyl]oxy}thio-phene-2-carboxamide A mixture of 2.50 g of methyl 5-(1H-imidazo[4,5-b]pyridin-1-yl)-3-{[2-(trifluoromethyl)benzyl]oxy}thiophene-2-carboxylate (compound B5a) and 250 ml of a saturated solution of ammonia in methanol was stirred in an autoclave at 130° C. for 12 h. The reaction mixture was allowed to cool down to room temperature, concentrated, and the resulting residue was purified by flash chromatography (neutral alumina oxide, eluents: ethyl acetate/methanol). After crystallization from acetonitrile the title compound was obtained.

$^1$H NMR (400 MHz, D$_6$-DMSO): δ=5.55 (s, 2H), 6.78 (bs, 1H), 7.47 (dd, J=4.7 and 8.2 Hz, 1H), 7.66 (t, J=7.6 Hz, 1H), 7.72-7.74 (m, 2H), 7.79 (t, J=7.6 Hz, 1H), 7.84-7.86 (m, 2H), 8.27 (dd, J=1.3 and 8.2 Hz, 1H), 8.57 (dd, J=1.3 and 4.7 Hz, 1H), 8.94 (s, 1H).

MS (MH$^+$ found)=419.1

21. 5-(5,6-Dimethoxy-1H-imidazo[4,5-b]pyridin-1-yl)-3-{[2-(trifluoromethyl)benzyl]oxy}thiophene-2-carboxamide (compound 21A) and

5-(5,6-Dimethoxy-3H-imidazo[4,5-b]pyridin-3-yl)-3-{[2-(trifluoromethyl)benzyl]oxy}thiophene-2-carboxamide (compound 21B)

In a similar manner as described for example 16, 700 mg of an isomeric mixture of methyl 5-(5,6-dimethoxy-1H-imidazo[4,5-b]pyridin-1-yl)-3-{[2-(trifluoromethyl)benzyl]oxy}thiophene-2-carboxylate (compound B4a) and methyl 5-(5,6-dimethoxy-3H-imidazo[4,5-b]pyridin-3-yl)-3-{[2-(trifluoro-methyl)benzyl]oxy}thiophene-2-carboxylate (compound B4b) and 80 ml of a saturated solution of ammonia in methanol give the title compounds 21A and 21B.

Compound 21A:
$^1$H NMR (400 MHz, D$_6$-DMSO): δ=3.88 (s, 3H), 3.95 (s, 3H), 5.56 (s, 2H), 6.81 (bs, 1H), 7.61 (s, 1H), 7.63-7.67 (m, 2H), 7.72 (bs, 1H), 7.78 (t, J=7.6 Hz, 1H), 7.84-7.86 (m, 2H), 8.55 (s, 1H).

MS (MH$^+$ found)=479.0

Compound 21B:
$^1$H NMR (400 MHz, D$_6$-DMSO): δ=3.86 (s, 3H), 3.97 (s, 3H), 5.53 (s, 2H), 6.77 (bs, 1H), 7.63-7.67 (m, 2H), 7.76-7.86 (m, 5H), 8.78 (s, 1H)

MS (MH$^+$ found)=479.1

22. 5-(5-methoxy-3H-imidazo[4,5-b]pyridin-3-yl)-3-{[2-(trifluoromethyl)benzyl]oxy}thiophene-2-carboxamide A mixture of 0.74 g of methyl 5-(5-methoxy-3H-imidazo[4,5-b]pyridin-3-yl)-3-{[2-(trifluoromethyl)benzyl]oxy}thiophene-2-carboxylate (compound B7b) and 200 ml of a saturated solution of ammonia in methanol was stirred in an autoclave at 130° C. for 10 h. The reaction mixture was allowed to cool down to room temperature and concentrated to about half of the volume. The precipitated solid was filtered, dissolved in 4 ml methanol/DMSO (1:1) and purified by preparative HPLC (water/acetonitrile, elution gradient 9/1 to 1/9 (v/v)). After lyophilization the obtained solid was crystallized with dichloromethane/n-hexane to give the title compound.

The structural assignment of the regioisomer was unequivocally established by two-dimensional $^1$H NMR experiments (NOESY, COSY).

$^1$H NMR (400 MHz, D$_6$-DMSO): δ=3.96 (s, 3H), 5.54 (s, 2H), 6.78 (bs, 1H), 6.85 (d, J=8.8 Hz, 1H), 7.62-7.67 (m, 2H), 7.79 (t, J=7.5 Hz, 1H), 7.85-7.87 (m, 3H), 8.13 (d, J=8.5 Hz, 1H), 8.88 (s, 1H).

MS (MH$^+$ found)=448.9

23. 5-(5-methoxy-1H-imidazo[4,5-b]pyridin-1-yl)-3-{[2-(trifluoromethyl)benzyl]oxy}thiophene-2-carboxamide In a similar manner as described for example 22, 1.5 g of methyl 5-(5-methoxy-1H-imidazo[4,5-b]pyridin-1-yl)-3-{[2-(trifluoromethyl)benzyl]oxy}thio-phene-2-carboxylate (compound B7a) and 200 ml of a saturated solution of ammonia in methanol yield the title compound.

The structural assignment of the regioisomer was unequivocally established by two-dimensional $^1$H NMR experiments (NOESY, COSY).

$^1$H NMR (400 MHz, D$_6$-DMSO): δ=3.93 (s, 3H), 5.55 (s, 2H), 6.76 (bs, 1H), 6.89 (d, J=8.8 Hz, 1H), 7.64-7.69 (m, 3H), 7.79 (t, J=7.6 Hz, 1H), 7.84-7.86 (m, 2H), 8.18 (d, J=8.8 Hz, 1H), 8.76 (s, 1H).

MS (MH$^+$ found)=449.0

24. 5-{6-[(4-methylpiperazin-1-yl)methyl]-1H-imidazo[4,5-c]pyridin-1-yl}-3-{(1R)-1-[2-(trifluoromethyl)phenyl]ethoxy}thiophene-2-carboxamide A mixture of 3.6 g of [1-(5-carbamoyl-4-{(1R)-1-[2-(trifluoro-methyl)phenyl]ethoxy}-2-thienyl)-1H-imidazo[4,5-c]pyridin-6-yl]methyl methanesulfonate and 3.7 ml of 1-methylpiperazine in 80 ml dichloromethane is stirred at 40° C. for 2 hours. The reaction mixture is concentrated to dryness and the resulting residue is purified by flash chromatography [silica gel, eluent: dichloromethane/methanol/triethylamine, elution gradient 99.7/0/0.3 (v/v/v) to 89.7/10/0.3 (v/v/v)]. The obtained product is filtered through a short plug of Flash-NH2 silica gel [eluent: dichloro-methane/methanol, 9/1 (v/v)] in a further purification step. After evaporation of the solvents, the resulting oil is treated with 5 ml diethyl ether, resulting in precipitation of the product. After filtration the title compound is obtained as white solid.

$^1$H NMR (300 MHz, D$_6$-DMSO): δ=1.82 (d, J=6.2 Hz, 3H), 2.30 (s, 3H), 2.49-2.56 (m, 8H), 3.75 (d, J=1.8 Hz, 2H), 5.84-5.92 (m, 2H), 6.67 (s, 1H), 7.20 (br s, 1H), 7.46-7.51 (m, 2H), 7.62-7.75 (m, 3H), 7.94 (s, 1H), 9.09 (d, J=0.9 Hz, 1H).

MS (MH$^+$ found)=545.1 mp.: 191-192° C.

25. 5-[6-(hydroxymethyl)-1H-imidazo[4,5-c]pyridin-1-yl]-3-{(1R)-1-[2-(trifluoromethyl)phenyl]ethoxy}thiophene-2-carboxamide 2.31 g of 5-[6-({[tert-butyl(dimethyl)silyl]oxy}methyl)-1H-imidazo[4,5-c]pyridin-1-yl]-3-{(1R)-1-[2-(trifluoromethyl)phenyl]ethoxy}thiophene-2-carboxamide are dissolved in 100 ml tetrahydrofuran and to this solution 1.1 ml of tetra-n-butylammonium fluoride (~75% in H2O) are added at 0° C. The reaction mixture is allowed to warm to room temperature and stirred for 90 minutes.

The solvent is evaporated under reduced pressure and the residue is treated with 100 ml dichloromethane and 100 ml saturated aqueous NaHCO$_3$ solution. The mixture is left for one hour at 4° C. and the resulting precipitate is collected by filtration.

The filter cake is washed with water and diethyl ether and dried under vacuum to yield the title compound as a white solid.

$^1$H NMR (300 MHz, D$_6$-DMSO): δ=1.76 (d, J=6.2 Hz, 3H), 4.68 (s, 2H), 5.46 (br s, 1H), 5.92 (q, J=6.0 Hz, 1H), 7.13 (br s, 1H), 7.24 (s, 1H), 7.54-7.60 (m, 1H), 7.62 (d, J=0.7 Hz, 1H), 7.76-7.85 (m, 3H), 7.97 (d, J=8.0 Hz, 1H), 8.65 (s, 1H), 8.96 (d, J=0.7 Hz, 1H).

MS (MH+ found)=463.0

26. Maleate salt of 5-{6-[(4-methylpiperazin-1-yl)methyl]-1H-imidazo[4,5-c]pyridin-1-yl}-3-{(1R)-1-[2-(trifluoromethyl)phenyl]ethoxy}thiophene-2-carboxamide To a solution of 140 mg of 5-{6-[(4-methylpiperazin-1-yl)methyl]-1H-imidazo[4,5-c]pyridin-1-yl}-3-{(1R)-1-[2-(trifluoromethyl)phenyl]ethoxy}thiophene-2-carboxamide in 2 ml acetone is added a solution of 32.5 mg malic acid in 1 ml aceton at 60° C. The reaction mixture is stirred for 10 minutes at 60° C. The solvent is evaporated under reduced pressure and the resulting residue is suspended in 3 ml diethyl ether. The precipitate is filtered off and washed with diethyl ether to yield the title compound.

$^1$H NMR (300 MHz, D$_6$-DMSO): δ=1.77 (d, J=6.2 Hz, 3H), 2.74 (s, 3H), 3.31 (br m, 8H, +H2O), 3.85 (s, 2H), 5.94 (q, J=5.7 Hz, 1H), 6.04 (s, 2H), 7.14 (br s, 1H), 7.25 (s, 1H), 7.56-7.62 (m, 2H), 7.76-7.82 (m, 2H), 7.87 (br s, 1H), 7.98 (d, J=7.9 Hz, 1H), 8.69 (s, 1H), 9.02 (d, J=0.7 Hz, 1H).

MS (MH+ found)=545.1

27. 3-[1-(2-chlorophenyl)-2,2,2-trifluoroethoxy]-5-[6-(hydroxymethyl)-1H-imidazo[4,5-c]pyridin-1-yl]thiophene-2-carboxamide A mixture of 470 mg of methyl 5-[6-({[tert-butyl(dimethyl)silyl]oxy}methyl)-1H-imidazo[4,5-c]pyridin-1-yl]-3-[1-(2-chlorophenyl)-2,2,2-trifluoroethoxy]thiophene-2-carboxylate and 40 ml of a saturated solution of ammonia in methanol is stirred in a microwave vial at 125° C. for 4 h in the microwave cavity. The reaction mixture is concentrated to dryness and the resulting residue is purified by flash chromatography (ethyl acetate/methanol, 90/10 (v/v)) to yield the title compound.

$^1$H NMR (300 MHz, D$_6$-DMSO): δ=4.70 (d, J=5.6 Hz, 2H), 5.47 (t, J=5.6 Hz, 1H), 6.71 (q, J=6.0 Hz, 1H), 6.92 (br s, 1H), 7.34 (s, 1H), 7.52-7.57 (m, 2H), 7.67-7.65 (m, 1H), 7.68 (s, 1H), 7.84-7.87 (m, 1H), 8.01 (br s, 1H), 8.64 (s, 1H), 8.96 (s, 1H).

LC-MS (MH+ found)=483.1

28. 5-(3H-imidazo[4,5-c]pyridin-3-yl)-3-{[4-(trifluoromethyl)benzyl]oxy}thiophene-2-carboxamide A mixture of 41 mg of methyl 5-(3H-imidazo[4,5-c]pyridin-3-yl)-3-{[4-(trifluoromethyl)benzyl]oxy}thiophene-2-carboxylate and 5 ml of a saturated solution of ammonia in methanol is stirred in a microwave vial at 125° C. for 4 h in the microwave cavity. The reaction mixture is concentrated to dryness, the resulting residue is dissolved in 5 ml dichloromethane and purified by flash chromatography (dichloromethane/methanol, 95/5 (v/v)) to yield the title compound.

$^1$H NMR (300 MHz, D$_6$-DMSO): δ=5.55 (s, 2H), 7.10 (br s, 1H), 7.72 (s, 1H), 7.75 (br s, 1H), 7.78-7.83 (m, 5H), 8.51 (d, J=5.4 Hz, 1H), 8.83 (s, 1H), 9.13 (d, J=1.1 Hz, 1H).

MS (MH+ found)=419.0

29. 5-(3H-imidazo[4,5-c]pyridin-3-yl)-3-{[2-(trifluoromethoxy)benzyl]oxy}thiophene-2-carboxamide In a similar manner as described for example 28, 57 mg of methyl 5-(3H-imidazo[4,5-c]pyridin-3-yl)-3-{[2-(trifluoromethoxy)benzyl]oxy}thiophene-2-carboxylate and 6 ml of a saturated solution of ammonia in methanol yield the title compound.

$^1$H NMR (400 MHz, D$_6$-DMSO): δ=5.50 (s, 2H), 6.85 (br s, 1H), 7.47-7.50 (m, 2H), 7.55-7.60 (m, 1H), 7.75-7.77 (m, 2H), 7.80 (s, 1H), 7.83 (dd, J=0.7 and 5.6 Hz, 1H), 8.52 (d, J=5.6 Hz, 1H), 8.86 (s, 1H), 9.17 (d, J=0.7 Hz, 1H).

MS (MH+ found)=435.0

30. 5-(3H-imidazo[4,5-c]pyridin-3-yl)-3-{[3-(trifluoromethyl)benzyl]oxy}thiophene-2-carboxamide In a similar manner as described for example 28, 65 mg of methyl 5-(3H-imidazo[4,5-c]pyridin-3-yl)-3-{[3-(trifluoromethyl)benzyl]oxy}thiophene-2-carboxylate and 7 ml of a saturated solution of ammonia in methanol yield the title compound.

$^1$H NMR (300 MHz, D$_6$-DMSO): δ=5.53 (s, 2H), 7.12 (br s, 1H), 7.65-7.76 (m, 4H), 7.83 (dd, J=1.1 and 5.5 Hz, 1H), 7.88 (d, J=7.4 Hz, 1H), 7.96 (s, 1H), 8.51 (d, J=5.5 Hz, 1H), 8.83 (s, 1H), 9.12 (d, J=1.1 Hz, 1H).

MS (MH+ found)=418.9

31. 3-[(2-fluorobenzyl)oxy]-5-(3H-imidazo[4,5-c]pyridin-3-yl)thiophene-2-carboxamide Step 1: In a similar manner as described for example B11, 81.7 mg of 1-(bromomethyl)-2-fluorobenzene, 100 mg of methyl 3-hydroxy-5-(3H-imidazo[4,5-c]pyridin-3-yl)thiophene-2-carboxylate, and 59.7 mg of potassium carbonate in 3 ml anhydrous DMF give methyl 3-[(2-fluorobenzyl)oxy]-5-(3H-imidazo[4,5-c]pyridin-3-yl)thiophene-2-carboxylate as crude material that is used for step 2 without further purification.

Step 2: In a similar manner as described for example 28, 86 mg of methyl 3-[(2-fluorobenzyl)oxy]-5-(3H-imidazo[4,5-c]pyridin-3-yl)thiophene-2-carboxylate (product of step 1) and 20 ml of a saturated solution of ammonia in methanol yield the title compound.

$^1$H NMR (400 MHz, D$_6$-DMSO): δ=5.51 (s, 2H), 6.90 (br s, 1H), 7.27-7.33 (m, 2H), 7.45-7.51 (m, 1H), 7.63-7.68 (m, 1H), 7.73 (br s, 1H), 7.81 (s, 1H), 7.83 (dd, J=0.6 and 5.5 Hz, 1H), 8.52 (d, J=5.5 Hz, 1H), 8.86 (s, 1H), 9.18 (s, 1H).

MS (MH+ found)=369.1

32. 3-[(1R)-1-(2-chlorophenyl)ethoxy]-5-(3H-imidazo[4,5-c]pyridin-3-yl)thiophene-2-carboxamide Under a nitrogen atmosphere 100 mg of methyl 3-hydroxy-5-(3H-imidazo[4,5-c]pyridin-3-yl)thiophene-2-carboxylate, 57.2 mg of (1S)-1-(2-chlorophenyl)ethanol and 95.7 mg triphenylphosphine are dissolved in 1 ml anhydrous THF. To this mixture a solution of 80.9 mg diisopropyl azodicarboxylate in 0.5 ml anhydrous THF is added dropwise and the mixture is stirred for 14 h at room temperature. The solvent is evaporated under vacuum. After extraction with ethyl acetate and a saturated solution of sodium chloride, the organic phase is dried over MgSO$_4$. The solvent is removed under vacuum and the remaining residue is dissolved in 2 ml dichloromethane and filtered through a short plug of silica gel (eluent: ethyl acetate). After evaporation of the solvent, the remaining residue and 20 ml of a saturated solution of ammonia in methanol are stirred in a microwave vial at 125° C. for 8 h in the microwave cavity. Subsequently the solvent is removed under vacuum. The remaining residue is dissolved in 2 ml dichloromethane and is purified by flash chromatography (eluent: ethyl acetate, followed by ethyl acetate/methanol 95/5 (v/v)) to yield the title compound.

$^1$H NMR (400 MHz, D$_6$-DMSO): δ=1.74 (d, J=6.4 Hz, 3H), 6.03 (q, J=6.4 Hz, 1H), 7.13 (br s, 1H), 7.35 (s, 1H), 7.38 (dd, J=1.7 and 7.6 Hz, 1H), 7.41-7.45 (m, 1H), 7.50 (dd, J=1.2 and 7.8 Hz, 1H), 7.70 (dd, J=1.7 and 7.6 Hz, 1H), 7.80 (dd, J=1.2 and 5.6 Hz, 1H), 7.83 (br s, 1H), 8.49 (d, J=5.6 Hz, 1H), 8.79 (s, 1H), 8.94 (d, J=0.7 Hz, 1H).

MS (MH+ found)=399.0

33. 5-(1H-imidazo[4,5-c]pyridin-1-yl)-3-{[2-(trifluoromethoxy)benzyl]oxy}thiophene-2-carboxamide A mixture of 26.8 mg of methyl 5-(1H-imidazo[4,5-c]pyridin-1-yl)-3-{[2-(trifluoromethoxy)benzyl]oxy}thiophene-2-carboxylate and 5 ml of a saturated solution of ammonia in methanol is stirred in a microwave vial at 125° C. for 4 h in the microwave cavity. The reaction mixture is concentrated to dryness, the resulting residue is dissolved in ethyl acetate and purified by flash chromatography [Silica gel, eluent: ethyl acetate/methanol, elution gradient of 100/0 (v/v) to 95/5 (v/v)] to yield the title compound.

$^1$H NMR (400 MHz, D$_6$-DMSO): δ=5.48 (s, 2H), 6.84 (br s, 1H), 7.47-7.51 (m, 2H), 7.56-7.60 (m, 1H), 7.76-7.77 (m, 3H), 7.85 (d, J=5.6 Hz, 1H), 8.53 (d, J=5.6 Hz, 1H), 8.80 (s, 1H), 9.10 (s, 1H).

MS (MH+ found)=435.1

34. 3-{[4-fluoro-2-(trifluoromethyl)benzyl]oxy}-5-(1H-imidazo[4,5-c]pyridin-1-yl)thiophene-2-carboxamide In a similar manner as described for example 33, 45.5 mg of methyl 3-{[4-fluoro-2-(trifluoromethyl)benzyl]oxy}-5-(1H-imidazo[4,5-c]pyridin-1-yl)thiophene-2-carboxylate and 5 ml of a saturated solution of ammonia in methanol yield the title compound.

$^1$H NMR (300 MHz, D$_6$-DMSO): δ=5.52 (s, 2H), 6.77 (br s, 1H), 7.64-7.78 (m, 4H), 7.86 (dd, J=1.1 and 5.7 Hz, 1H), 7.90-7.95 (m, 1H), 8.54 (d, J=5.7 Hz, 1H), 8.81 (s, 1H), 9.10 (d, J=1.1 Hz, 1H).

MS (MH+ found)=437.0

35. 5-(1H-imidazo[4,5-c]pyridin-1-yl)-3-{[3-(trifluoromethyl)benzyl]oxy}thiophene-2-carboxamide In a similar manner as described for example 33, 27.5 mg of methyl 5-(1H-imidazo[4,5-c]pyridin-1-yl)-3-{[3-(trifluoromethyl)benzyl]oxy}thiophene-2-carboxylate and 5 ml of a saturated solution of ammonia in methanol yield the title compound.

$^1$H NMR (400 MHz, D$_6$-DMSO): δ=5.51 (s, 2H), 7.12 (br s, 1H), 7.66-7.77 (m, 5H), 7.88 (d, J=7.6 Hz, 1H), 7.97 (s, 1H), 8.51 (d, J=5.6 Hz, 1H), 8.77 (s, 1H), 9.09 (s, 1H).

MS (MH+ found)=419.1

36. 5-(1H-imidazo[4,5-c]pyridin-1-yl)-3-{[4-(trifluoromethyl)benzyl]oxy}thiophene-2-carboxamide In a similar manner as described for example 33, 45.8 mg of methyl 5-(1H-imidazo[4,5-c]pyridin-1-yl)-3-{[4-(trifluoromethyl)benzyl]oxy}thiophene-2-carboxylate and 5 ml of a saturated solution of ammonia in methanol yield the title compound.

$^1$H NMR (400 MHz, D$_6$-DMSO): δ=5.53 (s, 2H), 7.10 (br s, 1H), 7.67-7.82 (m, 7H), 8.52 (d, J=5.6 Hz, 1H), 8.77 (s, 1H), 9.09 (s, 1H).

MS (MH+ found)=419.0

37. 5-{6-[(4-methylpiperazin-1-yl)methyl]-3H-imidazo[4,5-c]pyridin-3-yl}-3-{[2-(trifluoromethyl)benzyl]oxy}thiophene-2-carboxamide Step 1: In a similar manner as described for example A1, 346 mg of 5-[6-(hydroxymethyl)-3H-imidazo[4,5-c]pyridin-3-yl]-3-{[2-(trifluoromethyl)benzyl]oxy}thiophene-2-carboxamide, 97.3 mg of methanesulfonic anhydride, and 93.7 mg of triethylamine in 10.5 ml dichloromethane give [3-(5-carbamoyl-4-{[2-(trifluoromethyl)benzyl]oxy}-2-thienyl)-3H-imidazo[4,5-c]pyridin-6-yl]methyl methanesulfonate as crude material that is used for step 2 without further purification.

Step 2: To a solution of 160 mg of [3-(5-carbamoyl-4-{[2-(trifluoromethyl)benzyl]oxy}-2-thienyl)-3H-imidazo[4,5-c]pyridin-6-yl]methyl methanesulfonate (product of step 1) in 15 ml of dichloromethane are added 300 mg of 1-methylpiperazine, and the reaction mixture is stirred at room temperature for 3 h. The mixture is concentrated to dryness under vacuum and the residue is dissolved in acetonitrile/ammonium bicarbonate buffer and purified by preparative HPLC (acetonitrile/ammonium bicarbonate buffer, elution gradient 30/70 to 90/10 (v/v)) to obtain the title compound.

$^1$H NMR (300 MHz, D$_6$-DMSO): δ=2.16 (s, 3H), 2.34-2.47 (br m, 8H), 3.73 (s, 2H), 5.56 (s, 2H), 6.79 (br s, 1H), 7.63-7.81 (m, 6H), 7.85 (d, J=8.1 Hz, 1H), 8.84 (s, 1H), 9.07 (d, J=0.9 Hz, 1H).

MS (MH+ found)=531.1

38. 3-{[2-(difluoromethoxy)benzyl]oxy}-5-(3H-imidazo[4,5-c]pyridin-3-yl)thiophene-2-carboxamide A mixture of 37.5 mg of methyl 3-{[2-(difluoromethoxy)benzyl]oxy}-5-(3H-imidazo[4,5-c]pyridin-3-yl)thiophene-2-carboxylate and 5 ml of a saturated solution of ammonia in methanol is stirred in a microwave vial at 125° C. for 4 h in the microwave cavity. The reaction mixture is concentrated to dryness, the resulting residue is dissolved in a mixture of acetonitrile and methanol (9:1 (v/v)) and purified by preparative HPLC (water/acetonitrile, elution gradient 9/1 to 1/9 (v/v)) to obtain the title compound.

$^1$H NMR (300 MHz, D$_6$-DMSO): δ=5.45 (s, 2H), 6.90 (br s, 1H), 7.29-7.35 (m, 3H), 7.47-7.56 (m, 1H), 7.66-7.69 (m, 2H), 7.79 (s, 1H), 7.83 (dd, J=1.1 Hz, 1H), 8.51 (d, J=5.6 Hz, 1H), 8.86 (s, 1H), 9.17 (d, J=1.1 Hz, 1H).

MS (MH+ found)=417.0

39. 3-[(2-cyanobenzyl)oxy]-5-(1H-imidazo[4,5-c]pyridin-1-yl)thiophene-2-carboxamide In a similar manner as described for example 38, 55 mg of methyl 3-[(2-cyanobenzyl)oxy]-5-(1H-imidazo[4,5-c]pyridin-1-yl)thiophene-2-carboxylate and 20 ml of a saturated solution of ammonia in methanol yield the title compound.

$^1$H NMR (300 MHz, D$_6$-DMSO): δ=5.62 (s, 2H), 6.91 (br s, 1H), 7.58-7.65 (m, 1H), 7.77-7.85 (m, 5H), 7.95-7.98 (m, 1H), 8.52 (d, J=5.5 Hz, 1H), 8.86 (s, 1H), 9.18 (d, J=1.1 Hz, 1H).

MS (MH+ found)=376.0

40. 3-[(2-fluorobenzyl)oxy]-5-(1H-imidazo[4,5-c]pyridin-1-yl)thiophene-2-carboxamide A mixture of 50 mg of methyl 3-[(2-fluorobenzyl)oxy]-5-(1H-imidazo[4,5-c]pyridin-1-yl)thiophene-2-carboxylate and 15 ml of a saturated solution of ammonia in methanol is stirred in a microwave vial at 125° C. for 4 h in the microwave cavity. The reaction mixture is concentrated to dryness, the resulting residue is recrystallized from 5 ml ethanol to yield the title compound.

MS (MH+ found)=369.0

41. 3-{[4-fluoro-2-(trifluoromethyl)benzyl]oxy}-5-(3H-imidazo[4,5-c]pyridin-3-yl)thiophene-2-carboxamide In a similar manner as described for example 38, 92.1 mg of methyl 3-{[4-fluoro-2-(trifluoromethyl)benzyl]oxy}-5-(3H-imidazo[4,5-c]pyridin-3-yl)thiophene-2-carboxylate and 15 ml of a saturated solution of ammonia in methanol yield the title compound.

$^1$H NMR (300 MHz, D$_6$-DMSO): δ=5.54 (s, 2H), 6.78 (br s, 1H), 7.64-7.78 (m, 4H), 7.83 (dd, J=1.0 Hz and 5.7 Hz, 1H), 7.90-7.95 (m, 1H), 8.52 (d, J=5.5 Hz, 1H), 8.87 (s, 1H), 9.19 (d, J=1.0 Hz, 1H).

MS (MH+ found)=437.0

42. 3-{[2-(difluoromethoxy)benzyl]oxy}-5-(1H-imidazo[4,5-c]pyridin-1-yl)thiophene-2-carboxamide In a similar manner as described for example 38, 110 mg of methyl 3-{[2-(difluoromethoxy)benzyl]oxy}-5-(1H-imidazo[4,5-c]pyridin-1-yl)thiophene-2-carboxylate and 20 ml of a saturated solution of ammonia in methanol yield the title compound.

$^1$H NMR (300 MHz, D$_6$-DMSO): δ=5.43 (s, 2H), 6.90 (br s, 1H), 7.29-7.35 (m, 4H), 7.47-7.56 (m, 2H), 7.66-7.74 (m, 4H), 7.84 (dd, J=1.0 Hz and 5.7 Hz, 1H), 8.53 (d, J=5.6 Hz, 1H), 8.80 (s, 1H), 9.10 (d, J=1.0 Hz, 1H).

MS (MH+ found)=417.0

43. 3-[(2,6-dichlorobenzyl)oxy]-5-(3H-imidazo[4,5-c]pyridin-3-yl)thiophene-2-carboxamide In a similar manner as described for example 38, 123.1 mg of methyl 3-[(2,6-dichlorobenzyl)oxy]-5-(3H-imidazo[4,5-c]pyridin-3-yl)thiophene-2-carboxylate and 15 ml of a saturated solution of ammonia in methanol yield the title compound.

$^1$H NMR (300 MHz, D$_6$-DMSO): δ=5.61 (s, 2H), 6.64 (br s, 1H), 7.50-7.55 (m, 1H), 7.61 (s, 1H), 7.64 (d, J=1.4 Hz, 1H), 7.70 (br s, 1H), 7.84 (dd, J=1.0 Hz and 5.6 Hz, 1H), 7.92 (s, 1H), 8.53 (d, J=5.6 Hz, 1H), 8.90 (s, 1H), 9.24 (d, J=1.0 Hz, 1H).

MS (MH+ found)=419.0

44. 5-[6-(hydroxymethyl)-1H-imidazo[4,5-c]pyridin-1-yl]-3-{1-[2-(trifluoromethyl)phenyl]ethoxy}thiophene-2-carboxamide 0.75 g of 5-[6-({[tert-butyl(dimethyl)silyl]oxy}methyl)-1H-imidazo[4,5-c]pyridin-1-yl]-3-{1-[2-(trifluoromethyl)phenyl]ethoxy}thiophene-2-carboxamide are dissolved in 100 ml tetrahydrofuran and to this solution 0.48 ml of tetra-n-butylammonium fluoride (~75% in H$_2$O) is added at 0° C. The reaction mixture is allowed to warm to room temperature and stirred for 60 minutes.

The solvent is then evaporated under reduced pressure and the residue is treated with 50 ml dichloromethane and 40 ml saturated aqueous NaHCO$_3$ solution. The mixture is stored for one hour at 4° C. and the resulting precipitate is collected by filtration. The filter cake is washed with H$_2$O and diethyl ether and dried under vacuum to yield the title product as a white solid.

$^1$H NMR (300 MHz, D$_6$-DMSO): δ=1.76 (d, J=6.2 Hz, 3H), 4.68 (d, J=4.9 Hz, 2H), 5.46 (t, J=5.3 Hz, 1H), 5.94 (q, J=6.2 Hz, 1H), 7.12 (br s, 1H), 7.24 (s, 1H), 7.57 (m, 2H), 7.79 (m, 3H), 7.85 (br s, 1H), 8.65 (s, 1H), 8.96 (d, J=0.8 Hz, 1H).

MS (MH+ found)=463.1

45. 5-{6-[(4-methylpiperazin-1-yl)methyl]-1H-imidazo[4,5-c]pyridin-1-yl}-3-{-1-[2-(trifluoromethyl)phenyl]ethoxy}thiophene-2-carboxamide Step 1: In a similar manner as described for example 49 (step 1), 900 mg of 5-[6-(hydroxymethyl)-1H-imidazo[4,5-c]pyridin-1-yl]-3-{1-[2-(trifluoromethyl)phenyl]ethoxy}thiophene-2-carboxamide, 423.8 mg of methanesulfonyl chloride, and 393.6 mg of triethylamine in 32 ml dichloromethane give [1-(5-carbamoyl-4-{1-[2-(trifluoromethyl)phenyl]ethoxy}-2-thienyl)-1H-imidazo[4,5-c]pyridin-6-yl]methyl methanesulfonate as crude material that is used for step 2 without further purification.

Step 2: A mixture of 200 mg of crude [1-(5-carbamoyl-4-{1-[2-(trifluoromethyl)phenyl]ethoxy}-2-thienyl)-1H-imidazo[4,5-c]pyridin-6-yl]methyl methanesulfonate (step 1) and 1-methylpiperazine (0.41 ml) in 5 ml dichloromethane is stirred at 40° C. for 2 hours. The reaction mixture is then concentrated to dryness and the resulting residue is purified by flash-chromatography [Silica gel, eluent: dichloromethane/methanol/triethylamine, 94.5/5/4.5 (v/v/v)]. The obtained product is filtered through a short plug of silica gel Flash NH$_2$ [eluent: dichloromethane/methanol, 98/2 (v/v)] in a further purification step. After evaporation of the solvents, the resulting oil is treated with 5 ml diethyl ether whereby the product precipitated. After filtration the title product is obtained as a white solid.

$^1$H NMR (300 MHz, CDCl$_3$): δ=1.82 (d, J=6.3 Hz, 3H), 2.29 (s, 3H), 2.48-2.55 (br m, 8H), 3.74 (d, J=1.8 Hz, 2H), 5.86 (q, J=6.3 Hz, 1H), 5.90 (brs, 1H), 6.68 (s, 1H), 7.20 (br s, 1H), 7.48 (m, 2H), 7.68 (m, 3H), 7.94 (s, 1H), 9.09 (d, J=0.8 Hz, 1H).

MS (MH+ found)=545.0

46. 5-[6-(hydroxymethyl)-1H-imidazo[4,5-c]pyridin-1-yl]-3-{(1S)-1-[2-(trifluoromethyl)phenyl]ethoxy}thiophene-2-carboxamide A mixture of 230 mg of 5-[6-({[tert-butyl(dimethyl)silyl]oxy}methyl)-1H-imidazo[4,5-c]pyridin-1-yl]-3-{(1S)-1-[2-

(trifluoromethyl)phenyl]ethoxy}thiophene-2-carboxamide in 5 ml THF is cooled to 0° C. At 0° C. 0.14 ml tetra-n-butylammonium fluoride (~75% in H₂0) are added. The reaction mixture is allowed to warm to room temperature and stirred for 90 minutes.

The solvent is evaporated under reduced pressure and the residue is then treated with 9 ml dichloromethane and 7 ml saturated aqueous NaHCO₃ solution. The phases are separated. The organic phase is concentrated to dryness under reduced pressure.

The residue is purified by flash chromatography on silica gel [eluent: dichloromethane/methanol, with a gradient from 95/5 to 90/10 (v/v)] to obtain the title product.

¹H NMR (300 MHz, D₆-DMSO): δ=1.76 (d, J=6.3 Hz, 3H), 4.68 (d, J=5.6 Hz, 2H), 5.45 (t, J=5.7 Hz, 1H), 5.93 (m, 1H), 7.12 (br s, 1H), 7.24 (s, 1H), 7.54-7.62 (m, 2H), 7.76-7.81 (m, 2H), 7.85 (br s, 1H), 7.97 (d, 1H), 8.65 (s, 1H), 8.96 (d, J=0.8 Hz, 1H).

MS (MH+ found)=463.0

47. 5-[6-(hydroxymethyl)-3H-imidazo[4,5-c]pyridin-3-yl]-3-{(1R)-1-[2-(trifluoromethyl)phenyl]ethoxy}thiophene-2-carboxamide In a similar manner as described for example 51, 370 mg of 5-[6-({[tert-butyl(dimethyl)silyl]oxy}methyl)-3H-imidazo[4,5-c]pyridin-3-yl]-3-{(1R)-1-[2-(trifluoromethyl)phenyl]ethoxy}thiophene-2-carboxamide and 166 mg of tetra-n-butylammonium fluoride (~75% in H₂0) in 6 ml THF yield the title compound.

¹H NMR (300 MHz, D₆-DMSO): δ=1.76 (d, J=6.2 Hz, 3H), 4.69 (d, J=5.6 Hz, 2H), 5.45 (t, J=5.8 Hz, 1H), 5.99 (q, J=6.3 Hz, 1H), 7.14 (br s, 1H), 7.25 (s, 1H), 7.57 (t, J=7.6 Hz, 1H), 7.77-7.81 (m, 3H), 7.84 (br s, 1H), 7.96 (d, J=7.9 Hz, 1H), 8.73 (s, 1H), 8.80 (s, 1H).

MS (MH+ found)=463.0

48. 5-{6-[(4-methylpiperazin-1-yl)methyl]-1H-imidazo[4,5-c]pyridin-1-yl}-3-{(1S)-1-[2-(trifluoromethyl)phenyl]ethoxy}thiophene-2-carboxamide Step 1: In a similar manner as described for example 49 (step 1), 120 mg of 5-[6-(hydroxymethyl)-1H-imidazo[4,5-c]pyridin-1-yl]-3-{(1S)-1-[2-(trifluoromethyl)phenyl]ethoxy}thiophene-2-carboxamide, 57 mg of methanesulfonyl chloride, and 53 mg of triethylamine in 3 ml dichloromethane give [1-(5-carbamoyl-4-{(1S)-1-[2-(trifluoromethyl)phenyl]ethoxy}-2-thienyl)-1H-imidazo[4,5-c]pyridin-6-yl]methyl methanesulfonate as crude material that is used for step 2 without further purification.

Step 2: A mixture of 155 mg of crude [1-(5-carbamoyl-4-{(1S)-1-[2-(trifluoromethyl)phenyl]ethoxy}-2-thienyl)-1H-imidazo[4,5-c]pyridin-6-yl]methyl methanesulfonate (from step 1) and 1-methylpiperazine (0.16 ml) in dichloromethane is stirred at 40° C. for 1 hour. The reaction mixture is then concentrated to dryness and the resulting residue is purified by flash chromatography [Silica gel, eluent: dichloromethane/7 N solution of ammonia in methanol, with a gradient from 100/0 to 90/10 (v/v)]. The obtained product is purified a second time by preparative HPLC (ammonium formate buffer/acetonitrile, elution gradient 97/3 to 0/100 (v/v)) to obtain the title product.

¹H NMR (300 MHz, CDCl₃): δ=1.82 (d, J=6.3 Hz, 3H), 2.30 (s, 3H), 2.50-2.56 (br m, 8H), 3.75 (d, J=1.7 Hz, 2H), 5.84 (br s, 1H), 5.88 (m, 1H), 6.67 (s, 1H), 7.20 (br s, 1H), 7.48 (m, 2H), 7.67-7.75 (m, 3H), 7.94 (s, 1H), 9.09 (d, J=0.9 Hz, 1H).

MS (MH+ found)=545.1

49. 5-{6-[(4-methylpiperazin-1-yl)methyl]-3H-imidazo[4,5-c]pyridin-3-yl}-3-{(1R)-1-[2-(trifluoromethyl)phenyl]ethoxy}thiophene-2-carboxamide Step 1: A suspension of 224 mg of 5-[6-(hydroxymethyl)-3H-imidazo[4,5-c]pyridin-3-yl]-3-{(1R)-1-[2-(trifluoromethyl)phenyl]ethoxy}thiophene-2-carboxamide and 0.135 ml triethylamine in 5.5 ml anhydrous dichloromethane is cooled to 0° C. Under nitrogen atmosphere, 0.07 ml methanesulfonyl chloride is added dropwise.

The reaction mixture is stirred at 0° C. for 10 minutes and then 3 h at room temperature. Water is added (5 ml) and the layers are separated. The aqueous phase is extracted with 2×5 ml dichloromethane. The organic phases are combined, dried over MgSO₄ and evaporated under reduced pressure to give crude [3-(5-carbamoyl-4-{(1R)-1-[2-(trifluoromethyl)phenyl]ethoxy}-2-thienyl)-3H-imidazo[4,5-c]pyridin-6-yl]methyl methanesulfonate, which is used for the next step without further purification.

Step 2: In a similar manner as described for example 58, 289 mg of crude [3-(5-carbamoyl-4-{(1R)-1-[2-(trifluoromethyl)phenyl]ethoxy}-2-thienyl)-3H-imidazo[4,5-c]pyridin-6-yl]methyl methanesulfonate (from step 1) and 0.27 ml N-methylpiperazine in dichloromethane yield the title compound.

¹H NMR (300 MHz, CDCl₃): δ=1.81 (d, J=6.2 Hz, 3H), 2.47 (s, 3H), 2.71-2.81 (br m, 8H), 3.83 (s, 2H), 5.86 (m, 2H), 6.72 (s, 1H), 7.20 (br s, 1H), 7.48 (m, 1H), 7.62-7.75 (m, 3H), 7.79 (s, 1H), 8.02 (s, 1H), 8.78 (d, J=1.0 Hz, 1H).

50. 5-[6-(aminomethyl)-3H-imidazo[4,5-c]pyridin-3-yl]-3-{(1R)-1-[2-(trifluoromethyl)phenyl]ethoxy}thiophene-2-carboxamide A suspension of 150 mg of crude [3-(5-carbamoyl-4-{(1R)-1-[2-(trifluoromethyl)phenyl]ethoxy}-2-thienyl)-3H-imidazo[4,5-c]pyridin-6-yl]methyl methanesulfonate (example 49, step 1) in 5 ml of a saturated solution of ammonia in methanol is stirred in a microwave vial at 80° C. for 1 h in the microwave cavity. The solvent is removed under reduced pressure. 20 ml of water and 20 ml dichloromethane is added to the residue, the organic phase is separated and the aqueous phase is extracted with 2×10 ml dichloromethane. The combined organic layers are dried over MgSO₄, filtered and evaporated under reduced pressure. The resulting residue is purified by flash chromatography [silica gel, eluent: dichloromethane/methanol/7 N solution of ammonia in methanol, 9/1/0.3 (v/v/v)] to yield the title product.

¹H NMR (300 MHz, D₆-DMSO): δ=1.76 (d, J=6.2 Hz, 3H), 3.97 (s, 2H), 5.99 (q, J=6.5 Hz, 1H), 7.14 (br s, 1H), 7.25 (s, 1H), 7.57 (t, J=7.9 Hz, 1H), 7.76-7.82 (m, 4H), 7.95 (d, J=7.8 Hz, 1H), 8.73 (s, 1H), 8.83 (d, J=0.9 Hz, 1H).

MS (MH+ found)=462.0

51. 3-{1-[4-fluoro-2-(trifluoromethyl)phenyl]ethoxy}-5-[6-(hydroxymethyl)-1H-imidazo[4,5-c]pyridin-1-yl]thiophene-2-carboxamide A mixture of 1.48 g of 5-[6-({[tert-butyl(dimethyl)silyl]oxy}methyl)-1H-imidazo[4,5-c]pyridin-1-yl]-3-{-1-[4-fluoro-2-(trifluoromethyl)phenyl]ethoxy}thiophene-2-carboxamide in 25 ml THF is cooled to 0° C. At 0° C. 0.91 ml tetra-n-butylammonium fluoride (~75% in H₂0) are added. The reaction mixture is allowed to warm to room temperature and stirred for 90 minutes.

The solvent is evaporated under reduced pressure and the residue is filtered through a short plug of silica gel [eluent: dichloromethane/methanol, with a gradient from 9/1 to 8/2 (v/v)]. It is then treated with 25 ml dichloromethane and 15 ml saturated aqueous $NaHCO_3$ solution. The phases are separated; the aqueous phase is extracted with 2×25 ml dichloromethane. A white solid precipitates in the aqueous phase. It is collected by filtration and washed with $H_2O$ to obtain the title product.

$^1$H NMR (300 MHz, $D_6$-DMSO): δ=1.75 (d, J=6.2 Hz, 3H), 4.68 (d, J=5.4 Hz, 2H), 5.46 (t, J=5.5 Hz, 1H), 5.89 (q, J=6.2 Hz, 1H), 7.13 (br s, 1H), 7.23 (s, 1H), 7.63-7.69 (m, 3H), 7.83 (br s, 1H), 7.70 (m, 1H), 8.65 (s, 1H), 8.95 (d, J=1.0 Hz, 1H).

MS (MH+ found)=481.0

52. 3-[(1R)-1-(2-bromophenyl)ethoxy]-5-[6-(hydroxymethyl)-1H-imidazo[4,5-c]pyridin-1-yl]thiophene-2-carboxamide A mixture of 1.23 g of 3-[(1R)-1-(2-bromophenyl)ethoxy]-5-[6-({[tert-butyl(dimethyl)silyl]oxy}methyl)-1H-imidazo[4,5-c]pyridin-1-yl]thiophene-2-carboxamide in 21 ml THF is cooled to 0° C. At 0° C. 0.76 ml tetra-n-butylammonium fluoride (~75% in $H_2O$) are added. The reaction mixture is allowed to warm to room temperature and stirred for 90 minutes.

The solvent is evaporated under reduced pressure and the residue is filtered through a short plug of silica gel [eluent: dichloromethane/methanol, with a gradient from 9/1 to 8/2 (v/v)]. It is then treated with 20 ml dichloromethane and 15 ml saturated aqueous $NaHCO_3$ solution. The phases are separated; the aqueous phase is extracted with 2×20 ml dichloromethane. A white solid precipitates in the aqueous phase. It is collected by filtration and washed with $H_2O$ to obtain the title product.

$^1$H NMR (300 MHz, $D_6$-DMSO): δ=1.72 (d, J=6.3 Hz, 3H), 4.69 (d, J=5.7 Hz, 2H), 5.48 (t, J=5.8 Hz, 1H), 5.90 (q, J=6.3 Hz, 1H), 7.13 (br s, 1H), 7.26-7.31 (m, 2H), 7.48 (m, 1H), 7.64-7.71 (m, 3H), 7.83 (br s, 1H), 8.67 (s, 1H), 8.95 (d, J=0.9 Hz, 1H).

MS (MH+ found)=472.9

53. 3-{(1-[2-(difluoromethoxy)phenyl]ethoxy}-5-[6-(hydroxymethyl)-1H-imidazo[4,5-c]pyridin-1-yl]thiophene-2-carboxamide A mixture of 1.44 g of 5-[6-({[tert-butyl(dimethyl)silyl]oxy}methyl)-1H-imidazo[4,5-c]pyridin-1-yl]-3-{-1-[2-(difluoromethoxy)phenyl]ethoxy}thiophene-2-carboxamide in 25 ml THF is cooled to 0° C. At 0° C., 0.91 ml tetra-n-butylammonium fluoride (~75% in $H_2O$) are added. The reaction mixture is allowed to warm to room temperature and stirred for 90 minutes.

The solvent is evaporated under reduced pressure and the residue is filtered through a short plug of silica gel [eluent: dichloromethane/methanol, with a gradient from 9/1 to 8/2 (v/v)]. It is then treated with 25 ml dichloromethane and 20 ml saturated aqueous $NaHCO_3$ solution. The phases are separated; the aqueous phase is extracted with 2×30 ml dichloromethane. A white solid precipitates in the aqueous phase. It is collected by filtration and washed with $H_2O$ to obtain the title product.

$^1$H NMR (300 MHz, $D_6$-DMSO): δ=1.72 (d, J=6.4 Hz, 3H), 4.70 (d, J=5.7 Hz, 2H), 5.49 (t, J=5.7 Hz, 1H), 5.90 (q, J=6.3 Hz, 1H), 7.1 (br s, 1H), 7.24-7.34 (m, 5H), 7.68 (m, 2H), 7.82 (br s, 1H), 8.66 (s, 1H), 8.96 (d, J=0.9 Hz, 1H).

MS (MH+ found)=460.9

54. 3-[(1R)-1-(2-chlorophenyl)ethoxy]-5-[6-(hydroxymethyl)-1H-imidazo[4,5-c]pyridin-1-yl]thiophene-2-carboxamide A mixture of 1.57 g of 5-[6-({[tert-butyl(dimethyl)silyl]oxy}methyl)-1H-imidazo[4,5-c]pyridin-1-yl]-3-[(1R)-1-(2-chlorophenyl)ethoxy]thiophene-2-carboxamide in 30 ml THF is cooled to 0° C. At 0° C., 1.05 ml tetra-n-butylammonium fluoride (~75% in $H_2O$) are added. The reaction mixture is allowed to warm to room temperature and stirred for 90 minutes.

The solvent is evaporated under reduced pressure and the residue is filtered through a short plug of silica gel [eluent: dichloromethane/methanol, with a gradient from 9/1 to 8/2 (v/v)]. It is then treated with 30 ml dichloromethane and 25 ml saturated aqueous $NaHCO_3$ solution. The phases are separated; the aqueous phase is extracted with 2×30 ml dichloromethane whereby the title compound partly precipitates in the aqueous phase. After filtration and separation the organic layer is treated with 40 ml saturated aqueous $NaHCO_3$ solution. After separation of the organic layer and evaporation of the solvent a second batch of title compound is obtained.

$^1$H NMR (300 MHz, $D_6$-DMSO): δ=1.75 (d, J=6.4 Hz, 3H), 4.69 (s, 2H), 5.49 (br s, 1H), 5.95 (q, J=6.3 Hz, 1H), 7.12 (br s, 1H), 7.34-7.51 (m, 4H), 7.68-7.72 (m, 2H), 7.83 (br s, 1H), 8.68 (s, 1H), 8.95 (d, J=0.8 Hz, 1H).

MS (MH+ found)=429.0

55. 3-[(1R)-1-(2-fluorophenyl)ethoxy]-5-[6-(hydroxymethyl)-1H-imidazo[4,5-c]pyridin-1-yl]thiophene-2-carboxamide A mixture of 1.42 g of 5-[6-({[tert-butyl(dimethyl)silyl]oxy}methyl)-1H-imidazo[4,5-c]pyridin-1-yl]-3-[(1R)-1-(2-fluorophenyl)ethoxy]thiophene-2-carboxamide in 25 ml THF is cooled to 0° C. At 0° C., 0.98 ml tetra-n-butylammonium fluoride (~75% in $H_2O$) are added. The reaction mixture is allowed to warm to room temperature and stirred for 90 minutes.

The solvent is evaporated under reduced pressure and the residue is filtered through a short plug of silica gel [eluent: dichloromethane/methanol, with a gradient from 9/1 to 8/2 (v/v)]. It is then treated with 100 ml dichloromethane and 75 ml saturated aqueous $NaHCO_3$ solution. The phases are separated; the aqueous phase is extracted with 2×75 ml dichloromethane whereby the title compound partly precipitates in the aqueous phase. After filtration and separation the organic layer is treated with 40 ml saturated aqueous $NaHCO_3$ solution. After separation of the organic layer and evaporation of the solvent a second batch of title compound is obtained.

$^1$H NMR (300 MHz, $D_6$-DMSO): δ=1.75 (d, J=6.4 Hz, 3H), 4.70 (d, J=5.8 Hz, 2H), 5.52 (t, J=5.8 Hz, 1H), 5.94 (q, J=6.4 Hz, 1H), 7.08 (br s, 1H), 7.22-729 (m, 2H), 7.37-7.44 (m, 1H), 7.58 (s, 1H), 7.64 (td, J=1.8 Hz and 7.6 Hz, 1H), 7.73 (d, J=0.8 Hz, 1H), 7.83 (br s, 1H), 8.70 (s, 1H), 8.96 (d, J=0.9 Hz, 1H).

MS (MH+ found)=413.0

56. 3-{[1-(2-chlorophenyl)propyl]oxy}-5-[6-(hydroxymethyl)-1H-imidazo[4,5-c]pyridin-1-yl]thiophene-2-carboxamide A mixture of 1.92 g of 5-[6-({[tert-butyl(dimethyl)silyl]oxy}methyl)-1H-imidazo[4,5-c]pyridin-1-yl]-3-{[-1-(2-chlorophenyl)propyl]oxy}thiophene-2-carboxamide in 35 ml THF is cooled to 0° C. At 0° C. 1.25 ml tetra-n-butylammonium fluoride (~75% in H$_2$0) are added. The reaction mixture is allowed to warm to room temperature and stirred for 90 minutes.

The solvent is evaporated under reduced pressure and the residue is filtered through a short plug of silica gel [eluent: dichloromethane/methanol, with a gradient from 9/1 to 8/2 (v/v)]. It is then treated with 50 ml dichloromethane and 40 ml saturated aqueous NaHCO$_3$ solution. The phases are separated; the aqueous phase is extracted with 2×100 ml dichloromethane. The organic phases are combined and concentrated to dryness under reduced pressure. The residue is treated again with 50 ml dichloromethane and 25 ml saturated aqueous NaHCO$_3$ solution. A white solid precipitates which is collected by filtration, washed with water to obtain the title product.

$^1$H NMR (300 MHz, D$_6$-DMSO): δ=1.00 (t, J=7.4 Hz, 3H), 1.97 (m, 1H), 2.21 (m, 1H), 4.69 (d, J=5.7 Hz, 2H), 5.48 (t, J=5.8 Hz, 1H), 5.74 (m, 1H), 7.15 (br s, 1H), 7.26 (s, 1H), 7.33-7.51 (m, 3H), 7.66 (s, 1H), 7.68 (d, J=1.8 Hz, 1H), 7.85 (br s, 1H), 8.66 (s, 1H), 8.95 (d, 0.8 Hz, 1H).

MS (MH+ found)=443.1

57. 3-[(1-(2-fluorophenyl)ethoxy]-5-[6-(hydroxymethyl)-1H-imidazo[4,5-c]pyridin-1-yl]thiophene-2-carboxamide A mixture of 1.84 g of 5-[6-({[tert-butyl(dimethyl)silyl]oxy}methyl)-1H-imidazo[4,5-c]pyridin-1-yl]-3-[-1-(2-fluorophenyl)ethoxy]thiophene-2-carboxamide in 35 ml THF is cooled to 0° C. At 0° C., 1.27 ml tetra-n-butylammonium fluoride (~75% in H$_2$0) are added. The reaction mixture is allowed to warm to room temperature and stirred for 90 minutes.

The solvent is evaporated under reduced pressure and the residue is filtered through a short plug of silica gel [eluent: dichloromethane/methanol, with a gradient from 9/1 to 8/2 (v/v)]. After evaporation of the solvent the remaining residue is then treated with 50 ml dichloromethane and 35 ml saturated aqueous NaHCO$_3$ solution. The phases are separated; the aqueous phase is extracted with 2×75 ml dichloromethane. A white solid precipitates in the aqueous phase. It is collected by filtration and washed with H$_2$O to obtain the title product.

$^1$H NMR (300 MHz, D$_6$-DMSO): δ=1.74 (d, J=6.4 Hz, 3H), 4.71 (s, 2H), 5.52 (br s, 1H), 5.92 (q, J=6.4 Hz, 1H), 7.07 (br s, 1H), 7.22-7.29 (m, 2H), 7.37-7.44 (m, 1H), 7.58 (s, 1H), 7.64 (td, J=1.8 and 7.5 Hz, 1H), 7.72 (d, J=0.8 Hz, 1H), 7.82 (br s, 1H), 8.70 (s, 1H), 8.96 (d, J=0.9 Hz, 1H).

MS (MH+ found)=413.0

58. 5-(6-{[4-(phenylsulfonyl)piperazin-1-yl]methyl}-1H-imidazo[4,5-c]pyridin-1-yl)-3-{(1R)-1-[2-(trifluoromethyl)phenyl]ethoxy}thiophene-2-carboxamide 100 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate are dissolved in 2.5 ml dichloromethane. Under N$_2$ atmosphere benzenesulfonyl piperazine (209 mg) is added. The reaction mixture is stirred at 40° C. for 1 hour and then concentrated to dryness under vacuum. The residue is purified by preparative HPLC (ammonium formate buffer/acetonitrile, elution gradient 97/3 to 0/100 (v/v)) to obtain the title product.

$^1$H NMR (300 MHz, CDCl$_3$): δ=1.79 (d, J=6.2 Hz, 3H), 2.58 (m, 4H), 3.08 (m, 4H), 3.71 (s, 2H), 5.83 (m, 2H), 6.64 (s, 1H), 7.18 (br s, 1H), 7.34 (d, J=0.8 Hz, 1H), 7.45-7.77 (m, 9H), 7.93 (s, 1H), 9.07 (d, J=0.9 Hz, 1H).

MS (MH+ found)=671.0

59. 5-{6-[(4-phenylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 59 is synthesized starting with 100 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 150 mg 1-phenylpiperazine.

$^1$H NMR (300 MHz, CDCl$_3$): δ=1.80 (d, J=6.2 Hz, 3H), 2.69 (m, 4H), 3.23 (m, 4H), 3.81 (d, J=1.5 Hz, 2H), 5.85 (m, 2H), 6.68 (s, 1H), 6.82 (t, J=7.3 Hz, 1H), 6.91 (dd, J=0.9 and 8.9 Hz, 2H), 7.23 (br s, 1H), 7.24-7.61 (m, 2H), 7.46 (m, 1H), 7.53 (d, J=0.8 Hz, 1H), 7.64 (t, J=7.4 Hz, 2H), 7.71 (t, J=7.4 Hz, 1H), 7.95 (s, 1H), 9.10 (d, J=1 Hz, 1H).

MS (MH+ found)=607.4

60. 5-{6-[(4-cyclopropylpiperazin-1-yl)methyl]-1H-imidazo[4,5-c]pyridin-1-yl}-3-{(1R)-1-[2-(trifluoromethyl)phenyl]ethoxy}thiophene-2-carboxamide 100 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 205 mg triethylamine are dissolved in 2.5 ml dichloromethane. Under N$_2$ atmosphere 1-cyclopropylpiperazine dihydrochloride (184 mg) is added. The reaction mixture is stirred at 40° C. for 1 hour and then concentrated to dryness under vacuum. The residue is purified by preparative HPLC (ammonium formate buffer/acetonitrile, elution gradient 97/3 to 0/100 (v/v)) to obtain the title product.

$^1$H NMR (300 MHz, CDCl$_3$): δ=0.42 (m, 4H), 1.45 (m, 1H), 1.81 (d, J=6.2 Hz, 3H), 2.52-2.67 (br m, 8H), 3.74 (d, J=1.8 Hz, 2H), 5.88 (m, 2H), 6.67 (s, 1H), 7.19 (br s, 1H), 7.50 (m, 2H), 7.62-7.75 (m, 3H), 7.93 (s, 1H), 9.08 (d, J=0.9 Hz, 1H).

MS (MH+ found)=571.1

61. 5-(6-{[4-(2-hydroxyethyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 61 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 0.12 ml of N-(2-hydroxyethyl)piperazine.

$^1$H NMR (300 MHz, CDCl$_3$): δ=1.81 (d, J=6.2 Hz, 3H), 2.55-2.61 (m, 10H), 2.95 (t, J=4.9 Hz, 1H), 3.60 (td, J=2.3 and 5.3 Hz, 2H), 3.81 (s, 2H), 5.85 (q, J=6.1 Hz, 1H), 5.91 (br s, 1H), 6.68 (s, 1H), 7.19 (br s, 1H), 7.50 (m, 2H), 7.62-7.75 (m, 3H), 7.94 (s, 1H), 9.09 (d, J=0.9 Hz, 1H).

MS (MH+ found)=575.0

62. 5-[6-(morpholin-4-ylmethyl)-1H-imidazo[4,5-c]pyridin-1-yl]-3-{(1R)-1-[2-(trifluoromethyl)phenyl]ethoxy}thiophene-2-carboxamide In a similar manner as described for example 58, compound 62 is synthesized starting with 108 mg of [1-(5-carbamoyl-4-{(1R)-1-[2-(trifluoromethyl)phenyl]ethoxy}-2- thienyl)-1H-imidazo[4,5-c]pyridin-6-yl]methyl methanesulfonate and 87.1 mg of morpholine.

¹H NMR (300 MHz, CDCl₃): δ=1.81 (d, J=6.3 Hz, 3H), 2.52 (t, J=4.6 Hz, 4H), 3.74 (m, 6H), 5.88 (m, 2H), 6.68 (s, 1H), 7.19 (br s, 1H), 7.48 (m, 2H), 7.62-7.74 (m, 3H), 7.94 (s, 1H), 9.09 (d, J=1 Hz, 1H).

MS (MH+ found)=532.0

63. 5-{6-[(1,1-dioxidothiomorpholin-4-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 63 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 135.2 mg of thiomorpholine 1,1-dioxide.

¹H NMR (300 MHz, CDCl₃): δ=1.81 (d, J=6.2 Hz, 3H), 3.08 (s, 8H), 3.90 (s, 2H), 5.87 (m, 1H), 5.90 (br s, 1H), 6.68 (s, 1H), 7.60 (br s, 1H), 7.47-7.52 (m, 2H), 7.63-7.75 (m, 3H), 7.97 (s, 1H), 9.09 (d, J=0.9 Hz, 1H).

MS (MH+ found)=580.0

64. 5-{6-[(4-hydroxypiperidin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 64 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 101.1 mg of piperidin-4-ol.

¹H NMR (300 MHz, D₆-DMSO): δ=1.35-1.44 (m, 2H), 1.69 (m, 2H), 1.72 (d, J=6.2 Hz, 3H), 2.16 (t, J=10.7 Hz, 2H), 2.73 (m, 2H), 3.46 (m, 1H), 3.66 (s, 2H), 4.51 (br s, 1H), 5.94 (q, J=6.2 Hz, 1H), 7.14 (br s, 1H), 7.19 (s, 1H), 7.52-7.60 (m, 2H), 7.79 (t, J=8.1 Hz, 2H), 7.85 (br s, 1H), 7.95 (d, J=7.9 Hz, 1H), 8.64 (s, 1H), 8.95 (d, J=0.8 Hz, 1H).

MS (MH+ found)=546.0

65. 5-(6-{[4-(dimethylamino)piperidin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 65 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 128.2 mg of N,N-dimethylpiperidin-4-amine.

¹H NMR (300 MHz, CDCl₃): δ=1.64 (m, 2H), 1.81 (d, J=6.3 Hz, 3H), 2.11 (m, 5H), 2.34 (s, 6H), 2.95 (m, 2H), 3.73 (s, 2H), 5.88 (q, J=6.0 Hz, 1H), 5.90 (br s, 1H), 6.67 (s, 1H), 7.20 (br s, 1H), 7.45-7.51 (m, 2H), 7.62-7.74 (m, 3H), 7.93 (s, 1H), 9.07 (d, J=0.9 Hz, 1H).

MS (MH+ found)=573.1

66. 5-(6-{[4-(methylsulfonyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 66 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 164.1 mg of 1-(methylsulfonyl)piperazine.

¹H NMR (300 MHz, CDCl₃): δ=1.81 (d, J=6.3 Hz, 3H), 2.63 (m, 4H), 2.78 (s, 3H), 3.28 (t, J=4.9 Hz, 4H), 3.79 (s, 2H), 5.85 (q, J=6.3 Hz, 1H), 5.91 (br s, 1H), 6.68 (s, 1H), 7.19 (br s, 1H), 7.46-7.51 (m, 2H), 7.63-7.75 (m, 3H), 7.96 (s, 1H), 9.10 (d, J=0.9 Hz, 1H).

MS (MH+ found)=609.0

67. 4-{[1-(5-carbamoyl-4-{(1R)-1-[2-(trifluoromethyl)phenyl]ethoxy}-2-thienyl)-1H-imidazo[4,5-c]pyridin-6-yl]methyl}piperazine-1-carboxamide In a similar manner as described for example 60, compound 67 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate, 165.6 mg of piperazine-1-carboxamide hydrochloride and 0.15 ml triethylamine.

¹H NMR (300 MHz, CDCl₃): δ=1.80 (d, J=6.3 Hz, 3H), 2.54 (t, J=5.0 Hz, 4H), 3.43 (m, 4H), 3.77 (s, 2H), 4.46 (s, 2H), 5.87 (m, 2H), 6.67 (s, 1H), 7.19 (br s, 1H), 7.48-7.52 (m, 2H), 7.62-7.74 (m, 3H), 7.95 (s, 1H), 9.09 (d, J=0.8 Hz, 1H).

MS (MH+ found)=573.9

68. 4-{[1-(5-carbamoyl-4-{(1R)-1-[2-(trifluoromethyl)phenyl]ethoxy}-2-thienyl)-1H-imidazo[4,5-c]pyridin-6-yl]methyl}-N,N-dimethylpiperazine-1-carboxamide In a similar manner as described for example 58, compound 68 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 157.2 mg of N,N-dimethylpiperazine-1-carboxamide.

¹H NMR (300 MHz, D₆-DMSO): δ=1.77 (d, J=6.2 Hz, 3H), 2.44 (m, 4H), 2.71 (s, 6H), 3.11 (m, 4H), 3.72 (s, 2H), 5.95 (q, J=6.3 Hz, 1H), 7.14 (br s, 1H), 7.20 (s, 1H), 7.54-7.59 (m, 2H), 7.79 (t, J=8.3 Hz, 2H), 7.85 (br s, 1H), 7.95 (d, J=7.7 Hz, 1H), 8.65 (s, 1H), 8.98 (d, J=0.9 Hz, 1H).

MS (MH+ found)=602.1

69. 5-(6-{[4-(2-methoxyethyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 69 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 144.2 mg of 1-(2-methoxyethyl)piperazine.

MS (MH+ found)=589.1

70. 5-[6-({4-[2-(dimethylamino)ethyl]piperazin-1-yl}methyl)-1H-imidazo[4,5-c]pyridin-1-yl]-3-{(1R)-1-[2-(trifluoromethyl)phenyl]ethoxy}thiophene-2-carboxamide In a similar manner as described for example 58, compound 70 is synthesized starting with 108 mg of [1-(5-carbamoyl-4-{(1R)-1-[2-(trifluoromethyl)phenyl]ethoxy}-2- thienyl)-1H-imidazo[4,5-c]pyridin-6-yl]methyl methanesulfonate and 157.3 mg of N,N-dimethyl-2-piperazin-1-ylethanamine.

$^1$H NMR (300 MHz, D$_6$-DMSO): δ=1.76 (d, J=6.2 Hz, 3H), 2.13 (s, 6H), 2.30-2.42 (m, 12H), 3.68 (s, 2H), 5.92 (q, J=6.2 Hz, 1H), 7.13 (br s, 1H), 7.21 (s, 1H), 7.54 (m, 2H), 7.79 (t, J=8.6 Hz, 2H), 7.85 (br s, 1H), 7.97 (d, J=7.8 Hz, 1H), 8.64 (s, 1H), 8.96 (d, J=0.9 Hz, 1H).

MS (MH+ found)=602.0

71. 5-[6-({4-[(dimethylamino)sulfonyl]piperazin-1-yl}methyl)-1H-imidazo[4,5-c]pyridin-1-yl]-3-{(1R)-1-[2-(trifluoromethyl)phenyl]ethoxy}thiophene-2-carboxamide In a similar manner as described for example 58, compound 71 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 193.3 mg of N,N-dimethylpiperazine-1-sulfonamide.

$^1$H NMR (300 MHz, CDCl$_3$): δ=1.81 (d, J=6.3 Hz, 3H), 2.55-2.56 (m, 4H), 2.83 (s, 6H), 3.31 (m, 4H), 3.77 (s, 2H), 5.88 (q, J=6.3 Hz, 1H), 5.90 (br s, 1H), 6.67 (s, 1H), 7.20 (br s, 1H), 7.49 (m, 2H), 7.63-7.75 (m, 3H), 7.95 (s, 1H), 9.09 (d, J=0.9 Hz, 1H).

MS (MH+ found)=638.0

72. 5-{6-[(4-methyl-3-oxopiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 60, compound 72 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate, 150.6 mg of 1-methylpiperazin-2-one hydrochloride and 0.15 ml triethylamine.

$^1$H NMR (300 MHz, CDCl$_3$): δ=1.80 (d, J=6.2 Hz, 3H), 2.77 (m, 2H), 2.96 (s, 3H), 3.20 (s, 2H), 3.33 (m, 2H), 3.80 (s, 2H), 5.85 (q, J=6.3 Hz, 1H), 6.00 (br s, 1H), 6.68 (s, 1H), 7.20 (br s, 1H), 7.51 (m, 2H), 7.62-7.74 (m, 3H), 7.96 (s, 1H), 9.08 (d, J=0.9 Hz, 1H).

MS (MH+ found)=559.0

73. 5-(6-{[(1-methylpiperidin-4-yl)amino]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 73 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 114.2 mg of 1-methylpiperidin-4-amine.

$^1$H NMR (300 MHz, CDCl$_3$): δ=1.80 (m, 3H), 2.43 (s, 3H), 2.71-2.85 (m, 9H), 3.90 (s, 2H), 5.80 (br s, 1H), 5.85 (q, J=6.3 Hz, 1H), 6.68 (s, 1H), 7.19 (br s, 1H), 7.48 (m, 1H), 7.61 (s, 1H), 7.62-7.75 (m, 4H), 7.93 (s, 1H), 9.06 (d, J=0.9 Hz, 1H).

MS (MH+ found)=559.0

74. 5-{6-[(3,4-dimethylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 60, compound 74 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate, 150.7 mg of 1,2-dimethylpiperazine hydrochloride and 0.15 ml triethylamine.

$^1$H NMR (300 MHz, CDCl$_3$): δ=1.02 (dd, J=1.8 and 6.2 Hz, 3H), 1.81 (d, J=6.2 Hz, 3H), 2.02 (m, 1H), 2.24 (m, 1H), 2.30 (s, 3H), 2.39 (m, 2H), 2.68-2.79 (m, 3H), 3.73 (s, 2H), 5.81 (br s, 1H), 5.85 (q, J=6.2 Hz, 1H), 6.67 (s, 1H), 7.19 (br s, 1H), 7.48 (m, 2H), 7.61-7.75 (m, 3H), 7.94 (s, 1H), 9.09 (d, J=0.9 Hz, 1H).

MS (MH+ found)=559.0

75. 5-{6-[(4-pyridin-4-ylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 75 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 163.2 mg of 1-pyridin-4-ylpiperazine.

$^1$H NMR (300 MHz, CDCl$_3$): δ=1.80 (d, J=6.3 Hz, 3H), 2.65 (m, 4H), 3.38 (m, 4H), 3.80 (s, 2H), 5.87 (q, J=6.4 Hz, 1H), 5.91 (br s, 1H), 6.66 (m, 3H), 7.19 (br s, 1H), 7.47 (t, J=7.5 Hz, 1H), 7.56 (d, J=0.8 Hz, 1H), 7.62-7.74 (m, 3H), 7.95 (s, 1H), 8.26 (dd, J=1.5 and 5 Hz, 2H), 9.10 (d, J=0.9 Hz, 1H).

MS (MH+ found)=608.0

76. 3-[1-(2-chlorophenyl)-2,2,2-trifluoroethoxy]-5-{6-[(4-methylpiperazin-1-yl)methyl]-1H-imidazo[4,5-c]pyridin-1-yl}thiophene-2-carboxamide Step 1: In a similar manner as described for example 49 (step 1), 170 mg of 3-[1-(2-chlorophenyl)-2,2,2-trifluoroethoxy]-5-[6-(hydroxymethyl)-1H-imidazo[4,5-c]pyridin-1-yl]thiophene-2-carboxamide, 76.7 mg of methanesulfonyl chloride, and 70.8 mg of triethylamine in 3 ml dichloromethane give (1-{5-carbamoyl-4-[1-(2-chlorophenyl)-2,2,2-trifluoroethoxy]-2-thienyl}-1H-imidazo[4,5-c]pyridin-6-yl)methyl methanesulfonate as crude material that is used for step 2 without further purification.

Step 2: 230 mg of crude (1-{5-carbamoyl-4-[1-(2-chlorophenyl)-2,2,2-trifluoroethoxy]-2-thienyl}-1H-imidazo[4,5-c]pyridin-6-yl)methyl methanesulfonate (from step 1) are dissolved in 5 ml dichloromethane. Under N$_2$ atmosphere 200 mg 1-methylpiperazine is added. The reaction mixture is stirred at 40° C. for 1 hour and then concentrated to dryness under vacuum. The residue is purified by preparative HPLC (ammonium formate buffer/acetonitrile, elution gradient 97/3 to 0/100 (v/v)) to obtain the title product.

$^1$H NMR (300 MHz, CDCl$_3$): δ=2.31 (s, 3H), 2.51-2.58 (br m, 8H), 3.77 (d, J=1.5 Hz, 2H), 5.90 (br s, 1H), 6.21 (q, J=5.7 Hz, 1H), 6.63 (d, J=2.3 Hz, 1H), 6.91 (br s, 1H), 7.26-7.57 (m, 4H), 7.65 (dd, J=1.6 and 6.9 Hz, 1H), 7.98 (s, 1H), 9.10 (d, J=1.0 Hz, 1H).

MS (MH+ found)=565.0

77. 5-{6-[(4-pyrimidin-2-ylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 77 is synthesized starting with 108 mg of [1-(5-carbamoyl-4-{(1R)-1-[2-(trifluoromethyl)phenyl]ethoxy}-2- thienyl)-1H-imidazo[4,5-c]pyridin-6-yl]methyl methanesulfonate and 164.2 mg of 2-piperazin-1-ylpyrimidine.

$^1$H NMR (300 MHz, CDCl$_3$): δ=1.82 (d, J=6.3 Hz, 3H), 2.58 (m, 4H), 3.79 (s, 2H), 3.85 (m, 4H), 5.83 (q, J=6.2 Hz, 1H), 5.90 (br s, 1H), 6.47 (t, J=4.7 Hz, 1H), 6.68 (s, 1H), 7.19 (br s, 1H), 7.47 (t, J=7.2 Hz, 1H), 7.55 (d, J=0.9 Hz, 1H), 7.62-7.74 (m, 3H), 7.95 (s, 1H), 8.31 (d, J=4.8 Hz, 2H), 9.10 (d, J=0.9 Hz, 1H).

MS (MH+ found)=609.1

78. 5-{6-[(4-benzoylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 78 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 190.2 mg of 1-benzoylpiperazine.

$^1$H NMR (300 MHz, CDCl$_3$): δ=1.83 (d, J=6.2 Hz, 3H), 2.18 (br s, 4H), 3.48 (br s, 4H), 3.79 (s, 2H), 5.85 (q, J=6.2 Hz, 1H), 6.03 (br s, 1H), 6.67 (s, 1H), 7.20 (br s, 1H), 7.40 (s, 5H), 7.48 (m, 1H), 7.53 (d, J=0.8 Hz, 1H), 7.62-7.74 (m, 3H), 7.95 (s, 1H), 9.09 (d, J=1.0 Hz, 1H).

MS (MH+ found)=635.1

79. 5-{6-[(4-benzylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 79 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 190.2 mg of 1-benzylpiperazine.

$^1$H NMR (300 MHz, CDCl$_3$): δ=1.81 (d, J=6.2 Hz, 3H), 2.58 (br s, 8H), 3.58 (s, 2H), 3.77 (s, 2H), 5.83 (q, J=6.2 Hz, 1H), 5.96 (br s, 1H), 6.67 (s, 1H), 7.23 (br s, 1H), 7.31 (m, 5H), 7.45-7.50 (m, 2H), 7.62-7.74 (m, 3H), 7.93 (s, 1H), 9.07 (d, J=0.9 Hz, 1H).

MS (MH+ found)=621.1

80. 5-(6-{[4-(2-morpholin-4-ylethyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 80 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 199.3 mg of 4-(2-piperazin-1-ylethyl)morpholine.

$^1$H NMR (300 MHz, CDCl$_3$): δ=1.81 (d, J=6.2 Hz, 3H), 2.47-2.58 (m, 16H), 3.66-3.75 (m, 4H), 3.80 (s, 2H), 5.85 (q, J=6.3 Hz, 1H), 5.90 (br s, 1H), 6.67 (s, 1H), 7.20 (br s, 1H), 7.46-7.51 (m, 2H), 7.62-7.75 (m, 3H), 7.94 (s, 1H), 9.08 (d, J=1.0 Hz, 1H).

MS (MH+ found)=644.1

81. 5-{6-[(4-acetyl-1,4-diazepan-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 81 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 142.2 mg of 1-acetyl-1,4-diazepane.

$^1$H NMR (300 MHz, CDCl$_3$): δ=1.83 (d, J=6.3 Hz, 3H), 1.90 (m, 2H), 2.11 (2s, 3H), 2.69-2.81 (m, 4H), 3.55 (t, J=6.3 Hz, 2H), 3.62-3.69 (m, 2H), 3.90 (s, 2H), 5.84 (q, J=6.3 Hz, 1H), 5.91 (br s, 1H), 6.68 (d, J=1.3 Hz, 1H), 7.26 (br s, 1H), 7.48 (t, J=7.5 Hz, 1H), 7.57 (m, 1H), 7.62-7.74 (m, 3H), 7.94 (d, J=1.8 Hz, 1H), 9.07 (dd, J=0.9 and 2.7 Hz, 1H).

MS (MH+ found)=587.0

82. 5-(6-{[4-(2-cyanoethyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 82 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 139.2 mg of 3-piperazin-1-ylpropanenitrile.

$^1$H NMR (300 MHz, CDCl$_3$): δ=1.81 (d, J=6.2 Hz, 3H), 2.51 (t, J=7.1 Hz, 2H), 2.58 (s, 8H), 2.72 (t, J=7.1 Hz, 2H), 3.82 (s, 2H), 5.86 (q, J=6.3 Hz, 1H), 6.00 (br s, 1H), 6.68 (s, 1H), 7.20 (br s, 1H), 7.46 (d, J=7.2 Hz, 1H), 7.51 (d, J=0.8 Hz, 1H), 7.62-7.75 (m, 3H), 7.95 (s, 1H), 9.09 (d, J=0.9 Hz, 1H).

MS (MH+ found)=584.1

83. 5-{6-[(2,5-dimethylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 83 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 114.2 mg of 2,5-dimethylpiperazine.

$^1$H NMR (300 MHz, CDCl$_3$): δ=1.00 (t, J=5.5 Hz, 3H), 1.15 (m, 3H), 1.82 (d, J=6.2 Hz, 3H), 1.90 (td, J=4.6 and 10.8 Hz, 1H), 2.42 (br m, 1H), 2.64-2.76 (m, 2H), 2.90-3.00 (m, 2H), 3.45 (dd, J=10.5 and 14.1 Hz, 1H), 4.26 (t, J=13.0 Hz, 1H), 5.88 (q, J=6.2 Hz, 1H), 6.06 (br s, 1H), 6.68 (d, J=2.8 Hz, 1H), 7.20 (br s, 1H), 7.48 (t, J=7.2 Hz, 1H), 7.53 (d, J=3.8 Hz, 1H), 7.62-7.72 (m, 3H), 7.94 (d, J=3.1 Hz, 1H), 9.07 (s, 1H).

MS (MH+ found)=559.1

84. 5-{6-[(4-pyrazin-2-ylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 84 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 164.2 mg of 2-piperazin-1-ylpyrazine.

$^1$H NMR (300 MHz, CDCl$_3$): δ=1.82 (d, J=6.3 Hz, 3H), 2.62-2.65 (m, 4H), 3.61-3.65 (m, 4H), 3.85 (s, 2H), 5.85 (q, J=6.2 Hz, 1H), 5.98 (br s, 1H), 6.68 (s, 1H), 7.19 (br s, 1H), 7.47 (t, J=7.3 Hz, 1H), 7.56 (d, J=0.8 Hz, 1H), 7.64-7.74 (m, 3H), 7.84 (d, J=2.6 Hz, 1H), 7.96 (s, 1H), 8.05 (dd, J=1.6 and 2.6 Hz, 1H), 8.13 (d, J=1.5 Hz, 1H), 9.11 (d, J=1.0 Hz, 1H).

MS (MH+ found)=609.0

85. 5-[6-({4-[(1-methylpiperidin-4-yl)methyl]piperazin-1-yl}methyl)-1H-imidazo[4,5-c]pyridin-1-yl]-3-{(1R)-1-[2-(trifluoromethyl)phenyl]ethoxy}thiophene-2-carboxamide In a similar manner as described for example 58, compound 85 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 197.3 mg of 1-[(1-methylpiperidin-4-yl)methyl]piperazine.

$^1$H NMR (300 MHz, CDCl$_3$): δ=1.21 (m, 2H), 1.34 (m, 1H), 1.74 (m, 2H), 1.80 (d, J=6.2 Hz, 3H), 1.93-2.01 (m, 2H), 2.18 (d, J=7.0 Hz, 2H), 2.30 (s, 3H), 2.45-2.53 (br m, 8H), 2.89 (m, 2H), 3.79 (s, 2H), 5.85 (q, J=6.3 Hz, 1H), 5.89 (br s, 1H), 6.67 (s, 1H), 7.19 (br s, 1H), 7.48 (m, 2H), 7.61-7.74 (m, 3H), 8.13 (s, 1H), 9.08 (d, J=0.9 Hz, 1H).

MS (MH+ found)=642.1

86. 5-{6-[(4-{2-[methyl(phenyl)amino]-2-oxoethyl}piperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 86 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 233.3 mg of N-methyl-N-phenyl-2-piperazin-1-ylacetamide.

$^1$H NMR (300 MHz, CDCl$_3$): δ=1.82 (d, J=6.2 Hz, 3H), 2.50 (br s, 8H), 2.93 (s, 2H), 3.27 (s, 3H), 3.71 (d, J=2.0 Hz, 2H), 5.85 (q, J=6.3 Hz, 1H), 5.91 (br s, 1H), 6.65 (s, 1H), 7.19 (m, 3H), 7.32-7.50 (m, 5H), 7.62-7.74 (m, 3H), 7.92 (s, 1H), 9.06 (d, J=0.9 Hz, 1H).

MS (MH+ found)=678.1

87. 5-[6-({4-[2-(dimethylamino)-2-oxoethyl]piperazin-1-yl}methyl)-1H-imidazo[4,5-c]pyridin-1-yl]-3-{(1R)-1-[2-(trifluoromethyl)phenyl]ethoxy}thiophene-2-carboxamide In a similar manner as described for example 58, compound 87 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 171.2 mg of N,N-dimethyl-2-piperazin-1-ylacetamide.

$^1$H NMR (300 MHz, CDCl$_3$): δ=1.81 (d, J=6.2 Hz, 3H), 2.57 (s, 8H), 2.94 (s, 3H), 3.08 (s, 3H), 3.17 (s, 2H), 3.75 (d, J=1.2 Hz, 2H), 5.86 (q, J=6.3 Hz, 1H), 5.95 (br s, 1H), 6.67 (s, 1H), 7.20 (br s, 1H), 7.50 (m, 2H), 7.62-7.74 (m, 3H), 7.93 (s, 1H), 9.08 (d, J=0.9 Hz, 1H).

MS (MH+ found)=616.1

88. 5-[6-({[2-(4-methylpiperazin-1-yl)ethyl]amino}methyl)-1H-imidazo[4,5-c]pyridin-1-yl]-3-{(1R)-1-[2-(trifluoromethyl)phenyl]ethoxy}thiophene-2-carboxamide In a similar manner as described for example 60, compound 88 is synthesized starting with 100 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate, 150.0 mg of 2-(4-methylpiperazin-1-yl)ethanamine and 0.16 ml triethylamine.

$^1$H NMR (300 MHz, CDCl$_3$): δ=1.80 (d, J=6.2 Hz, 3H), 2.30 (s, 3H), 2.43-2.57 (m, 10H), 2.74 (t, J=6.2 Hz, 2H), 2.81 (t, J=6.2 Hz, 1H), 4.02 (s, 2H), 5.85 (q, J=6.3 Hz, 1H), 5.89 (br s, 1H), 6.67 (s, 1H), 7.19 (br s, 1H), 7.40 (d, J=0.9 Hz, 1H), 7.48 (t, J=7.1 Hz, 1H), 7.62-7.75 (m, 3H), 7.94 (s, 1H), 9.06 (d, J=0.9 Hz, 1H).

MS (MH+ found)=588.2

89. 5-(6-{[4-(4-methylpiperazin-1-yl)piperidin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 60, compound 89 is synthesized starting with 100 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 225 mg of 1-methyl-4-piperidin-4-ylpiperazine and 103 mg triethylamine.

MS (MH+ found)=628.1

90. 5-(6-{[(methylsulfonyl)amino]methyl}-3H-imidazo[4,5-c]pyridin-3-yl)-3-{(1R)-1-[2-(trifluoromethyl)phenyl]ethoxy}thiophene-2-carboxamide A mixture of 48.7 mg of 5-[6-(aminomethyl)-3H-imidazo[4,5-c]pyridin-3-yl]-3-{(1R)-1-[2-(trifluoromethyl)phenyl]ethoxy}thiophene-2-carboxamide and 26.1 mg triethylamine in 1 ml anhydrous dichloromethane is stirred at room temperature. Under nitrogen atmosphere, 14 mg methanesulfonyl chloride is added. The reaction mixture is stirred at room temperature for 14 h. The solvent is removed under pressure and the residue is purified by preparative HPLC (ammonium formate buffer/acetonitrile, elution gradient 97/3 to 0/100 (v/v)) to obtain the title product.

$^1$H NMR (300 MHz, D$_6$-DMSO): δ=1.77 (d, J=6.2 Hz, 3H), 2.93 (s, 3H), 4.39 (d, J=6.3 Hz, 2H), 5.98 (q, J=6.1 Hz, 1H), 7.14 (br s, 1H), 7.25 (s, 1H), 7.56 (t, J=7.6 Hz, 1H), 7.68 (t, J=6.2 Hz, 1H), 7.75 (m, 3H), 7.84 (br s, 1H), 7.97 (d, J=7.7 Hz, 1H), 8.76 (s, 1H), 8.84 (d, J=0.8 Hz, 1H).

MS (MH+ found)=540.0

91. 5-[6-({4-[(4-methylpiperazin-1-yl)carbonyl]piperidin-1-yl}methyl)-1H-imidazo[4,5-c]pyridin-1-yl]-3-{(1R)-1-[2-(trifluoromethyl)phenyl]ethoxy}thiophene-2-carboxamide In a similar manner as described for example 60, compound 91 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate, 211.3 mg of 1-methyl-4-(piperidin-4-ylcarbonyl)piperazine and 0.16 ml triethylamine.

$^1$H NMR (300 MHz, D$_6$-DMSO): δ=1.1 (t, J=7.2 Hz, 2H), 1.58 (br m, 3H), 1.77 (d, J=6.2 Hz, 3H), 2.09-2.30 (m, 7H), 2.87 (m, 2H), 3.15 (s, 1H), 3.20-3.50 (m, 5H+H$_2$O), 3.70 (s, 2H), 5.92 (q, J=6.1 Hz, 1H), 7.14 (br s, 1H), 7.18 (s, 1H), 7.51 (s, 1H), 7.57 (t, J=7.5 Hz, 1H), 7.77-7.86 (m, 1H), 7.89 (br s, 1H), 7.95 (d, J=7.9 Hz, 1H), 8.17 (s, 1H), 8.64 (s, 1H), 8.96 (s, 1H).

MS (MH+ found)=656.1

92. 5-[(6-(piperazin-1-ylmethyl)-1H-imidazo[4,5-c]pyridin-1-yl)-3-{(1R)-1-[2-(trifluoromethyl)phenyl]ethoxy}thiophene-2-carboxamide A mixture of 270 mg of [1-(5-carbamoyl-4-{(1R)-1-[2-(trifluoro-methyl)phenyl]ethoxy}-2-thienyl)-1H-imidazo[4, 5-c]pyridin-6-yl]methyl methanesulfonate and 258 mg of piperazine in 10 ml dichloromethane is stirred at room temperature for 16 hours. Water (20 ml) is added to the mixture. After separation of the organic layer, the aqueous layer is extracted with dichloromethane (2×10 ml). The combined organic layers are dried over MgSO$_4$. After filtration the solvent is removed under reduced pressure. The resulting residue is purified by flash chromatography [silica gel, eluent: ethyl acetate/methanol/aqueous solution of ammonia, 20/4/1 (v/v/v) to give the title compound.

$^1$H NMR (300 MHz, D$_6$-DMSO): δ=1.76 (d, J=6.1 Hz, 3H), 2.40 (m, 4H), 2.74 (m, 3H), 3.42 (s, 2H), 3.67 (s, 2H), 5.94 (m, 1H), 7.13 (br s, 1H), 7.20 (s, 1H), 7.53-7.60 (m, 2H), 7.79 (m, 2H), 7.83 (br s, 1H), 7.98 (d, J=7.5 Hz, 1H), 8.64 (d, J=3.2 Hz, 1H), 8.96 (d, J=0.8 Hz, 1H).

MS (MH+ found)=531.0

93. 5-{6-[(4-methylpiperidin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 93 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 99.2 mg of 4-methylpiperidine.

$^1$H NMR (300 MHz, CDCl$_3$): δ=0.93 (d, J=5.6 Hz, 3H), 1.38 (m, 3H), 1.61-1.65 (m, 2H), 1.81 (d, J=6.2 Hz, 3H), 2.18-2.25 (m, 2H), 2.96-3.00 (m, 2H), 3.85 (s, 2H), 5.88 (q, J=6.2 Hz, 1H), 6.01 (br s, 1H), 6.70 (s, 1H), 7.20 (br s, 1H), 7.48 (t, J=7.2 Hz, 1H), 7.58 (d, J=0.8 Hz, 1H), 7.62-7.74 (m, 3H), 7.95 (s, 1H), 9.07 (d, J=0.9 Hz, 1H).

MS (MH+ found)=544.1

94. 5-{6-[(3-hydroxypyrrolidin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 94 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 87.1 mg of pyrrolidin-3-ol.

$^1$H NMR (300 MHz, CDCl$_3$): δ=1.80 (d, J=6.3 Hz, 3H), 1.93 (m, 1H), 2.26 (m, 1H), 2.78 (m, 1H), 2.94 (m, 1H), 3.08 (m, 1H), 3.23 (m, 1H), 4.10 (s, 2H), 4.45 (m, 1H), 5.88 (q, J=6.2 Hz, 1H), 5.96 (br s, 1H), 6.72 (d, J=1.1 Hz, 1H), 7.20 (br s, 1H), 7.48 (m, 1H), 7.63-7.74 (m, 4H), 7.98 (d, J=0.8 Hz, 1H), 9.09 (d, J=0.9 Hz, 1H).

MS (MH+ found)=532.0

95. 5-{6-[(1S,4S)-2,5-diazabicyclo[2.2.1]hept-2-ylmethyl]-1H-imidazo[4,5-c]pyridin-1-yl}-3-{(1R)-1-[2-(trifluoromethyl)phenyl]ethoxy}thiophene-2-carboxamide Step 1: 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate are dissolved in 2.5 ml dichloromethane. Under N$_2$ atmosphere tert-butyl (1S,4S)-2,5-diazabicyclo[2.2.1]heptane-2-carboxylate (198 mg) is added. The reaction mixture is stirred at 40° C. for 1 hour and then concentrated to dryness under vacuum. The residue is purified by preparative HPLC (ammonium formate buffer/acetonitrile, elution gradient 97/3 to 0/100 (v/v)) to obtain tert-butyl (1S,4S)-5-{[1-(5-carbamoyl-4-{(1R)-1-[2-(trifluoromethyl)phenyl]ethoxy}-2-thienyl)-1H-imidazo[4,5-c]pyridin-6-yl]methyl}-2,5-diazabicyclo[2.2.1]heptane-2-carboxylate.

MS (MH+ found)=642.9

Step 2: 33.9 mg of tert-butyl (1S,4S)-5-{[1-(5-carbamoyl-4-{(1R)-1-[2-(trifluoromethyl)phenyl]ethoxy}-2-thienyl)-1H-imidazo[4,5-c]pyridin-6-yl]methyl}-2,5-diazabicyclo[2.2.1]heptane-2-carboxylate is dissolved in 0.5 ml dichloromethane and 0.5 ml trifluoroacetic acid is added at 0° C. After 90 minutes at 0° C. the reaction mixture is concentrated to dryness. The residue is treated with 1.5 ml dichloromethane and 1.5 ml of a saturated aqueous solution of sodium bicarbonate. The aqueous phase is separated and extracted with dichloromethane. The combined organic phases are dried over Na$_2$SO$_4$, filtered and evaporated under reduced pressure. The resulting residue is purified by flash chromatography [silica gel Flash NH$_2$, eluent: dichloromethane/methanol, 9/1 (v/v)] to yield the title product.

$^1$H NMR (300 MHz, CDCl$_3$): δ=1.01 (s, 1H), 1.80 (d, J=6.3 Hz, 3H), 1.87 (d, J=9.3 Hz, 1H), 2.48 (d, J=9.6 Hz, 1H), 2.85 (dd, J=2.2 and 10.2 Hz, 1H), 2.94 (dd, J=2.3 and 9.7 Hz, 1H), 3.26 (d, J=10.2 Hz, 1H), 3.42 (s, 1H), 3.49 (s, 1H), 3.57 (s, 1H), 3.96 (d, J=3.6 Hz, 2H), 5.87 (m, 2H), 6.67 (s, 1H), 7.21 (br s, 1H), 7.45 (m, 1H), 7.61-7.74 (m, 4H), 7.92 (s, 1H), 9.05 (d, J=0.9 Hz, 1H).

MS (MH+ found)=543.1

96. Formate salt of 5-{6-[(3-hydroxyazetidin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 60, compound 96 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate, 109.6 mg of azetidin-3-ol hydrochloride and 0.16 ml triethylamine.

$^1$H NMR (300 MHz, CDCl$_3$): δ=1.81 (d, J=6.2 Hz, 3H), 3.71 (dd, J=4.1 and 10.8 Hz, 2H), 4.04 (m, 2H), 4.12 (s, 2H), 4.51 (m, 1H), 5.85 (m, 2H), 6.72 (s, 1H), 7.15 (br s, 1H), 7.50 (m, 1H), 7.57 (d, J=0.9 Hz, 1H), 7.65-7.74 (m, 3H), 7.95 (s, 1H), 8.36 (s, 1H), 9.08 (d, J=1.0 Hz, 1H).

MS (MH+ found)=518.0

97. 3-{1-[4-fluoro-2-(trifluoromethyl)phenyl]ethoxy}-5-{6-[(4-methylpiperazin-1-yl)methyl]-1H-imidazo[4,5-c]pyridin-1-yl}thiophene-2-carboxamide Step 1: In a similar manner as described for example 49 (step 1), 120 mg of 3-{1-[4-fluoro-2-(trifluoromethyl)phenyl]ethoxy}-5-[6-(hydroxymethyl)-1H-imidazo[4,5-c]pyridin-1-yl]thiophene-2-carboxamide, 57 mg of methanesulfonyl chloride, and 51 mg of triethylamine in 3 ml dichloromethane give [1-(5-carbamoyl-4-{1-[4-fluoro-2-(trifluoromethyl)phenyl]ethoxy}-2-thienyl)-1H-imidazo[4,5-c]pyridin-6-yl]methyl methanesulfonate as crude material that is used for step 2 without further purification.

Step 2: 166 mg of crude [1-(5-carbamoyl-4-{1-[4-fluoro-2-(trifluoromethyl)phenyl]ethoxy}-2-thienyl)-1H-imidazo[4,5-c]pyridin-6-yl]methyl methanesulfonate (from step 1) are dissolved in 3 ml dichloromethane. Under N$_2$ atmosphere 1-methylpiperazine (125 mg) is added. The reaction mixture is stirred at 40° C. for 3 hours and then concentrated to dryness under vacuum. The residue is purified by preparative HPLC (ammonium formate buffer/acetonitrile, elution gradient 97/3 to 0/100 (v/v)) to obtain the title product.

¹H NMR (300 MHz, CDCl₃): δ=1.79 (d, J=6.2 Hz, 3H), 2.43 (s, 3H), 2.62-2.81 (br m, 8H), 3.78 (s, 2H), 5.83 (q, J=6.2 Hz, 1H), 6.06 (br s, 1H), 6.67 (s, 1H), 7.14 (br s, 1H), 7.36 (td, J=2.6 and 8.1 Hz, 1H), 7.44 (dd, J=2.6 and 8.7 Hz, 1H), 7.50 (d, J=0.9 Hz, 1H), 7.69-7.73 (m, 1H), 7.97 (s, 1H), 9.1 (d, J=0.9 Hz, 1H).

MS (MH+ found)=563.0

98. 3-[(1R)-1-(2-bromophenyl)ethoxy]-5-{6-[(4-methylpiperazin-1-yl)methyl]-1H-imidazo[4,5-c]pyridin-1-yl}thiophene-2-carboxamide Step 1: In a similar manner as described for example 49 (step 1), 357 mg of 3-[(1R)-1-(2-bromophenyl)ethoxy]-5-[6-(hydroxymethyl)-1H-imidazo[4,5-c]pyridin-1-yl]thiophene-2-carboxamide, 173 mg of methanesulfonyl chloride, and 153 mg of triethylamine in 7.5 ml dichloromethane give (1-{4-[(1R)-1-(2-bromophenyl)ethoxy]-5-carbamoyl-2-thienyl}-1H-imidazo[4,5-c]pyridin-6-yl)methyl methanesulfonate as crude material that is used for step 2 without further purification.

Step 2: 159 mg of crude (1-{4-[(1R)-1-(2-bromophenyl)ethoxy]-5-carbamoyl-2-thienyl}-1H-imidazo[4,5-c]pyridin-6-yl)methyl methanesulfonate (from step 1) are dissolved in 3 ml dichloromethane. Under N₂ atmosphere 1-methylpiperazine (125 mg) is added. The reaction mixture is stirred at 40° C. for 3 hours and then concentrated to dryness under vacuum. The residue is purified by preparative HPLC (ammonium formate buffer/acetonitrile, elution gradient 97/3 to 0/100 (v/v)) to obtain the title product.

¹H NMR (300 MHz, CDCl₃): δ=1.77 (d, J=6.3 Hz, 3H), 2.34 (s, 3H), 2.58 (br s, 8H), 3.76 (d, J=1.3 Hz, 2H), 5.83 (q, J=6.3 Hz, 1H), 5.91 (br s, 1H), 6.65 (s, 1H), 7.21 (m, 2H), 7.37 (td, J=1.1 and 7.4 Hz, 1H), 7.46 (m, 2H), 7.61 (dd, J=1.1 and 8.0 Hz, 1H), 7.99 (s, 1H), 9.10 (d, J=0.9 Hz, 1H).

MS (MH+ found)=555.0

99. 3-{1-[2-(difluoromethoxy)phenyl]ethoxy}-5-{6-[(4-methylpiperazin-1-yl)methyl]-1H-imidazo[4,5-c]pyridin-1-yl}thiophene-2-carboxamide Step 1: In a similar manner as described for example 49 (step 1), 115 mg of 3-{(1-[2-(difluoromethoxy)phenyl]ethoxy}-5-[6-(hydroxymethyl)-1H-imidazo[4,5-c]pyridin-1-yl]thiophene-2-carboxamide, 57 mg of methanesulfonyl chloride, and 51 mg of triethylamine in 3 ml dichloromethane give [1-(5-carbamoyl-4-{1-[2-(difluoromethoxy)phenyl]ethoxy}-2-thienyl)-1H-imidazo[4,5-c]pyridin-6-yl]methyl methanesulfonate as crude material that is used for step 2 without further purification.

Step 2: 128 mg of crude [1-(5-carbamoyl-4-{1-[2-(difluoromethoxy)phenyl]ethoxy}-2-thienyl)-1H-imidazo[4,5-c]pyridin-6-yl]methyl methanesulfonate (from step 1) are dissolved in 3 ml dichloromethane. Under N₂ atmosphere 1-methylpiperazine (125 mg) is added. The reaction mixture is stirred at 40° C. for 3 hours and then concentrated to dryness under vacuum. The residue is purified by preparative HPLC (ammonium formate buffer/acetonitrile, elution gradient 97/3 to 0/100 (v/v)) to obtain the title product.

¹H NMR (300 MHz, CDCl₃): δ=1.77 (d, J=6.4 Hz, 3H), 2.39 (s, 3H), 2.57-2.64 (br m, 8H), 3.77 (s, 2H), 5.81 (q, J=6.4 Hz, 1H), 5.90 (br s, 1H), 6.45, 6.94, 6.69, (2s, d, 1H), 6.75 (s, 1H), 7.20-7.51 (m, 6H), 7.99 (s, 1H), 9.10 (d, J=0.9 Hz, 1H).

MS (MH+ found)=543.1

100. 3-[(1R)-1-(2-chlorophenyl)ethoxy]-5-{6-[(4-methylpiperazin-1-yl)methyl]-1H-imidazo[4,5-c]pyridin-1-yl}thiophene-2-carboxamide Step 1: In a similar manner as described for example 49 (step 1), 428 mg of 3-[(1R)-1-(2-chlorophenyl)ethoxy]-5-[6-(hydroxymethyl)-1H-imidazo[4,5-c]pyridin-1-yl]thiophene-2-carboxamide, 229 mg of methanesulfonyl chloride, and 202 mg of triethylamine in 10 ml dichloromethane give (1-{5-carbamoyl-4-[(1R)-1-(2-chlorophenyl)ethoxy]-2-thienyl}-1H-imidazo[4,5-c]pyridin-6-yl)methyl methanesulfonate as crude material that is used for step 2 without further purification.

Step 2: 154 mg of crude (1-{5-carbamoyl-4-[(1R)-1-(2-chlorophenyl)ethoxy]-2-thienyl}-1H-imidazo[4,5-c]pyridin-6-yl)methyl methanesulfonate (from step 2) are dissolved in 3 ml dichloromethane. Under N₂ atmosphere 1-methylpiperazine (125 mg) is added. The reaction mixture is stirred at 40° C. for 3 hours and then concentrated to dryness under vacuum. The residue is purified by preparative HPLC (ammonium formate buffer/acetonitrile, elution gradient 97/3 to 0/100 (v/v)) to obtain the title product.

¹H NMR (300 MHz, CDCl₃): δ=1.78 (d, J=6.4 Hz, 3H), 2.40 (s, 3H), 2.65 (br s, 8H), 3.77 (s, 2H), 5.90 (q, J=6.4 Hz, 1H), 6.11 (br s, 1H), 6.66 (s, 1H), 7.18 (br s, 1H), 7.25-7.50 (m, 5H), 7.99 (s, 1H), 9.10 (d, J=1.0 Hz, 1H).

MS (MH+ found)=511.1

101. 3-[(1R)-1-(2-fluorophenyl)ethoxy]-5-{6-[(4-methylpiperazin-1-yl)methyl]-1H-imidazo[4,5-c]pyridin-1-yl}thiophene-2-carboxamide Step 1: In a similar manner as described for example 49 (step 1), 737 mg of 3-[(1R)-1-(2-fluorophenyl)ethoxy]-5-[6-(hydroxymethyl)-1H-imidazo[4,5-c]pyridin-1-yl]thiophene-2-carboxamide, 409 mg of methanesulfonyl chloride, and 362 mg of triethylamine in 18 ml dichloromethane give (1-{5-carbamoyl-4-[(1R)-1-(2-fluorophenyl)ethoxy]-2-thienyl}-1H-imidazo[4,5-c]pyridin-6-yl)methyl methanesulfonate as crude material that is used for step 2 without further purification.

Step 2: 145 mg of crude (1-{5-carbamoyl-4-[(1R)-1-(2-fluorophenyl)ethoxy]-2-thienyl}-1H-imidazo[4,5-c]pyridin-6-yl)methyl methanesulfonate (from step 1) are dissolved in 3 ml dichloromethane. Under N₂ atmosphere 1-methylpiperazine (125 mg) is added. The reaction mixture is stirred at 40° C. for 3 hours and then concentrated to dryness under vacuum. The residue is purified by preparative HPLC (ammonium formate buffer/acetonitrile, elution gradient 97/3 to 0/100 (v/v)) to obtain the title product.

¹H NMR (300 MHz, CDCl₃): δ=1.81 (d, J=6.4 Hz, 3H), 2.35 (s, 3H), 2.60 (br s, 8H), 3.78 (s, 2H), 5.77 (q, J=6.4 Hz, 1H), 5.87 (br s, 1H), 6.80 (s, 1H), 7.11-7.46 (m, 5H), 7.51 (d, J=0.9 Hz, 1H), 8.00 (s, 1H), 9.10 (d, J=1.0 Hz, 1H).

MS (MH+ found)=495.0

102. 3-{[1-(2-chlorophenyl)propyl]oxy}-5-{6-[(4-methylpiperazin-1-yl)methyl]-1H-imidazo[4,5-c]pyridin-1-yl}thiophene-2-carboxamide Step 1: In a similar manner as described for example 49 (step 1), 1 g of 3-{[1-(2-chlorophenyl)propyl]oxy}-5-[6-(hydroxymethyl)-1H-imidazo[4,5-c]pyridin-1-yl]thiophene-2-carboxamide, 517 mg of methanesulfonyl chloride, and 457 mg of triethylamine in 19 ml dichloromethane give [1-(5- carbamoyl-4-{[(2-chlorophenyl)propyl]oxy}-2-thienyl)-1H-imidazo[4,5-c]pyridin-6-yl]methyl methanesulfonate as crude material that is used for step 2 without further purification.

Step 2: 147 mg of crude ([1-(5-carbamoyl-4-{[(2-chlorophenyl)propyl]oxy}-2-thienyl)-1H-imidazo[4,5-c]pyridin-6-yl]methyl methanesulfonate (from step 1) are dissolved in 3 ml dichloromethane. Under $N_2$ atmosphere 1-methylpiperazine (125 mg) is added. The reaction mixture is stirred at 40° C. for 3 hours and then concentrated to dryness under vacuum. The residue is purified by preparative HPLC (ammonium formate buffer/acetonitrile, elution gradient 97/3 to 0/100 (v/v)) to obtain the title product.

$^1$H NMR (300 MHz, CDCl$_3$): δ=1.13 (t, J=7.4 Hz, 3H), 2.09 (m, 2H), 2.54 (s, 3H), 2.73 (br s, 4H), 2.91 (br s, 4H), 3.80 (s, 2H), 5.69 (t, J=5.5 Hz, 1H), 5.97 (br s, 1H), 6.66 (s, 1H), 7.23 (br s, 1H), 7.32-7.48 (m, 5H), 8.01 (s, 1H), 9.12 (d, J=0.9 Hz, 1H).

MS (MH+ found)=525.0

103. 3-[1-(2-fluorophenyl)ethoxy]-5-{6-[(4-methylpiperazin-1-yl)methyl]-1H-imidazo[4,5-c]pyridin-1-yl}thiophene-2-carboxamide Step 1: In a similar manner as described for example 49 (step 1), 1.06 g of 3-[(1-(2-fluorophenyl)ethoxy]-5-[6-(hydroxymethyl)-1H-imidazo[4,5-c]pyridin-1-yl]thiophene-2-carboxamide, 586 mg of methanesulfonyl chloride, and 518 mg of triethylamine in 19 ml dichloromethane give (1-{5-carbamoyl-4-[1-(2-fluorophenyl)ethoxy]-2-thienyl}-1H-imidazo[4,5-c]pyridin-6-yl)methyl methanesulfonate as crude material that is used for step 2 without further purification.

Step 2: 168 mg of crude (1-{5-carbamoyl-4-[1-(2-fluorophenyl)ethoxy]-2-thienyl}-1H-imidazo[4,5-c]pyridin-6-yl)methyl methanesulfonate (from step 1) are dissolved in 4 ml dichloromethane. Under $N_2$ atmosphere 1-methylpiperazine (125 mg) is added. The reaction mixture is stirred at 40° C. for 3 hours and then concentrated to dryness under vacuum. The residue is purified by preparative HPLC (ammonium formate buffer/acetonitrile, elution gradient 97/3 to 0/100 (v/v)) to obtain the title product.

$^1$H NMR (300 MHz, CDCl$_3$): δ=1.81 (d, J=6.4 Hz, 3H), 2.58 (s, 3H), 2.79 (br m, 4H), 2.97 (br m, 4H), 3.83 (s, 2H), 5.77 (q, J=6.4 Hz, 1H), 5.98 (br s, 1H), 6.81 (s, 1H), 7.12-7.25 (m, 3H), 7.34-7.48 (m, 3H), 8.03 (s, 1H), 9.12 (d, J=0.9 Hz, 1H).

MS (MH+ found)=495.1

104. 5-(6-{[(2-hydroxyethyl)amino]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 104 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 61.1 mg of 2-aminoethanol.

$^1$H NMR (300 MHz, CDCl$_3$): δ=1.80 (d, J=6.3 Hz, 3H), 2.93 (m, 2H), 3.77 (t, J=5.2 Hz, 2H), 4.13 (s, 2H), 5.85 (q, J=6.2 Hz, 1H), 6.06 (br s, 1H), 6.67 (s, 1H), 7.18 (br s, 1H), 7.39 (s, 1H), 7.49 (t, J=7.5 Hz, 1H), 7.62-7.76 (m, 3H), 7.97 (s, 1H), 9.07 (d, J=0.9 Hz, 1H).

MS (MH+ found)=506.0

105. 5-{6-[(cyclobutylamino)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 105 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 71.1 mg of cyclobutanamine.

$^1$H NMR (300 MHz, CDCl$_3$): δ=1.60-1.78 (m, 4H), 1.80 (d, J=6.3 Hz, 3H), 2.14-2.30 (m, 3H), 3.67 (q, J=7.8 Hz, 1H), 3.94 (s, 2H), 5.85 (q, J=6.2 Hz, 1H), 5.98 (br s, 1H), 6.66 (s, 1H), 7.19 (br s, 1H), 7.39 (s, 1H), 7.46-7.50 (m, 1H), 7.62-7.75 (m, 3H), 7.93 (s, 1H), 9.06 (d, J=0.9 Hz, 1H).

MS (MH+ found)=516.0

106. 5-{6-[(4-cyclohexylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 106 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 168.3 mg of 1-cyclohexylpiperazine.

$^1$H NMR (300 MHz, CDCl$_3$): δ=1.24 (m, 6H), 1.62-1.97 (m, 10H), 2.94 (br m, 6H), 3.75 (s, 2H), 5.88 (m, 2H), 6.67 (s, 1H), 7.20 (br s, 1H), 7.40 (d, J=0.8 Hz, 1H), 7.50 (t, J=7.5 Hz, 1H), 7.63-7.77 (m, 3H), 7.95 (s, 1H), 9.10 (d, J=0.9 Hz, 1H).

MS (MH+ found)=613.1

107. 5-{6-[(4-ethylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 107 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 114.2 mg of 1-ethylpiperazine.

$^1$H NMR (300 MHz, CDCl$_3$): δ=1.12 (t, J=7.2 Hz, 3H), 1.81 (d, J=6.3 Hz, 3H), 2.52 (q, J=7.2 Hz, 2H), 2.62 (br s, 8H), 3.76 (d, J=1.0 Hz, 2H), 5.86 (q, J=6.1 Hz, 1H), 5.95 (br s, 1H), 6.67 (s, 1H), 7.20 (br s, 1H), 7.46 (s, J=0.8 Hz, 1H), 7.49 (m, 1H), 7.62-7.75 (m, 3H), 7.94 (s, 1H), 9.09 (d, J=1.0 Hz, 1H).

MS (MH+ found)=559.1

108. 5-(6-{[4-(3-hydroxypropyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 108 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 144.2 mg of 3-piperazin-1-ylpropan-1-ol.

$^1$H NMR (300 MHz, CDCl$_3$): δ=1.73 (m, 2H), 1.80 (d, J=6.3 Hz, 3H), 2.52-2.72 (br m, 10H), 3.75 (s, 2H), 3.79 (t, J=5.3 Hz, 2H), 5.89 (m, 2H), 6.67 (s, 1H), 7.24 (br s, 1H), 7.45 (d, J=0.87 Hz, 1H), 7.49 (m, 1H), 7.62-7.76 (m, 3H), 7.94 (s, 1H), 9.09 (d, J=0.9 Hz, 1H).

MS (MH+ found)=589.1

109. 3-[(2,5-diethoxybenzyl)oxy]-5-[6-(hydroxymethyl)-1H-imidazo[4,5-c]pyridin-1-yl]thiophene-2-carboxamide A mixture of 450 mg of 5-[6-({[tert-butyl(dimethyl)silyl]oxy}methyl)-1H-imidazo[4,5-c]pyridin-1-yl]-3-[(2,5-diethoxybenzyl)oxy]thiophene-2-carboxamide in 20 ml THF is cooled to 0° C. At 0° C. 0.28 ml tetra-n-butylammonium fluoride (~75% in $H_2O$) is added. The reaction mixture is allowed to warm to room temperature and stirred over night.

The solvent is evaporated under reduced pressure and the residue is treated with ml dichloromethane and 10 ml saturated aqueous $NaHCO_3$ solution. The mixture is left for one hour at 4° C. and the resulting precipitate is collected by filtration. The filter cake is washed with $H_2O$ and diethyl ether and dried under vacuum to yield the title compound as a white solid.

$^1$H NMR (300 MHz, $D_6$-DMSO): δ=1.27 (m, 6H), 3.94 (q, J=7.0 Hz, 2H), 4.04 (q, J=7.0 Hz, 2H), 4.72 (s, 2H), 5.32 (s, 2H), 5.75 (br s, 1H), 6.89 (dd, J=3.0 Hz and 8.9 Hz, 1H), 6.98 (d, J=8.9 Hz, 1H), 7.04 (br s, 1H), 7.10 (d, J=3.0 Hz, 1H), 7.76 (s, 2H), 7.82 (s, 1H), 8.76 (s, 1H), 8.98 (d, J=0.9 Hz, 1H).

MS (MH+ found)=469.0

110. 5-[6-(hydroxymethyl)-1H-imidazo[4,5-c]pyridin-1-yl]-3-[1-(2-methylphenyl)ethoxy]thiophene-2-carboxamide A mixture of 650 mg of 5-[6-({[tert-butyl(dimethyl)silyl]oxy}methyl)-1H-imidazo[4,5-c]pyridin-1-yl]-3-[1-(2-methylphenyl)ethoxy]thiophene-2-carboxamide in 50 ml THF is cooled to 0° C. At 0° C. 0.45 ml tetra-n-butylammonium fluoride (~75% in $H_2O$) is added. The reaction mixture is allowed to warm to room temperature and stirred over night.

The solvent is evaporated under reduced pressure and the residue is treated with 40 ml dichloromethane and 40 ml saturated aqueous $NaHCO_3$ solution. The mixture is left for one hour at 4° C. and the resulting precipitate is collected by filtration. The filter cake is washed with $H_2O$ and diethyl ether and dried under vacuum to yield the title compound as a white solid.

$^1$H NMR (300 MHz, $D_6$-DMSO): δ=1.68 (d, J=6.3 Hz, 3H), 2.41 (s, 3H), 4.69 (s, 2H), 5.49 (br s, 1H), 5.83 (q, J=6.3 Hz, 1H), 7.10 (br s, 1H), 7.20-7.27 (m, 3H), 7.35 (s, 1H), 7.47 (d, J=6.7 Hz, 1H), 7.66 (d, J=0.8 Hz, 1H), 7.82 (br s, 1H), 8.68 (s, 1H), 8.95 (d, J=0.8 Hz, 1H).

MS (MH+ found)=408.9

111. 5-{6-[(cyclobutylamino)methyl]-3H-imidazo[4,5-c]pyridin-3-yl}-3-{-1-[2-(trifluoromethyl)phenyl]ethoxy}thiophene-2-carboxamide Step 1: In a similar manner as described for example 49 (step 1), 5.47 g of 5-[6-(hydroxymethyl)-3H-imidazo[4,5-c]pyridin-3-yl]-3-{1-[2-(trifluoromethyl)phenyl]ethoxy}thiophene-2-carboxamide, 2.57 g of methanesulfonyl chloride, and 2.39 g of triethylamine in 130 ml dichloromethane give [3-(5-carbamoyl-4-{1-[2-(trifluoromethyl)phenyl]ethoxy}-2-thienyl)-3H-imidazo[4,5-c]pyridin-6-yl]methyl methanesulfonate as crude material that is used for step 2 without further purification.

Step 2: 108 mg of [3-(5-carbamoyl-4-{1-[2-(trifluoromethyl)phenyl]ethoxy}-2-thienyl)-3H-imidazo[4,5-c]pyridin-6-yl]methyl methanesulfonate (from step 1) are dissolved in 2.5 ml dichloromethane. Under $N_2$ atmosphere cyclobutylamine (71 mg) is added. The reaction mixture is stirred over night at 50° C. and then concentrated to dryness under vacuum. The residue is purified by preparative HPLC (ammonium formate buffer/acetonitrile, elution gradient 97/3 to 0/100 (v/v)) to obtain the title product.

$^1$H NMR (300 MHz, $CDCl_3$): δ=1.57 (m, 4H), 1.80 (d, J=6.2 Hz, 3H), 2.15 (m, 2H), 3.29 (m, 1H), 3.95 (s, 2H), 5.83 (q, J=6.3 Hz, 1H), 5.94 (br s, 1H), 6.71 (s, 1H), 7.19 (br s, 1H), 7.46 (m, 1H), 7.62 (m, 4H), 8.00 (s, 1H), 8.76 (d, J=1.0 Hz, 1H).

MS (MH+ found)=516.1

112. 5-{6-[(ethylamino)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 112 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 45.1 mg of ethanamine.

$^1$H NMR (300 MHz, $CDCl_3$): δ=1.16 (t, J=7.1 Hz, 3H), 1.80 (d, J=6.2 Hz, 3H), 2.70 (q, J=7.1 Hz, 2H), 3.99 (s, 2H), 5.85 (m, 2H), 6.66 (s, 1H), 7.20 (br s, 1H), 7.39 (s, 1H), 7.48 (t, J=7.1 Hz, 1H), 7.62-7.75 (m, 3H), 7.94 (s, 1H), 9.06 (d, J=1.0 Hz, 1H).

MS (MH+ found)=490.0

113. 5-{6-[(propylamino)methyl]-1H-imidazo[4,5-c]pyridin-1-yl}-3-{1R)-1-[2-(trifluoromethyl)phenyl]ethoxy}thiophene-2-carboxamide)

In a similar manner as described for example 58, compound 113 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 59.1 mg of propan-1-amine.

$^1$H NMR (300 MHz, $CDCl_3$): δ=0.93 (t, J=7.4 Hz, 3H), 1.52 (m, 2H), 1.80 (d, J=6.3 Hz, 3H), 2.61 (t, J=7.2 Hz, 2H), 3.98 (s, 2H), 5.80 (br s, 1H), 5.85 (q, J=6.1 Hz, 1H), 6.66 (s, 1H), 7.19 (br s, 1H), 7.39 (s, 1H), 7.48 (m, 1H), 7.62-7.75 (m, 3H), 7.94 (s, 1H), 9.06 (d, J=0.9 Hz, 1H).

MS (MH+ found)=504.0

114. 5-{6-[(tert-butylamino)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 114 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 73.1 mg of 2-methylpropan-2-amine.

$^1$H NMR (300 MHz, $CDCl_3$): δ=1.22 (s, 9H), 1.80 (d, J=6.2 Hz, 3H), 3.97 (d, J=0.9 Hz, 2H), 5.85 (q, J=6.3 Hz, 1H), 5.95 (br s, 1H), 6.67 (s, 1H), 7.19 (br s, 1H), 7.45 (m, 2H), 7.62-7.74 (m, 3H), 7.93 (s, 1H), 9.05 (d, J=0.9 Hz, 1H).

MS (MH+ found)=518.0

115. 5-{6-[(cyclopropylamino)methyl]-3H-imidazo[4,5-c]pyridin-3-yl}-3-{(1R)-1-[2-(trifluoromethyl)phenyl]ethoxy}thiophene-2-carboxamide In a similar manner as described for example 58, 289 mg of crude [3-(5-carbamoyl-4-{(1R)-1-[2-(trifluoromethyl)phenyl]ethoxy}-2-thienyl)-3H-imidazo[4,5-c]pyridin-6-yl]methyl methanesulfonate (example 49, step 1) and 0.35 ml cyclopropylamine in 7 ml dichloromethane yield the title compound.

$^1$H NMR (300 MHz, D$_6$-DMSO): δ=0.27-0.37 (m, 4H), 1.75 (d, J=6.2 Hz, 3H), 2.10 (m, 1H), 3.96 (s, 2H), 6.00 (q, J=6.2 Hz, 1H), 7.13 (br s, 1H), 7.26 (s, 1H), 7.57 (m, 1H), 7.75 (m, 3H), 7.81 (br s, 1H), 7.95 (d, J=7.7 Hz, 1H), 8.71 (s, 1H), 8.83 (d, J=1.0 Hz, 1H).

MS (MH+ found)=501.9

116. 5-{6-[(methylamino)methyl]3H-imidazo[4,5-c]pyridin-3-yl}-3-{(1R)-1-[2-(trifluoromethyl)phenyl]ethoxy}thiophene-2-carboxamide A solution of 75 mg of crude [3-(5-carbamoyl-4-{(1R)-1-[2-(trifluoromethyl)phenyl]ethoxy}-2-thienyl)-3H-imidazo[4,5-c]pyridin-6-yl]methyl methanesulfonate (example 49, step 1) and 0.32 ml methylamine (2 M solution in methanol) in 1.5 ml methanol is stirred in a microwave vial at 120° C. for 6 h in the microwave cavity. The reaction mixture is concentrated to dryness and the resulting residue is purified by preparative HPLC (ammonium formate buffer/acetonitrile, elution gradient 97/3 to 0/100 (v/v)) to obtain the title product.

$^1$H NMR (300 MHz, D$_6$-DMSO): δ=1.75 (d, J=6.2 Hz, 3H), 3.39 (s, 3H), 4.61 (s, 2H), 6.00 (q, J=6.2 Hz, 1H), 7.14 (br s, 1H), 7.26 (s, 1H), 7.57 (t, J=7.7 Hz, 1H), 7.74-7.81 (m, 3H), 7.85 (br s, 1H), 7.95 (d, J=7.9 Hz, 1H), 8.75 (s, 1H), 8.84 (s, 1H).

MS (MH+ found)=476.9

117. 5-{6-[(ethylamino)methyl]-3H-imidazo[4,5-c]pyridin-3-yl}-3-{(1R)-1-[2-(trifluoromethyl)phenyl]ethoxy}thiophene-2-carboxamide In a similar manner as described for example 116, 200 mg of crude [3-(5-carbamoyl-4-{(1R)-1-[2-(trifluoromethyl)phenyl]ethoxy}-2-thienyl)-3H-imidazo[4,5-c]pyridin-6-yl]methyl methanesulfonate (example 49, step 1) and 0.925 ml ethylamine (2 M solution in THF) in 4 ml methanol give the title compound.

$^1$H NMR (300 MHz, D$_6$-DMSO): δ=1.08 (t, J=7.1 Hz, 3H), 1.75 (d, J=6.2 Hz, 3H), 2.64 (q, J=7.1 Hz, 2H), 3.99 (s, 2H), 6.00 (q, J=6.3 Hz, 1H), 7.14 (br s, 1H), 7.26 (s, 1H), 7.57 (t, J=7.5 Hz, 1H), 7.75-7.81 (m, 3H), 7.84 (br s, 1H), 7.95 (d, J=7.8 Hz, 1H), 8.73 (s, 1H), 8.85 (d, J=1.1 Hz, 1H).

MS (MH+ found)=490.0

118. 5-{6-[(4-acetylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 128.2 mg of 1-acetylpiperazine in 2.5 ml dichloromethane give the title compound.

$^1$H NMR (300 MHz, D$_6$-DMSO): δ=1.75 (d, J=6.3 Hz, 3H), 1.97 (s, 3H), 2.37-2.47 (m, 4H), 3.41 (m, 4H), 3.73 (s, 2H), 5.93 (q, J=6.1 Hz, 1H), 7.14 (br s, 1H), 7.21 (s, 1H), 7.55-7.60 (m, 2H), 7.76-7.81 (m, 2H), 7.86 (br s, 1H), 7.95 (d, J=7.7 Hz, 1H), 8.65 (s, 1H), 8.97 (d, J=1.0 Hz, 1H).

MS (MH+ found)=573.0

119. 5-(6-{[4-(1-phenylethyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 190.3 mg of 1-(1-phenylethyl)piperazine in 2.5 ml dichloromethane give the title compound.

$^1$H NMR (300 MHz, D$_6$-DMSO+CD$_3$OD)): δ=1.27 (d, J=6.6 Hz, 3H), 1.75 (d, J=6.3 Hz, 3H), 2.33-2.45 (br m, 8H), 3.35 (m, 1H), 3.68 (s, 2H), 5.91 (q, J=6.2 Hz, 1H), 7.15 (s, 1H), 7.21 (m, 1H), 7.29 (m, 4H), 7.50 (m, 2H), 7.73 (m, 2H), 7.93 (d, J=7.8 Hz, 1H), 8.60 (s, 1H), 8.94 (d, J=0.9 Hz, 1H).

MS (MH+ found)=635.1

120. 5-{6-[(4-isobutylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 142.2 mg of 1-isobutylpiperazine in 2.5 ml dichloromethane give the title compound.

$^1$H NMR (300 MHz, D$_6$-DMSO): δ=0.82 (d, J=6.6 Hz, 6H), 1.68-1.77 (m, 4H), 2.00 (d, J=7.4 Hz, 2H), 2.27-2.45 (br m, 8H), 3.69 (s, 2H), 5.92 (q, J=6.1 Hz, 1H), 7.13 (br s, 1H), 7.20 (s, 1H), 7.54 (m, 2H), 7.75 (m, 2H), 7.84 (br s, 1H), 7.98 (d, J=7.6 Hz, 1H), 8.64 (s, 1H), 8.96 (s, 1H).

MS (MH+ found)=587.1

121. 5-{6-[(4-isopropylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 128.2 mg of 1-isopropylpiperazin in 2.5 ml dichloromethane give the title compound.

$^1$H NMR (300 MHz, D$_6$-DMSO): δ=0.94 (d, J=6.6 Hz, 6H), 1.75 (d, J=6.3 Hz, 3H), 2.44 (br s, 8H), 3.68 (s, 2H), 5.92 (q, J=6.2 Hz, 1H), 7.12 (br s, 1H), 7.20 (s, 1H), 7.54 (d, J=0.7 Hz, 1H), 7.57 (m, 2H), 7.76 (m, 2H), 7.83 (br s, 1H), 7.95 (d, J=7.9 Hz, 1H), 8.64 (s, 1H), 8.96 (d, J=0.9 Hz, 1H).

MS (MH+ found)=573.0

122. 5-{6-[(4-allylpiperazin-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 126.2 mg of 1-allylpiperazin in 2.5 ml dichloromethane give the title compound.

$^1$H NMR (300 MHz, D$_6$-DMSO): δ=1.75 (d, J=6.2 Hz, 3H), 2.38-2.45 (br m, 8H), 2.93 (d, J=6.3 Hz, 2H), 3.69 (s, 2H), 5.08-5.19 (m, 2H), 5.73-5.86 (m, 1H), 5.92 (q, J=6.4 Hz, 1H), 7.13 (br s, 1H), 7.20 (s, 1H), 7.53 (d, J=0.7 Hz, 1H), 7.57 (d, J=7.6 Hz, 1H), 7.79 (m, 2H), 7.85 (br s, 1H), 7.96 (d, J=7.8 Hz, 1H), 8.64 (s, 1H), 8.96 (d, J=0.8 Hz, 1H).

MS (MH+ found)=571.1

123. 3-[1-(2-chloro-4-cyanophenyl)ethoxy]-5-[6-(hydroxymethyl)-1H-imidazo[4,5-c]pyridin-1-yl]thiophene-2-carboxamide A mixture of 350 mg of 5-[6-({[tert-butyl(dimethyl)silyl]oxy}methyl)-1H-imidazo[4,5-c]pyridin-1-yl]-3-[1-(2-chloro-4-cyanophenyl)ethoxy]thiophene-2-carboxamide in 20 ml THF is cooled to 0° C. At 0° C. 0.23 ml tetra-n- butylammonium fluoride (~75% in H₂0) is added. The reaction mixture is allowed to warm to room temperature and stirred over night.

The solvent is evaporated under reduced pressure and the residue is treated with 10 ml dichloromethane and 10 ml saturated aqueous NaHCO₃ solution. The mixture is left for one hour at 4° C. and the resulting precipitate is collected by filtration. The filter cake is washed with H₂O, dichloromethane and diethyl ether and then dried under vacuum to yield the title compound as a white solid.

¹H NMR (300 MHz, D₆-DMSO): δ=1.73 (d, J=6.3 Hz, 3H), 4.70 (s, 2H), 5.54 (br s, 1H), 5.94 (q, J=6.4 Hz, 1H), 7.17 (br s, 1H), 7.28 (s, 1H), 7.68 (s, 1H), 7.85 (br s, 1H), 7.87-7.95 (m, 2H), 8.10 (d, J=0.8 Hz, 1H), 8.67 (s, 1H), 8.95 (d, J=0.8 Hz, 1H).

MS (MH+ found)=453.9

124. 5-(6-{[4-(2-morpholin-4-yl-2-oxoethyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 213.3 mg of 4-(piperazin-1-ylacetyl)morpholine in 2.5 ml dichloromethane give the title compound.

¹H NMR (300 MHz, CDCl₃): δ=1.72 (d, J=6.2 Hz, 3H), 2.59 (br s, 8H), 3.22 (s, 2H), 3.62-3.67 (br m, 8H), 3.78 (s, 2H), 5.86 (q, J=6.3 Hz, 1H), 5.97 (br s, 1H), 6.68 (s, 1H), 7.20 (br s, 1H), 7.51 (m, 1H), 7.53 (d, J=0.9 Hz, 1H), 7.61-7.74 (m, 3H), 7.95 (s, 1H), 9.08 (d, J=0.9 Hz, 1H).

MS (MH+ found)=658.1

125. 3-[-1-(2-chlorophenyl)ethoxy]-5-[6-(hydroxymethyl)-3H-imidazo[4,5-c]pyridin-3-yl]thiophene-2-carboxamide A mixture of 8.19 g of 5-[6-({[tert-butyl(dimethyl)silyl]oxy}methyl)-3H-imidazo[4,5-c]pyridin-3-yl]-3-[-1-(2-chlorophenyl)ethoxy]thiophene-2-carboxamide in 550 ml THF is cooled to 0° C. At 0° C. 4.14 ml tetra-n-butylammonium fluoride (~75% in H₂0) are added. The reaction mixture is allowed to warm to room temperature and stirred for one hour.

The solvent is evaporated under reduced pressure and the residue is treated with 100 ml dichloromethane and 125 ml saturated aqueous NaHCO₃ solution. The mixture is left at 4° C. over night and the resulting precipitate is collected by filtration. The filter cake is washed with H₂O and dichloromethane and then dried under vacuum to yield the title compound as a white solid.

¹H NMR (300 MHz, D₆-DMSO): δ=1.73 (d, J=6.4 Hz, 3H), 4.69 (s, 2H), 5.45 (br s, 1H), 6.01 (q, J=6.3 Hz, 1H), 7.13 (br s, 1H), 7.33-7.52 (m, 4H), 7.68 (dd, J=1.8 and 7.6 Hz, 1H), 7.78 (s, 1H), 7.82 (br s, 1H), 8.76 (s, 1H), 8.84 (d, J=0.9 Hz, 1H).

MS (MH+ found)=429.0

126. 5-(6-{[2-(hydroxymethyl)-4-methylpiperazin-1-yl]methyl}-1H-imidazo[4,5-c]pyridin-1-yl)-3-{(1R)-1-[2-(trifluoromethyl)phenyl]ethoxy}thiophene-2-carboxamide A mixture of 270 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 130 mg of (4-methylpiperazin-2-yl)methanol (synthesized starting from commercially available 1-(tert-butoxycarbonyl)piperazine-2-carboxylic acid in one step in analogy to the synthesis of (2S)-1-(tert-butoxycarbonyl)piperazine-2-carboxylic acid described in patent application WO2005/026152) in 10 ml dichloromethane is stirred at room temperature for 16 hours. 505 mg triethylamine is added and the reaction mixture is stirred additional 24 h at room temperature. Water (20 ml) is added to the mixture. After separation of the organic layer, the aqueous layer is extracted with dichloromethane (2×20 ml). The combined organic layers are dried over MgSO₄. After filtration the solvent is removed under reduced pressure. The resulting residue is purified by flash chromatography [silica gel, eluent: ethyl acetate/methanol/aqueous solution of ammonia, 20/4/1 (v/v/v) and subsequently by preparative HPLC (ammonium formate buffer/acetonitrile, elution gradient 65/35 to 15/85 (v/v)) to give the title product.

¹H NMR (300 MHz, CDCl₃): δ=1.81 (d, J=6.2 Hz, 3H), 2.33-2.56 (m, 7H), 2.74-2.89 (m, 3H), 3.41 (dd, J=1.8 and 11.3 Hz, 1H), 3.73-3.75 (m, 2H), 3.83 (dd, J=4.0 and 11.3 Hz, 1H), 5.86 (m, 2H), 6.67 (s, 1H), 7.19 (br s, 1H), 7.46-7.51 (m, 2H), 7.62-7.75 (m, 3H), 7.94 (s, 1H), 9.09 (d, J=0.9 Hz, 1H).

MS (MH+ found)=575.0

127. 3-[(1R)-1-(2-chlorophenyl)ethoxy]-5-(6-{[4-(2-hydroxyethyl)piperazin-1-yl]methyl}-1H-imidazo[4,5-c]pyridin-1-yl)thiophene-2-carboxamide Step 1: In a similar manner as described for example 49 (step 1), 428 mg of 3-[(1R)-1-(2-chlorophenyl)ethoxy]-5-[6-(hydroxymethyl)-1H-imidazo[4,5-c]pyridin-1-yl]thiophene-2-carboxamide, 229 mg of methanesulfonyl chloride, and 202 mg of triethylamine in 10 ml dichloromethane give (1-{5-carbamoyl-4-[(1R)-1-(2-chlorophenyl)ethoxy]-2-thienyl}-1H-imidazo[4,5-c]pyridin-6-yl)methyl methanesulfonate as crude material that is used for step 2 without further purification.

Step 2: 130 mg of crude (1-{5-carbamoyl-4-[(1R)-1-(2-chlorophenyl)ethoxy]-2-thienyl}-1H-imidazo[4,5-c]pyridin-6-yl)methyl methanesulfonate (from step 1) are dissolved in 4 ml dichloromethane. Under N₂ atmosphere 2-piperazin-1-ylethanol (167 mg) is added. The reaction mixture is stirred at 40° C. for 2 hours and then concentrated to dryness under vacuum. The residue is purified by preparative HPLC (ammonium formate buffer/acetonitrile, elution gradient 45/55 to 15/85 (v/v)) to obtain the title product.

¹H NMR (300 MHz, CDCl₃): δ=1.80 (d, J=6.4 Hz, 3H), 2.55 (br s, 10H), 3.62 (t, J=5.3 Hz, 2H), 3.77 (s, 2H), 5.88 (m, 2H), 6.66 (s, 1H), 7.19 (br s, 1H), 7.29-7.50 (m, 5H), 7.98 (s, 1H), 9.09 (s, 1H).

MS (MH+ found)=541.0

128. 4-[(1-{5-carbamoyl-4-[(1R)-1-(2-chlorophenyl)ethoxy]-2-thienyl}-1H-imidazo[4,5-c]pyridin-6-yl)methyl]-N,N-dimethylpiperazine-1-carboxamide In a similar manner as described for example 127, compound 128 is synthesized starting with 130 mg of crude (1-{5-carbamoyl-4-[(1R)-1-(2-chlorophenyl)ethoxy]-2-thienyl}-1H-imidazo[4,5-c]pyridin-6-yl)methyl methanesulfonate and 202 mg of N,N-dimethylpiperazine-1-carboxamide.

¹H NMR (300 MHz, CDCl₃): δ=1.78 (d, J=6.3 Hz, 3H), 2.52 (t, J=4.7 Hz, 4H), 2.82 (s, 6H), 3.28 (t, J=4.7 Hz, 4H), 3.77 (s, 2H), 5.85 (m, 2H), 6.66 (s, 1H), 7.22 (br s, 1H), 7.30-7.51 (m, 5H), 7.98 (s, 1H), 9.09 (s, 1H).

MS (MH+ found)=568.0

129. 3-[(1R)-1-(2-chlorophenyl)ethoxy]-5-{6-[(4-methyl-1,4-diazepan-1-yl)methyl]-1H-imidazo[4,5-c]pyridin-1-yl}thiophene-2-carboxamide In a similar manner as described for example 127, compound 129 is synthesized starting with 130 mg of crude (1-{5-carbamoyl-4-[(1R)-1-(2-chlorophenyl)ethoxy]-2-thienyl}-1H-imidazo[4,5-c]pyridin-6-yl)methyl methanesulfonate and 147 mg of 1-methyl-1,4-diazepane.

$^1$H NMR (300 MHz, CDCl$_3$): δ=1.79 (d, J=6.4 Hz, 3H), 1.99-2.05 (m, 2H), 2.58 (s, 3H), 2.86 (t, J=6.0 Hz, 2H), 2.92 (br m, 4H), 2.99-3.03 (m, 2H), 3.93 (s, 2H), 5.78 (br s, 1H), 5.90 (q, J=6.4 Hz, 1H), 6.68 (m, 1H), 7.19 (br s, 1H), 7.29-7.38 (m, 2H), 7.43-7.50 (m, 2H), 7.58 (s, 1H), 7.99 (s, 1H), 9.08 (s, 1H).

MS (MH+ found)=525.1

130. 3-[(1R)-1-(2-chlorophenyl)ethoxy]-5-{6-[(4-ethylpiperazin-1-yl)methyl]-1H-imidazo[4,5-c]pyridin-1-yl}thiophene-2-carboxamide In a similar manner as described for example 127, compound 130 is synthesized starting with 130 mg of crude (1-{5-carbamoyl-4-[(1R)-1-(2-chlorophenyl)ethoxy]-2-thienyl}-1H-imidazo[4,5-c]pyridin-6-yl)methyl methanesulfonate and 147 mg of 1-ethylpiperazine.

$^1$H NMR (300 MHz, CDCl$_3$): δ=1.08 (t, J=7.2 Hz, 3H), 1.79 (d, J=6.4 Hz, 3H), 2.43 (q, J=7.2 Hz, 2H), 2.52-2.58 (br m, 8H), 3.77 (s, 2H), 5.86-5.92 (m, 2H), 6.66 (m, 1H), 7.20 (br s, 1H), 7.29-7.38 (m, 2H), 7.43-7.50 (m, 3H), 7.97 (s, 1H), 9.09 (s, 1H).

MS (MH+ found)=525.0

131. 3-[(1R)-1-(2-chlorophenyl)ethoxy]-5-{6-[(4-pyridin-4-ylpiperazin-1-yl)methyl]-1H-imidazo[4,5-c]pyridin-1-yl}thiophene-2-carboxamide In a similar manner as described for example 127, compound 131 is synthesized starting with 130 mg of crude (1-{5-carbamoyl-4-[(1R)-1-(2-chlorophenyl)ethoxy]-2-thienyl}-1H-imidazo[4,5-c]pyridin-6-yl)methyl methanesulfonate and 209 mg of 1-pyridin-4-ylpiperazine.

$^1$H NMR (300 MHz, CDCl$_3$): δ=1.78 (d, J=6.3 Hz, 3H), 2.64-2.67 (m, 4H), 3.35-3.39 (m, 4H), 3.81 (s, 2H), 5.85-5.91 (m, 2H), 6.64-6.66 (m, 3H), 7.18 (br s, 1H), 7.29-7.37 (m, 2H), 7.41-7.49 (m, 2H), 7.56 (s, 1H), 7.99 (s, 1H), 8.27 (d, J=6.4 Hz, 2H), 9.11 (s, 1H).

MS (MH+ found)=574.0

132. 3-[(1R)-1-(2-chlorophenyl)ethoxy]-5-[6-({4-[2-(dimethylamino)ethyl]piperazin-1-yl}methyl)-1H-imidazo[4,5-c]pyridin-1-yl]thiophene-2-carboxamide In a similar manner as described for example 127, compound 132 is synthesized starting with 130 mg of crude (1-{5-carbamoyl-4-[(1R)-1-(2-chlorophenyl)ethoxy]-2-thienyl}-1H-imidazo[4,5-c]pyridin-6-yl)methyl methanesulfonate and 202 mg of N,N-dimethyl-2-piperazin-1-ylethanamine.

$^1$H NMR (300 MHz, CDCl$_3$): δ=1.78-1.80 (m, 8H), 2.25 (s, 6H), 2.42-2.56 (m, 7H), 3.76 (s, 2H), 5.83-5.92 (m, 2H), 6.66 (s, 1H), 7.20 (br s, 1H), 7.30-7.38 (m, 2H), 7.42-7.49 (m, 3H), 7.97 (s, 1H), 9.09 (s, 1H).

MS (MH+ found)=568.0

133. 3-[(1R)-1-(2-bromophenyl)ethoxy]-5-(6-{[4-(2-hydroxyethyl)piperazin-1-yl]methyl}-1H-imidazo[4,5-c]pyridin-1-yl)thiophene-2-carboxamide 143 mg of (1-{4-[(1R)-1-(2-bromophenyl)ethoxy]-5-carbamoyl-2-thienyl}-1H-imidazo[4,5-c]pyridin-6-yl)methyl methanesulfonate (example 98, step 1) are dissolved in 4 ml dichloromethane. Under N$_2$ atmosphere N,N-dimethylpiperazine-1-carboxamide (204 mg) is added. The reaction mixture is stirred at 40° C. for 75 minutes and then concentrated to dryness under vacuum. The residue is purified by preparative HPLC (ammonium formate buffer/acetonitrile, elution gradient 45/55 to 15/85 (v/v)) to obtain the title product.

$^1$H NMR (300 MHz, CDCl$_3$): δ=1.78 (d, J=6.4 Hz, 3H), 2.50-2.53 (m, 4H), 2.82 (s, 6H), 3.26-3.29 (m, 4H), 3.77 (s, 2H), 5.77-5.87 (m, 2H), 6.65 (s, 1H), 7.18-7.23 (m, 2H), 7.37-7.42 (m, 1H), 7.46-7.49 (m, 1H), 7.52 (s, 1H), 7.60-7.62 (m, 1H), 7.99 (s, 1H), 9.09 (s, 1H).

MS (MH+ found)=612.0

134. 4-{[1-(5-carbamoyl-4-{1-[2-(difluoromethoxy)phenyl]ethoxy}-2-thienyl)-1H-imidazo[4,5-c]pyridin-6-yl]methyl}-N,N-dimethylpiperazine-1-carboxamide Step 1: In a similar manner as described for example 49 (step 1), 511 mg of 3-{(1-[2-(difluoromethoxy)phenyl]ethoxy)-5-[6-(hydroxymethyl)-1H-imidazo[4,5-c]pyridin-1-yl]thiophene-2-carboxamide, 252 mg of methanesulfonyl chloride, and 223 mg of triethylamine in 11 ml dichloromethane give [1-(5-carbamoyl-4-{1-[2-(difluoromethoxy)phenyl]ethoxy}-2-thienyl)-1H-imidazo[4,5-c]pyridin-6-yl]methyl methanesulfonate as crude material that is used for step 2 without further purification.

Step 2: 122 mg of crude [1-(5-carbamoyl-4-{1-[2-(difluoromethoxy)phenyl]ethoxy}-2-thienyl)-1H-imidazo[4,5-c]pyridin-6-yl]methyl methanesulfonate (from step 1) are dissolved in 4 ml dichloromethane. Under N$_2$ atmosphere N,N-dimethylpiperazine-1-carboxamide (178 mg) is added. The reaction mixture is stirred at 40° C. for 2 hours and then concentrated to dryness under vacuum. The residue is purified by preparative HPLC (ammonium formate buffer/acetonitrile, elution gradient 45/55 to 15/85 (v/v)) to obtain the title product.

$^1$H NMR (300 MHz, CDCl$_3$): δ=1.78 (d, J=6.4 Hz, 3H), 2.50-2.53 (m, 4H), 2.82 (s, 6H), 3.26-3.29 (m, 4H), 3.77 (s, 2H), 5.81-5.87 (m, 2H), 6.42, 6.68, 6.92 (s, 1H), 6.75 (s, 1H), 7.19-7.21 (m, 2H), 7.30-7.32 (m, 1H), 7.36-7.39 (m, 1H), 7.48-7.51 (m, 1H), 7.53 (s, 1H), 7.98 (s, 1H), 9.09 (s, 1H).

MS (MH+ found)=600.0

135. 3-{1-[2-(difluoromethoxy)phenyl]ethoxy}-5-{6-[(4-ethylpiperazin-1-yl)methyl]-1H-imidazo[4,5-c]pyridin-1-yl}thiophene-2-carboxamide In a similar manner as described for example 134, compound 135 is synthesized starting with 122 mg of crude [1-(5-carbamoyl-4-{1-[2-(difluoromethoxy)phenyl]ethoxy}-2-thienyl)-1H-imidazo[4,5-c]pyridin-6-yl]methyl methanesulfonate and 129 mg of 1-ethylpiperazine.

$^1$H NMR (300 MHz, CDCl$_3$): δ=1.08 (d, J=7.2 Hz, 3H), 1.78 (d, J=6.4 Hz, 3H), 2.43 (q, J=7.2 Hz, 2H), 2.52-2.58 (br m, 8H), 3.77 (s, 2H), 5.81-5.87 (m, 2H), 6.43, 6.67, 6.92 (s,

1H), 6.75 (s, 1H), 7.19-7.21 (m, 2H), 7.30-7.33 (m, 1H), 7.36-7.42 (m, 1H), 7.48-7.51 (m, 2H), 7.97 (s, 1H), 9.09 (s, 1H).

MS (MH+ found)=557.1

136. 5-[6-({4-[2-(dimethylamino)ethyl]piperazin-1-yl}methyl)-1H-imidazo[4,5-c]pyridin-1-yl]-3-[(1R)-1-(2-fluorophenyl)ethoxy]thiophene-2-carboxamide 136 mg of crude (1-{5-carbamoyl-4-[(1R)-1-(2-fluorophenyl)ethoxy]-2-thienyl}-1H-imidazo[4,5-c]pyridin-6-yl)methyl methanesulfonate (example 101, step 1) are dissolved in 5 ml dichloromethane. Under N₂ atmosphere N,N-dimethyl-2-piperazin-1-ylethanamine (218 mg) is added. The reaction mixture is stirred at 40° C. for 2 hours and 2 hours at room temperature. It is then concentrated to dryness under vacuum. The residue is purified by preparative HPLC (ammonium formate buffer/acetonitrile, elution gradient 97/3 to 0/100 (v/v)) to obtain the title product.

¹H NMR (300 MHz, CDCl₃): δ=1.82 (d, J=6.4 Hz, 3H), 2.41 (s, 6H), 2.59-2.65 (m, 12H), 3.78 (s, 2H), 5.74-5.81 (m, 2H), 6.80 (s, 1H), 7.11-7.25 (m, 3H), 7.33-7.46 (m, 2H), 7.54 (s, 1H), 8.00 (s, 1H), 9.09 (s, 1H).

MS (MH+ found)=552.1

137. 4-{[1-(5-carbamoyl-4-{[1-(2-chlorophenyl)propyl]oxy}-2-thienyl)-1H-imidazo[4,5-c]pyridin-6-yl]methyl}-N,N-dimethylpiperazine-1-carboxamide 110 mg of crude [1-(5-carbamoyl-4-{[(2-chlorophenyl)propyl]oxy}-2-thienyl)-1H-imidazo[4,5-c]pyridin-6-yl]methyl methanesulfonate (example 102, step 1) are dissolved in 5 ml dichloromethane. Under N₂ atmosphere N,N-dimethylpiperazine-1-carboxamide (167 mg) is added. The reaction mixture is stirred at 40° C. for 2 hours and 2 hours at room temperature. It is then concentrated to dryness under vacuum. The residue is purified by preparative HPLC (ammonium formate buffer/acetonitrile, elution gradient 97/3 to 0/100 (v/v)) to obtain the title product.

¹H NMR (300 MHz, CDCl₃): δ=1.13 (t, J=7.4 Hz, 3H), 2.01-2.19 (m, 2H), 2.52-2.55 (m, 4H), 2.82 (s, 6H), 3.27-3.50 (m, 4H), 3.79 (s, 2H), 5.69 (dd, J=5.7 Hz and 7.2 Hz, 1H), 6.01 (br s, 1H), 6.67 (s, 1H), 7.21 (br s, 1H), 7.30-7.38 (m, 2H), 7.42-7.46 (m, 2H), 7.52 (s, 1H), 7.99 (s, 1H), 9.10 (s, 1H).

MS (MH+ found)=582.0

138. Formic acid salt of 3-{[1-(2-chlorophenyl)propyl]oxy}-5-(6-{[4-(2-hydroxyethyl)piperazin-1-yl]methyl}-1H-imidazo[4,5-c]pyridin-1-yl)thiophene-2-carboxamide In a similar manner as described for example 137, compound 138 is synthesized starting with 110 mg of crude [1-(5-carbamoyl-4-{[(2-chlorophenyl)propyl]oxy}-2-thienyl)-1H-imidazo[4,5-c]pyridin-6-yl]methyl methanesulfonate (example 102, step 1) and 138 mg of 2-piperazin-1-ylethanol.

¹H NMR (300 MHz, CDCl₃): δ=1.13 (t, J=7.5 Hz, 3H), 2.02-2.19 (m, 2H), 2.74-2.77 (m, 4H), 2.87 (t, J=5.1 Hz, 2H), 3.00-3.04 (m, 4H), 3.81-3.84 (m, 4H), 5.69 (dd, J=5.7 Hz and 7.1 Hz, 1H), 5.95 (br s, 1H), 6.66 (s, 1H), 7.21 (br s, 1H), 7.33-7.36 (m, 2H), 7.43-7.49 (m, 3H), 8.00 (s, 1H), 8.42 (s, 1H), 9.11 (s, 1H).

MS (MH+ found)=555.0

139. 3-{[1-(2-chlorophenyl)propyl]oxy}-5-(6-{[4-(2-methoxyethyl)piperazin-1-yl]methyl}-1H-imidazo[4,5-c]pyridin-1-yl)thiophene-2-carboxamide In a similar manner as described for example 137, compound 139 is synthesized starting with 110 mg of crude [1-(5-carbamoyl-4-{[(2-chlorophenyl)propyl]oxy}-2-thienyl)-1H-imidazo[4,5-c]pyridin-6-yl]methyl methanesulfonate (example 102, step 1) and 153 mg of 1-(2-methoxyethyl)piperazine.

¹H NMR (300 MHz, CDCl₃): δ=1.13 (t, J=7.4 Hz, 3H), 2.02-2.19 (m, 2H), 2.70-2.96 (m, 10H), 3.33 (s, 3H), 3.59 (t, J=5.3 Hz, 2H), 3.81 (s, 2H), 5.69 (dd, J=5.7 Hz and 7.2 Hz, 1H), 5.95 (br s, 1H), 6.66 (s, 1H), 7.21 (br s, 1H), 7.32-7.36 (m, 2H), 7.42-7.47 (m, 3H), 7.99 (s, 1H), 9.10 (d, J=0.8 Hz, 1H).

MS (MH+ found)=569.0

140. 3-{[1-(2-chlorophenyl)propyl]oxy}-5-{6-[(4-cyclopropylpiperazin-1-yl)methyl]-1H-imidazo[4,5-c]pyridin-1-yl}thiophene-2-carboxamide In a similar manner as described for example 137, compound 140 is synthesized starting with 110 mg of crude [1-(5-carbamoyl-4-{[(2-chlorophenyl)propyl]oxy}-2-thienyl)-1H-imidazo[4,5-c]pyridin-6-yl]methyl methanesulfonate (example 102, step 1), 211 mg of 1-cyclopropylpiperazine dihydrochloride and 258 mg of triethylamine.

¹H NMR (300 MHz, CDCl₃): δ=0.48-0.45 (m, 4H), 1.13 (t, J=7.4 Hz, 3H), 1.62-1.68 (m, 1H), 2.02-2.19 (m, 2H), 2.55 (br m, 4H), 2.71 (br m, 4H), 3.78 (s, 2H), 5.67-5.71 (m, 1H), 5.92 (br s, 1H), 6.67 (s, 1H), 7.21 (br s, 1H), 7.30-7.37 (m, 2H), 7.43-7.46 (m, 2H), 7.51 (s, 1H), 7.98 (s, 1H), 9.09 (s, 1H).

MS (MH+ found)=551.1

141. 3-{[1-(2-chlorophenyl)propyl]oxy}-5-{6-[(4-methyl-1,4-diazepan-1-yl)methyl]-1H-imidazo[4,5-c]pyridin-1-yl}thiophene-2-carboxamide In a similar manner as described for example 137, compound 141 is synthesized starting with 110 mg of crude [1-(5-carbamoyl-4-{[(2-chlorophenyl)propyl]oxy}-2-thienyl)-1H-imidazo[4,5-c]pyridin-6-yl]methyl methanesulfonate (example 102, step 1) and 121 mg of 1-methyl-1,4-diazepane.

¹H NMR (300 MHz, CDCl₃): δ=1.13 (t, J=7.4 Hz, 3H), 1.91-2.01 (m, 2H), 2.04-2.19 (m, 2H), 2.52 (s, 3H), 2.82-2.87 (m, 6H), 2.94 (t, J=5.7 Hz, 2H), 3.92 (s, 2H), 5.70 (t, J=5.6 Hz, 1H), 5.89 (br s, 1H), 6.67 (s, 1H), 7.20 (br s, 1H), 7.30-7.37 (m, 2H), 7.42-7.46 (m, 2H), 7.53 (s, 1H), 7.98 (s, 1H), 9.07 (s, 1H).

MS (MH+ found)=539.1

142. Formic acid salt of 3-{[1-(2-chlorophenyl)propyl]oxy}-5-{(6-[(4-ethylpiperazin-1-yl)methyl]1H-imidazo[4,5-c]pyridin-1-yl}thiophene-2-carboxamide In a similar manner as described for example 137, compound 142 is synthesized starting with 110 mg of crude [1-(5-carbamoyl-4-{[(2-chlorophenyl)propyl]oxy}-2-thienyl)-1H-imidazo[4,5-c]pyridin-6-yl]methyl methanesulfonate (example 102, step 1) and 121 mg of 1-ethylpiperazine.

¹H NMR (300 MHz, CDCl₃): δ=1.13 (t, J=7.4 Hz, 3H), 1.23 (t, J=7.3 Hz, 3H), 2.02-2.19 (m, 2H), 2.75-2.84 (m, 6H), 2.93 (br s, 4H), 3.80 (s, 2H), 5.67-5.71 (m, 1H), 5.96 (br s,

1H), 6.66 (s, 1H), 7.21 (br s, 1H), 7.33-7.36 (m, 2H), 7.41-7.49 (m, 3H), 8.00 (s, 1H), 8.46 (s, 1H), 9.11 (s, 1H).
MS (MH+ found)=539.1

143. 3-{[1-(2-chlorophenyl)propyl]oxy}-5-{6-[(4-pyridin-4-ylpiperazin-1-yl)methyl]-1H-imidazo[4,5-c]pyridin-1-yl}thiophene-2-carboxamide In a similar manner as described for example 137, compound 143 is synthesized starting with 110 mg of crude [1-(5-carbamoyl-4-{[(2-chlorophenyl)propyl]oxy}-2-thienyl)-1H-imidazo[4,5-c]pyridin-6-yl]methyl methanesulfonate (example 102, step 1) and 173 mg of 1-pyridin-4-ylpiperazine.
$^1$H NMR (300 MHz, D$_6$-DMSO): δ=0.98 (t, J=7.4 Hz, 3H), 1.95-2.04 (m, 1H), 2.14-2.26 (m, 1H), 2.56-2.59 (m, 4H), 3.30-3.34 (m, 4H), 3.78 (s, 2H), 5.73-5.78 (m, 1H), 6.79-6.81 (m, 2H), 7.15 (br s, 1H), 7.29-7.49 (m, 4H), 7.61 (d, J=0.7 Hz, 1H), 7.67 (dd, J=1.8 Hz, 1H), 7.84 (br s, 1H), 8.14-8.16 (m, 2H), 8.68 (s, 1H), 8.99 (d, J=0.9 Hz, 1H).
MS (MH+ found)=588.1

144. 5-(6-{[3-(dimethylamino)pyrrolidin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 114.2 mg of 3-(dimethylamino)pyrrolidine in 2.5 ml dichloromethane give the title compound.
$^1$H NMR (300 MHz, CDCl$_3$): δ=1.68-1.78 (m, 1H), 1.81 (d, J=6.2 Hz, 3H), 1.99-2.06 (m, 1H), 2.22 (s, 6H), 2.39-2.44 (m, 1H), 2.54-2.64 (m, 1H), 2.75-2.93 (m, 3H), 3.77-3.94 (m, 2H), 5.87 (q, J=6.4 Hz, 1H), 5.97 (br s, 1H), 6.67 (s, 1H), 7.20 (br s, 1H), 7.45-7.51 (m, 2H), 7.62-7.74 (m, 3H), 7.93 (s, 1H), 9.06 (s, 1H).
MS (MH+ found)=559.0

145. 5-(6-{[4-(2-oxo-2-pyrrolidin-1-ylethyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 197.3 mg of 1-(2-oxo-2-pyrrolidin-1-ylethyl)piperazine in 2.5 ml dichloromethane give the title compound.
$^1$H NMR (300 MHz, CDCl$_3$): δ=1.81-1.98 (m, 7H), 2.63 (br s, 8H), 3.14 (s, 2H), 3.45-3.51 (m, 4H), 3.78 (s, 2H), 5.88 (q, J=6.2 Hz, 1H), 6.09 (br s, 1H), 6.69 (s, 1H), 7.21 (br s, 1H), 7.46-7.51 (m, 2H), 7.62-7.75 (m, 3H), 7.94 (s, 1H), 9.08 (d, J=0.7 Hz, 1H).
MS (MH+ found)=642.1

146. 3-[(1R)-1-(2-chlorophenyl)-2-hydroxyethoxy]-5-[6-(hydroxymethyl)-1H-imidazo[4,5-c]pyridin-1-yl]thiophene-2-carboxamide A mixture of 236 mg of 3-[(1R)-2-{[tert-butyl(dimethyl)silyl]oxy}-1-(2-chlorophenyl)ethoxy]-5-[6-({[tert-butyl(dimethyl)silyl]oxy}methyl)-1H-imidazo[4,5-c]pyridin-1-yl]thiophene-2-carboxamide in 15 ml THF is cooled to 0° C. At 0° C. 0.26 ml tetra-n-butylammonium fluoride (~75% in H$_2$0) are added. The reaction mixture is allowed to warm to room temperature and stirred for one hour. The solvent is evaporated under reduced pressure and the residue is treated with 15 ml dichloromethane and 10 ml saturated aqueous NaHCO$_3$ solution. The phases are separated; the aqueous phase is extracted with 10 ml dichloromethane. The combined organic phase is dried over Na$_2$SO$_4$, filtered and concentrated to dryness. The raw product is purified by flash chromatography over silica gel Flash NH$_2$ [eluent: dichloromethane/methanol, with a gradient of 100/0 to 90/10 (v/v)]. The title product is obtained after a second purification in preparative HPLC (ammonium formate buffer/acetonitrile, elution gradient 80/20 to 30/70 (v/v)).
$^1$H NMR (300 MHz, D$_6$-DMSO): δ=3.78-3.93 (m, 2H), 4.68 (d, J=5.6 Hz, 2H), 5.47 (t, J=5.8 Hz, 1H), 5.57 (t, J=6.0 Hz, 1H), 5.76-5.80 (m, 1H), 7.11 (s, 1H), 7.33-7.44 (m, 3H), 7.49-7.52 (m, 1H), 7.57-7.60 (m, 1H), 7.63 (d, J=1.0 Hz, 1H), 7.87 (br s, 1H), 8.64 (s, 1H), 8.94 (d, J=0.9 Hz, 1H).
Contains 6.8 mol % TBAF δ=0.94 (t, 12H), 1.28-1.35 (m, 8H), 1.52-1.60 (m, 8H), 3.14-3.19 (m, 8H).
MS (MH+ found)=445.1

147. 5-(6-{[[(2-morpholin-4-ylethyl)amino]methyl}-1H-imidazo[4,5-c]pyridin-1-yl)-3-{(1R)-1-[2-(trifluoromethyl)phenyl]ethoxy}thiophene-2-carboxamide In a similar manner as described for example 60, compound 147 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate, 130 mg 2-morpholin-4-ylethanamine and 0.15 ml triethylamine.
$^1$H NMR (300 MHz, CDCl$_3$): δ=1.81 (d, J=6.2 Hz, 3H), 2.40-2.54 (m, 7H), 2.73 (t, J=6.2 Hz, 2H), 3.63-3.71 (m, 4H), 4.0 (s, 2H), 5.83-5.89 (m, 2H), 6.66 (s, 1H), 7.18 (br s, 1H), 7.43-7.50 (m, 2H), 7.62-7.75 (m, 3H), 7.93 (s, 1H), 9.06 (d, J=1.0 Hz, 1H).
MS (MH+ found)=575.1

148. 3-[1-(2-methylphenyl)ethoxy]-5-{6-[(4-methylpiperazin-1-yl)methyl]-1H-imidazo[4,5-c]pyridin-1-yl}thiophene-2-carboxamide Step 1: In a similar manner as described for example 49 (step 1), 410 mg of 5-[6-(hydroxymethyl)-1H-imidazo[4,5-c]pyridin-1-yl]-3-[1-(2-methylphenyl)ethoxy]thiophene-2-carboxamide, 0.15 ml of methanesulfonyl chloride, and 0.28 ml triethylamine in 15 ml dichloromethane give (1-{5-carbamoyl-4-[1-(2-methylphenyl)ethoxy]-2-thienyl}-1H-imidazo[4,5-c]pyridin-6-yl)methyl methanesulfonate as crude material that is used for step 2 without further purification.
Step 2: 97.3 mg of crude (1-{5-carbamoyl-4-[1-(2-methylphenyl)ethoxy]-2-thienyl}-1H-imidazo[4,5-c]pyridin-6-yl)methyl methanesulfonate (from step 1) are dissolved in 2.5 ml dichloromethane. Under N$_2$ atmosphere 1-methylpiperazine (100 mg) is added. The reaction mixture is stirred at 40° C. for 90 minutes and then concentrated to dryness under vacuum. The residue is purified by preparative HPLC (ammonium formate buffer/acetonitrile, elution gradient 60/40 to 25/75 (v/v)) to obtain the title product.
$^1$H NMR (300 MHz, CDCl$_3$): δ=1.77 (d, J=6.4 Hz, 3H), 2.30 (s, 3H), 2.42 (s, 3H), 2.49-2.57 (br m, 8H), 3.74 (d, J=2.0 Hz, 2H), 5.62 (q, J=6.4 Hz, 1H), 5.81 (br s, 1H), 6.50 (s, 1H), 7.21-7.30 (m, 4H), 7.37-7.43 (m, 2H), 7.93 (s, 1H), 9.09 (d, J=1.0 Hz, 1H).
MS (MH+ found)=491.1

149. 5-{6-[(4-isopropylpiperazin-1-yl)methyl]-1H-imidazo[4,5-c]pyridin-1-yl}-3-[1-(2-methylphenyl)ethoxy]thiophene-2-carboxamide In a similar manner as described for example 148, compound 149 is synthesized starting with 97.3 mg of (1-{5-carbamoyl-4-[1-(2-methylphenyl)ethoxy]-2-thienyl}-1H-imidazo[4,5-c]pyridin-6-yl)methyl methanesulfonate and 1-isopropylpiperazine (128 mg).

$^1$H NMR (300 MHz, CDCl$_3$): δ=1.05 (t, J=6.4 Hz, 6H), 1.77 (d, J=6.4 Hz, 3H), 2.42 (s, 3H), 2.57-2.70 (m, 9H), 3.75 (d, J=2.6 Hz, 2H), 5.62 (q, J=6.4 Hz, 1H), 5.81 (br s, 1H), 6.50 (s, 1H), 7.21-7.30 (m, 4H), 7.37-7.43 (m, 2H), 7.93 (s, 1H), 9.09 (d, J=1.0 Hz, 1H).

MS (MH$^+$ found)=519.1

150. 5-{6-[(4-ethylpiperazin-1-yl)methyl]-1H-imidazo[4,5-c]pyridin-1-yl}-3-[1-(2-methylphenyl)ethoxy]thiophene-2-carboxamide In a similar manner as described for example 148, compound 150 is synthesized starting with 97.3 mg of (1-{5-carbamoyl-4-[1-(2-methylphenyl)ethoxy]-2-thienyl}-1H-imidazo[4,5-c]pyridin-6-yl)methyl methanesulfonate and 1-ethyl piperazine (114 mg).

$^1$H NMR (300 MHz, CDCl$_3$): δ=1.08 (t, J=7.2 Hz, 3H), 1.77 (d, J=6.4 Hz, 3H), 2.39-2.58 (m, 13H), 3.75 (d, J=2.5 Hz, 2H), 5.62 (q, J=6.3 Hz, 1H), 5.80 (br s, 1H), 6.50 (s, 1H), 7.21-7.30 (m, 4H), 7.38-7.42 (m, 2H), 7.93 (s, 1H), 9.09 (d, J=0.9 Hz, 1H).

MS (MH$^+$ found)=505.1

151. 3-{[1-(2-chlorophenyl)propyl]oxy}-5-[6-({4-[2-(dimethylamino)ethyl]piperazin-1-yl}methyl)-1H-imidazo[4,5-c]pyridin-1-yl]thiophene-2-carboxamide In a similar manner as described for example 137, compound 151 is synthesized starting with 110 mg of crude [1-(5-carbamoyl-4-{[(2-chlorophenyl)propyl]oxy}-2-thienyl)-1H-imidazo[4,5-c]pyridin-6-yl]methyl methanesulfonate (example 102, step 1) and 167 mg of N,N-dimethyl-2-piperazin-1-ylethanamine.

$^1$H NMR (300 MHz, CDCl$_3$): δ=1.13 (t, J=7.4 Hz, 3H), 2.01-2.19 (m, 2H), 2.24 (s, 6H), 2.40-2.56 (m, 12H), 3.76 (d, J=1.0 Hz, 2H), 5.66-5.71 (m, 1H), 5.78 (br s, 1H), 6.66 (s, 1H), 7.20 (br s, 1H), 7.30-7.37 (m, 2H), 7.42-7.46 (m, 2H), 7.50 (d, J=0.9 Hz, 1H), 7.97 (s, 1H), 9.09 (d, J=0.9 Hz, 1H).

MS (MH$^+$ found)=582.1

152. 5-{6-[(4-ethylpiperazin-1-yl)methyl]-1H-imidazo[4,5-c]pyridin-1-yl}-3-[1-(2-fluorophenyl)ethoxy]thiophene-2-carboxamide Step 1: In a similar manner as described for example 49 (step 1), 1.06 g of 3-[(1-(2-fluorophenyl)ethoxy]-5-[6-(hydroxymethyl)-1H-imidazo[4,5-c]pyridin-1-yl]thiophene-2-carboxamide, 586 mg of methanesulfonyl chloride, and 518 mg of triethylamine in 19 ml dichloromethane give ((1-{5-carbamoyl-4-[1-(2-fluorophenyl)ethoxy]-2-thienyl}-1H-imidazo[4,5-c]pyridin-6-yl)methyl methanesulfonate as crude material that is used for step 2 without further purification.

Step 2: 161 mg of crude ((1-{5-carbamoyl-4-[1-(2-fluorophenyl)ethoxy]-2-thienyl}-1H-imidazo[4,5-c]pyridin-6-yl)methyl methanesulfonate (from step 1) are dissolved in 5 ml dichloromethane. Under N$_2$ atmosphere N,N-dimethyl-2-piperazin-1-ylethanamine (258 mg) is added. The reaction mixture is stirred at 40° C. for 3 hours and then concentrated to dryness under vacuum. The title product is obtained after two purifications in preparative HPLC (ammonium formate buffer/acetonitrile, elution gradient 97/3 to 0/100 (v/v)).

$^1$H NMR (300 MHz, CDCl$_3$): δ=1.08 (t, J=7.3 Hz, 3H), 1.82 (d, J=6.6 Hz, 3H), 2.43 (q, J=7.3 Hz, 2H), 2.52-2.59 (br m, 8H), 3.78 (s, 2H), 5.77 (q, J=6.4 Hz, 2H), 6.79 (s, 1H), 7.13-7.25 (m, 3H), 7.33-7.46 (m, 2H), 7.53 (d, J=0.9 Hz, 1H), 7.99 (s, 1H), 9.10 (d, J=1.0 Hz, 1H).

MS (MH$^+$ found)=509.1

153. 3-[(2-ethylbenzyl)oxy]-5-{6-[(4-methylpiperazin-1-yl)methyl]-1H-imidazo[4,5-c]pyridin-1-yl}thiophene-2-carboxamide Step 1: In a similar manner as described for example 49 (step 1), 210 mg of 3-[(2-ethylbenzyl)oxy]-5-[6-(hydroxymethyl)-1H-imidazo[4,5-c]pyridin-1-yl]thiophene-2-carboxamide, 112 mg of methanesulfonyl chloride, and 104 mg of triethylamine in 5 ml DMF give 3-[(2-ethylbenzyl)oxy]-5-{6-[(methylsulfonyl)methyl]-1H-imidazo[4,5-c]pyridin-1-yl}thiophene-2-carboxamid as crude material that is used for step 2 without further purification.

Step 2: 225 mg of crude 3-[(2-ethylbenzyl)oxy]-5-{6-[(methylsulfonyl)methyl]-1H-imidazo[4,5-c]pyridin-1-yl}thiophene-2-carboxamide (from step 1) are dissolved in 3.5 ml dichloromethane. Under N$_2$ atmosphere N-methylpiperazine (125 mg) is added. The reaction mixture is stirred at 40° C. for 3 hours and then concentrated to dryness under vacuum. The residue is purified by preparative HPLC (ammonium formate buffer/acetonitrile, elution gradient 97/3 to 0/100 (v/v)) to obtain the title product.

$^1$H NMR (300 MHz, CDCl$_3$): δ=1.29 (t, J=7.5 Hz, 3H), 1.85 (s, 3H), 2.50-2.60 (br m, 8H), 2.78 (q, J=7.7 Hz, 2H), 3.81 (s, 2H), 5.31 (s, 2H), 5.72 (br s, 1H), 6.97 (br s, 1H), 7.04 (s, 1H), 7.28-7.43 (m, 4H), 7.69 (s, 1H), 8.11 (s, 1H), 9.12 (d, J=1.0 Hz, 1H).

MS (MH$^+$ found)=491.1

154. 3-[(2-ethylbenzyl)oxy]-5-{6-[(4-ethylpiperazin-1-yl)methyl]-1H-imidazo[4,5-c]pyridin-1-yl}thiophene-2-carboxamide In a similar manner as described for example 153, compound 154 is synthesized starting with 225 mg of 3-[(2-ethylbenzyl)oxy]-5-{6-[(methylsulfonyl)methyl]-1H-imidazo[4,5-c]pyridin-1-yl}thiophene-2-carboxamide and 142 mg of N-ethylpiperazine.

$^1$H NMR (300 MHz, CDCl$_3$): δ=1.08 (t, J=7.3 Hz, 3H), 1.29 (t, J=7.5 Hz, 3H), 2.44 (q, J=7.3 Hz, 2H), 2.55-2.62 (br m, 8H), 2.76 (q, J=7.5 Hz, 2H), 3.82 (s, 2H), 5.31 (s, 2H), 5.58 (br s, 1H), 6.96 (br s, 1H), 7.04 (s, 1H), 7.28-7.35 (m, 2H), 7.38-7.43 (m, 2H), 7.69 (d, J=0.9 Hz, 1H), 8.11 (s, 1H), 9.13 (d, J=1.1 Hz, 1H).

MS (MH$^+$ found)=505.1

155. 3-[(2,5-diethoxybenzyl)oxy]-5-{6-[(4-methylpiperazin-1-yl)methyl]-1H-imidazo[4,5-c]pyridin-1-yl}thiophene-2-carboxamide Step 1: In a similar manner as described for example 49 (step 1), 250 mg of 3-[(2,5-diethoxybenzyl)oxy]-5-[6-(hydroxymethyl)-1H-imidazo[4,5-c]pyridin-1-yl]thiophene-2-carboxamide, 115.4 mg of methanesulfonyl chloride, and 0.15 ml triethylamine in 6 ml dichloromethane give a 70:30 mixture of 5-[6-(chloromethyl)-1H-imidazo[4,5-c]pyridin- 1-yl]-3-[(2,5-diethoxybenzyl)oxy]thiophene-2-carboxamide and (1-{5-carbamoyl-4-[(2,5-diethoxybenzyl)oxy]-2-thienyl}-1H-imidazo[4,5-c]pyridin-6-yl)methyl methanesulfonate as crude material that is used for step 2 without further purification.

Step 2: 257.6 mg of a crude 70:30 mixture of 5-[6-(chloromethyl)-1H-imidazo[4,5-c]pyridin-1-yl]-3-[(2,5-diethoxybenzyl)oxy]thiophene-2-carboxamide and (1-{5-carbamoyl-4-[(2,5-diethoxybenzyl)oxy]-2-thienyl}-1H-imidazo[4,5-c]pyridin-6-yl)methyl methanesulfonate (from step 1) are dissolved in 5 ml dichloromethane. Under $N_2$ atmosphere N-methylpiperazine (261 mg) is added. The reaction mixture is stirred at 40° C. for 24 hours and then concentrated to dryness under vacuum. The residue is purified by flash chromatography [silica gel, eluent: dichloromethane/methanol/triethylamine, with an elution gradient of 99.7/0/0.3 to 84.7/15/0.3 (v/v)]. The title product is obtained after a further purification step (filtration through a short plug of Flash-$NH_2$ silica gel [eluent: dichloromethane/methanol, 9/1 (v/v)].

$^1$H NMR (300 MHz, $CDCl_3$): δ=1.35-1.42 (m, 6H), 2.28 (s, 3H), 2.48-2.58 (br m, 8H), 3.80 (s, 2H), 3.95-4.09 (m, 4H), 5.31 (s, 2H), 5.64 (br s, 1H), 6.88 (d, J=1.7 Hz, 2H), 6.94-6.95 (m, 1H), 7.06 (s, 1H), 7.20 (br s, 1H), 7.68 (d, J=0.9 Hz, 1H), 8.08 (s, 1H), 9.12 (d, J=0.9 Hz, 1H).

MS ($MH^+$ found)=551.1

156. 3-[-1-(2-fluorophenyl)ethoxy]-5-(6-{[(1-methylpiperidin-4-yl)amino]methyl}-3H-imidazo[4,5-c]pyridin-3-yl)thiophene-2-carboxamide Step 1: In a similar manner as described for example 49 (step 1), 2.9 g of 3-[-1-(2-fluorophenyl)ethoxy]-5-[6-(hydroxymethyl)-3H-imidazo[4,5-c]pyridin-3-yl]thiophene-2-carboxamide, 1.53 g of methanesulfonyl chloride, and 1.42 g of triethylamine in 70 ml dichloromethane give (3-{5-carbamoyl-4-[-1-(2-fluorophenyl)ethoxy]-2-thienyl}-3H-imidazo[4,5-c]pyridin-6-yl)methyl methanesulfonate as crude material that is used for step 2 without further purification.

Step 2: 290 mg of crude (3-{5-carbamoyl-4-[-1-(2-fluorophenyl)ethoxy]-2-thienyl}-3H-imidazo[4,5-c]pyridin-6-yl)methyl methanesulfonate (from step 1) are dissolved in 7.5 ml dichloromethane. Under $N_2$ atmosphere 1-methylpiperidin-4-amine (342.6 mg) is added. The reaction mixture is stirred at 40° C. for 50 hours and then concentrated to dryness under vacuum. The residue is purified by preparative HPLC (ammonium formate buffer/acetonitrile, elution gradient 85/15 to 40/60 (v/v)) to obtain the title product.

MS ($MH^+$ found)=509.1

157. 3-[-1-(2-fluorophenyl)ethoxy]-5-(6-{[4-(2-methoxyethyl)piperazin-1-yl]methyl}-3H-imidazo[4,5-c]pyridin-3-yl)thiophene-2-carboxamide In a similar manner as described for example 156, compound 157 is synthesized starting with 290 mg of (3-{5-carbamoyl-4-[-1-(2-fluorophenyl)ethoxy]-2-thienyl}-3H-imidazo[4,5-c]pyridin-6-yl)methyl methanesulfonate and 1-(2-methoxyethyl)piperazine (432.7 mg).

$^1$H NMR (300 MHz, $CDCl_3$): δ=1.81 (d, J=6.6 Hz, 3H), 2.58-2.62 (m, 10H), 3.34 (s, 3H), 3.51 (t, J=5.8 Hz, 2H), 3.81 (s, 2H), 5.76 (q, J=6.5 Hz, 1H), 5.86 (br s, 1H), 6.83 (s, 1H), 7.10-7.24 (m, 3H), 7.32-7.44 (m, 2H), 7.83 (d, J=0.7 Hz, 1H), 8.07 (s, 1H), 8.82 (d, J=0.9 Hz, 1H).

MS (MH+ found)=539.1

158. 3-[-1-(2-fluorophenyl)ethoxy]-5-[6-(morpholin-4-ylmethyl)-3H-imidazo[4,5-c]pyridin-3-yl]thiophene-2-carboxamide In a similar manner as described for example 156, compound 158 is synthesized starting with 290 mg of (3-{5-carbamoyl-4-[-1-(2-fluorophenyl)ethoxy]-2-thienyl}-3H-imidazo[4,5-c]pyridin-6-yl)methyl methanesulfonate and morpholine (261.4 mg).

$^1$H NMR (300 MHz, $CDCl_3$): δ=1.80 (d, J=6.4 Hz, 3H), 2.53-2.57 (m, 4H), 3.74-3.77 (m, 4H), 3.80 (s, 2H), 5.76 (q, J=6.4 Hz, 1H), 5.89 (br s, 1H), 6.84 (s, 1H), 7.10-7.24 (m, 3H), 7.32-7.38 (m, 1H), 7.42 (td, J=1.8 Hz and 7.5 Hz, 1H), 7.84 (s, 1H), 8.08 (s, 1H), 8.84 (d, J=1.0 Hz, 1H).

MS (MH+ found)=482.1

159. 5-(6-{[4-(trifluoroacetyl)piperazin-1-yl]methyl}-1H-imidazo[4,5-c]pyridin-1-yl)-3-{(1R)-1-[2-(trifluoromethyl)phenyl]ethoxy}thiophene-2-carboxamide In a similar manner as described for example 58, compound 159 is synthesized starting with 108 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate, 182.1 mg of 1-(trifluoroacetyl)piperazine.

$^1$H NMR (300 MHz, $CDCl_3$): δ=1.83 (d, J=6.2 Hz, 3H), 2.57 (m, 4H), 3.64 (m, 2H), 3.71 (m, 2H), 3.78 (d, J=1.6 Hz, 2H), 5.85 (m, 2H), 6.68 (s, 1H), 7.19 (br s, 1H), 7.46 (m, 2H), 7.62-7.74 (m, 3H), 7.96 (s, 1H), 9.10 (d, J=0.9 Hz, 1H).

MS (MH+ found)=627.1

160. 5-{6-[(4-benzoylpiperazin-1-yl)methyl]3H-imidazo[4,5-c]pyridin-3-yl}-3-[-1-(2-fluorophenyl)ethoxy]thiophene-2-carboxamide In a similar manner as described for example 156, compound 160 is synthesized starting with 290 mg of (3-{5-carbamoyl-4-[-1-(2-fluorophenyl)ethoxy]-2-thienyl}-3H-imidazo[4,5-c]pyridin-6-yl)methyl methanesulfonate and 1-benzoylpiperazine (570.8 mg).

$^1$H NMR (300 MHz, $CDCl_3$): δ=1.80 (d, J=6.5 Hz, 3H), 2.61 (br s, 4H), 3.49 (br s, 4H), 3.85 (s, 2H), 5.74 (q, J=6.5 Hz, 1H), 5.83 (br s, 1H), 6.84 (s, 1H), 7.10-7.23 (m, 3H), 7.32-7.44 (m, 7H), 7.83 (d, J=0.9 Hz, 1H), 8.08 (s, 1H), 8.84 (d, J=0.9 Hz, 1H).

MS (MH+ found)=585.2

161. 5-{6-[(1,1-dioxidothiomorpholin-4-yl)methyl]-3H-imidazo[4,5-c]pyridin-3-yl}-3-[-1-(2-fluorophenyl)ethoxy]thiophene-2-carboxamide In a similar manner as described for example 156, compound 161 is synthesized starting with 290 mg of (3-{5-carbamoyl-4-[-1-(2-fluorophenyl)ethoxy]-2-thienyl}-3H-imidazo[4,5-c]pyridin-6-yl)methyl methanesulfonate and thiomorpholine 1,1-dioxide (405.6 mg).

$^1$H NMR (300 MHz, $CDCl_3$): δ=1.81 (s, J=6.5 Hz, 3H), 3.10 (s, 8H), 3.96 (s, 2H), 5.75 (q, J=6.4 Hz, 1H), 5.92 (br s, 1H), 6.85 (s, 1H), 7.10-7.24 (m, 3H), 7.33-7.45 (m, 2H), 7.80 (d, J=0.8 Hz, 1H), 8.10 (s, 1H), 8.84 (d, J=1.0 Hz, 1H).

MS (MH+ found)=530.0

162. 3-[(2-ethylbenzyl)oxy]-5-[6-(hydroxymethyl)-1H-imidazo[4,5-c]pyridin-1-yl]thiophene-2-carboxamide A mixture of 460 mg of 5-[6-({[tert-butyl(dimethyl)silyl]oxy}methyl)-1H-imidazo[4,5-c]pyridin-1-yl]-3-[(2-ethylbenzyl)oxy]thiophene-2-carboxamide in 30 ml THF is cooled to 0° C. At 0° C. 0.32 ml tetra-n-butylammonium fluoride (~75% in H$_2$O) are added. The reaction mixture is allowed to warm to room temperature and stirred for one hour.

The solvent is evaporated under reduced pressure and the residue is treated with 15 ml dichloromethane and 15 ml saturated aqueous NaHCO$_3$ solution. The mixture is left over night at 4° C. and the resulting precipitate is collected by filtration. The filter cake is washed with water and diethyl ether and dried under vacuum to obtain the title product.

$^1$H NMR (300 MHz, D$_6$-DMSO): δ=1.21 (t, J=7.5 Hz, 3H), 2.72 (q, J=7.5 Hz, 2H), 4.72 (s, 2H), 5.42 (s, 2H), 5.54 (s, 1H), 6.82 (br s, 1H), 7.24-7.38 (m, 3H), 7.51 (d, J=7.3 Hz, 1H), 7.72 (br s, 1H), 7.79 (s, 1H), 7.84 (d, J=0.7 Hz, 1H), 8.77 (s, 1H), 8.98 (d, J=0.8 Hz, 1H).

MS (MH+ found)=409.0

163. 3-[-1-(2-fluorophenyl)ethoxy]-5-[6-(hydroxymethyl)-3H-imidazo[4,5-c]pyridin-3-yl]thiophene-2-carboxamide A mixture of 4.44 g of 5-[6-({[tert-butyl(dimethyl)silyl]oxy}methyl)-3H-imidazo[4,5-c]pyridin-3-yl]-3-[1-(2-fluorophenyl)ethoxy]thiophene-2-carboxamide in 300 ml THF is cooled to 0° C. At 0° C. 2.31 ml tetra-n-butylammonium fluoride (~75% in H$_2$O) are added. The reaction mixture is allowed to warm to room temperature and stirred over night.

The solvent is evaporated under reduced pressure and the residue is treated with 100 ml dichloromethane and 100 ml saturated aqueous NaHCO$_3$ solution. The mixture is left at 4° C. for 4 hours and the resulting precipitate is collected by filtration. The filter cake is washed with water and diethyl ether and dried under vacuum to obtain the title product.

$^1$H NMR (300 MHz, D$_6$-DMSO): δ=1.74 (d, J=6.4 Hz, 3H), 4.69 (d, J=5.6 Hz, 2H), 5.45 (t, J=5.8 Hz, 1H), 5.96 (q, J=6.3 Hz, 1H), 7.08 (br s, 1H), 7.22-7.29 (m, 2H), 7.37-7.45 (m, 1H), 7.58 (s, 1H), 7.61 (td, J=1.9 and 8.1 Hz, 1H), 7.78 (d, J=0.8 Hz, 1H), 7.81 (br s, 1H), 8.78 (s, 1H), 8.91 (d, J=1.0 Hz, 1H).

MS (MH+ found)=413.0

164. 5-{6-[(4-methyl-1,4-diazepan-1-yl)methyl]-1H-imidazo[4,5-c]pyridin-1-yl}-3-{(1R)-1-[2-(trifluoromethyl)phenyl]ethoxy}thiophene-2-carboxamide In a similar manner as described for example 58, compound 164 is synthesized starting with 216 mg of [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate and 228 mg 1-methyl-1,4-diazepane.

$^1$H NMR (300 MHz, CDCl$_3$): δ=1.67-1.77 (m, 5H), 2.24 (s, 3H), 2.51-2.58 (m, 4H), 2.68-2.74 (m, 4H), 3.84 (s, 2H), 5.93 (q, J=Hz, 1H), 7.12 (br s, 1H), 7.22 (s, 1H), 7.55-7.62 (m, 2H), 7.76-7.82 (m, 3H), 7.98 (d, J=7.8 Hz, 1H), 8.64 (s, 1H), 8.96 (d, J=0.9 Hz, 1H).

MS (MH+ found)=559.1

165. 5-[6-(hydroxymethyl)-3H-imidazo[4,5-c]pyridin-3-yl]-3-{1-[2-(trifluoromethyl)phenyl]ethoxy}thiophene-2-carboxamide In a similar manner as described for example 44, 10.18 g of 5-[6-({[tert-butyl(dimethyl)silyl]oxy}methyl)-3H-imidazo[4,5-c]pyridin-3-yl]-3-{1-[2-(trifluoromethyl)phenyl]ethoxy}thiophene-2-carboxamide and 4.61 g of tetra-n-butylammonium fluoride (~75% in H$_2$O) in 670 ml THF yield the title compound.

$^1$H NMR (300 MHz, D$_6$-DMSO): δ=1.76 (d, J=6.2 Hz, 3H), 4.69 (s, 2H), 5.44 (br s, 1H), 5.99 (q, J=6.2 Hz, 1H), 7.14 (br s, 1H), 7.25 (s, 1H), 7.54-7.59 (m, 1H), 7.76-7.81 (m, 3H), 7.84 (br s, 1H), 7.96 (d, J=8.1 Hz, 1H), 8.78 (s, 1H), 8.80 (d, J=0.9 Hz, 1H).

Intermediate Compounds of Type (Ie) and (Ic)

A1. [1-(5-Carbamoyl-4-{[2-(trifluoromethyl)benzyl]oxy}-2-thienyl)-1H-imidazo[4,5-c]pyridin-6-yl]methyl methanesulfonate To a suspension of 336 mg of 5-(6-hydroxymethyl-imidazo[4,5-c]pyridin-1-yl)-3-(2-trifluoromethyl-benzyloxy)-thiophene-2-carboxylic acid amide (compound 9) in 15 ml anhydrous dichloromethane were added 265 mg triethylamine and then 209 mg methanesulfonic anhydride at 0° C. under nitrogen atmosphere. The reaction mixture was allowed to warm to room temperature and was stirred for one hour. 100 ml dichloromethane was added and the organic layer was washed twice with 30 ml of saturated NaHCO$_3$ solution. The organic layers were combined, dried with MgSO$_4$ and concentrated in vacuum. The residue was dissolved in ethyl acetate and filtered through a short plug of silica gel. After evaporation of the solvent the title compound was obtained.

$^1$H NMR (300 MHz, D$_6$-DMSO): δ=3.29 (s, 3H), 5.46 (s, 2H), 5.54 (s, 2H), 6.81 (bs, 1H), 7.63-7.68 (m, 1H), 7.75-7.87 (m, 5H), 8.00 (d, J=0.9 Hz, 1H), 8.86 (s, 1H), 9.12 (d, J=0.9 Hz, 1H).

MS (MH$^+$ found)=526.9

A2. 5-[6-({[Tert-butyl(dimethyl)silyl]oxy}methyl)-3H-imidazo[4,5-c]pyridin-3-yl]-3-{[2-(trifluoromethyl)benzyl]oxy}thiophene-2-carboxamide A mixture of 1.05 g of methyl 5-[6-({[tert-butyl(dimethyl)silyl]oxy}methyl)-3H-imidazo[4,5-c]pyridin-3-yl]-3-{[2-(trifluoromethyl)benzyl]oxy}thiophene-2-carboxylate (compound B2a) and 100 ml of a saturated solution of ammonia in methanol was stirred in an autoclave at 120° C. for 3.5 h. The reaction mixture was allowed to cool down to room temperature, concentrated to dryness, dissolved in dichloromethane and filtered through a plug of silica gel (eluents: dichloromethane/ethyl acetate) to yield the title product.

$^1$H NMR (300 MHz, D$_6$-DMSO): δ=0.13 (s, 6H), 0.95 (s, 9H), 4.90 (s, 2H), 5.57 (s, 2H), 6.8 (bs, 1H), 7.63-7.87 (m, 7H), 8.86 (s, 1H), 9.08 (s, 1H).

MS (MH$^+$ found)=562.9

A3. [1-(5-carbamoyl-4-{(1R)-1-[2-(trifluoromethyl)phenyl]ethoxy}-2-thienyl)-1H-imidazo[4,5-c]pyridin-6-yl]methyl methanesulfonate A suspension of 1.66 g of 5-[6-(hydroxymethyl)-1H-imidazo[4,5-c]pyridin-1-yl]-3-{(1R)-1-[2-(trifluoromethyl)phenyl]ethoxy}thiophene-2-carboxamide and 1.0 ml triethylamine in 60 ml anhydrous dichloromethane was cooled to 0° C. Under nitrogen atmosphere, 0.53 ml methanesulfonyl chloride was added dropwise.

The reaction mixture was stirred at 0° C. for 30 minutes. 50 ml water were added and the layers were separated. The aqueous layer was extracted with 2×40 ml dichloromethane. The organic layers were combined, dried over Na$_2$SO$_4$ and evaporated under reduced pressure to give the compound which was used for the next step without further purification.

MS (MH$^+$ found)=541.0

A4. 5-[6-({[tert-butyl(dimethyl)silyl]oxy}methyl)-1H-imidazo[4,5-c]pyridin-1-yl]-3-{(1R)-1-[2-(trifluoromethyl)phenyl]ethoxy}thiophene-2-carboxamide A mixture of 5.1 g of methyl 5-[6-({[tert-butyl(dimethyl)silyl]oxy}methyl)-1H-imidazo[4,5-c]pyridin-1-yl]-3-{(1R)-1-[2-(trifluoromethyl)phenyl]ethoxy}thio-phene-2-carboxylate and 500 ml of a 7 N solution of ammonia in methanol is stirred in an autoclave at 125° C. for 4 hours. The mixture is allowed to cool down to room temperature and concentrated to dryness. During the reaction the TBDMS group of the title product is partially removed. The crude is purified by flash chromatography [silica gel, eluent: cyclohexane/ethyl acetate/methanol, elution gradient of 40/60/0 (v/v/v) to 0/100/0 (v/v/v) and then to 0/90/10 (v/v)] to give the title compound. Additionally, 5-[6-(hydroxymethyl)-1H-imidazo[4,5-c]pyridin-1-yl]-3-{(1R)-1-[2-(trifluoromethyl)phenyl]ethoxy}thiophene-2-carboxamide is obtained.

$^1$H NMR (300 MHz, D$_6$-DMSO): δ=0.11 (2s, 6H), 0.92 (s, 9H), 1.76 (d, J=6.4 Hz, 3H), 4.87 (s, 2H), 5.89 (q, J=5.6 Hz, 1H), 7.10 (br s, 1H), 7.27 (s, 1H), 7.54-7.59 (m, 1H), 7.66 (s, 1H), 7.73-7.81 (m, 3H), 7.98 (d, J=7.7 Hz, 1H), 8.66 (s, 1H), 8.98 (s, 1H).

MS (MH+ found)=577.0

A5. 5-[6-({[tert-butyl(dimethyl)silyl]oxy}methyl)-1H-imidazo[4,5-c]pyridin-1-yl]-3-{-1-[4-fluoro-2-(trifluoromethyl)phenyl]ethoxy}thiophene-2-carboxamide A mixture of 2.22 g of methyl 5-[6-({[tert-butyl(dimethyl)silyl]oxy}methyl)-1H-imidazo[4,5-c]pyridin-1-yl]-3-{-1-[4-fluoro-2-(trifluoromethyl)phenyl]ethoxy}thiophene-2-carboxylate and 168 ml of a saturated solution of ammonia in methanol is stirred in a microwave vial at 125-130° C. for 4 h in the microwave cavity. The reaction mixture is concentrated to dryness and the resulting residue is purified by flash chromatography [Silica gel, eluent: ethyl acetate/cyclohexane, elution gradient of 0/100 (v/v) to 70/30 (v/v)] to yield the title product.

$^1$H NMR (300 MHz, D$_6$-DMSO): δ=0.11 (2 s, 6H), 0.92 (3 s, 9H), 1.75 (d, J=6.2 Hz, 3H), 4.88 (s, 2H), 5.86 (d, J=6.3 Hz, 1H), 7.10 (br s, 1H), 7.27 (s, 1H), 7.62-7.70 (m, 3H), 7.81 (br s, 1H), 8.05 (dd, J=5.4 and 8.6 Hz, 1H), 8.66 (s, 1H), 8.99 (d, J=0.9 Hz, 1H).

MS (MH+ found)=595.0

A6. 5-[6-({[tert-butyl(dimethyl)silyl]oxy}methyl)-1H-imidazo[4,5-c]pyridin-1-yl]-3-{(1S)-1-[2-(trifluoromethyl)phenyl]ethoxy}thiophene-2-carboxamide In a similar manner as described for example A5, 368 mg of methyl 5-[6-({[tert-butyl(dimethyl)silyl]oxy}methyl)-1H-imidazo[4,5-c]pyridin-1-yl]-3-{(1S)-1-[2-(trifluoromethyl)phenyl]ethoxy}thiophene-2-carboxylate and 41 ml of a saturated solution of ammonia in methanol yield the title compound.

$^1$H NMR (300 MHz, D$_6$-DMSO): δ=0.10 (2 s, 6H), 0.92 (s, 9H), 1.75 (d, J=6.2 Hz, 3H), 4.87 (s, 2H), 5.89 (d, J=6.3 Hz, 1H), 7.09 (s, 1H), 7.27 (s, 1H), 7.54-7.99 (m, 6H), 8.66 (s, 1H), 8.98 (s, 1H).

MS (MH+ found)=577.0

A7. 5-[6-({[tert-butyl(dimethyl)silyl]oxy}methyl)-3H-imidazo[4,5-c]pyridin-3-yl]-3-{(1R)-1-[2-(trifluoromethyl)phenyl]ethoxy}thiophene-2-carboxamide A mixture of 12 g of methyl 5-[6-({[tert-butyl(dimethyl)silyl]oxy}methyl)-3H-imidazo[4,5-c]pyridin-3-yl]-3-{(1R)-1-[2-(trifluoromethyl)phenyl]ethoxy}thiophene-2-carboxylate and 1.3 l of a 7 N solution of ammonia in methanol is stirred in an autoclave at 125° C. for 4 hours. The reaction mixture is concentrated to dryness and the resulting residue is purified by flash chromatography [silica gel, eluent: toluol/dioxane, elution gradient of 7/3 (v/v) to 1/1 (v/v)] to yield the title product.

$^1$H NMR (300 MHz, D$_6$-DMSO): δ=0.12 (2 s, 6H), 0.94 (3 s, 9H), 1.76 (d, J=6.2 Hz, 3H), 4.88 (s, 2H), 5.99 (d, J=6.3 Hz, 1H), 7.14-7.23 (m, 1H), 7.25 (s, 1H), 7.56 (t, J=7.6 Hz, 1H), 7.73-7.84 (m, 4H), 7.96 (d, J=7.8 Hz, 1H), 8.75 (s, 1H), 8.82 (d, J=0.8 Hz 1H).

MS (MH+ found)=576.9

A8. 3-[(1R)-2-{[tert-butyl(dimethyl)silyl]oxy}-1-(2-chlorophenyl)ethoxy]-5-[6-({[tert-butyl(dimethyl)silyl]oxy}methyl)-1H-imidazo[4,5-c]pyridin-1-yl]thiophene-2-carboxamide In a similar manner as described for example A5, 500 mg of methyl 3-[(1R)-2-{[tert-butyl(dimethyl)silyl]oxy}-1-(2-chlorophenyl)ethoxy]-5-[6-({[tert-butyl(dimethyl)silyl]oxy}methyl)-1H-imidazo[4,5-c]pyridin-1-yl]thiophene-2-carboxylate and 40 ml of a saturated solution of ammonia in methanol yield the title compound.

$^1$H NMR (300 MHz, D$_6$-DMSO): δ=−0.03-0.01 (m, 6H), 0.10-0.11 (2 s, 6H), 0.79 (s, 9H), 0.93-0.94 (d, J=2.9 Hz, 9H), 4.02-4.16 (m, 2H), 4.88 (s, 2H), 5.81-5.85 (m, 1H), 7.21 (br s, 1H), 7.26 (s, 1H), 7.36-7.69 (m, 5H), 7.93 (s, 1H), 8.68 (s, 1H), 8.97-8.98 (d, J=0.9 Hz, 1H).

MS (MH+ found)=673.0

A9. 5-[6-({[tert-butyl(dimethyl)silyl]oxy}methyl)-1H-imidazo[4,5-c]pyridin-1-yl]-3-[1-(2-chloro-4-cyanophenyl)ethoxy]thiophene-2-carboxamide 1.50 g of methyl 5-[6-({[tert-butyl(dimethyl)silyl]oxy}methyl)-1H-imidazo[4,5-c]pyridin-1-yl]-3-[-1-(2-chloro-4-cyanophenyl)ethoxy]thiophene-2-carboxylate are dissolved in 60 ml of a 7 N solution of ammonia in methanol. The reaction mixture is stirred for 5 hours at 125° C. under microwave radiation.

The mixture is then concentrated under vacuum and the residue is purified by flash-chromatography on silica gel [eluent: ethyl acetate/methanol with a gradient from 100/0 to 90/10 (v/v)] to yield the title product.

$^1$H NMR (300 MHz, D$_6$-DMSO): δ=0.11 (2 s, 6H), 0.92 (3 s, 9H), 1.74 (d, J=6.3 Hz, 3H), 4.88 (s, 2H), 5.93 (q, J=6.4 Hz, 1H), 7.14 (br s, 1H), 7.32 (s, 1H), 7.71 (s, 1H), 7.76 (br s, 1H), 7.81 (br s, 1H), 7.88-7.95 (m, 2H), 8.84 (s, 1H), 8.98 (d, J=0.9 Hz, 1H).

MS (MH+ found)=568.0

A10. 3-[(1R)-1-(2-bromophenyl)ethoxy]-5-[6-({[tert-butyl(dimethyl)silyl]oxy}methyl)-1H-imidazo[4,5-c]pyridin-1-yl]thiophene-2-carboxamide In a similar manner as described for example A5, 2.11 g of methyl 3-[(1R)-1-(2-bromophenyl)ethoxy]-5-[6-({[tert-butyl(dimethyl)silyl]oxy}methyl)-1H-imidazo[4,5-c]pyridin-1-yl]thiophene-2-carboxylate and 168 ml of a saturated solution of ammonia in methanol yield the title compound.

$^1$H NMR (300 MHz, D$_6$-DMSO): δ=0.11 (2 s, 6H), 0.93 (s, 9H), 1.73 (d, J=6.3 Hz, 3H), 4.88 (s, 2H), 5.86 (q, J=6.2 Hz, 1H), 7.09 (br s, 1H), 7.26-7.31 (m, 2H), 7.45-7.50 (m, 1H), 7.63-7.72 (m, 3H), 7.80 (br s, 1H), 8.69 (s, 1H), 8.98 (s, 1H).
MS (MH+ found)=586.9

A11. 5-[6-({[tert-butyl(dimethyl)silyl]oxy}methyl)-1H-imidazo[4,5-c]pyridin-1-yl]-3-{-1-[2-(difluoromethoxy)phenyl]ethoxy}thiophene-2-carboxamide In a similar manner as described for example A5, 2.78 g of methyl 5-[6-({[tert-butyl(dimethyl)silyl]oxy}methyl)-1H-imidazo[4,5-c]pyridin-1-yl]-3-{-1-[2-(difluoromethoxy)phenyl]ethoxy}thiophene-2-carboxylate and 115 ml of a saturated solution of ammonia in methanol yield the title compound.

$^1$H NMR (300 MHz, D$_6$-DMSO): δ=0.11 (2 s, 6H), 0.93 (s, 9H), 1.72 (d, J=6.4 Hz, 3H), 4.88 (s, 2H), 5.89 (q, J=6.4 Hz, 1H), 7.09 (br s, 1H), 7.22-7.44 (m, 5H), 7.66-7.72 (m, 2H), 7.79 (br s, 1H) 8.69 (s, 1H), 8.99 (s, 1H).
MS (MH+ found)=575.0

A12. 5-[6-({[tert-butyl(dimethyl)silyl]oxy}methyl)-1H-imidazo[4,5-c]pyridin-1-yl]-3-[(1R)-1-(2-chlorophenyl)ethoxy]thiophene-2-carboxamide In a similar manner as described for example A5, 2.60 g of methyl 5-[6-({[tert-butyl(dimethyl)silyl]oxy}methyl)-1H-imidazo[4,5-c]pyridin-1-yl]-3-[(1R)-1-(2-chlorophenyl)ethoxy]thiophene-2-carboxylate and 92 ml of a saturated solution of ammonia in methanol yield the title compound.

$^1$H NMR (300 MHz, D$_6$-DMSO): δ=0.11 (2 s, 6H), 0.94 (3 s, 9H), 1.74 (d, J=6.3 Hz, 3H), 4.88 (s, 2H), 5.94 (q, J=6.3 Hz, 1H), 7.10 (br s, 1H), 7.34-7.50 (m, 4H), 7.70-7.73 (m, 2H), 7.80 (br s, 1H) 7.77 (s, 1H), 8.99 (d, J=0.9 Hz, 1H).
MS (MH+ found)=543.0

A13. 5-[6-({[tert-butyl(dimethyl)silyl]oxy}methyl)-1H-imidazo[4,5-c]pyridin-1-yl]-3-[(1R)-1-(2-fluorophenyl)ethoxy]thiophene-2-carboxamide In a similar manner as described for example A5, 2.50 g of methyl 5-[6-({[tert-butyl(dimethyl)silyl]oxy}methyl)-1H-imidazo[4,5-c]pyridin-1-yl]-3-[(1R)-1-(2-fluorophenyl)ethoxy]thiophene-2-carboxylate and 92 ml of a saturated solution of ammonia in methanol yield the title compound.

$^1$H NMR (300 MHz, D$_6$-DMSO): δ=0.11 (2 s, 6H), 0.93 (s, 9H), 1.75 (d, J=6.4 Hz, 3H), 4.89 (s, 2H), 5.90 (q, J=6.4 Hz, 1H), 7.05 (br s, 1H), 7.21-7.28 (m, 2H), 7.37-7.44 (m, 1H), 7.59-7.66 (m, 2H), 7.74 (s, 1H), 7.78 (br s, 1H), 8.73 (s, 1H), 8.99 (d, J=0.7 Hz, 1H).
MS (MH+ found)=526.9

A14. 5-[6-({[tert-butyl(dimethyl)silyl]oxy}methyl)-1H-imidazo[4,5-c]pyridin-1-yl]-3-{[-1-(2-chlorophenyl)propyl]oxy}thiophene-2-carboxamide In a similar manner as described for example A5, 3.64 g of methyl 5-[6-({[tert-butyl(dimethyl)silyl]oxy}methyl)-1H-imidazo[4,5-c]pyridin-1-yl]-3-{[1-(2-chlorophenyl)propyl]oxy}thiophene-2-carboxylate and 115 ml of a saturated solution of ammonia in methanol yield the title compound.

$^1$H NMR (300 MHz, D$_6$-DMSO): δ=0.11 (2 s, 6H), 0.94 (2 s, 9H), 1.02 (t, J=7.3 Hz, 3H), 1.97-2.25 (m, 2H), 4.88 (s, 2H), 5.71 (q, J=6.4 Hz, 1H), 7.15 (br s, 1H), 7.25 (s, 1H), 7.32-7.69 (m, 5H), 7.83 (br s, 1H), 8.68 (s, 1H), 8.98 (s, 1H).
MS (MH+ found)=557.0

A15. 5-[6-({[tert-butyl(dimethyl)silyl]oxy}methyl)-1H-imidazo[4,5-c]pyridin-1-yl]-3-[-1-(2-fluorophenyl)ethoxy]thiophene-2-carboxamide In a similar manner as described for example A5, 2.98 g of methyl 5-[6-({[tert-butyl(dimethyl)silyl]oxy}methyl)-1H-imidazo[4,5-c]pyridin-1-yl]-3-[1-(2-fluorophenyl)ethoxy]thiophene-2-carboxylate and 115 ml of a saturated solution of ammonia in methanol yield the title compound.

$^1$H NMR (300 MHz, D$_6$-DMSO): δ=0.11 (2 s, 6H), 0.93 (2 s, 9H), 1.75 (d, J=6.4 Hz, 3H), 4.89 (s, 2H), 5.91 (q, J=6.4 Hz, 1H), 7.05 (br s, 1H), 7.21-7.66 (m, 5H), 7.74 (s, 1H), 7.79 (br s, 1H), 8.73 (s, 1H), 8.99 (d, 1H).
MS (MH+ found)=527.0

A16. 5-[6-({[tert-butyl(dimethyl)silyl]oxy}methyl)-3H-imidazo[4,5-c]pyridin-3-yl]-3-[-1-(2-chlorophenyl)ethoxy]thiophene-2-carboxamide In a similar manner as described for example A7, 15.69 g of methyl 5-[6-({[tert-butyl(dimethyl)silyl]oxy}methyl)-3H-imidazo[4,5-c]pyridin-3-yl]-3-[-1-(2-chlorophenyl)ethoxy]thiophene-2-carboxylate and 1.4 l of a saturated solution of ammonia in methanol yield the title compound.

$^1$H NMR (300 MHz, D$_6$-DMSO): δ=0.13 (s, 6H), 0.95 (s, 9H), 1.74 (d, J=6.3 Hz, 3H), 4.89 (s, 2H), 6.02 (q, J=6.4 Hz, 1H), 7.12 (br s, 1H), 7.33 (s, 1H), 7.36-7.51 (m, 3H), 7.69 (dd, J=1.9 Hz and 7.7 Hz, 1H), 7.74 (d, J=0.9 Hz, 1H), 7.82 (br s, 1H), 8.77 (s, 1H), 8.66 (d, J=0.9 Hz, 1H).

A17. 5-[6-({[tert-butyl(dimethyl)silyl]oxy}methyl)-1H-imidazo[4,5-c]pyridin-1-yl]-3-[(2-ethylbenzyl)oxy]thiophene-2-carboxamide In a similar manner as described for example A5, 1.0 g of methyl 5-[6-({[tert-butyl(dimethyl)silyl]oxy}methyl)-1H-imidazo[4,5-c]pyridin-1-yl]-3-[(2-ethylbenzyl)oxy]thiophene-2-carboxylate and 60 ml of a saturated solution of ammonia in methanol yield the title compound.

$^1$H NMR (300 MHz, D$_6$-DMSO): δ=0.12 (s, 6H), 0.94 (s, 9H), 1.21 (t, J=7.4 Hz, 3H), 2.75 (q, J=7.4 Hz, 2H), 4.91 (s, 2H), 5.4 (s, 2H), 6.79 (br s, 1H), 7.24-7.39 (m, 3H), 7.49-7.51 (m, 1H), 7.67 (br s, 1H), 7.80 (s, 1H), 7.83 (d, J=0.9 Hz, 1H), 8.80 (s, 1H), 9.01 (d, J=0.9 Hz, 1H).

A18. 5-[6-({[tert-butyl(dimethyl)silyl]oxy}methyl)-3H-imidazo[4,5-c]pyridin-3-yl]-3-[1-(2-fluorophenyl)ethoxy]thiophene-2-carboxamide In a similar manner as described for example A7, 10.1 g of methyl 5-[6-({[tert-butyl(dimethyl)silyl]oxy}methyl)-3H-imidazo[4,5-c]pyridin-3-yl]-3-[1-(2-fluorophenyl)ethoxy]thiophene-2-carboxylate and 950 ml of a saturated solution of ammonia in methanol yield the title compound.

$^1$H NMR (300 MHz, D$_6$-DMSO): δ=0.13 (s, 6H), 0.95 (s, 9H), 1.75 (d, J=6.4 Hz, 3H), 4.89 (s, 2H), 6.0 (q, J=6.4 Hz, 1H), 7.07 (br s, 1H), 7.22-7.28 (m, 2H), 7.37-7.45 (m, 1H), 7.59 (s, 1H), 7.61-7.67 (m, 1H), 7.75 (d, J=0.9 Hz, 1H), 7.81 (br s, 1H), 8.79 (s, 1H), 8.93 (d, J=0.9 Hz, 1H).

A19. 5-[6-({[tert-butyl(dimethyl)silyl]oxy}methyl)-1H-imidazo[4,5-c]pyridin-1-yl]-3-[(2,5-diethoxybenzyl)oxy]thiophene-2-carboxamide In a similar manner as described for example A9, 1.50 g of methyl 5-[6-({[tert-butyl(dimethyl)silyl]oxy}methyl)-1H- imidazo[4,5-c]pyridin-1-yl]-3-[(2,5-diethoxybenzyl)oxy]thiophene-2-carboxylate and 250 ml of a saturated solution of ammonia in methanol yield the title compound.

$^1$H NMR (300 MHz, D$_6$-DMSO): δ=0.11 (s, 6H), 0.93 (s, 9H), 1.23-1.30 (m, 8H), 3.92-4.06 (m, 4H), 4.50 (s, 2H), 5.30 (s, 2H), 6.88-6.92 (m, 1H), 6.97 (s, 1H), 7.00 (s, 1H), 7.09 (d, J=3.1 Hz, 1H), 7.71 (br s, 1H), 7.76 (s, 1H), 7.81 (d, J=0.8 Hz, 1H).

MS (MH+ found)=583.1

A20. 5-[6-({[tert-butyl(dimethyl)silyl]oxy}methyl)-1H-imidazo[4,5-c]pyridin-1-yl]-3-[1-(2-methylphenyl)ethoxy]thiophene-2-carboxamide In a similar manner as described for example A9, 1.25 g of methyl 5-[6-({[tert-butyl(dimethyl)silyl]oxy}methyl)-1H-imidazo[4,5-c]pyridin-1-yl]-3-[1-(2-methylphenyl)ethoxy]thiophene-2-carboxylate and 60 ml of a saturated solution of ammonia in methanol yield the title compound.

$^1$H NMR (300 MHz, D$_6$-DMSO): δ=0.11 (2 s, 6H), 0.93 (s, 9H), 1.68 (d, J=6.4 Hz, 3H), 2.40 (s, 3H), 4.87 (s, 2H), 5.83 (q, J=6.4 Hz, 1H), 7.06 (br s, 1H), 7.19-7.26 (m, 3H), 7.40 (s, 1H), 7.48-7.51 (m, 1H), 7.67 (s, 1H), 7.78 (br s, 1H), 8.70 (s, 1H), 8.89 (d, J=0.9 Hz, 1H).

MS (MH+ found)=523.1

A21. 5-[6-({[tert-butyl(dimethyl)silyl]oxy}methyl)-3H-imidazo[4,5-c]pyridin-3-yl]-3-{1-[2-(trifluoromethyl)phenyl]ethoxy}thiophene-2-carboxamide In a similar manner as described for example A7, 14.1 g of methyl 5-[6-({[tert-butyl(dimethyl)silyl]oxy}methyl)-3H-imidazo[4,5-c]pyridin-3-yl]-3-{1-[2-(trifluoromethyl)phenyl]ethoxy}thiophene-2-carboxylate and 1.6 l of a saturated solution of ammonia in methanol yield the title compound.

$^1$H NMR (300 MHz, D$_6$-DMSO): δ=0.12 (s, 6H), 0.94 (s, 9H), 1.76 (d, J=6.1 Hz, 3H), 4.88 (s, 2H), 5.99 (q, J=6.1 Hz, 1H), 7.13 (br s, 1H), 7.25 (s, 1H), 7.54-7.59 (m, 1H), 7.73-7.81 (m, 3H), 7.84 (br s, 1H), 7.96 (d, J=7.9 Hz, 1H), 8.75 (s, 1H), 8.82 (d, J=0.9 Hz, 1H).

Intermediate Compounds of Type (IIa)

B1. Methyl 5-(1H-imidazo[4,5-c]pyridin-1-yl)-3-{[2-(trifluoromethyl)benzyl]oxy}thiophene-2-carboxylate (compound B1a) and

Methyl 5-(3H-imidazo[4,5-c]pyridin-3-yl)-3-{[2-(trifluoromethyl)benzyl]oxy}thiophene-2-carboxylate (compound B1b)

In a similar manner as described for example B3, 7.92 g of an isomeric mixture of methyl 3-hydroxy-5-(1H-imidazo[4,5-c]pyridin-1-yl)thiophene-2-carboxylate and methyl 3-hydroxy-5-(3H-imidazo[4,5-c]pyridin-3-yl)thiophene-2-carboxylate (example C1) and 4.77 g of K$_2$CO$_3$ and 8.23 g of 1-(bromomethyl)-2-(trifluoromethyl)benzene in 60 ml N,N-dimethylformamide yield compound B1a and compound B1b.

Compound B1a:

$^1$H NMR (200 MHz, D$_6$-DMSO): δ=3.80 (s, 3H), 5.52 (s, 2H), 7.59-7.67 (m, 1H), 7.77-8.00 (m, 5H), 8.55 (d, J=5.7 Hz, 1H), 8.88 (s, 1H), 9.11 (s, 1H).

Compound B1b:

$^1$H NMR (200 MHz, D$_6$-DMSO): δ=3.80 (s, 3H), 5.54 (s, 2H), 7.59-7.66 (m, 1H), 7.77-7.86 (m, 4H), 7.99 (d, J=7.6 Hz, 1H), 8.54 (d, J=5.5 Hz, 1H), 8.94 (s, 1H), 9.23 (d, J=0.7 Hz, 1H).

B2. Methyl 5-[6-({[tert-butyl(dimethyl)silyl]oxy}methyl)-3H-imidazo[4,5-c]pyridin-3-yl]-3-{[2-(trifluoromethyl)benzyl]oxy}thiophene-2-carboxylate (compound B2a) and

Methyl 5-[6-({[tert-butyl(dimethyl)silyl]oxy}methyl)-1H-imidazo[4,5-c]pyridin-1-yl]-3-{[2-(trifluoromethyl)benzyl]oxy}thiophene-2-carboxylate (compound B2b)

In a similar manner as described for example B3, 2.08 g of an isomeric mixture of methyl 5-[6-({[tert-butyl(dimethyl)silyl]oxy}methyl)-3H-imidazo[4,5-c]pyridin-3-yl]-3-hydroxythiophene-2-carboxylate and methyl 5-[6-({[tert-butyl(dimethyl)silyl]oxy}methyl)-1H-imidazo[4,5-c]pyridin-1-yl]-3-hydroxythiophene-2-carboxylate (example C3) and 0.82 g of K$_2$CO$_3$ and 1.42 g of 1-(bromomethyl)-2-(trifluoromethyl)benzene in 15 ml N,N-dimethylformamide yield compound B2a and compound B2b.

Compound B2a:

$^1$H NMR (300 MHz, D$_6$-DMSO): δ=0.13 (s, 6H), 0.95 (s, 9H), 3.79 (s, 3H), 4.90 (s, 2H), 5.53 (s, 2H), 7.62 (t, J=7.7 Hz, 1H), 7.77-7.83 (m, 4H), 7.98 (d, J=7.5 Hz, 1H), 8.92 (s, 1H), 9.12 (d, J=0.9 Hz, 1H).

MS (MH$^+$ found)=577.9

Compound B2b:

$^1$H NMR (300 MHz, D$_6$-DMSO): δ=0.13 (s, 6H), 0.96 (s, 9H), 3.79 (s, 3H), 4.91 (s, 2H), 5.48 (s, 2H), 7.63 (d, J=7.7 Hz, 1H), 7.78-7.83 (m, 3H), 7.90 (d, J=0.7 Hz, 1H), 7.98 (d, J=7.7 Hz, 1H), 8.91 (s, 1H), 9.01 (d, J=0.7 Hz, 1H).

MS (MH$^+$ found)=578.0

B3. Methyl 5-(6-chloro-1H-imidazo[4,5-c]pyridin-1-yl)-3-{[2-(trifluoromethyl)benzyl]oxy}thiophene-2-carboxylate (compound B3a) and

Methyl 5-(6-chloro-3H-imidazo[4,5-c]pyridin-3-yl)-3-{[2-(trifluoromethyl)benzyl]oxy}thiophene-2-carboxylate (compound B3b)

To a solution of 557 mg of an isomeric mixture of methyl 5-(6-chloro-1H-imidazo[4,5-c]pyridin-1-yl)-3-hydroxythiophene-2-carboxylate and methyl 5-(6-chloro-3H-imidazo[4,5-c]pyridin-3-yl)-3-hydroxythiophene-2-carboxylate (example C2) in 25 ml anhydrous N,N-dimethylformamide were added 248 mg K$_2$CO$_3$ and 428 mg 1-(bromomethyl)-2-(trifluoromethyl)benzene under a nitrogen atmosphere. The reaction mixture was stirred for 12 h at room temperature, poured into 500 ml of ice water, then 40 ml of a saturated solution of KCl were added and the mixture was allowed to stand for 12 h at 0° C. The resulting solid was filtered and washed with water. The filter cake was dissolved in dichloromethane, the organic layer was washed with water, dried with MgSO$_4$ and concentrated under vacuum. The isomeric mixture was separated and purified by flash chromatography [(Silicagel, hexane/ethylacetate (7/3 v/v)]. The separated isomers were crystallized from dichloromethane/hexane to yield compound B3a and compound B3b. The structural assignment of the regioisomers was unequivocally established by two-dimensional $^1$H NMR experiments (NOESY, COSY).

Compound B3a:

$^1$H NMR (400 MHz, D$_6$-DMSO): δ=3.80 (s, 3H), 5.53 (s, 2H), 7.63 (t, J=7.7 Hz, 1H), 7.78-7.83 (m, 3H), 7.91-7.98 (m, 2H), 8.88 (s, 1H), 8.92 (s, 1H).

Compound B3b:
 $^1$H NMR (400 MHz, D$_6$-DMSO): δ=3.80 (s, 3H), 5.53 (s, 2H), 7.63 (t, J=7.6 Hz, 1H), 7.78-7.82 (m, 3H), 7.98-7.99 (m, 2H), 9.01 (s, 1H), 9.02 (s, 1H).

B4. Methyl 5-(5,6-dimethoxy-1H-imidazo[4,5-b] pyridin-1-yl)-3-{[2-(trifluoromethyl)benzyl] oxy}thiophene-2-carboxylate (compound B4a) and

Methyl 5-(5,6-dimethoxy-3H-imidazo[4,5-b]pyridin-3-yl)-3-{[2-(trifluoromethyl)benzyl]oxy}thiophene-2-carboxylate (compound B4b)

To a solution of an isomeric mixture of 1.76 g of methyl 5-(5,6-dimethoxy-1H-imidazo[4,5-b]pyridin-1-yl)-3-hydroxythiophene-2-carboxylate and methyl 5-(5,6-dimethoxy-3H-imidazo[4,5-b]pyridin-3-yl)-3-hydroxythiophene-2-carboxylate (example C7) in 20 ml anhydrous N,N-dimethylformamide were added 0.86 g K$_2$CO$_3$ and 1.51 g of 1-(bromomethyl)-2-(trifluoromethyl)benzene under a nitrogen atmosphere. The reaction mixture was stirred for 12 h at room temperature, poured into 200 ml of ice water and stirred for 1 h. The solid was filtered, dissolved in acetonitrile and the isomeric mixture was separated and purified by preparative HPLC to yield compound B4a and compound B4b. The structural assignment of compound B4a was unequivocally established by two-dimensional $^1$H NMR experiments (NOESY, COSY).
Compound B4a:
 $^1$H NMR (400 MHz, D$_6$-DMSO): δ=3.79 (s, 3H), 3.90 (s, 3H), 3.96 (s, 3H), 5.53 (s, 2H), 7.60-7.65 (m, 2H), 7.70 (s, 1H), 7.78-7.83 (m, 2H), 7.97 (d, J=7.7 Hz, 1H), 8.80 (s, 1H).
 MS (MH$^+$ found)=494.1
Compound B4b:
 MS (MH$^+$ found)=494.1

B5. Methyl 5-(1H-imidazo[4,5-b]pyridin-1-yl)-3-{[2-(trifluoromethyl)benzyl]oxy}thiophene-2-carboxylate (compound B5a) and

Methyl 5-(3H-imidazo[4,5-b]pyridin-3-yl)-3-{[2-(trifluoromethyl)benzyl]oxy}thiophene-2-carboxylate (compound B5b)

In a similar manner as described for example B3, 12.49 g of an isomeric mixture of methyl 3-hydroxy-5-(1H-imidazo[4,5-b]pyridin-1-yl)thiophene-2-carboxylate and methyl 3-hydroxy-5-(3H-imidazo[4,5-b]pyridin-3-yl)thiophene-2-carboxylate (example C8) and 7.45 g of K$_2$CO$_3$ and 12.91 g of 1-(bromomethyl)-2-(trifluoromethyl)benzene in 200 ml N,N-dimethylformamide yield compound B5a and compound B5b.
Compound B5a:
 $^1$H NMR (400 MHz, D$_6$-DMSO): δ=3.79 (s, 3H), 5.52 (s, 2H), 7.48 (dd, J=4.7 and 8.2 Hz, 1H), 7.63 (t, J=7.7 Hz, 1H), 7.80-7.84 (m, 3H), 7.98 (d, J=7.7 Hz, 1H), 8.33 (dd, J=1.4 and 8.2 Hz, 1H), 8.58 (dd, J=1.4 and 4.7 Hz, 1H), 9.25 (s, 1H).
 MS (MH$^+$ found)=434.1
Compound B5b:
 $^1$H NMR (400 MHz, D$_6$-DMSO): δ=3.79 (s, 3H), 5.49 (s, 2H), 7.49 (dd, J=4.8 and 8.1 Hz, 1H), 7.63 (t, J=7.7 Hz, 1H), 7.79-7.84 (m, 2H), 7.94 (s, 1H), 8.01 (d, J=7.1 Hz, 1H), 8.28 (dd, J=0.8 and 8.0 Hz, 1H), 8.56 (d, J=4.8 Hz, 1H), 9.25 (s, 1H).
 MS (MH$^+$ found)=434.1

B6. Methyl 5-(6-methoxy-3H-imidazo[4,5-c]pyridin-3-yl)-3-{[2-(trifluoromethyl)benzyl]oxy}thiophene-2-carboxylate (compound B6a) and

Methyl 5-(6-methoxy-1H-imidazo[4,5-c]pyridin-1-yl)-3-{[2-(trifluoromethyl)benzyl]oxy}thiophene-2-carboxylate (compound B6b)

To a solution of 1.20 g of an isomeric mixture of methyl 3-hydroxy-5-(6-methoxy-3H-imidazo[4,5-c]pyridin-3-yl) thiophene-2-carboxylate and methyl 3-hydroxy-5-(6-methoxy-1H-imidazo[4,5-c]pyridin-1-yl)thiophene-2-carboxylate (example C6) in 15 ml anhydrous N,N-dimethylformamide were added 0.65 g of K$_2$CO$_3$ and 1.12 g of 1-(bromomethyl)-2-(trifluoromethyl)benzene under a nitrogen atmosphere. The reaction mixture was stirred for 12 h at room temperature and poured into 400 ml of ice water. The resulting solid was filtered, washed with water and dried under vacuum to give the crude title compounds as an isomeric mixture. The isomeric mixture was used for the next steps (examples 16, 17 and 18) without further purification.
 MS (MH$^+$ found)=464.1

B7. Methyl 5-(5-methoxy-1H-imidazo[4,5-b]pyridin-1-yl)-3-{[2-(trifluoromethyl)benzyl] oxy}thiophene-2-carboxylate (Compound B7a) and

Methyl 5-(5-methoxy-3H-imidazo[4,5-b]pyridin-3-yl)-3-{[2-(trifluoromethyl)benzyl]oxy}thiophene-2-carboxylate (Compound B7b)

In a similar manner as described for example B3, 1.4 g of an isomeric mixture of methyl 3-hydroxy-5-(5-methoxy-1H-imidazo[4,5-b]pyridin-1-yl)thiophene-2-carboxylate and methyl 3-hydroxy-5-(5-methoxy-3H-imidazo[4,5-b]pyridin-3-yl)thiophene-2-carboxylate (example C9) and 0.76 g K$_2$CO$_3$ and 1.31 g 1-(bromomethyl)-2-(trifluoromethyl)benzene in 20 ml N,N-dimethylformamide yield compound B7a and compound B7b as crude material. These compounds were used for the next step (examples 22 and 23) without further purification.
 LC-MS (MH$^+$ found)=464.1 (compound B7a and B7b)

B8. Methyl 5-{6-[(2-methoxyethyl)carbamoyl]-1H-imidazo[4,5-c]pyridin-1-yl}-3-{[2-(trifluoromethyl) benzyl]oxy}thiophene-2-carboxylate To a solution of 1.5 g of methyl 3-hydroxy-5-{6-[(2-methoxyethyl)carbamoyl]-1H-imidazo[4,5-c]pyridin-1-yl}thiophene-2-carboxylate (compound C5) in 10 ml anhydrous N,N-dimethylformamide were added 610 mg K$_2$CO$_3$ and 1.14 g 1-(bromomethyl)-2-(trifluoromethyl)benzene under a nitrogen atmosphere. The reaction mixture was stirred for 12 h at room temperature, poured into 400 ml of ice water and the resulting precipitate was filtered. The filter cake was washed with water, dissolved in 300 ml ethyl acetate and washed with 50 ml saturated aqueous KCl solution. The organic layer was separated, dried with MgSO$_4$ and concentrated under vacuum. The residue was crystallized from methanol to yield the title compound.
 $^1$H NMR (200 MHz, D$_6$-DMSO): δ=3.31 (s, 3H), 3.52 (m, 4H), 3.81 (s, 3H), 5.51 (s, 2H), 7.59-7.67 (m, 1H), 7.78-7.85 (m, 2H), 7.89 (s, 1H), 8.0 (d, J=7.9 Hz, 1H), 8.42 (s, 1H), 8.80 (bs, 1H), 9.02 (s, 1H), 9.15 (s, 1H).
 LC-MS (MH$^+$ found)=535.0

B9. Methyl 5-{6-[(2-morpholin-4-ylethyl)carbamoyl]-1H-imidazo[4,5-c]pyridin-1-yl}-3-{[2-(trifluoromethyl)benzyl]oxy}thiophene-2-carboxylate In a similar manner as described for example B8, 1.03 g of methyl 3-hydroxy-5-{6-[(2-morpholin-4-ylethyl)carbamoyl]-1H-imidazo[4,5-c]pyridin-1-yl}thiophene-2-carboxylate (compound C4), 326 mg $K_2CO_3$ and 683 mg 1-(bromomethyl)-2-(trifluoromethyl)benzene in 11 ml of N,N-dimethylformamide yield the title compound as crude material. The compound was used for the next step (examples 5 and 11) without further purification.

MS ($MH^+$ found)=590.1

B10. Methyl 5-[6-({[tert-butyl(dimethyl)silyl]oxy}methyl)-1H-imidazo[4,5-c]pyridin-1-yl]-3-{(1R)-1-[2-(trifluoromethyl)phenyl]ethoxy}thiophene-2-carboxylate Under a nitrogen atmosphere, 4.45 g of methyl 5-[6-({[tert-butyl(dimethyl)silyl]oxy}methyl)-1H-imidazo[4,5-c]pyridin-1-yl]-3-hydroxythiophene-2-carboxylate and 3.02 g of (1S)-1-[2-(trifluoromethyl)phenyl]ethanol are dissolved in 140 ml anhydrous dichloromethane. 7.07 g triphenylphosphine (polymer bound, ~3 mmol/g) and 4.88 g of di-tert-butyl azodicarboxylate are added. The reaction mixture is stirred at room temperature for 90 minutes and then filtered. The filter cake is washed with 10 ml dichloromethane and 10 ml methanol. The filtrate is concentrated to dryness under reduced pressure.

The crude is purified by flash chromatography [silica gel, eluent: ethyl acetate/cyclohexane, elution gradient of 0/100 (v/v) to 60/40 (v/v) to yield the title product.

$^1$H NMR (300 MHz, D6-DMSO): δ=0.12 (2s, 6H), 0.95 (s, 9H), 1.66 (d, J=6.0 Hz, 3H), 3.84 (s, 3H), 4.89 (s, 2H), 5.93 (q, J=6.0 Hz, 1H), 7.52-7.58 (m, 2H), 7.71-7.82 (m, 3H), 8.04 (d, J=7.9 Hz, 1H), 8.79 (s, 1H), 9.00 (d, J=0.9 Hz, 1H).

MS (MH+ found)=592.1

B11. Methyl 5-(3H-imidazo[4,5-c]pyridin-3-yl)-3-{[2-(trifluoromethoxy)benzyl]oxy}thiophene-2-carboxylate 110 mg of 2-(trifluoromethoxy)benzyl bromide is added to a mixture of 100 mg of methyl 3-hydroxy-5-(3H-imidazo[4,5-c]pyridin-3-yl)thiophene-2-carboxylate and 59.7 mg of potassium carbonate in 3 ml anhydrous DMF. The mixture is stirred for 14 h at room temperature. Ice water is added and the organic phase is extracted with dichloromethane. The organic phase is poured on a phase separator and the solvent is removed under vacuum. The residue is dissolved in ethyl acetate and filtered through a short plug of silica gel (eluent: ethyl acetate) to yield the title compound.

$^1$H NMR (400 MHz, $D_6$-DMSO): δ=3.79 (s, 3H), 5.46 (s, 2H), 7.47-7.55 (m, 3H), 7.82-7.85 (m, 3H), 8.53 (d, 5.5 Hz, 1H), 8.92 (s, 1H), 9.22 (d, J=0.7 Hz, 1H).

MS ($MH^+$ found)=450.0

B12. Methyl 5-(3H-imidazo[4,5-c]pyridin-3-yl)-3-{[3-(trifluoromethyl)benzyl]oxy}thiophene-2-carboxylate In a similar manner as described for example B11, 102.8 mg of 3-(trifluoromethyl)benzyl bromide, 100 mg of methyl 3-hydroxy-5-(3H-imidazo[4,5-c]pyridin-3-yl)thiophene-2-carboxylate, 59.7 mg of potassium carbonate in 3 ml anhydrous DMF yield the title compound.

$^1$H NMR (400 MHz, $D_6$-DMSO): δ=3.82 (s, 3H), 5.53 (s, 2H), 7.67-7.75 (m, 2H), 7.79-7.82 (m, 2H), 7.84 (dd, J=0.7 Hz and 5.5 Hz, 1H), 7.93 (s, 1H), 8.53 (d, J=5.7 Hz, 1H), 8.90 (s, 1H), 9.21 (d, J=0.6 Hz, 1H).

MS ($MH^+$ found)=433.9

B13. Methyl 5-(3H-imidazo[4,5-c]pyridin-3-yl)-3-{[4-(trifluoromethyl)benzyl]oxy}thiophene-2-carboxylate In a similar manner as described for example B11, 102.8 mg of 4-(trifluoromethyl)benzyl bromide, 100 mg of methyl 3-hydroxy-5-(3H-imidazo[4,5-c]pyridin-3-yl)thiophene-2-carboxylate, 59.7 mg of potassium carbonate in 3 ml anhydrous DMF yield the title compound.

$^1$H NMR (300 MHz, $D_6$-DMSO): δ=3.82 (s, 3H), 5.54 (s, 2H), 7.72-7.85 (m, 6H), 8.53 (d, J=5.5 Hz, 1H), 8.90 (s, 1H), 9.20 (d, J=1.1 Hz, 1H).

MS ($MH^+$ found)=433.9

B14. Methyl 5-(1H-imidazo[4,5-c]pyridin-1-yl)-3-{[2-(trifluoromethoxy)benzyl]oxy}thiophene-2-carboxylate 110 mg of 2-(trifluoromethoxy)benzyl bromide is added to a mixture of 100 mg of methyl 3-hydroxy-5-(1H-imidazo[4,5-c]pyridin-1-yl)thiophene-2-carboxylate and 59.7 mg of potassium carbonate in 3 ml anhydrous DMF. The mixture is stirred for 14 h at room temperature. Ice water is added and the organic phase is extracted with dichloromethane. The organic phase is poured on a phase separator and the solvent is removed under vacuum. The residue is dissolved in 2 ml of dichloromethane and filtered through a short plug of silica gel (eluent: hexane/ethyl acetate 1/1 (v/v) to 0/100 (v/v)) to yield the title compound.

$^1$H NMR (300 MHz, $D_6$-DMSO): δ=3.78 (s, 3H), 5.43 (s, 2H), 7.43-7.58 (m, 3H), 7.81-7.84 (m, 2H), 7.90 (dd, J=1.1 Hz and 5.6 Hz, 1H), 8.54 (d, J=5.6 Hz, 1H), 8.86 (s, 1H), 9.11 (d, J=0.8 Hz, 1H).

MS ($MH^+$ found)=449.9

B15. Methyl 3-{[4-fluoro-2-(trifluoromethyl)benzyl]oxy}-5-(1H-imidazo[4,5-c]pyridin-1-yl)thiophene-2-carboxylate In a similar manner as described for example B14, 110.5 mg of 4-fluoro-2-(trifluoromethyl)benzyl bromide, 100 mg of methyl 3-hydroxy-5-(1H-imidazo[4,5-c]pyridin-1-yl)thiophene-2-carboxylate, 59.7 mg of potassium carbonate in 3 ml anhydrous DMF yield the title compound.

$^1$H NMR (300 MHz, $D_6$-DMSO): δ=3.79 (s, 3H), 5.48 (s, 2H), 7.66-7.75 (m, 2H), 7.80 (s, 1H), 7.91 (dd, J=1.1 Hz and 5.6 Hz, 1H), 8.00-8.04 (m, 1H), 8.55 (d, J=5.5 Hz, 1H), 8.87 (s, 1H), 9.11 (d, J=0.9 Hz, 1H).

MS ($MH^+$ found)=451.9

B16. Methyl 5-(1H-imidazo[4,5-c]pyridin-1-yl)-3-{[3-(trifluoromethyl)benzyl]oxy}thiophene-2-carboxylate In a similar manner as described for example B14, 102.8 mg of 3-(trifluoromethyl)benzyl bromide, 100 mg of methyl 3-hydroxy-5-(1H-imidazo[4,5-c]pyridin-1-yl)thiophene-2-carboxylate, 59.7 mg of potassium carbonate in 3 ml anhydrous DMF yield the title compound.

¹H NMR (300 MHz, D₆-DMSO): δ=3.80 (s, 3H), 5.51 (s, 2H), 7.66-7.82 (m, 4H), 7.87 (dd, J=1.1 Hz and 5.6 Hz, 1H), 7.93 (br s, 1H), 8.00-8.04 (m, 1H), 8.55 (d, J=5.5 Hz, 1H), 8.84 (s, 1H), 9.11 (d, J=1.0 Hz, 1H).
MS (MH⁺ found)=434.0

B17. Methyl 5-(1H-imidazo[4,5-c]pyridin-1-yl)-3-{[4-(trifluoromethyl)benzyl]oxy}thiophene-2-carboxylate In a similar manner as described for example B14, 102.8 mg of 4-(trifluoromethyl)benzyl bromide, 100 mg of methyl 3-hydroxy-5-(1H-imidazo[4,5-c]pyridin-1-yl)thiophene-2-carboxylate, 59.7 mg of potassium carbonate in 3 ml anhydrous DMF yield the title compound.
¹H NMR (300 MHz, D₆-DMSO): δ=3.82 (s, 3H), 5.52 (s, 2H), 7.73-7.75 (m, 3H), 7.81-7.83 (m, 2H), 7.87 (dd, J=0.9 Hz and 5.7 Hz, 1H), 8.53 (d, J=5.7 Hz, 1H), 8.83-8.84 (m, 1H), 9.11 (d, J=0.9 Hz, 1H).
MS (MH⁺ found)=433.9

B18. Methyl 3-{[2-(difluoromethoxy)benzyl]oxy}-5-(3H-imidazo[4,5-c]pyridin-3-yl)thiophene-2-carboxylate 207.7 mg of 2-(difluoromethoxy)benzyl bromide is added to a mixture of 200 mg of methyl 3-hydroxy-5-(3H-imidazo[4,5-c]pyridin-3-yl)thiophene-2-carboxylate and 110.9 mg of potassium carbonate in 6 ml anhydrous DMF. The mixture is stirred for 14 h at room temperature. Additional 207.7 mg of 2-(Difluoromethoxy)benzyl bromide and 110.9 mg of potassium carbonate are added and the mixture is stirred at 75° C. for 3 h. Ice water is added to the mixture at room temperature and the organic phase is extracted with dichloromethane. The organic phase is poured on a phase separator and the solvent is removed under vacuum. The residue is dissolved in ethyl acetate and purified by flash column chromatography (eluent: hexane/ethyl acetate 1/1 (v/v) to 0/100 (v/v)) to yield the title compound.
¹H NMR (300 MHz, D₆-DMSO): δ=3.79 (s, 3H), 5.42 (s, 2H), 7.25-7.30 (m, 2H), 7.36 (td, J=1.1 Hz and 7.5 Hz, 1H), 7.46-7.51 (m, 1H), 7.73 (dd, J=1.6 Hz and 7.6 Hz, 1H), 7.83-7.85 (m, 2H), 8.53 (d, J=5.5 Hz, 1H), 8.93 (s, 1H), 9.23 (d, J=1.1 Hz, 1H).
MS (MH⁺ found)=432.0

B19. Methyl 3-[(2-cyanobenzyl)oxy]-5-(1H-imidazo[4,5-c]pyridin-1-yl)thiophene-2-carboxylate In a similar manner as described for example B18, 171.7 mg of 2-(bromomethyl)benzonitrile, 200 mg of methyl 3-hydroxy-5-(3H-imidazo[4,5-c]pyridin-3-yl)thiophene-2-carboxylate, 110.9 mg of potassium carbonate in 6 ml anhydrous DMF yield the title compound.
¹H NMR (300 MHz, D₆-DMSO): δ=3.79 (s, 3H), 5.55 (s, 2H), 7.60 (td, J=1.7 Hz and 7.4 Hz, 1H), 7.78-7.87 (m, 3H), 7.90-7.96 (m, 2H), 8.55 (d, J=5.7 Hz, 1H), 8.87 (s, 1H), 9.11 (d, J=0.9 Hz, 1H).
MS (MH⁺ found)=391.0

B20. Methyl 3-[(2-fluorobenzyl)oxy]-5-(1H-imidazo[4,5-c]pyridin-1-yl)thiophene-2-carboxylate In a similar manner as described for example B11, 172 mg of 1-(bromomethyl)-2-fluorobenzene, 200 mg of methyl 3-hydroxy-5-(1H-imidazo[4,5-c]pyridin-1-yl)thiophene-2-carboxylate, 121 mg of potassium carbonate in 5 ml anhydrous DMF yield the title compound.
¹H NMR (300 MHz, D₆-DMSO): δ=3.78 (s, 3H), 5.46 (s, 2H), 7.25-7.32 (m, 2H), 7.42-7.50 (m, 1H), 7.66-7.72 (m, 1H), 7.83-7.85 (m, 2H), 8.53 (d, J=5.7 Hz, 1H), 8.92 (s, 1H), 9.23 (d, J=0.9 Hz, 1H).
MS (MH⁺ found)=384.0

B21. Methyl 3-{[4-fluoro-2-(trifluoromethyl)benzyl]oxy}-5-(3H-imidazo[4,5-c]pyridin-3-yl)thiophene-2-carboxylate In a similar manner as described for example B11, 110.5 mg of 4-fluoro-2-(trifluoromethyl)benzyl bromide, 100 mg of methyl 3-hydroxy-5-(3H-imidazo[4,5-c]pyridin-3-yl)thiophene-2-carboxylate, 59.7 mg of potassium carbonate in 3 ml anhydrous DMF yield the title compound.
¹H NMR (300 MHz, D₆-DMSO): δ=3.79 (s, 3H), 5.51 (s, 2H), 7.66-7.75 (m, 2H), 7.84-7.85 (m, 2H), 8.00-8.05 (m, 1H), 8.53 (d, J=5.4 Hz, 1H), 8.93 (s, 1H), 9.23 (d, J=0.9 Hz, 1H).
MS (MH⁺ found)=452.0

B22. Methyl 3-{[2-(difluoromethoxy)benzyl]oxy}-5-(1H-imidazo[4,5-c]pyridin-1-yl)thiophene-2-carboxylate In a similar manner as described for example B18, 207.7 mg of 2-(difluoromethoxy)benzyl bromide, 200 mg of methyl 3-hydroxy-5-(1H-imidazo[4,5-c]pyridin-1-yl)thiophene-2-carboxylate, 110.9 mg of potassium carbonate in 6 ml anhydrous DMF yield the title compound.
¹H NMR (300 MHz, D₆-DMSO): δ=3.78 (s, 3H), 5.40 (s, 2H), 7.25-7.38 (m, 3H), 7.46-7.51 (m, 1H), 7.73 (dd, J=1.6 Hz and 7.4 Hz, 1H), 7.79 (s, 1H), 7.91 (dd, J=1.1 Hz and 5.6 Hz, 1H), 8.54 (d, J=5.7 Hz, 1H), 8.87 (s, 1H), 9.11 (d, J=0.8 Hz, 1H).
MS (MH⁺ found)=432.0

B23. Methyl 3-[(2,6-dichlorobenzyl)oxy]-5-(3H-imidazo[4,5-c]pyridin-3-yl)thiophene-2-carboxylate In a similar manner as described for example B11, 103.5 mg of 2,6-dichlorobenzyl bromide, 100 mg of methyl 3-hydroxy-5-(3H-imidazo[4,5-c]pyridin-3-yl)thiophene-2-carboxylate, 59.7 mg of potassium carbonate in 3 ml anhydrous DMF yield the title compound.
¹H NMR (400 MHz, D₆-DMSO): δ=3.72 (s, 3H), 5.55 (s, 2H), 7.49-7.53 (m, 1H), 7.59-7.62 (m, 2H), 7.85 (dd, J=0.9 Hz and 5.5 Hz, 1H), 7.91 (s, 1H), 8.54 (d, J=5.6 Hz, 1H), 8.94 (s, 1H), 9.11 (d, J=0.6 Hz, 1H).
MS (MH⁺ found)=433.9

B24. Methyl 5-[6-({[tert-butyl(dimethyl)silyl]oxy}methyl)-3H-imidazo[4,5-c]pyridin-3-yl]-3-{(1R)-1-[2-(trifluoromethyl)phenyl]ethoxy}thiophene-2-carboxylate In a similar manner as described for example B31, 7.3 g of methyl 5-[6-({[tert-butyl(dimethyl)silyl]oxy}methyl)-3H-imidazo[4,5-c]pyridin-3-yl]-3-hydroxythiophene-2-carboxylate, 5.0 g of (1S)-1-[2-(trifluoromethyl)phenyl]ethanol, 9.2 g of triphenylphosphine (polymer bound, ~3 mmol/g) and 8.1 g of di-tert-butyl azodicarboxylate in 180 ml anhydrous dichloromethane yield the title compound.
¹H NMR (300 MHz, D₆-DMSO): δ=0.13 (s, 6H), 0.95 (s, 9H), 1.66 (d, J=6.2 Hz, 3H), 3.85 (s, 3H), 4.89 (s, 2H), 6.02 (q, J=6.2 Hz, 1H), 7.52-7.57 (m, 2H), 7.72-7.81 (m, 3H), 8.02 (d, J=7.8 Hz, 1H), 8.83 (s, 1H), 8.92 (s, 1H).
MS (MH+ found)=592.0

B25. Methyl 5-[6-({[tert-butyl(dimethyl)silyl]oxy}methyl)-1H-imidazo[4,5-c]pyridin-1-yl]-3-{1-[2-(trifluoromethyl)phenyl]ethoxy}thiophene-2-carboxylate (compound B25a) and methyl 5-[6-({[tert-butyl(dimethyl)silyl]oxy}methyl)-3H-imidazo[4,5-c]pyridin-3-yl]-3-{1-[2-(trifluoromethyl)phenyl]ethoxy}thiophene-2-carboxylate (compound B25b)

In a similar manner as described for example B3, 8.0 g of an isomeric mixture of methyl 5-[6-({[tert-butyl(dimethyl)silyl]oxy}methyl)-3H-imidazo[4,5-c]pyridin-3-yl]-3-hydroxythiophene-2-carboxylate and methyl 5-[6-({[tert-butyl(dimethyl)silyl]oxy}methyl)-1H-imidazo[4,5-c]pyridin-1-yl]-3-hydroxythiophene-2-carboxylate (example C3) and 3.15 g of $K_2CO_3$ and 5.95 g of 1-(1-bromoethyl)-2-(trifluoromethyl)benzene in 240 ml anhydrous N,N-dimethylformamide yield compound B25a and compound B25b.
Compound B25a:
$^1$H NMR (300 MHz, $D_6$-DMSO): δ=0.11 (s, 6H), 0.95 (s, 9H), 1.66 (d, J=6.1 Hz, 3H), 3.84 (s, 3H), 4.89 (s, 2H), 5.93 (q, J=6.1 Hz, 1H), 7.53-7.58 (m, 2H), 7.74-7.85 (m, 3H), 8.03 (d, J=7.8 Hz, 1H), 8.80 (s, 1H), 9.00 (s, 1H).
MS (MH+ found)=592.1
Compound B25b:
$^1$H NMR (300 MHz, $D_6$-DMSO): δ=0.12 (s, 6H), 0.94 (s, 9H), 1.66 (d, J=6.1 Hz, 3H), 3.84 (s, 3H), 4.91 (s, 2H), 6.02 (q, J=6.1 Hz, 1H), 7.51-7.57 (m, 2H), 7.72-7.81 (m, 3H), 8.01 (d, J=7.9 Hz, 1H), 8.82 (s, 1H), 8.92 (s, 1H).
MS (MH+ found)=592.1

B26. Methyl 5-[6-({[tert-butyl(dimethyl)silyl]oxy}methyl)-1H-imidazo[4,5-c]pyridin-1-yl]-3-{(1S)-1-[2-(trifluoromethyl)phenyl]ethoxy}thiophene-2-carboxylate In a similar manner as described for example B31, 441 mg of methyl 5-[6-({[tert-butyl(dimethyl)silyl]oxy}methyl)-1H-imidazo[4,5-c]pyridin-1-yl]-3-hydroxythiophene-2-carboxylate, 300 mg of (1R)-1-[2-(trifluoromethyl)phenyl]ethanol, 672 mg of triphenylphosphine (polymer bound, ~3 mmol/g) and 484 mg of di-tert-butyl azodicarboxylate in 12 ml anhydrous dichloromethane yield the title compound.
$^1$H NMR (300 MHz, $D_6$-DMSO): δ=0.12 (s, 6H), 0.94 (s, 9H), 1.66 (d, J=6.1 Hz, 3H), 3.84 (s, 3H), 4.89 (s, 2H), 5.93 (q, J=6.1 Hz, 1H), 7.51-7.57 (m, 2H), 7.71-7.82 (m, 3H), 8.03 (d, J=7.8 Hz, 1H), 8.80 (s, 1H), 8.99 (s, 1H).
MS (MH+ found)=592.1

B27. Methyl 3-[(1R)-2-{[tert-butyl(dimethyl)silyl]oxy}-1-(2-chlorophenyl)ethoxy]-5-[6-({[tert-butyl(dimethyl)silyl]oxy}methyl)-1H-imidazo[4,5-c]pyridin-1-yl]thiophene-2-carboxylate In a similar manner as described for example B31, 0.5 g of methyl 5-[6-({[tert-butyl(dimethyl)silyl]oxy}methyl)-1H-imidazo[4,5-c]pyridin-1-yl]-3-hydroxythiophene-2-carboxylate, 0.44 g of (1S)-2-{[tert-butyl(dimethyl)silyl]oxy}-1-(2-chlorophenyl)ethanol (synthesized starting from (S)-(+)-2-chloromandelic acid in a two step sequence including reduction with $LiAlH_4$ and protection of the primary hydroxy group using tert-butyldimethylsilylchloride), 0.63 g of triphenylphosphine (polymer bound, ~3 mmol/g) and 0.55 g of di-tert-butyl azodicarboxylate in 10 ml anhydrous dichloromethane yield the title compound.
$^1$H NMR (300 MHz, $D_6$-DMSO): δ=−0.02 (s, 6H), 0.12 (s, 6H), 0.75-0.77 (t, J=2.9 Hz, 9H), 0.95-0.96 (t, J=2.9 Hz, 9H), 3.84 (s, 3H), 3.91-4.03 (m, 2H), 4.90 (s, 2H), 5.89-5.93 (m, 1H), 7.34-7.50 (m, 3H), 7.57 (s, 1H), 7.74-7.82 (m, 1H), 7.82 (s, 1H), 8.82 (s, 1H), 9.00 (d, J=0.9 Hz, 1H).
MS (MH+ found)=688.0

B28. Methyl 5-[6-({[tert-butyl(dimethyl)silyl]oxy}methyl)-1H-imidazo[4,5-c]pyridin-1-yl]-3-[(2,5-diethoxybenzyl)oxy]thiophene-2-carboxylate In a similar manner as described for example B31, 1.5 g of methyl 5-[6-({[tert-butyl(dimethyl)silyl]oxy}methyl)-1H-imidazo[4,5-c]pyridin-1-yl]-3-hydroxythiophene-2-carboxylate, 0.91 g of (2,5-diethoxyphenyl)methanol, 2.4 g of triphenylphosphine (polymer bound, ~3 mmol/g) and 1.66 g of di-tert-butyl azodicarboxylate in 40 ml anhydrous dichloromethane yield the title compound.
$^1$H NMR (300 MHz, $D_6$-DMSO): δ=0.13 (s, 6H), 0.96 (t, 9H), 1.26-1.33 (m, 6H), 3.78 (s, 3H), 3.95-4.06 (m, 4H), 4.91 (s, 2H), 5.28 (s, 2H), 6.87 (dd, J=3.1 Hz and 8.9 Hz, 1H), 6.96 (d, J=8.9 Hz, 1H), 7.17 (d, J=3.0 Hz, 1H), 7.78 (s, 1H), 7.91 (d, J=0.8 Hz, 1H), 8.91 (s, 1H), 9.01 (d, J=0.9 Hz, 1H).
MS (MH+ found)=598.0

B29. Methyl 5-[6-({[tert-butyl(dimethyl)silyl]oxy}methyl)-1H-imidazo[4,5-c]pyridin-1-yl]-3-[-1-(2-chloro-4-cyanophenyl)ethoxy]thiophene-2-carboxylate In a similar manner as described for example B31, 1.42 g of methyl 5-[6-({[tert-butyl(dimethyl)silyl]oxy}methyl)-1H-imidazo[4,5-c]pyridin-1-yl]-3-hydroxythiophene-2-carboxylate, 0.8 g of 3-chloro-4-(1-hydroxyethyl)benzonitrile, 2.26 g of triphenylphosphine (polymer bound, ~3 mmol/g) and 1.56 g of di-tert-butyl azodicarboxylate in 40 ml anhydrous dichloromethane yield the title compound.
$^1$H NMR (300 MHz, $D_6$-DMSO): δ=0.12 (s, 6H), 0.95 (s, 9H), 1.65 (d, J=6.3 Hz, 3H), 3.84 (s, 3H), 4.90 (s, 2H), 5.96 (q, J=6.3 Hz, 1H), 7.67 (s, 1H), 7.84 (d, J=0.8 Hz, 1H), 7.94-8.00 (m, 2H), 8.10 (d, J=0.6 Hz, 1H), 8.85 (s, 1H), 9.00 (d, J=0.9 Hz, 1H).
MS (MH+ found)=583.0

B30. Methyl 5-[6-({[tert-butyl(dimethyl)silyl]oxy}methyl)-1H-imidazo[4,5-c]pyridin-1-yl]-3-[1-(2-methylphenyl)ethoxy]thiophene-2-carboxylate In a similar manner as described for example B31, 1.50 g of methyl 5-[6-({[tert-butyl(dimethyl)silyl]oxy}methyl)-1H-imidazo[4,5-c]pyridin-1-yl]-3-hydroxythiophene-2-carboxylate, 0.63 g of 1-(2-methylphenyl)ethanol, 2.4 g of triphenylphosphine (polymer bound, ~3 mmol/g) and 1.66 g of di-tert-butyl azodicarboxylate in 40 ml anhydrous dichloromethane yield the title compound.
$^1$H NMR (300 MHz, $D_6$-DMSO): δ=0.2 (s, 6H), 0.95 (s, 9H), 1.60 (d, J=6.3 Hz, 3H), 2.40 (s, 3H), 3.82 (s, 3H), 4.89 (s, 2H), 5.86 (q, J=6.3 Hz, 1H), 7.18-7.27 (m, 3H), 7.58-7.61 (m, 1H), 7.63 (s, 1H), 7.80 (d, J=0.8 Hz, 1H), 8.83 (s, 1H), 9.00 (d, J=0.9 Hz, 1H).
MS (MH+ found)=538.0

B31. Methyl 5-[6-({[tert-butyl(dimethyl)silyl]oxy}methyl)-1H-imidazo[4,5-c]pyridin-1-yl]-3-{1-[4-fluoro-2-(trifluoromethyl)phenyl]ethoxy}thiophene-2-carboxylate Under a nitrogen atmosphere, 2.1 g of methyl 5-[6-({[tert-butyl(dimethyl)silyl]oxy}methyl)-1H-imidazo[4,5-c]pyridin-1-yl]-3-hydroxythiophene-2-carboxylate are dissolved in 60 ml anhydrous dichloromethane. Consecutively, 1.56 g of 1-[4-fluoro-2-(trifluoromethyl)phenyl]ethanol, 3.3 g triphenylphosphine (polymer bound, ~3 mmol/g) and 2.3 g of di-tert-butyl azodicarboxylate are added to the solution. The reaction mixture is stirred at room temperature for 15 h and then filtered. The filter cake is washed with 50 ml of a dichloromethane/methanol mixture (95:5). The filtrate is concentrated to dryness under reduced pressure. The crude is purified by flash chromatography [Silica gel, eluent: ethyl acetate/cyclohexane, elution gradient of 5/95 (v/v) to 70/30 (v/v) to yield the title product.

$^1$H NMR (300 MHz, D$_6$-DMSO): δ=0.11-0.12 (2 s, 6H), 0.94-0.96 (3 s, 9H), 1.64-1.66 (d, J=6.2 Hz, 3H), 3.84 (s, 3H), 4.90 (s, 2H), 5.90-5.92 (q, J=6.2 Hz, 1H), 7.58-7.72 (m, 3H), 7.80 (d, J=0.9 Hz, 1H), 8.06-8.10 (m, 1H), 8.80 (s, 1H), 9.00 (d, J=0.9 Hz, 1H).

MS (MH+ found)=609.9

B32. Methyl 3-[(1R)-1-(2-bromophenyl)ethoxy]-5-[6-({[tert-butyl(dimethyl)silyl]oxy}methyl)-1H-imidazo[4,5-c]pyridin-1-yl]thiophene-2-carboxylate In a similar manner as described for example B31, 1.68 g of methyl 5-[6-({[tert-butyl(dimethyl)silyl]oxy}methyl)-1H-imidazo[4,5-c]pyridin-1-yl]-3-hydroxythiophene-2-carboxylate, 960 mg of (1S)-1-(2-bromophenyl)ethanol, 2.67 g of triphenylphosphine (polymer bound, ~3 mmol/g) and 1.842 g of di-tert-butyl azodicarboxylate in 50 ml anhydrous dichloromethane yield the title compound.

$^1$H NMR (300 MHz, D$_6$-DMSO): δ=0.14-0.16 (2 s, 6H), 0.95-0.96 (3 s, 9H), 1.63-1.65 (d, J=6.3 Hz, 3H), 3.83 (s, 3H), 4.90 (s, 2H), 5.84-5.87 (q, J=6.2 Hz, 1H), 7.25-7.31 (m, 1H), 7.47-7.65 (m, 3H), 7.76-7.82 (m, 2H), 8.84 (s, 1H), 9.00 (d, J=0.8 Hz, 1H).

MS (MH+ found)=603.9

B33. Methyl 5-[6-({[tert-butyl(dimethyl)silyl]oxy}methyl)-1H-imidazo[4,5-c]pyridin-1-yl]-3-{-1-[2-(difluoromethoxy)phenyl]ethoxy}thiophene-2-carboxylate In a similar manner as described for example B31, 2.1 g of methyl 5-[6-({[tert-butyl(dimethyl)silyl]oxy}methyl)-1H-imidazo[4,5-c]pyridin-1-yl]-3-hydroxythiophene-2-carboxylate, 1.41 g of 1-[2-(difluoromethoxy)phenyl]ethanol, 3.33 g of triphenylphosphine (polymer bound, ~3 mmol/g) and 2.3 g of di-tert-butyl azodicarboxylate in 60 ml anhydrous dichloromethane yield the title compound.

$^1$H NMR (300 MHz, D$_6$-DMSO): δ=0.11-0.12 (2 s, 6H), 0.94-0.96 (3 s, 9H), 1.62-1.64 (d, J=6.3 Hz, 3H)), 3.82 (s, 3H), 4.90 (s, 2H), 5.86-5.92 (q, J=6.3 Hz, 1H), 7.21-7.43 (m, 4H), 7.60 (s, 1H), 7.74-7.76 (dd, J=1.8 Hz and 7.6 Hz, 1H), 7.83 (d, J=0.8 Hz, 1H), 8.83 (s, 1H), 9.00 (d, J=0.9 Hz, 1H).

MS (MH+ found)=590.0

B34. Methyl 5-[6-({[tert-butyl(dimethyl)silyl]oxy}methyl)-1H-imidazo[4,5-c]pyridin-1-yl]-3-[(1R)-1-(2-chlorophenyl)ethoxy]thiophene-2-carboxylate In a similar manner as described for example B31, 2.1 g of methyl 5-[6-({[tert-butyl(dimethyl)silyl]oxy}methyl)-1H-imidazo[4,5-c]pyridin-1-yl]-3-hydroxythiophene-2-carboxylate, 1.18 g of (1S)-1-(2-chlorophenyl)ethanol, 3.33 g of triphenylphosphine (polymer bound, ~3 mmol/g) and 2.3 g of di-tert-butyl azodicarboxylate in 60 ml anhydrous dichloromethane yield the title compound.

$^1$H NMR (300 MHz, D$_6$-DMSO): δ=0.12-0.14 (2 s, 6H), 0.95 (2 s, 9H), 1.63-1.65 (d, J=6.4 Hz, 3H), 3.83 (s, 3H), 4.90 (s, 2H), 5.90-5.96 (q, J=6.3 Hz, 1H), 7.33-7.49 (m, 3H), 7.62 (s, 1H), 7.78-7.83 (m, 2H), 8.85 (s, 1H) 9.00 (d, J=0.9 Hz, 1H).

MS (MH+ found)=558.0

B35. Methyl 5-[6-({[tert-butyl(dimethyl)silyl]oxy}methyl)-1H-imidazo[4,5-c]pyridin-1-yl]-3-[(1R)-1-(2-fluorophenyl)ethoxy]thiophene-2-carboxylate In a similar manner as described for example B31, 2.31 g of methyl 5-[6-({[tert-butyl(dimethyl)silyl]oxy}methyl)-1H-imidazo[4,5-c]pyridin-1-yl]-3-hydroxythiophene-2-carboxylate, 0.92 g of (1S)-1-(2-fluorophenyl)ethanol, 3.67 g of triphenylphosphine (polymer bound, ~3 mmol/g) and 2.53 g of di-tert-butyl azodicarboxylate in 65 ml anhydrous dichloromethane yield the title compound.

$^1$H NMR (300 MHz, D$_6$-DMSO): δ=0.12-0.13 (2 s, 6H), 0.95-0.97 (3 s, 9H), 1.64-1.67 (d, J=6.3 Hz, 3H), 3.82 (s, 3H), 4.90 (s, 2H), 5.90-5.96 (q, J=6.4 Hz, 1H), 7.19-7.42 (m, 3H), 7.68-7.71 (dd, J=1.8 Hz and 7.6 Hz, 2H), 7.84-7.85 (d, J=0.9 Hz, 1H), 8.85 (s, 1H) 9.00 (d, J=0.9 Hz, 1H).

MS (MH+ found)=542.0

B36. Methyl 5-[6-({[tert-butyl(dimethyl)silyl]oxy}methyl)-1H-imidazo[4,5-c]pyridin-1-yl]-3-{[1-(2-chlorophenyl)propyl]oxy}thiophene-2-carboxylate In a similar manner as described for example B31, 3.0 g of methyl 5-[6-({[tert-butyl(dimethyl)silyl]oxy}methyl)-1H-imidazo[4,5-c]pyridin-1-yl]-3-hydroxythiophene-2-carboxylate, 1.83 g of 1-(2-chlorophenyl)propan-1-ol, 4.76 g of triphenylphosphine (polymer bound, ~3 mmol/g) and 3.29 g of di-tert-butyl azodicarboxylate in 85 ml anhydrous dichloromethane yield the title compound.

$^1$H NMR (300 MHz, D$_6$-DMSO): δ=0.11-0.12 (2 s, 6H), 0.95-0.96 (3 s, 9H), 0.96-1.00 (d, J=7.3 Hz, 2H), 2.00-2.05 (t, J=7.3 Hz, 3H), 3.84 (s, 3H), 4.89 (s, 2H), 5.78-5.82 (t, J=5.8 Hz, 1H), 7.31-7.47 (m, 4H), 7.66-7.69 (dd, J=1.7 Hz and 7.6 Hz, 1H), 7.78 (d, J=0.9 Hz, 1H), 8.80 (s, 1H) 8.99 (d, J=0.9 Hz, 1H).

MS (MH+ found)=571.9

B37. Methyl 5-[6-({[tert-butyl(dimethyl)silyl]oxy}methyl)-1H-imidazo[4,5-c]pyridin-1-yl]-3-[1-(2-fluorophenyl)ethoxy]thiophene-2-carboxylate In a similar manner as described for example B31, 3.0 g of methyl 5-[6-({[tert-butyl(dimethyl)silyl]oxy}methyl)-1H-imidazo[4,5-c]pyridin-1-yl]-3-hydroxythiophene-2-carboxylate, 1.50 g of 1-(2-fluorophenyl)ethanol, 4.76 g of triphenylphosphine (polymer bound, ~3 mmol/g) and 3.29 g of di-tert-butyl azodicarboxylate in 85 ml anhydrous dichloromethane yield the title compound.

$^1$H NMR (300 MHz, D$_6$-DMSO): δ=0.12-0.13 (2 s, 6H), 0.94-0.96 (3 s, 9H), 1.64-1.66 (d, J=6.3 Hz, 3H), 3.82 (s, 3H), 4.90 (s, 2H), 5.89-5.96 (q, J=6.3 Hz, 1H), 7.18-7.42 (m, 3H), 7.62-7.84 (m, 2H), 7.84 (s, 1H), 8.85 (s, 1H) 8.99-9.00 (d, J=0.9 Hz, 1H).

MS (MH+ found)=541.9

B38. Methyl 5-[6-({[tert-butyl(dimethyl)silyl]oxy}methyl)-3H-imidazo[4,5-c]pyridin-3-yl]-3-[-1-(2-chlorophenyl)ethoxy]thiophene-2-carboxylate In a similar manner as described for example B31, 8.9 g of methyl 5-[6-({[tert-butyl(dimethyl)silyl]oxy}methyl)-3H-imidazo[4,5-c]pyridin-3-yl]-3-hydroxythiophene-2-carboxylate, 5.0 g of 1-(2-chlorophenyl)ethanol, 11.2 g of triphenylphosphine (polymer bound, ~3 mmol/g) and 9.8 g of di-tert-butyl azodicarboxylate in 260 ml anhydrous dichloromethane yield the title compound.

$^1$H NMR (300 MHz, D$_6$-DMSO): δ=0.13 (s, 6H), 0.95 (s, 9H), 1.64 (d, J=6.3 Hz, 3H), 3.84 (s, 3H), 4.89 (s, 2H), 6.01 (q, J=6.3 Hz, 1H), 7.32-7.49 (m, 3H), 7.56 (s, 1H), 7.75-7.78 (m, 2H), 7.86 (s, 1H), 8.96 (d, J=1.0 Hz, 1H).

B39. Methyl 5-[6-({[tert-butyl(dimethyl)silyl]oxy}methyl)-1H-imidazo[4,5-c]pyridin-1-yl]-3-[(2-ethylbenzyl)oxy]thiophene-2-carboxylate In a similar manner as described for example B31, 845.5 mg of methyl 5-[6-({[tert-butyl(dimethyl)silyl]oxy}methyl)-1H-imidazo[4,5-c]pyridin-1-yl]-3-hydroxythiophene-2-carboxylate, 412 mg of (2-ethylphenyl)methanol, 1.06 g of triphenylphosphine (polymer bound, ~3 mmol/g) and 928 mg of di-tert-butyl azodicarboxylate in 25 ml anhydrous dichloromethane yield the title compound.

$^1$H NMR (300 MHz, D$_6$-DMSO): δ=0.13 (s, 6H), 0.96 (s, 9H), 1.20 (t, J=7.6 Hz, 3H), 2.73 (q, J=7.6 Hz, 2H), 3.76 (s, 3H), 4.92 (s, 2H), 5.36 (s, 2H), 7.23-7.37 (m, 3H), 7.55 (d, J=7.4 Hz, 1H), 7.88 (m, 2H), 8.90 (s, 1H), 9.02 (d, J=0.9 Hz, 1H).

B40. Methyl 5-[6-({[tert-butyl(dimethyl)silyl]oxy}methyl)-3H-imidazo[4,5-c]pyridin-3-yl]-3-[1-(2-fluorophenyl)ethoxy]thiophene-2-carboxylate In a similar manner as described for example B31, 5.92 g of methyl 5-[6-({[tert-butyl(dimethyl)silyl]oxy}methyl)-3H-imidazo[4,5-c]pyridin-3-yl]-3-hydroxythiophene-2-carboxylate, 2.96 mg of 1-(2-fluorophenyl)ethanol, 7.39 g of triphenylphosphine (polymer bound, ~3 mmol/g) and 6.49 g of di-tert-butyl azodicarboxylate in 200 ml anhydrous dichloromethane yield the title compound.

$^1$H NMR (300 MHz, D$_6$-DMSO): δ=0.13 (s, 6H), 0.95 (s, 9H), 1.64 (d, J=6.3 Hz, 3H), 3.83 (s, 3H), 4.89 (s, 2H), 6.02 (q, J=6.4 Hz, 1H), 7.19-7.40 (m, 3H), 7.67-7.75 (m, 3H), 8.86 (s, 1H), 8.99 (d, J=1.0 Hz, 1H).

B41. Methyl 5-[6-({[tert-butyl(dimethyl)silyl]oxy}methyl)-1H-imidazo[4,5-c]pyridin-1-yl]-3-[1-(2-chlorophenyl)-2,2,2-trifluoroethoxy]thiophene-2-carboxylate In a similar manner as described for example B31, 1.53 g of methyl 5-[6-({[tert-butyl(dimethyl)silyl]oxy}methyl)-1H-imidazo[4,5-c]pyridin-1-yl]-3-hydroxythiophene-2-carboxylate, 1.0 g of 1-(2-chlorophenyl)-2,2,2-trifluoroethanol, 2.43 g of triphenylphosphine (polymer bound, ~3 mmol/g) and 1.68 g of di-tert-butyl azodicarboxylate in 40 ml anhydrous dichloromethane yield the title compound.

$^1$H NMR (300 MHz, D$_6$-DMSO): δ=0.11 (2 s, 6H), 0.94 (s, 9H), 3.85 (s, 3H), 4.89 (s, 2H), 6.60 (q, J=6.0 Hz, 1H), 7.51-7.60 (m, 3H), 7.71 (s, 1H), 7.79 (d, J=0.9 Hz, 1H), 7.84-7.87 (m, 1H), 8.77 (s, 1H), 9.0 (d, J=0.9 Hz, 1H).

LC-MS (MH+ found)=612.1

B42. Methyl 5-[6-({[tert-butyl(dimethyl)silyl]oxy}methyl)-3H-imidazo[4,5-c]pyridin-3-yl]-3-{1-[2-(trifluoromethyl)phenyl]ethoxy}thiophene-2-carboxylate In a similar manner as described for example B31, 10.0 g of methyl 5-[6-({[tert-butyl(dimethyl)silyl]oxy}methyl)-3H-imidazo[4,5-c]pyridin-3-yl]-3-hydroxythiophene-2-carboxylate, 6.8 g of 1-[2-(trifluoromethyl)phenyl]ethanol, 12.5 g of triphenylphosphine (polymer bound, ~3 mmol/g) and 11.0 g of di-tert-butyl azodicarboxylate in 300 ml anhydrous dichloromethane yield the title compound.

$^1$H NMR (300 MHz, D$_6$-DMSO): δ=0.13 (s, 6H), 0.95 (s, 9H), 1.77 (d, J=6.3 Hz, 3H), 3.85 (s, 3H), 4.89 (s, 2H), 6.00 (q, J=6.3 Hz, 1H), 7.52-7.67 (m, 2H), 7.72-7.82 (m, 3H), 8.03 (d, J=8.0 Hz, 1H), 8.83 (s, 1H), 8.92 (s, 1H).

MS (MH+ found)=592.1

Intermediate Compounds of Type (IIIa)

C1. Methyl 3-hydroxy-5-(1H-imidazo[4,5-c]pyridin-1-yl)thiophene-2-carboxylate (Compound C1a) and Methyl 3-hydroxy-5-(3H-imidazo[4,5-c]pyridin-3-yl)thiophene-2-carboxylate (compound C1b)

A suspension of 17.27 g of 1H-imidazo[4,5-c]pyridine in 4 l chloroform was sonicated at 40° C. until the solid has been dissolved. To this solution a solution of 13.29 g methyl 2-chloro-3-oxo-2,3-dihydrothiophene-2-carboxylate in 120 ml chloroform was added dropwise and the mixture was stirred for 18 h at room temperature. The precipitated solid (1H-imidazo[4,5-c]pyridine hydrochloride) was filtered off. The filtrate was concentrated under reduced pressure to a volume of 400 ml and the precipitated solid (1H-imidazo[4,5-c]pyridine hydrochloride) was filtered off. The filtrate was washed with water (2×40 ml). The organic layer was separated and concentrated under reduced pressure to a volume of about 200 ml. This solution was triturated with 400 ml of n-hexane and stored at 0° C. The precipitated solid (predominantly title compounds) was collected by filtration and washed with n-hexane. The filtrate was evaporated to dryness and the residue triturated with 600 ml ethyl acetate at 60° C. The mixture was filtered and the organic layer concentrated under reduced pressure. The resulting solid (predominantly title compounds) was filtered and washed with ethyl acetate. The combined solids were dried under vacuum to yield the crude title compounds. The isomeric mixture was used for the next step (example B1) without further purification.

LC-MS (MH$^+$ found)=276.0 (isomeric mixture)

C1.1. Methyl 3-hydroxy-5-(1H-imidazo[4,5-c]pyridin-1-yl)thiophene-2-carboxylate and Methyl 3-hydroxy-5-(3H-imidazo[4,5-c]pyridin-3-yl)thiophene-2-carboxylate To a suspension of 6 g of 1H-imidazo[4,5-c]pyridine in 300 ml of anhydrous dichloromethane is slowly added a solution of 4.8 g of methyl 2-chloro-3-oxo-2,3-dihydrothiophene-2- carboxylate. The reaction mixture is stirred for 14 h at room temperature. The solvent is removed under reduced pressure and the residue is purified by flash chromatography [silica gel, elution gradient of toluene/ethyl acetate/acetic acid, 80/20/1 (v/v/v)] to 30/70/1 (v/v/v) to give the separated title compounds along with a small fraction of the isomeric mixture.

Methyl 3-hydroxy-5-(1H-imidazo[4,5-c]pyridin-1-yl)thiophene-2-carboxylate

The structural assignment of the regioisomer is unequivocally established by two-dimensional $^1$H NMR experiments (NOESY, COSY).
$^1$H NMR (400 MHz, D6-DMSO): δ=3.81 (s, 3H), 7.20 (s, 1H), 7.84 (dd, J=0.8 Hz and 5.6 Hz, 1H), 8.52 (d, J=5.7 Hz, 1H), 8.83 (s, 1H), 9.09 (s, 1H), 10.90 (br s, 1H).
MS (MH+ found)=276.0

Methyl 3-hydroxy-5-(3H-imidazo[4,5-c]pyridin-3-yl)thiophene-2-carboxylate

The structural assignment of the regioisomer is unequivocally established by two-dimensional $^1$H NMR experiments (NOESY, COSY).
$^1$H NMR (400 MHz, D6-DMSO): δ=3.81 (s, 3H), 7.25 (s, 1H), 7.83 (dd, J=0.9 Hz and 5.4 Hz, 1H), 8.51 (d, J=5.3 Hz, 1H), 8.90 (s, 1H), 9.14 (s, 1H), 10.90 (br s, 1H).
MS (MH+ found)=276.0

C2. Methyl 5-(6-chloro-M-imidazo[4,5-c]pyridin-1-yl)-3-hydroxythiophene-2-carboxylate (compound C2a) and methyl 5-(6-chloro-3H-imidazo[4,5-c]pyridin-3-yl)-3-hydroxythiophene-2-carboxylate (compound C2b)

To a mixture of 0.68 g of 6-chloro-1H-imidazo[4,5-c]pyridine and 0.65 g of 2,2,6,6-tetramethylpiperidine in 100 ml chloroform were slowly added a solution of 0.87 g of methyl 2-chloro-3-oxo-2,3-dihydrothiophene-2-carboxylate in 40 ml chloroform. The reaction mixture was stirred for 12 h at room temperature. After washing with water (3×50 ml) the organic layer was separated, dried with MgSO$_4$ and concentrated to a volume of about 100 ml. The residue was treated with n-hexane until precipitation takes place. The solid was filtered and the procedure was repeated once again. The combined solids were dried under vacuum to yield the title compounds as an isomeric mixture, which was used for the next step (example B3) without further purification.
LC-MS (MH$^+$ found)=310.0 (isomeric mixture)

C3. Methyl 5-[6-({[tert-butyl(dimethyl)silyl]oxy}methyl)-3H-imidazo[4,5-c]pyridin-3-yl]-3-hydroxythiophene-2-carboxylate (compound C3a) and Methyl 5-[6-({[tert-butyl(dimethyl)silyl]oxy}methyl)-1H-imidazo[4,5-c]pyridin-1-yl]-3-hydroxythiophene-2-carboxylate (compound C3b)

To a mixture of 21.2 g of 6-({[tert-butyl(dimethyl)silyl]oxy}methyl)-1H-imidazo[4,5-c]pyridine and 11.36 g of 2,2,6,6-tetramethylpiperidine in 2 l dichloromethane was slowly added a solution of 8.77 g of methyl 2-chloro-3-oxo-2,3-dihydrothiophene-2-carboxylate in 300 ml chloroform at 30-40° C. The reaction mixture was stirred for 12 h, washed with water (2×200 ml) and concentrated under vacuum. The residue was purified by flash chromatography (eluents: ethyl acetate/methanol/triethylamine) two times and after precipitation from ethyl acetate/n-hexane the title compounds were obtained as a mixture of regioisomers.
$^1$H NMR (300 MHz, D$_6$-DMSO) (isomeric mixture): δ=0.13 (s, 6H), 0.14 (s, 6H), 0.95 (s, 9H), 0.96 (s, 9H), 3.79 (s, 3H), 3.80 (s, 3H), 4.89 (s, 2H), 4.91 (s, 2H), 7.16 (s, 1H), 7.22 (s, 1H), 7.76 (s, 1H), 7.88 (s, 1H), 8.84 (s, 1H), 8.88 (s, 1H), 9.00 (s, 1H), 9.04 (s, 1H).
LC-MS (MH$^+$ found)=420.0 (isomeric mixture)

C3.1. Methyl 5-[6-({[tert-butyl(dimethyl)silyl]oxy}methyl)-1H-imidazo[4,5-c]pyridin-1-yl]-3-hydroxythiophene-2-carboxylate and methyl 5-[6-({[tert-butyl(dimethyl)silyl]oxy}methyl)-3H-imidazo[4,5-c]pyridin-3-yl]-3-hydroxythiophene-2-carboxylate To a mixture of 5.2 g of 6-({[tert-butyl(dimethyl)silyl]oxy}methyl)-1H-imidazo[4,5-c]pyridine and 3.2 g of 1-methyl-1H-imidazole in 100 ml of anhydrous dichloromethane is added
4.5 g of methyl 2-chloro-3-oxo-2,3-dihydrothiophene-2-carboxylate at 5° C. The reaction mixture is stirred for 2 h at 5° C. and after that for 16 h at room temperature. The organic phase is washed with 100 ml of water and 100 ml of a saturated solution of sodium hydrogen carbonate. The aqueous phase is separated and extracted with dichloromethane (2×100 ml). The combined organic phases are dried over MgSO$_4$, filtered and concentrated to a volume of 50 ml under reduced pressure. The isomeric mixture is purified and separated by flash chromatography [silica gel, eluent: toluene/dioxane/acetic acid, elution gradient of 60/40/1 (v/v/v) to 40/60/1 (v/v/v)]. The isolated fractions that contain the separated isomers are washed with 400 ml of water and 400 ml of a saturated solution of sodium hydrogen carbonate. The organic layers are filtered and evaporated under reduced pressure to yield the title compounds.

Methyl 5-[6-({[tert-butyl(dimethyl)silyl]oxy}methyl)-1H-imidazo[4,5-c]pyridin-1-yl]-3-hydroxythiophene-2-carboxylate The structural assignment of the regioisomer is unequivocally established by two-dimensional $^1$H NMR experiments (NOESY, COSY).
$^1$H NMR (400 MHz, D6-DMSO): δ=0.13 (s, 6H), 0.97 (s, 9H), 3.81 (s, 3H), 4.91 (s, 2H), 7.20 (s, 1H), 7.88 (s, 1H), 8.86 (s, 1H), 9.00 (s, 1H).
MS (MH+ found)=419.9

Methyl 5-[6-({[tert-butyl(dimethyl)silyl]oxy}methyl)-3H-imidazo[4,5-c]pyridin-3-yl]-3-hydroxythiophene-2-carboxylate The structural assignment of the regioisomer is unequivocally established by two-dimensional $^1$H NMR experiments (NOESY, COSY).
$^1$H NMR (400 MHz, D6-DMSO): δ=0.13 (s, 6H), 0.95 (s, 9H), 3.81 (s, 3H), 4.89 (s, 2H), 7.24 (s, 1H), 7.76 (s, 1H), 8.89 (s, 1H), 9.04 (s, 1H).
MS (MH+ found)=419.8

C4. Methyl 3-hydroxy-5-{6-[(2-morpholin-4-yl-ethyl)carbamoyl]1H-imidazo[4,5-c]pyridin-1-yl}thiophene-2-carboxylate To a solution of 2.27 g of 1H-imidazo[4,5-c]pyridine-6-carboxylic acid (2-morpholin-4-yl-ethyl)-amide in 150 ml chloroform was slowly added a solution of 1.27 g of methyl 2-chloro-3-oxo-2,3-dihydrothiophene-2-carboxylate in 100 ml chloroform and the reaction mixture was stirred for 12 h at room temperature. The reaction mixture was washed with water (3×50 ml) and the organic layer was dried with $MgSO_4$ and concentrated under vacuum. The residue was dissolved in dichloromethane and purified by flash chromatography (dichloromethane/methanol, elution gradient 10/0 to 9/1 (v/v))) to give the title compound.
MS ($MH^+$ found)=432.0

C5. Methyl 3-hydroxy-5-{6-[(2-methoxyethyl)carbamoyl]1H-imidazo[4,5-c]pyridin-1-yl}thiophene-2-carboxylate In a similar manner as described for example C3, 1.81 g of 1H-imidazo[4,5-c]pyridine-6-carboxylic acid (2-methoxyethyl)-amide and 1.27 g of methyl 2-chloro-3-oxo-2,3-dihydrothiophene-2-carboxylate in 300 ml chloroform yield the title compound which was used for the next step without further purification (example B8).
LC-MS ($MH^+$ found)=377.0

C6. Methyl 3-hydroxy-5-(6-methoxy-1H-imidazo[4,5-c]pyridin-1-yl)thio-phene-2-carboxylate (compound C6a) and

Methyl 3-hydroxy-5-(6-methoxy-3H-imidazo[4,5-c]pyridin-3-yl)thio-phene-2-carboxylate (compound C6b)

To a solution of 2.00 g of 6-methoxy-1H-imidazo[4,5-c]pyridine in 50 ml of chloroform were added 1.25 g of methyl 2-chloro-3-oxo-2,3-dihydrothiophene-2-carboxylate in portions and the reaction mixture was stirred for 120 h at room temperature. The reaction mixture was washed with water (3×50 ml) and the organic layer was dried and concentrated under vacuum. The residue was recrystallized from methanol to yield the title compounds as an isomeric mixture.
$^1$H NMR (400 MHz, $CDCl_3$) of isomeric mixture: δ=3.95 (s, 6H), 4.02 (s, 6H), 6.84 (s, 1H), 6.88 (s, 1H), 6.98 (s, 1H), 7.16 (s, 1H), 8.01 (s, 1H), 8.16 (s, 1H), 8.68 (s, 1H), 8.74 (s, 1H), 9.79 (bs, 2H).

C7. Methyl 5-(5,6-dimethoxy-1H-imidazo[4,5-b]pyridin-1-yl)-3-hydroxythio-phene-2-carboxylate (compound C7a) and

Methyl 5-(5,6-dimethoxy-3H-imidazo[4,5-b]pyridin-3-yl)-3-hydroxythio-phene-2-carboxylate (compound C7b)

A suspension of 11.6 g of 2-azido-5,6-dimethoxy-3-nitropyridine (example E5) in 600 ml methanol was treated with 1.7 g Pd/C (10% Pd) and hydrogenated for 16 h under atmospheric pressure. The reaction mixture was rapidly filtered through a plug of CELITE® (diatomaceous earth), the filtrate was concentrated under vacuum and the residue was refluxed in 100 ml of formic acid for 18 h. The formic acid was removed under vacuum and the resulting residue was dried under vacuum at 100-110° C. to yield crude 5,6-dimethoxy-1H-imidazo[4,5-b]pyridine (as formic acid salt and/or as free base) that was used for the following step without further purification (MS ($MH^+$ found)=180.2).
In a similar manner as described for example C6, 1.50 g of the above-synthesized 5,6-dimethoxy-1H-imidazo[4,5-b]pyridine and 0.81 g of methyl 2-chloro-3-oxo-2,3-dihydrothiophene-2-carboxylate in 40 ml chloroform yield the title compounds as an isomeric mixture which was used for the next step without further purification (example B4).
$^1$H NMR (400 MHz, $CDCl_3$) of isomeric mixture: δ=3.94 (s, 3H), 3.95 (s, 3H), 3.97 (s, 6H), 4.16 (s, 3H), 4.21 (s, 3H), 6.84 (s, 1H), 7.16 (s, 1H), 7.36 (s, 1H), 7.53 (s, 1H), 8.07 (s, 1H), 8.16 (s, 1H), 9.83 (bs, 2H).

C8. Methyl 3-hydroxy-5-(1H-imidazo[4,5-b]pyridin-1-yl)thiophene-2-carboxylate (compound C8a) and

Methyl 3-hydroxy-5-(3H-imidazo[4,5-b]pyridin-3-yl)thiophene-2-carboxylate (compound C8b)

In a similar manner as described for example C6, 30.0 g of 1H-imidazo[4,5-b]pyridine and 19.26 g of methyl 2-chloro-3-oxo-2,3-dihydrothiophene-2-carboxylate in 2 l chloroform give 3-hydroxy-5-imidazo[4,5-b]pyridin-3-yl-thiophene-2-carboxylic acid methyl ester (compound C8b) and the crude title compounds as an isomeric mixture which was used for the next step without further purification (example B5). The structural assignment of compound C8b was unequivocally established by two-dimensional $^1$H NMR experiment (NOESY, COSY).
Compound C8b:
$^1$H NMR (400 MHz, $D_6$-DMSO): δ=3.81 (s, 3H), 7.40 (s, 1H), 7.46 (dd, J=4.8 and 8.0 Hz, 1H), 8.25 (dd, J=1.3 and 8.0 Hz, 1H), 8.53 (dd, J=1.3 and 4.8 Hz, 1H), 9.11 (s, 1H), 10.61 (bs, 1H).
MS ($MH^+$ found)=276.0

C9. Methyl 3-hydroxy-5-(5-methoxy-1H-imidazo[4,5-b]pyridin-1-yl)thio-phene-2-carboxylate (compound C9a) and

Methyl 3-hydroxy-5-(5-methoxy-3H-imidazo[4,5-b]pyridin-3-yl)thio-phene-2-carboxylate (compound C9b)

10.19 g of 6-methoxypyridine-2,3-diamine dihydrochloride were dissolved in 100 ml formic acid and stirred under reflux for 72 h. The formic acid was evaporated under vacuum and the residue was dried under vacuum at 95° C. to give crude 5-methoxy-1H-imidazo[4,5-b]pyridine (as hydrochloride and/or as formic acid salt and/or as free base) that was used for the following step without further purification.
In a similar manner as described for example C2, 8.54 g of the above-synthesized 5-methoxy-1H-imidazo[4,5-b]pyridine and 4.46 g of methyl 2-chloro-3-oxo-2,3-dihydrothiophene-2-carboxylate and 13.07 g of 2,2,6,6-tetramethylpiperidine in 620 ml chloroform yield the title compounds as an isomeric mixture which was used for the next step (example B7) without further purification.
LC-MS ($MH^+$ found)=306.0

Intermediate Compounds of Type (IVa)

D1. 6-({[Tert-butyl(dimethyl)silyl]oxy}methyl)-1H-imidazo[4,5-c]pyridine 17.7 g of methyl 1H-imidazo[4,5-c]pyridine-6-carboxylate (example D2) were added in portions to a suspension of 19.0 g lithiumaluminium hydride in 0.6 l anhydrous tetrahydrofuran under nitrogen atmosphere at 0° C. After the addition was completed, the ice/water bath was removed and the mixture was stirred at room temperature for 12 h. 30 ml ethyl acetate followed by 100 ml methanol are slowly added at 0° C. (until gas evolution has stopped). Water (50 ml) was slowly added and the resulting precipitate was filtered. The precipitate was suspended in 1 l methanol and filtered through a plug of CELITE® (diatomaceous earth). The combined filtrates are evaporated under vacuum to give crude 1H-imidazo[4,5-c]pyridin-6-ylmethanol as a brown solid that was used for the next step without further purification. To a N,N-dimethylformamide solution (140 ml) of 1H-imidazo[4,5-c]pyridin-6-ylmethanol were added 28.0 g tert-butyldimethylsilyl chloride and 19.4 g imidazole. The mixture was stirred at room temperature for 12 h and then poured into ice water (2.5 l). The resulting solid was filtered, washed with 100 ml water and dissolved in 0.5 l ethyl acetate. The organic layer was dried with $MgSO_4$ and then concentrated under vacuum to a volume of about 100 ml. 50 ml n-hexane were added and the precipitating solid was filtered and washed with 50 ml n-hexane. The filtrate was concentrated and the resulting precipitate was washed with n-hexane. Both batches of solid were combined and dried under vacuum to yield the title compound as a yellow solid.

$^1$H NMR (300 MHz, $D_6$-DMSO): δ=0.11 (s, 9H), 0.94 (s, 6H), 4.84 (s, 2H), 7.56 (s, 1H), 8.32 (s, 1H), 8.83 (s, 1H), 12.70 (br s, 1H).

MS ($MH^+$ found)=264.1

D2. Methyl 1H-imidazo[4,5-c]pyridine-6-carboxylate 68.5 g methyl (6S)-4,5,6,7-tetrahydro-1H-imidazo[4,5-c]pyridine-6-carboxylate dihydrochloride, 81.8 g triethylamine and 63.3 g selenium dioxide were suspended in 1.1 l anhydrous 1,4-dioxane. The mixture was refluxed for 2 h. 26.3 g triethylamine were added and the mixture was allowed to cool down to room temperature and stirred overnight. The solvent was removed under reduced pressure and the residue was suspended in 300 ml methanol. 46.8 g triethylamine were added to adjust to pH 8-9. The resulting precipitate was filtered and washed with 70 ml methanol. The precipitate was treated with 500 ml N,N-dimethylformamide, stirred at 140° C. for 30 minutes and filtered hot. Upon cooling to room temperature, precipitation takes place. The precipitate was filtered, washed with 80 ml cold methanol and dried under vacuum to yield the title compound.

$^1$H NMR (200 MHz, $D_6$-DMSO): 3.89 (s, 3H), 8.31 (s, 1H), 8.58 (s, 1H), 9.02 (s, 1H), 13.2 (br s, 1H).

MS ($MH^+$ found)=178.0

D2.1. Methyl (6S)-4,5,6,7-tetrahydro-imidazo[4,5-c]pyridine-6-carboxylate

Into a mixture of 188.25 g methyl (6S)-4,5,6,7-tetrahydro-imidazo[4,5-c]pyridine-6-carboxylate dihydrochloride in 3 l dichloromethane at 10-15° C. is lead gaseous ammonia until saturation takes place (about one hour). 200 ml methanol are added and the mixture is filtered. The filter cake is washed with 2×100 ml DCM/MeOH (8/2 v/v). The filtrate is concentrated under reduced pressure and the resulting solid is dried under vacuum to give 128.4 g of the title product.

$^1$H NMR (300 MHz, $D_6$-DMSO): δ=2.60-2.79 (m, 2H), 3.65 (s, 3H), 3.67-3.79 (m, 3H), 7.42 (s, 1H).

MS ($MH^+$ found)=182.0

D2.2. Methyl-1H-imidazo[4,5-c]pyridine-6-carboxylate

A mixture of 59.9 g methyl (6S)-4,5,6,7-tetrahydro-imidazo[4,5-c]pyridine-6-carboxylate and 172.5 g $MnO_2$ in 2 l anhydrous 1,4-dioxane is refluxed for 4 hours. The reaction mixture is allowed to come to 60-70° C. whereupon 1 l methanol is slowly added. The suspension is filtered hot and the filtrate is concentrated under reduced pressure to give a first batch of the title product. The filter cake is washed with hot methanol (2 l) and concentrated under reduced pressure to a volume of about 50 ml. 80 ml 1,4-dioxane is added whereupon precipitation takes place. After filtration a second batch of the title product is obtained. The washing procedure of the initial filter cakes is repeated once again to give a third batch of the title product.

$^1$H NMR (300 MHz, $D_6$-DMSO): δ=3.89 (s, 3H), 8.32 (s, 1H), 8.58 (s, 1H), 9.02 (d, J=0.7 Hz, 1H), 13.18 (br s, 1H).

MS ($MH^+$ found)=178.0

D3. 6-Chloro-1H-imidazo[4,5-c]pyridine

A suspension of 1.04 g of 2-chloro-5-nitropyridin-4-amine (example E6) in 100 ml ethanol was treated with 50 mg Pd/C (10% Pd) and hydrogenated for 12 h under atmospheric pressure. The reaction mixture was filtered through a plug of CELITE® (diatomaceous earth) and the filtrate was concentrated under vacuum. The resulting oil was treated with 4 ml diethoxymethyl acetate and stirred for 2 h at room temperature and for one hour at 90° C. The reaction mixture was allowed to cool down to room temperature, 20 ml di-chloromethane were added and the organic layer was extracted with water (4×20 ml). The combined aqueous layers were concentrated to a volume of 10 ml and purified by preparative HPLC to yield the title compound.

$^1$H NMR (200 MHz, $D_6$-DMSO): δ=7.69 (d, J=0.8 Hz, 1H), 8.46 (s, 1H), 8.75 (d, J=0.8 Hz, 1H), 13.0 (bs, 1H).

MS ($MH^+$ found)=154.1

D4. 6-Methoxy-1H-imidazo[4,5-c]pyridine

A solution of 15.51 g of 2-methoxy-5-nitropyridin-4-amine (example E7) in 1.55 l methanol was treated with 4.65 g Pd/C (10% Pd) and hydrogenated for 12 h under atmospheric pressure. The reaction mixture was filtered through a plug of CELITE® (diatomaceous earth) and the filtrate was concentrated under vacuum. The resulting residue was treated with 181 ml formic acid and the mixture was refluxed for 50 h. The formic acid was distilled off and the residue was repeatedly purified by flash chromatography (neutral alumina oxide, ethyl acetate/methanol) to yield the title compound.

$^1$H NMR (200 MHz, $D_6$-DMSO): δ=3.87 (s, 3H), 6.85 (d, J=0.9 Hz, 1H), 8.24 (s, 1H), 8.54 (d, J=0.9 Hz, 1H), 12.5 (bs, 1H).

MS ($MH^+$ found)=150.1

D5. N-(2-Morpholin-4-ylethyl)-1H-imidazo[4,5-c]pyridine-6-carboxamide 2.0 g of methyl-1H-imidazo[4,5-c]pyridine-6-carboxylate (example D2), 22.1 g of 2-morpholin-4-ylethanamine and 70 ml methanol were placed in an autoclave for 2 h at 140° C. The methanol and 2-morpholin-4-ylethanamine were distilled off the reaction mixture under reduced pressure and the residue was purified by flash chromatography. After crystallization from ethyl acetate/n-hexane the title compound was obtained.

$^1$H NMR (200 MHz, $D_6$-DMSO): δ=2.41-2.54 (m, 6H), 3.42-3.51 (m, 2H), 3.56-3.61 (m, 4H), 8.25 (d, J=0.95 Hz, 1H), 8.53 (s, 1H), 8.70 (t, J=5.8 Hz, 1H), 8.97 (d, J=0.95 Hz, 1H).

MS ($MH^+$ found)=276.1

D6. N-(2-Methoxyethyl)-1H-imidazo[4,5-c]pyridine-6-carboxamide

In a similar manner as described for example D5, 2.0 g of methyl-1H-imidazo[4,5-c]pyridine-6-carboxylate (example D2) and 8.5 g of 2-methoxyethanamine in 50 ml methanol yield the title compound.

LC-MS (MH$^+$ found)=221.0

Further Intermediates

E1. 2,6-Dibromopyridin-3-ol

To 1 l 10% (w/v) aqueous NaOH solution were added 49 ml Br$_2$ at 0° C. To this mixture an ice cold solution of 30.0 g pyridin-3-ol in 30 ml 10% (w/v) aqueous NaOH solution was slowly added and the reaction mixture was stirred for 2 h at 0° C. and then for 2 h at room temperature. The resulting precipitate was filtered and the filtrate was acidified with aqueous HCl solution (pH 1). The resulting precipitate was filtered and dried under vacuum to yield the title compound.

$^1$H NMR (400 MHz, D$_6$-DMSO): δ=7.25 (d, J=8.0 Hz, 1H), 7.47 (d, J=8.0 Hz, 1H), 11.10 (s, 1H).

E2. 2,6-Dibromo-3-methoxypyridine

To a solution of 52.5 g 2,6-dibromopyridin-3-ol (example E1) in 90 ml DMSO were added 26.2 g K$_2$CO$_3$ and 43.8 ml methyl iodide and the reaction mixture was stirred under reflux for one hour. The mixture was allowed to cool down to room temperature and poured into 1 l of water and stirred for 3 h at 80° C. After cooling to room temperature the resulting solid was filtered, the filter cake was washed with ice cold water and dried under vacuum to yield the title compound.

$^1$H NMR (400 MHz, CDCl$_3$): δ=3.91 (s, 3H), 7.04 (d, J=8.0 Hz, 1H), 7.38 (d, J=8.0 Hz, 1H).

E3. 2,6-Dibromo-3-methoxy-5-nitropyridine

To 150 ml of concentrated sulfuric acid were added at 0° C. 150 ml fuming nitric acid. 40.0 g of 2,6-dibromo-3-methoxypyridine (example E2) were added portionwise to this mixture at 0° C. The reaction mixture was stirred for 45 minutes at 0° C. and then heated to 65° C. for 2 h. The mixture was poured into 2 l of crushed ice and stored at 0° C. overnight. The resulting precipitate was filtered, washed with water and dried under vacuum to yield the title compound.

$^1$H NMR (400 MHz, CDCl$_3$): δ=4.01 (s, 3H), 7.63 (s, 1H).

E4. 2-Bromo-5,6-dimethoxy-3-nitropyridine 20 g of 2,6-dibromo-3-methoxy-5-nitropyridine (example E3) were dissolved in 550 ml of anhydrous methanol at 30-40° C. 4.6 g sodium methoxide dissolved in 30 ml anhydrous methanol were added to this solution. The reaction mixture was stirred for one hour at room temperature, poured into 700 ml of water and stored in the refrigerator overnight. The precipitate was filtered, washed with ice cold water and dried under vacuum to yield the title compound.

$^1$H NMR (400 MHz, CDCl$_3$): δ=3.95 (s, 3H), 4.12 (s, 3H), 7.69 (s, 1H).

$^{13}$C NMR (100 MHz, CDCl$_3$): δ=55.68, 56.73, 115.33, 121.89, 143.18, 155.10.

E5. 2-Azido-5,6-dimethoxy-3-nitropyridine

To a suspension of 22.0 g of 2-bromo-5,6-dimethoxy-3-nitropyridine (example E4) in 50 ml DMSO were added 16.0 g sodium azide. The reaction mixture was stirred for 24 h at 50° C. Additional 3.20 g sodium azide were added and after stirring for additional 44 h the reaction was completed. The solvent was removed under vacuum and the resulting residue was extracted with dichloromethane (3×100 ml). The solvent was removed and the residue was purified by flash chromatography (petroleum ether/ethyl acetate) to yield the title compound.

$^1$H NMR (400 MHz, CDCl$_3$): δ=3.96 (s, 3H), 4.17 (s, 3H), 6.65 (s, 1H).

E6. 2-Chloro-5-nitropyridin-4-amine 357.5 g of 2-chloropyridin-4-amine were added in portions to 2.28 l of cold concentrated sulfuric acid. 0.86 l of nitric acid (90%) were slowly added so that the temperature of the reaction mixture always stays below 10° C. After the addition the mixture was stirred for one hour at room temperature and poured into 4 l of water containing 10 kg of ice. 6.2125% (w/v) aqueous NH$_3$ solution were slowly added. The resulting precipitate was filtered, washed with ice water and dried under vacuum to give 316.6 g of the 2-chloro-N-nitropyridin-4-amine. 316.2 g of this intermediate compound were treated with 2.35 l concentrated sulfuric acid and stirred for 30 minutes at 88-94° C. The mixture was cooled to room temperature and poured into 2 l of water containing 5 kg ice. 6.5 l 25% (w/v) aqueous NH$_3$ solution were slowly added. The resulting precipitate was filtered and pre-dried under reduced pressure. Finally the residue was dried by azeotropic distillation with benzene. After crystallization from benzene the title compound was obtained.

$^1$H NMR (200 MHz, D$_6$-DMSO): δ=6.96 (s, 1H), 8.07 (bs, 2H), 8.84 (s, 1H).

E7. 2-Methoxy-5-nitropyridin-4-amine

To a suspension of 36.9 g of 2-chloro-5-nitropyridin-4-amine (example E6) in 500 ml methanol were added 250 ml of a freshly prepared solution of sodium methoxide in methanol (5.7 g sodium) and the reaction mixture was refluxed for 12 h. About 500 ml methanol were distilled off and 500 ml of water were added. The resulting precipitate was filtered, washed with ice water and dried under vacuum to the title compound.

$^1$H NMR (400 MHz, D$_6$-DMSO): δ=8.82 (s, 1H), 7.65 (bs, 2H), 6.15 (s, 1H), 3.85 (s, 3H).

E8. 3-Chloro-4-(1-hydroxyethyl)benzonitrile

To a solution of 1.5 g of 4-acetyl-3-chlorobenzonitrile in 25 ml anhydrous THF is added 158 mg sodium boron hybrid at 0° C. The ice bath is removed and the reaction mixture is stirred for 18 h at room temperature. The reaction mixture is poured into 90 ml of 1N aqueous HCl solution. The aqueous layer is extracted with ethyl acetate (3×50 ml). The combined organic layers are washed with a saturated solution of sodium chloride (100 ml), dried over MgSO$_4$ and evaporated to dryness under reduced pressure. The remaining residue is purified by flash chromatography (n-hexane/ethyl acetate, 6/4 (v/v)) to yield the title compound.

$^1$H NMR (300 MHz, D$_6$-DMSO): δ=1.31 (d, J=6.3 Hz, 3H), 5.00-5.07 (m, 1H), 5.60 (d, J=4.2 Hz, 1H), 7.77-7.86 (m, 2H), 7.98 (d, J=1.5 Hz, 1H).

MS (MH$^+$ found)=181.1

E9. 4-Acetyl-3-chlorobenzonitrile

A mixture of 59 mg of zinc, 528 mg of zinc cyanide, 2.1 g of 1-(4-bromo-2-chlorophenyl)ethanone and 367 mg of [1,1'- bis(diphenylphosphino)ferrocene]dichloropalladium(II) in 10 ml N,N-dimethylacetamide is stirred for 4 h at 160° C. The reaction mixture is allowed to cool down to room temperature and stirred for 14 h at room temperature. The solvent is removed under reduced pressure and the resulting residue is purified by flash chromatography (n-hexane/ethyl acetate, 85/15 (v/v)) to yield the title compound.

$^1$H NMR (300 MHz, D$_6$-DMSO): δ=2.60 (s, 3H), 7.83, 7.86 (s, 1H), 7.96 (dd, J=1.6 Hz and 7.9 Hz, 1H), 8.17 (d, J=1.1 Hz, 1H).

MS (MH$^+$ found)=179.3

E10. 1-(4-Bromo-2-chlorophenyl)ethanone

Step 1: To a mixture of 15 g of 4-bromo-2-chlorobenzoic acid in 25 ml DMF is added 10 ml thionyl chloride at room temperature and the reaction mixture is stirred for 16 h at 75° C. Excess of thionyl chloride is removed under reduced pressure to give 4-bromo-2-chlorobenzoyl chloride as crude material that is used for the next step without further purification.

Step 2: 5 g of crude 4-bromo-2-chlorobenzoyl chloride (from step 1) are dissolved in 120 ml anhydrous THF. 45.6 ml of tributylphosphine is added dropwise at −22° C., and after 20 minutes 141 ml of methyl magnesium bromide is added dropwise and the reaction mixture is stirred for 40 minutes at −22° C. The reaction mixture is poured into 1N aqueous HCl solution and the aqueous layer is extracted with ethyl acetate (3×). The combined organic layers are washed with a saturated solution of sodium chloride, dried over MgSO$_4$ and evaporated to dryness under reduced pressure. The remaining residue is purified by flash chromatography (n-hexane/ethyl acetate, 9/1 (v/v)) to yield the title compound.

$^1$H NMR (300 MHz, D$_6$-DMSO): δ=2.58 (s, 3H), 7.67-7.68 (m, 2H), 7.84 (m, 1H).

MS (MH$^+$ found)=234.0

Commercial Utility

The compounds, salts thereof, and the stereoisomers of the compounds and the salts thereof according to the invention are hereinafter referred to as the compounds of the invention. In particular, the compounds of the invention are pharmaceutically acceptable.

The compounds of the invention have valuable pharmaceutical properties which make them commercially utilizable. Thus, one aspect of the invention relates to compounds according to formula I for use in the treatment or prophylaxis of diseases. In particular, as Plk1 inhibitors, they are able to interfere with the cell cycle of various cells, particularly neoplastic cells. In particular, the Plk1 inhibiting compounds of the invention can disrupt mitosis and drive cancer cells into apoptosis. The compounds of the invention are distinguished by valuable and desirable properties, such as, for example, high selectivity and low toxicity. On cellular level the compounds exhibit a cytotoxic effect only or preferentially on proliferating cells. The compounds are able to induce mitotic arrest in proliferating cells. Other valuable properties of the compounds of the invention include superior bioavailability in general (e.g. good enteral absorption), superior therapeutic window, superior pharmacokinetics (e.g. half-life), improved tolerability as compared to other anti-neoplastic agents, and further beneficial effects related with their therapeutic and pharmaceutical suitability.

Accordingly, the invention further relates to the compounds of the invention for use in the treatment or prophylaxis of diseases. Furtheron, the invention relates to the compounds of the invention for use in the treatment or prophylaxis of diseases alleviated by inhibition of kinases involved in cell division, preferably Polo-like kinases, even more preferably Plk1. In particular, the invention relates to the compounds of the invention for use in the treatment or prophylaxis of diseases characterized by increased Plk1 activity. Increased activity means that the activity of Plk1 in a given cell, group of cells, tissue, or region within a tissue is higher by a certain factor than it is in the healthy state. The factor by which Plk1 activity is increased can be, e.g., at least 1.5, at least 3, at least 10, or even at least 100. Without being meant as a limitation, the reason for said increased Plk1 activity may be increased expression ("overexpression") of the Plk1 gene or genes, which can be due to, among others, altered regulation of expression, mutations in the Plk1 promoter, gene duplication, gene amplification, genomic rearrangements, and so forth. Other processes leading to increased Plk1 activity might comprise reduced inhibition of Plk1 enzyme, enhanced Plk1 stability, reduced Plk1 inactivation or degradation, and altered availability of substrate(s) and/or cofactors.

Preferably, the invention further relates to the compounds of the invention for use in the treatment or prophylaxis of diseases comprising abnormal cell growth. In one embodiment, said abnormal cell growth is a cancer. In particular, the disease may be one of the following: Cancers of the colon including colorectal carcinoma, ovaries, breast, prostate, bladder, lung, gastrointestinal carcinomas, gastrointestinal stromal tumors, small cell lung cancer, head and neck cancer, cancers of cervix, pancreas, esophagus, kidney, larynx and hypopharynx, liver, endocrine glands, soft tissue, testis, retinoblastoma and Wilms tumor, endometrial tumors, malignant melanoma, non-Hodgekins lymphoma, Hodgekins lymphoma or other lymphomas, chronic and acute myeloic leukemia, acute lymphoblastic leukemia, T-cell lymphoma, plasma cell neoplasia, and leukemias, hematological malignancies including multiple myeloma, soft tissue sarcoma, osteosarcoma, fibrosarcoma, and other tumors of mesothelial origin, glioma, astrocytoma, cancers of unknown primary site, glioblastoma and other brain tumors and tumors of neuronal origin, germ cell cancers, myelodysplastic syndromes, myeloproliferative syndromes, disorders such as polycythemia vera, essential thrombocytopenia, myelofibrosis, hypereosinophilic syndrome, or other paraneoplastic syndromes. In another embodiment, said abnormal cell growth is a benign proliferative disease such as, e.g., benign prostatic hyperplasia, restenosis, fibrosis, or psoriasis, or any other kind of unwanted cell or tissue proliferation.

The invention also relates to the use of a compound of the invention in the manufacture of a pharmaceutical composition inhibiting Plk1, in particular a pharmaceutical composition for the treatment or prophylaxis of diseases alleviated by inhibition of Plk1, preferably, a pharmaceutical composition for the treatment or prophylaxis of the diseases exemplified above.

The invention further relates to a method of treating or preventing a disease comprising administering to a patient in need thereof a therapeutically effective amount of at least one of the compounds of the invention.

In particular, the invention relates to a method of treating or preventing one of the above mentioned diseases comprising administering to a patient in need thereof a therapeutically effective amount of at least one of the compounds of the invention.

Especially, the invention relates to a method of treating or preventing a disease which is alleviated by inhibition of Plk1 comprising administering to a patient in need thereof a therapeutically effective amount of at least one of the compounds of the invention.

Furthermore, the invention preferably relates to a method of treating or preventing cancers of the colon including colorectal carcinoma, ovaries, breast, prostate, bladder, lung, gastrointestinal carcinomas, gastrointestinal stromal tumors, small cell lung cancer, head and neck cancer, cancers of cervix, pancreas, esophagus, kidney, larynx and hypopharynx, liver, endocrine glands, soft tissue, testis, retinoblastoma and Wilms tumor, endometrial tumors, malignant melanoma, non-Hodgekins lymphoma, Hodgekins lymphoma or other lymphomas, chronic and acute myeloic leukemia, acute lymphoblastic leukemia, T-cell lymphoma, plasma cell neoplasia, and leukemias, hematological malignancies including multiple myeloma, soft tissue sarcoma, osteosarcoma, fibrosarcoma, and other tumors of mesothelial origin, glioma, astrocytoma, cancers of unknown primary site, glioblastoma and other brain tumors and tumors of neuronal origin, germ cell cancers, myelodysplastic syndromes, myeloproliferative syndromes, disorders such as polycythemia vera, essential thrombocytopenia, myelofibrosis, hypereosinophilic syndrome, or other paraneoplastic syndromes, or benign proliferative disease such as, e.g., benign prostatic hyperplasia, restenosis, fibrosis, or psoriasis, or any other kind of unwanted cell or tissue proliferation, comprising administering to a patient in need thereof a therapeutically effective amount of at least one of the compounds of the invention.

In the above methods, the patient is preferably a mammal, more preferably a human. Furthermore, in the above methods, at least one of the compounds of the invention can be used. Preferably, one or two of the compounds of the invention are used, more preferably, one of the compounds of the invention is used.

In a particularly preferred embodiment of the invention, the above methods of treating or preventing one of the above mentioned diseases comprise administering to a patient in need thereof a therapeutically effective amount of one compound of the examples according to the present invention.

The invention furthermore relates to a pharmaceutical composition which comprises at least one of the compounds of the invention together with at least one pharmaceutically acceptable carrier, diluent or excipient.

Preferably, the pharmaceutical composition comprises one or two of the compounds of the invention. More preferably, the pharmaceutical composition comprises one of the compounds of the invention.

In a particularly preferred embodiment of the invention, the pharmaceutical composition comprises a compound of the examples according to the present invention together with at least one pharmaceutically acceptable carrier, diluent or excipient.

The invention additionally relates to a pharmaceutical composition comprising at least one of the compounds of the invention, at least one pharmaceutically acceptable carrier, diluent or excipient, and at least one additional therapeutic agent with the proviso that the compound or compounds of the invention and the at least one additional therapeutic agent are therapeutically compatible. By therapeutically compatible it is meant that (a) the toxicity of the compound or compounds of the invention and the toxicity of the at least one additional therapeutic agent do not add up to an unacceptable toxicity, and (b) that the therapeutic effect of the compound or compounds of the invention is not modified or reduced in an unacceptable or undesired way by the at least one additional therapeutic agent, and vice versa. In a preferred embodiment, the therapeutic effect of the compound or compounds of the invention and the therapeutic effect of the at least one additional therapeutic agent are additive. In another preferred embodiment, the therapeutic effect of the compound or compounds of the invention and the therapeutic effect of the at least one additional therapeutic agent are synergistic, i.e., their combined effect is different from, preferably more beneficial than, the pure sum of the therapeutic effects when the compound or compounds and the agent(s) are administered alone, without any interaction of the effects the compound or compounds and the effects the agent(s) exert to the treated patient.

The invention also relates to a kit of parts, comprising at least one pharmaceutical composition comprising at least one of the compounds of the invention, and at least one pharmaceutical composition comprising at least one additional therapeutic agent.

Typical additional therapeutic agents useful in the present invention include, but are not limited to, anti-neoplastic agents in general, cytostatic agents, cytotoxic agents, antimetabolites, microtubule interfering agents, platinum derivatives, alkylating agents, topoisomerase I inhibitors, topoisomerase II inhibitors, signal transduction inhibitors, cell cycle signalling inhibitors, angiogenesis inhibitors including antibodies and receptor tyrosine kinase inhibitors, immunotherapeutic agents, monoclonal antibodies (including, but not limited to, murine, chimeric, and humanized monoclonal antibodies), proapoptotic agents, hormones, hormone analogues, antibiotic agents, anti-emetic agents, and analgetic agents.

In this respect, the therapeutic agent includes anti-neoplastic agents, cytostatic agents, cytotoxic agents, antimetabolites, microtubule interfering agents, platinum complexes, DNA alkylating agents, DNA intercalating agents, topoisomerase I inhibitors, topoisomerase II inhibitors, signal transduction inhibitors including kinase inhibitors, cell cycle signalling inhibitors, angiogenesis inhibitors including antibodies and receptor tyrosine kinase inhibitors, proapoptotic agents, hormones, hormone analogues, antibiotic agents, immunotherapeutic agents, monoclonal antibodies (including, but not limited to, murine, chimeric, and humanized monoclonal antibodies), anti-emetic agents, or analgetic agents in form of the free compounds, the pharmaceutically acceptable salts thereof, the pharmaceutically acceptable derivatives thereof (e.g., but not limited to, ester derivatives), the solvates thereof and the stereoisomers of the compounds, salts, derivatives and solvates.

Antimetabolites interfere with DNA synthesis. Purine analogues and pyrimidine analogues are incorporated, during the S phase of the cell cycle, into growing DNA strands and thereby suppress incorporation of the proper DNA building blocks, purines and pyrimidines. Examples for purine analogues and pyrimidine analogues include, but are not limited to, 5-fluorouracil, floxuridine, cytosine arabinose, mercaptopurine, thioguanine, fludarapine, pentostatin, and cladribine. Another class of antimetabolites prevents the synthesis of tetrahydrofolate, which is essential for purine and pyrimidine biosynthesis. Examples for antimetabolites suppressing synthesis of tetrahydrofolate include, but are not limited to, methotrexate and pemetrexed.

Microtubule interfering agents are chemotherapeutics that are directed against the formation of microtubules by tumor cells during M phase of the cell cycle. The group of anti-microtubule agents comprises vinca alkaloids and diterpenoids. Examples for vinca alkaloids include vinblastine, navelbine, vindesine, vinorelbine, and vincristine. Examples for diterpenoids include, but are not limited to, paclitaxel and docetaxel.

Platinum complexes are active against tumor cells by interacting with the cells' genomic DNA. More specifically, crosslinks are introduced into the DNA which introduces serious damage to the affected tumor cells. Examples for platinum complexes include, but are not limited to, cisplatin, carboplatin, and oxaliplatin.

Alkylating agents act by alkylating the genomic DNA of tumor cells, which interrupts normal function of the DNA and causes apoptosis. Examples for alkylating agents include, but are not limited to, alkyl sulfonates (e.g., busulfan), ethyleneimines and methylmelamines (e.g., hexamethylmelamine, thiotepa), nitrogen mustards (e.g., melphalan, cyclophosphamide, mechlorethamine, uramustine, and chlorambucil), nitrosoureas (e.g., carmustine, streptozocin), and triazenes (e.g., dacarbazine, temozolomide).

Inhibitors of topoisomerase I or topoisomerase II inhibit these enzymes' essential function in DNA supercoiling during cell division. Examples for inhibitors of topoisomerase I include, but are not limited to, camptothecins (e.g., irinotecan, topotecan). Examples for inhibitors of topoisomerase II include, but are not limited to, amsacrine, etoposide, etoposide phosphate, and teniposide.

Signal transduction inhibitors are compounds that interfere with certain cellular processes such as, e.g., cell division. Compounds useful for treatment of neoplasms include, but are not limited to, inhibitors of receptor and non-receptor tyrosine kinases, inhibitors of serine/threonine kinases, inhibitors of phosphoinositide 3-kinases, inhibitors of Ras oncogenes, myoinositol signaling inhibitors, and SH2/SH3 domain blockers. Examples for inhibitors of receptor tyrosine kinases include, but are not limited to, erlotinib (Tarceva), gefitinib (Iressa), dasatinib (Sprycel), sorafenib (Nexavar), SU11248 (Sutent), and lapatinib (Tycerb).

Cell cycle signalling inhibitors are intended to interfere with cell cycle progression by inhibiting the biological effect of crucial signalling molecules such as, e.g., cyclins/cyclindependent kinases and other essential cell cycle regulators.

Angiogenesis inhibitors such as, e.g., antibodies or receptor tyrosine kinase inhibitors inhibit the neovascularization of tumors. Examples include, but are not limited to, anti-VEGF antibodies such as, e.g., bevacizumab.

Monoclonal antibodies (including, but not limited to, murine, chimeric, and humanized monoclonal antibodies) are capable of binding to surface antigens specific for tumor cells, thus rendering susceptible the cancer cells to attack by the immune system. Examples for monoclonal antibodies as anti-tumor agents include, but are not limited to, trastuzumab (Herceptin), rituximab (Rituxan), gemtuzumab ozogamicin (Mylotarg), alemtuzumab (Campath), ibritumomab tiuxetan (Zevalin), tositumomab (Bexxar), cetuximab (Erbitux), bevacizumab (Avastin), and panitumumab (Vectibix).

Proapoptotic agents are intended to unblock apoptosis in cancer cells by reducing Bcl-2 activity in malignant cells characterized by upregulation of Bcl-2 activity. A proapoptotic effect is mediated by, for example, without being limited thereto, bcl-2 antisense oligonucleotides.

Hormones and hormone analogues are useful to treat neoplasms in which cell growth is affected by the level at which a certain hormone or hormones (or analogues thereof) are present. Examples for classes of hormones and hormone analogues include, but are not limited to, adrenocorticosteroids, androgens, anti-androgens, aromatase inhibitors, estrogens, anti-estrogens, gonadotropin-releasing hormone and its analogues, and progestrins. Examples for individual hormones and hormone analogues include, but are not limited to, aminoglutethimide, anastrozole, bicalutamide, cyproterone acetate, dexamethasone, droloxifene, dutasteride, exemestane, finasteride, flutamide, gosereline, iodoxyfene, letrazole, luprolide, megrestrol acetate, nilutamide, prednisolone, prednisone, raloxifene, tamoxifen, toremifene, and vorazole.

Antibiotic chemotherapeutic agents (antineoplastics) bind to or intercalate with DNA, which leads to cell death. Examples of antibiotic agents effective against cancer cells include, but are not limited to, actinomycin D, bleomycin, plicamycin, mitomycin, and anthracyclins such as, e.g., doxorubicin, daunorubicin, epirubicin, and others.

Immunotherapeutic agents are activating the immune system in order to attack cancer cells. Examples for immunotherapeutic agents include, but are not limited to, monoclonal antibodies, radiolabeled murine antibodies, and agents used for topic immunotherapy such as, e.g., imiquimod.

Anti-emetic agents are agents effective against nausea and vomiting, which can arise as side effects of chemotherapy. Examples for anti-emetic agents include, but are not limited to, $5HT_3$ receptor antagonists (e.g., dolasetron, granisetron, ondansetron, tropisetron, palonosetron, and others), dopamine antagonists (e.g., domperidone, metoclopramide, droperidol, haloperidol, chlorpromazine, promethazine, prochlorperazine, and others), antihistamines ($H_1R$ antagonists; cyclizine, diphenhydramine, dimenhydrinate, meclizine, hydroxyzine, and others), benzodiazepines such as, e.g., midazolam and others, cannabinoids such as, e.g., cannabis, marinol and others, and other anti-emetic agents not falling into one of the above groups, such as, e.g., emetrol, propofol, trimethobenzamide, and ginger extracts, among others.

Analgetic agents are compounds effective in relieving pain. Examples for analgetics include, but are not limited to, NSAIDs (non-steroidal anti-inflammatory drugs such as, e.g., Aspirin, rofecoxib, celecoxib, and others), paracetamol, carbamazepine, gabapentin, pregabalin, opiates, morphinomimetics (e.g., morphine, codeine, oxycodone, hydrocodone, diamorphine, pethidine, tramadol, buprenorphine, and others), and tricyclic antidepressants such as, e.g., amitriptyline.

In a preferred embodiment, the pharmaceutical composition comprises a compound of the invention in combination with an alkylating agent. In a particularly preferred embodiment, the pharmaceutical composition comprises:
a compound of the invention and cyclophosphamid,
a compound of the invention and chlorambucil,
a compound of the invention and melphalan,
a compound of the invention and BCNU (carmustin),
a compound of the invention and CCNU (lomustin),
a compound of the invention and thiotepa,
a compound of the invention and busulfan,
a compound of the invention and dacarbazine, or
a compound of the invention and temozolomide.

In a further preferred embodiment, the pharmaceutical composition comprises a compound of the invention in combination with an antimetabolite. In a particularly preferred embodiment, the pharmaceutical composition comprises:
a compound of the invention and aminopterin,
a compound of the invention and 5-fluorouracil,
a compound of the invention and methotrexate,
a compound of the invention and cytarabin,
a compound of the invention and mercaptopurin,
a compound of the invention and azathioprin,
a compound of the invention and azacytidine,
a compound of the invention and gemcitabine, or
a compound of the invention and capecitabine.

In a further preferred embodiment, the pharmaceutical composition comprises a compound of the invention in combination with an alkaloid. In a particularly preferred embodiment, the pharmaceutical composition comprises:
a compound of the invention and vinblastin,
a compound of the invention and vincristin, a compound of the invention and daunomycin,
a compound of the invention and adriamycin,
a compound of the invention and bleomycin,
a compound of the invention and bleomycin, or
a compound of the invention and procarbazin.

In a further preferred embodiment, the pharmaceutical composition comprises a compound of the invention in combination with a platinum derivative. In a particularly preferred embodiment, the pharmaceutical composition comprises:
a compound of the invention and cisplatin,
a compound of the invention and carboplatin,
a compound of the invention and oxaliplatin,
a compound of the invention and satraplatin.

In a further preferred embodiment, the pharmaceutical composition comprises a compound of the invention in combination with a tubulin inhibitor. In a particularly preferred embodiment, the pharmaceutical composition comprises:
a compound of the invention and paclitaxel, or
a compound of the invention and docetaxel.

In a further preferred embodiment, the pharmaceutical composition comprises a compound of the invention in combination with a topoisomerase inhibitor. In a particularly preferred embodiment, the pharmaceutical composition comprises:
a compound of the invention and irinotecan, or
a compound of the invention and topotecan.

In a further preferred embodiment, the pharmaceutical composition comprises a compound of the invention in combination with an inhibitor of the EGFR pathway. In a particularly preferred embodiment, the pharmaceutical composition comprises:
a compound of the invention and cetuximab,
a compound of the invention and trastuzumab,
a compound of the invention and gefitinib,
a compound of the invention and erlotinib,
a compound of the invention and lapatinib,
a compound of the invention and imatinib,
a compound of the invention and nilotinib, or
a compound of the invention and dasatinib.

In a further preferred embodiment, the pharmaceutical composition comprises a compound of the invention in combination with an inhibitor of farnesyltransferase. In a particularly preferred embodiment, the pharmaceutical composition comprises a compound of the invention and tipifarnib.

In a further preferred embodiment, the pharmaceutical composition comprises a compound of the invention in combination with an inhibitor of the VEGF-/VEGF-R signaling pathway. In a particularly preferred embodiment, the pharmaceutical composition comprises:
a compound of the invention and a VEGFR2 Mab,
a compound of the invention and bevacizumab,
a compound of the invention and sorafenib,
a compound of the invention and sunitinib, or
a compound of the invention and valatinib.

In a further preferred embodiment, the pharmaceutical composition comprises a compound of the invention in combination with a specific monoclonal antibody. In a particularly preferred embodiment, the pharmaceutical composition comprises:
a compound of the invention and trastuzumab,
a compound of the invention and rituximab,
a compound of the invention and gemtuzumab,
a compound of the invention and alemtuzumab,
a compound of the invention and ibritumomab,
a compound of the invention and tositumomab,
a compound of the invention and cetuximab,
a compound of the invention and bevacizumab,
a compound of the invention and panitumumab,
a compound of the invention and Anti-CD20 Mab, or
a compound of the invention and Anti-CD52 Mab.

In a further preferred embodiment, the pharmaceutical composition comprises a compound of the invention in combination with an Eg5 inhibitor. In a particularly preferred embodiment, the pharmaceutical composition comprises a compound of the invention and ispinesib.

In a further preferred embodiment, the pharmaceutical composition comprises a compound of the invention in combination with a proteasome inhibitor. In a particularly preferred embodiment, the pharmaceutical composition comprises a compound of the invention and bortezomib.

In a further preferred embodiment, the pharmaceutical composition comprises a compound of the invention in combination with a cyclin-dependent kinase inhibitor. In a particularly preferred embodiment, the pharmaceutical composition comprises:
a compound of the invention and flavopyridol, or
a compound of the invention and R-roscovitine.

In a further preferred embodiment, the pharmaceutical composition comprises a compound of the invention in combination with a multitarget enzyme inhibitor. In a particularly preferred embodiment, the pharmaceutical composition comprises a compound of the invention and pemetrexed.

In a further preferred embodiment, the pharmaceutical composition comprises a compound of the invention in combination with a histon deacetylase inhibitor. In a particularly preferred embodiment, the pharmaceutical composition comprises:
a compound of the invention and vorinostat,
a compound of the invention and belinostat,
a compound of the invention and LBH589,
a compound of the invention and depsipeptide,
a compound of the invention and 2-propylpentanoic acid,
a compound of the invention and BYK 397957,
a compound of the invention and BYK408740.

In a further preferred embodiment, the pharmaceutical composition comprises a compound of the invention in combination with a hypo- or demethylating agent. In a particularly preferred embodiment, the pharmaceutical composition comprises:
a compound of the invention and procaine,
a compound of the invention and azacitidine, or
a compound of the invention and decitabine.

The invention additionally relates to a pharmaceutical composition comprising at least one of the compounds of the invention, at least one pharmaceutically acceptable carrier, diluent or excipient, and two additional therapeutic agents with the proviso that the compound or compounds of the invention and the two additional therapeutic agents are therapeutically compatible. By therapeutically compatible it is meant that (a) the toxicity of the compound or compounds of the invention and the toxicity of the two additional therapeutic agents do not add up to an unacceptable toxicity, and (b) that the therapeutic effect of the compound or compounds of the invention is not modified or reduced in an unacceptable or undesired way by the two additional therapeutic agents, and vice versa. In a preferred embodiment, the therapeutic effect of the compound or compounds of the invention and the therapeutic effect of the two additional therapeutic agents are additive. In another preferred embodiment, the therapeutic effect of the compound or compounds of the invention and the therapeutic effect of the two additional therapeutic agents are synergistic, i.e., their combined effect is different from, preferably more beneficial than, the pure sum of all three therapeutic effects when the compound or compounds and the agents are administered alone, without any interaction of the effects the compound or compounds and the effects the agents exert to the treated patient.

In a further preferred embodiment, the first and the second additional therapeutic agents are independently selected from anti-neoplastic agents, cytostatic agents, cytotoxic agents, antimetabolites, microtubule interfering agents, platinum derivatives, DNA alkylating agents, DNA intercalating agents, topoisomerase I inhibitors, topoisomerase II inhibitors, signal transduction inhibitors including kinase inhibitors, cell cycle signalling inhibitors, angiogenesis inhibitors including antibodies and receptor tyrosine kinase inhibitors, proapoptotic agents, hormones, hormone analogues, antibiotic agents, immunotherapeutic agents, monoclonal antibodies (including, but not limited to, murine, chimeric, and humanized monoclonal antibodies), anti-emetic agents, and analgetic agents, in form of the free compounds, the pharmaceutically acceptable salts thereof, the pharmaceutically acceptable derivatives thereof (e.g., but not limited to, ester derivatives), the solvates thereof and the stereoisomers of the compounds, salts, derivatives and solvates.

In a particularly preferred embodiment, one of the two additional therapeutic agents is a taxane.

In a further particularly preferred embodiment, one of the two additional therapeutic agents is a platinum compound.

In a further particularly preferred embodiment, one of the two additional therapeutic agents is a hormone or hormone analogue.

In a further particularly preferred embodiment, one of the two additional therapeutic agents is a monoclonal antibody.

The invention also relates to a kit of parts, comprising at least one pharmaceutical composition comprising at least one of the compounds of the invention, and at least one pharmaceutical composition comprising two additional therapeutic agents.

The invention also relates to a kit of parts, comprising at least one pharmaceutical composition comprising at least one of the compounds of the invention and a first additional therapeutic agent, and at least one pharmaceutical composition comprising a second additional therapeutic agent.

The invention also relates to a kit of parts, comprising at least one pharmaceutical composition comprising at least one of the compounds of the invention, at least one pharmaceutical composition comprising a first additional therapeutic agent, and at least one pharmaceutical composition comprising a second additional therapeutic agent.

The above mentioned compound of the invention is preferably a compound according to the examples.

The invention furthermore relates to pharmaceutical compositions according to the invention, as defined above, inhibiting Plk1, especially for the treatment or prophylaxis of diseases alleviated by inhibition of Plk1, in particular for the treatment or prophylaxis of the diseases exemplified above.

The invention also encompasses pharmaceutical compositions according to the invention, as defined above, for the treatment or prophylaxis of the following diseases involving abnormal cell growth: Cancers of the colon including colorectal carcinoma, ovaries, breast, prostate, bladder, lung, gastrointestinal carcinomas, gastrointestinal stromal tumors, small cell lung cancer, head and neck cancer, cancers of cervix, pancreas, esophagus, kidney, larynx and hypopharynx, liver, endocrine glands, soft tissue, testis, retinoblastoma and Wilms tumor, endometrial tumors, malignant melanoma, non-Hodgekins lymphoma, Hodgekins lymphoma or other lymphomas, chronic and acute myeloic leukemia, acute lymphoblastic leukemia, T-cell lymphoma, plasma cell neoplasia, and leukemias, hematological malignancies including multiple myeloma, soft tissue sarcoma, osteosarcoma, fibrosarcoma, and other tumors of mesothelial origin, glioma, astrocytoma, cancers of unknown primary site, glioblastoma and other brain tumors and tumors of neuronal origin, germ cell cancers, myelodysplastic syndromes, myeloproliferative syndromes, disorders such as polycythemia vera, essential thrombocytopenia, myelofibrosis, hypereosinophilic syndrome, or other paraneoplastic syndromes. In another embodiment, said abnormal cell growth is a benign proliferative disease such as, e.g., benign prostatic hyperplasia, restenosis, fibrosis, or psoriasis, or any other kind of unwanted cell or tissue proliferation.

The pharmaceutical compositions according to the invention preferably contain the compound or compounds of the invention in a total amount of from 0.1 to 99.9 wt %, more preferably 5 to 95 wt %, in particular 20 to 80 wt %. In case at least one therapeutic agent selected from anti-neoplastic agents in general, cytostatic agents, cytotoxic agents, antimetabolites, microtubule interfering agents, platinum derivatives, alkylating agents, topoisomerase I inhibitors, topoisomerase II inhibitors, signal transduction inhibitors, cell cycle signalling inhibitors, angiogenesis inhibitors including antibodies and receptor tyrosine kinase inhibitors, immunotherapeutic agents, monoclonal antibodies (including, but not limited to, murine, chimeric, and humanized monoclonal antibodies), proapoptotic agents, hormones, hormone analogues, antibiotic agents, anti-emetic agents, and analgetic agents is present in the pharmaceutical compositions of the invention, the total amount of said therapeutic agent or therapeutic agents in the pharmaceutical compositions is preferably in the range of from 0.1 to 99.9 wt %, more preferably 5 to 95 wt %, in particular 20 to 80 wt %, with the proviso that the total amount of the compound or compounds of the invention and the therapeutic agent or therapeutic agents is less than 100 wt %. Preferably, the at least one compound of the invention and the at least one therapeutic agent are present in the pharmaceutical composition in a weight ratio of from 1000:1 to 1:1000.

As pharmaceutically acceptable auxiliaries, any auxiliaries known to be suitable for preparing pharmaceutical compositions can be used. Examples thereof include, but are not limited to, solvents, diluents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The pharmaceutical compositions can be formulated, for example, into tablets, coated tablets (dragees), pills, cachets, capsules (caplets), granules, powders, suppositories, solutions (e.g., but not limited to, sterile solutions), emulsions, suspensions, ointments, creams, lotions, pastes, oils, gels, sprays and patches (for example, without being limited thereto, transdermal therapeutic systems). Additionally, the pharmaceutical compositions can be prepared as, e.g., liposome delivery systems, systems in which the compound of the invention is coupled to monoclonal antibodies, and systems in which the compound of the invention is coupled to polymers (for example, without being limited thereto, soluble or biodegradable polymers).

In case of pharmaceutical compositions comprising at least one of the compounds of the invention and at least one therapeutic agent selected from anti-neoplastic agents in general, cytostatic agents, cytotoxic agents, antimetabolites, anti-microtubule agents, platinum derivatives, alkylating agents, topoisomerase I inhibitors, topoisomerase II inhibitors, signal transduction inhibitors, cell cycle signalling inhibitors, angiogenesis inhibitors including antibodies and receptor tyrosine kinase inhibitors, immunotherapeutic agents, monoclonal antibodies (including, but not limited to, murine, chimeric, and humanized monoclonal antibodies), proapoptotic agents, hormones, hormone analogues, antibiotic agents, anti-emetic agents, and analgetic agents, the compound of the invention and the therapeutic agent may be formulated together into the same dosage form (for example, without being limited thereto, tablets or solutions for injection), separately into the same dosage form (for example, without being limited thereto, tablets or solutions for injection), or into different dosage forms (for example, without being limited thereto, the compound of the invention may be formulated as tablet and the therapeutic agent may be formulated as powder, solution or suspension).

The pharmaceutical compositions can be manufactured in a manner known to a person skilled in the art, e.g. by dissolving, mixing, granulating, dragee-making, levigating, emulsifying, encapsulating, entrapping or lyophilizing processes.

The selected formulation depends inter alia on the route of administering the pharmaceutical composition. The pharmaceutical compositions of the invention can be administered by any suitable route, for example, by the oral, sublingual, buccal, intravenous, intraarterial, intramuscular, subcutaneous, intracutaneous, topical, transdermal, intranasal, intraocular, intraperitoneal, intrasternal, intracoronary, transurethral, rectal or vaginal route, by inhalation or by insufflation. Oral administration is preferred.

In case of pharmaceutical compositions comprising at least one of the compounds of the invention and at least one therapeutic agent selected from anti-neoplastic agents in general, cytostatic agents, cytotoxic agents, antimetabolites, anti-microtubule agents, platinum derivatives, alkylating agents, topoisomerase I inhibitors, topoisomerase II inhibitors, signal transduction inhibitors, cell cycle signalling inhibitors, angiogenesis inhibitors including antibodies and receptor tyrosine kinase inhibitors, immunotherapeutic agents, monoclonal antibodies (including, but not limited to, murine, chimeric, and humanized monoclonal antibodies), proapoptotic agents, hormones, hormone analogues, antibiotic agents, anti-emetic agents, and analgetic agents, the compound of the invention and the therapeutic agent may be administered by the same route, e.g., without limitation, orally, or by different routes, e.g., without limitation, the compound of the invention can be administered orally and the therapeutic agent can be administered topically or by injection.

Tablets, coated tablets (dragees), pills, cachets, capsules (caplets), granules, solutions, emulsions and suspensions are, e.g., suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g., under different pH conditions) or by coupling the compound of the invention to a biodegradable polymer.

Administration by inhalation is preferably made by using an aerosol. The aerosol is a liquid-gaseous dispersion, a solid-gaseous dispersion or a mixed liquid/solid-gaseous dispersion.

The aerosol may be generated by means of aerosol-producing devices such as dry powder inhalers (DPIs), pressurized metered dose inhalers (PMDIs) and nebulizers. Depending on the kind of the compound of the invention, and optionally the therapeutic agent, to be administered, the aerosol-producing device can contain the compound and, optionally, the therapeutic agent in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (co-solvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 µm, more preferably it is in the range of from 0.5 to 10 µm, in particular in the range of from 2 to 6 µm (D50 value, measured by laser diffraction).

Specific aerosol-producing devices which may be used for inhaled administration include, but are not limited to, Cyclohaler®, Diskhaler®, Rotadisk®, Turbohaler®, Autohaler®, Turbohaler®, Novolizer®, Easyhaler®, Aerolizer®, Jethaler®, Diskus®, Ultrahaler® and Mystic® inhalers. The aerosol-producing devices may be combined with spacers or expanders, e.g. Aerochamber®, Nebulator®, Volumatic® and Rondo®, for improving inhalation efficiency.

In case of topical administration, suitable pharmaceutical formulations are, for example, ointments, creams, lotions, pastes, gels, powders, solutions, emulsions, suspensions, oils, sprays, and patches (for example, without being limited thereto, transdermal therapeutic systems).

For parenteral modes of administration such as, for example, intravenous, intraarterial, intramuscular, subcutaneous, intracutaneous, intraperitoneal and intrasternal administration, preferably solutions (for example, without being limited thereto, sterile solutions or isotonic solutions) are used. They are preferably administered by injection or infusion techniques.

In case of intranasal administration, for example, sprays and solutions to be applied in drop form are preferred formulations.

For intraocular administration, solutions to be applied in drop form, gels and ointments are exemplified formulations.

Generally, the pharmaceutical compositions according to the invention can be administered such that the dose of the compound of the invention is in the range customary for Plk1 inhibitors. In particular, a dose in the range of from 0.01 to 5000 mg of the compound of the invention per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination. In case the pharmaceutical composition of the invention comprises at least one of the compounds of the invention and at least one therapeutic agent selected from anti-neoplastic agents in general, cytostatic agents, cytotoxic agents, antimetabolites, anti-microtubule agents, platinum derivatives, alkylating agents, topoisomerase I inhibitors, topoisomerase II inhibitors, signal transduction inhibitors, cell cycle signalling inhibitors, angiogenesis inhibitors including antibodies and receptor tyrosine kinase inhibitors, immunotherapeutic agents, monoclonal antibodies, proapoptotic agents, hormones, hormone analogues, antibiotic agents, anti-emetic agents, and analgetic agents, the same dose ranges apply to the therapeutic agent.

The pharmaceutical compositions according to the invention can be administered in a single dose per day or in multiple subdoses, for example, 2 to 4 doses per day. A single dose unit of the pharmaceutical composition can contain e.g. from 0.01 mg to 5000 mg, preferably 0.1 mg to 2000 mg, more preferably 0.5 to 1000 mg, most preferably 1 to 500 mg, of the compound of the invention. In case the pharmaceutical composition of the invention comprises at least one of the compounds of the invention and at least one therapeutic agent selected from anti-neoplastic agents in general, cytostatic agents, cytotoxic agents, antimetabolites, anti-microtubule agents, platinum derivatives, alkylating agents, topoisomerase I inhibitors, topoisomerase II inhibitors, signal transduction inhibitors, cell cycle signalling inhibitors, angiogenesis inhibitors including antibodies and receptor tyrosine kinase inhibitors, immunotherapeutic agents, monoclonal antibodies, proapoptotic agents, hormones, hormone analogues, antibiotic agents, anti-emetic agents, and analgetic agents, a single dose unit of the pharmaceutical composition can contain e.g. from 0.01 mg to 5000 mg, preferably 0.1 mg to 2000 mg, more preferably 0.5 to 1000 mg, most preferably 1 to 500 mg, of the therapeutic agent. Furthermore, the pharmaceutical composition can be adapted to weekly, monthly or even more infrequent administration, for example by using an implant, e.g. a subcutaneous or intramuscular implant, by using the compound of the invention in form of a sparingly soluble salt, or by using the compound of the invention coupled to a polymer. Administration of the pharmaceutical composition in a single dose per day is preferred.

In case the pharmaceutical composition of the invention comprises at least one of the compounds of the invention and at least one therapeutic agent selected from anti-neoplastic agents in general, cytostatic agents, cytotoxic agents, antimetabolites, anti-microtubule agents, platinum derivatives, alkylating agents, topoisomerase I inhibitors, topoisomerase II inhibitors, signal transduction inhibitors, cell cycle signalling inhibitors, angiogenesis inhibitors including antibodies and receptor tyrosine kinase inhibitors, immunotherapeutic agents, monoclonal antibodies, proapoptotic agents, hormones, hormone analogues, antibiotic agents, anti-emetic agents, and analgetic agents, administration of the compound of the invention and administration of the therapeutic agent can be made simultaneously or sequentially. In case of sequential administration, the compound of the invention can be administered before or after administration of the therapeutic agent.

Biological Investigations

The inhibition of Plk1 kinase activity can be measured using recombinant Plk1 protein expressed as an N-terminally histidine-tagged protein in SF9 insect cells and alpha casein as substrate. The Plk1 assay is run in 96 well plates by incubating 50 to 100 ng per well recombinant Plk1, 500 ng per well alpha casein (Sigma, # C-6780) as substrate, 10 µl of compound of invention (test compounds were dissolved as 20 mM solutions in dimethylsulfoxide (DMSO) and subsequently diluted), and 100 nM Li-ATP (including $^{33}$P-ATP) in 100 µl of reaction buffer (50 nM HEPES, pH 7.5; 3 mM MgCl$_2$; 3 mM MnCl$_2$; 3 µM Na-Orthovanadat; 1 mM DTT; 1 µg/ml PEG 8000) for 80 minutes at 30° C. The reactions are terminated by adding 100 µl stopping buffer (2% H$_3$PO$_4$ for 5 minutes) and are washed 3 times with washing solution (0.9% NaCl). Determining $^{33}$P incorporated into the protein substrate alpha casein, the detection is based on the adhesion of the phosphorylated protein to the surface of scintillator-coated flash plates (Perkin Elmer, USA; #SMP-200). Phosphorylation of alpha casein is measured by counting the radioactivity bound to the plate for 60 sec. using a plate reader (Perkin Elmer, USA; Wallac Microbeta). By this method, the IC$_{50}$ value of the Plk1 inhibition is determined as described above. Preferred compounds are characterized by an IC$_{50}$ value of Plk1 inhibition of below 1 µM.

TABLE 1

| compound (example #) | Plk1 inhibition |
|---|---|
| 1 | +++ |
| 2 | +++ |
| 3 | ++ |
| 4 | ++ |
| 5 | ++ |
| 6 | ++ |
| 7 | +++ |
| 8 | ++++ |
| 9 | +++ |
| 10 | ++ |
| 11 | + |
| 12 | ++++ |
| 13 | +++ |
| 14 | +++ |
| 15 | +++ |
| 16 | +++ |
| 17 | +++ |
| 18 | +++ |
| 19 | +++ |
| 20 | ++ |
| 21B | +++ |
| 21A | ++ |
| 22 | ++++ |
| 23 | +++ |
| 24 | ++++ |
| 25 | ++++ |
| 22 | ++++ |
| 23 | +++ |
| 24 | ++++ |
| 25 | ++++ |
| 26 | ++++ |
| 27 | 0 |
| 28 | ++ |
| 29 | +++ |
| 30 | ++ |
| 31 | +++ |
| 32 | ++++ |
| 33 | +++ |
| 34 | +++ |
| 35 | +++ |
| 36 | ++ |
| 37 | + |
| 38 | +++ |
| 39 | +++ |
| 40 | +++ |
| 41 | +++ |
| 42 | ++++ |
| 43 | +++ |
| 44 | ++++ |
| 45 | ++++ |
| 46 | ++ |
| 47 | +++ |
| 48 | +++ |
| 49 | + |
| 50 | +++ |
| 51 | ++++ |
| 52 | ++++ |
| 53 | ++++ |
| 54 | ++++ |
| 55 | ++++ |
| 56 | ++++ |
| 57 | ++++ |
| 58 | +++ |
| 59 | +++ |
| 60 | ++++ |

TABLE 1-continued

| compound (example #) | Plk1 inhibition |
|---|---|
| 61 | ++++ |
| 62 | +++ |
| 63 | +++ |
| 64 | ++++ |
| 65 | ++++ |
| 66 | ++++ |
| 67 | ++++ |
| 68 | ++++ |
| 69 | ++++ |
| 70 | +++ |
| 71 | +++ |
| 72 | ++++ |
| 73 | ++++ |
| 74 | ++++ |
| 75 | +++ |
| 76 | ++++ |
| 77 | +++ |
| 78 | +++ |
| 79 | +++ |
| 80 | +++ |
| 81 | +++ |
| 82 | +++ |
| 83 | +++ |
| 84 | +++ |
| 85 | ++ |
| 86 | +++ |
| 87 | +++ |
| 88 | +++ |
| 89 | +++ |
| 90 | +++ |
| 91 | +++ |
| 92 | ++++ |
| 93 | +++ |
| 94 | ++++ |
| 95 | ++++ |
| 96 | ++++ |
| 97 | ++++ |
| 98 | ++++ |
| 99 | ++++ |
| 100 | ++++ |
| 101 | ++++ |
| 102 | +++ |
| 103 | +++ |
| 104 | +++ |
| 105 | +++ |
| 106 | +++ |
| 107 | ++++ |
| 108 | ++++ |
| 109 | + |
| 110 | ++++ |
| 111 | ++ |
| 112 | +++ |
| 113 | +++ |
| 114 | +++ |
| 115 | +++ |
| 116 | +++ |
| 117 | ++ |
| 118 | +++ |
| 119 | ++++ |
| 120 | ++++ |
| 121 | ++++ |
| 122 | ++++ |
| 123 | ++++ |
| 124 | +++ |
| 125 | ++++ |
| 126 | ++++ |
| 127 | ++++ |
| 128 | ++++ |
| 129 | ++++ |
| 130 | ++++ |
| 131 | +++ |
| 132 | +++ |
| 133 | ++++ |
| 134 | ++++ |
| 135 | ++++ |
| 136 | ++ |
| 137 | +++ |
| 138 | +++ |
| 139 | +++ |
| 140 | +++ |
| 141 | +++ |
| 142 | ++++ |
| 143 | +++ |
| 144 | ++++ |
| 145 | +++ |
| 146 | ++++ |
| 147 | +++ |
| 148 | ++++ |
| 149 | +++ |
| 150 | +++ |
| 151 | ++ |
| 152 | +++ |
| 153 | ++++ |
| 154 | +++ |
| 155 | ++ |
| 156 | + |
| 157 | ++ |
| 158 | + |
| 159 | +++ |
| 160 | + |
| 161 | + |
| 162 | +++ |
| 163 | +++ |
| 164 | ++++ |
| 165 | 0 |

Plk1 inhibition as determined in enzymatic assays:
++++ $pIC_{50} > 8$
+++ $7 < pIC_{50} \leq 8$
++ $6 < pIC_{50} \leq 7$
+ $5 \leq pIC_{50} \leq 6$
− $pIC_{50} < 5$
0 $pIC_{50}$ not determined

The invention claimed is:
1. A compound of formula (I)

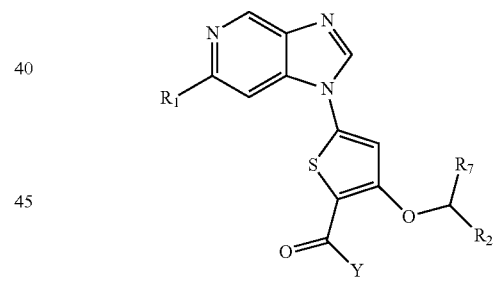

wherein
R1 is —CH$_2$N(R3)R4;
R2 is phenyl optionally having 1 to 3 substituents independently selected from the group consisting of —F, —Cl, —Br, —I, —CN, —OH, —NO$_2$, —SO$_2$CH$_3$, C1-C4 alkyl optionally being substituted with 1 to 3 F atoms, C1-C4 alkoxy optionally being substituted with 1 to 3 F atoms, C1-C4 alkylamino, and C1-C4 dialkylamino;
Y is —OH or —NH$_2$;
R3 and R4 together with the nitrogen atom they are bound to, form a saturated four- to seven-membered heterocycle,
  the heterocycle optionally containing one more heteroatoms selected from the group consisting of N, O and S, wherein S is optionally oxidized to a —SO— group or a —SO$_2$— group,
  and the heterocycle optionally being substituted by one or two substituents which independently are —OH, —F, amino, C1-C4 alkylamino, C1-C4 dialkylamino, C1-C4 alkyl optionally being substituted with 1 to 3 F atoms, C1-C4 acyl, benzoyl, phenoxy, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di(C1-C4 alkyl)aminoethyl, phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, N-methylpiperazinyl, N-methylpiperazinylcarbonyl, or oxo, and R7 is —H, methyl, ethyl, —CH$_2$OH or —CF$_3$;

or a salt thereof.

2. A compound according to claim 1, wherein

Y is —NH$_2$;

R3 and R4 together with the nitrogen atom they are bound to, form a piperazine ring or 1,4-diazepane ring, the piperazine or 1,4-diazepane optionally being substituted by one or two substituents independently being —F, C1-C4 alkyl, C1-C4 alkyl substituted with 1 to 3 F atoms, C1-C4 acyl, benzoyl, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di(C1-C4 alkyl)aminoethyl, phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, or oxo, and R7 is —H, methyl, —CH$_2$OH, or —CF$_3$;

or a salt thereof.

3. A compound according to claim 1, wherein

R2 is phenyl having a —F, —Cl, —Br, —I, trifluormethyl, difluormethoxy or trifluormethoxy substituent in the 2-position;

Y is —NH$_2$;

R3 and R4 together with the nitrogen atom they are bound to, form a piperazine ring or 1,4-diazepane ring, the piperazine or 1,4-diazepane optionally being substituted by one or two substituents independently being —F, C1-C4 alkyl optionally being substituted with 1 to 3 F atoms, C1-C4 acyl, benzoyl, 1-carboxamidyl optionally being substituted with C1-C4 alkyl or phenyl, 1-carboximidamidyl, sulfonyl optionally being substituted with C1-C4 alkyl or phenyl, 2-aminoethyl, 2-N—(C1-C4 alkyl)aminoethyl, 2-N,N-di(C1-C4 alkyl)aminoethyl; phenyl, pyridyl, pyrimidyl, benzyl, allyl, cyclopropyl, cyclobutyl, cyclopentyl, cyclohexyl, cyanomethyl, 2-cyanoethyl, 2-methansulfonylethyl, hydroxymethyl, 2-hydroxyethyl, 3-hydroxypropyl, (C1-C4 alkoxy)methyl, 2-(C1-C4 alkoxy)ethyl, 3-(C1-C4 alkoxy)propyl, N-methylpiperidyl, 1-phenylethyl, pyridylmethyl, N-methylpiperidylmethyl, 2-morpholinylethyl, morpholinocarbonylethyl, N,N-dimethylcarbonylmethyl, anilinocarbonylmethyl, N-methylanilinocarbonylmethyl, N-pyrrolidinocarbonylmethyl, N,N-dimethylsulfonyl, or oxo; and R7 is —H, methyl, —CH$_2$OH, or —CF$_3$;

or a salt thereof.

4. A compound according to claim 1, wherein R1 is N-methylpiperazine.

5. A compound according to claim 1, wherein R2 is 2-chlorphenyl or 2-trifluormethylphenyl.

6. A compound, which is

5-{6-[(Cyclopropylamino)methyl]-1H-imidazo[4,5-c]pyridin-1-yl}-3-{[2-(trifluoromethyl)benzyl]oxy}thiophene-2-carboxamide, or 5-{6-[(4-Methylpiperazin-1-yl)methyl]-1H-imidazo[4,5-c]pyridin-1-yl}-3-{[2-(trifluoromethyl)benzyl]oxy}thiophene-2-carboxamide, or a salt thereof.

7. A pharmaceutical composition comprising a compound according claim 1 or a salt thereof and at least one pharmaceutically acceptable auxiliary.

8. A pharmaceutical composition according to claim 7, further comprising at least one therapeutic agent being an anti-neoplastic agent, a cytostatic agent, a cytotoxic agent, an antimetabolite, a microtubule interfering agent, a platinum derivative, an alkylating agent, a topoisomerase I inhibitor, a topoisomerase II inhibitor, a signal transduction inhibitor, a cell cycle signaling inhibitor, an angiogenesis inhibitor including an antibody or a receptor tyrosine kinase inhibitor, an immunotherapeutic agent, a monoclonal antibody, a proapoptotic agent, a hormone, a hormone analogue, an antibiotic agent, an anti-emetic agent, or an analgetic agent.

9. A compound according to claim 6, which is

5-{6-[(Cyclopropylamino)methyl]-1H-imidazo[4,5-c]pyridin-1-yl}-3-{[2-(trifluoromethyl)benzyl]oxy}thiophene-2-carboxamide, or a salt thereof.

10. A compound according to claim 6, which is

5-{6-[(4-Methylpiperazin-1-yl)methyl]-1H-imidazo[4,5-c]pyridin-1-yl}-3-{[2-(trifluoromethyl)benzyl]oxy}thiophene-2-carboxamide, or a salt thereof.

11. A pharmaceutical composition comprising a compound according claim 6 or a salt thereof and at least one pharmaceutically acceptable auxiliary.

12. A compound according to claim 1, which is

5-{6-[(4-methylpiperazin-1-yl)methyl]-1H-imidazo[4,5-c]pyridin-1-yl}-3-{1-[2-(trifluoromethyl)phenyl]ethoxy}thiophene-2-carboxamide or a salt thereof.

13. A compound according to claim 12, which is

5-{6-[(4-methylpiperazin-1-yl)methyl]-1H-imidazo[4,5-c]pyridin-1-yl}-3-{(1R)-1-[2-(trifluoromethyl)phenyl]ethoxy}thiophene-2-carboxamide, or a salt thereof.

14. A compound according to claim 12, which is

5-{6-[(4-methylpiperazin-1-yl)methyl]-1H-imidazo[4,5-c]pyridin-1-yl}-3-{(1S)-1-[2-trifluoromethyl)phenyl]ethoxy}thiophene-2-carboxamide or a salt thereof.

15. A maleate salt of 5-{6-[(4-methylpiperazin-1-yl)methyl]-1H-imidazo[4,5-c]pyridin-1-yl}-3-{(1R)-1-[2-(trifluoromethyl)phenyl]ethoxy}thiophene-2-carboxamide according to claim 12.

16. A pharmaceutical composition comprising a compound according claim 12 or a salt thereof and at least one pharmaceutically acceptable auxiliary.

17. A compound according to claim 1, which is
4-{[1-(5-carbamoyl-4-{(1R)-1-[2-(trifluoromethyl)phenyl]ethoxy}-2-thienyl)-1H-imidazo[4,5-c]pyridin-6-yl]methyl}-N,N-dimethylpiperazine-1-carboxamide
5-{6-[(3,4-dimethylpiperazin-1-yl)methyl]-1H-imidazo[4,5-c]pyridin-1-yl}-3-{(1R)-1-[2-(trifluoromethyl)phenyl]ethoxy}thiophene-2-carboxamide
3-[1-(2-chlorophenyl)-2,2,2-trifluoroethoxy]-5-{6-[(4-methylpiperazin-1-yl)-methyl]-1H-imidazo[4,5-c]pyridin-1-yl}thiophene-2-carboxamide
5-{6-[(2,5-dimethylpiperazin-1-yl)methyl]-1H-imidazo[4,5-c]pyridin-1-yl}-3-{(1R)-1-[2-(trifluoromethyl)phenyl]ethoxy}thiophene-2-carboxamide
5-(6-{[4-(4-methylpiperazin-1-yl)piperidin-1-yl]methyl}-1H-imidazo[4,5-c]pyridin-1-yl)-3-{(1R)-1-[2-(trifluoromethyl)phenyl]ethoxy}thiophene-2-carboxamide
5-[6-({4-[(4-methylpiperazin-1-yl)carbonyl]piperidin-1-yl}methyl)-1H-imidazo[4,5-c]pyridin-1-yl]-3-{(1R)-1-[2-(trifluoromethyl)phenyl]ethoxy}thiophene-2-carboxamide
3-[(1R)-1-(2-bromophenyl)ethoxy]-5-{6-[(4-methylpiperazin-1-yl)methyl]-1H-imidazo[4,5-c]pyridin-1-yl}thiophene-2-carboxamide
3-{1-[2-(difluoromethoxy)phenyl]ethoxy}-5-{6-[(4-methylpiperazin-1-yl)methyl]-1H-imidazo[4,5-c]pyridin-1-yl}thiophene-2-carboxamide
or a salt thereof.

18. A compound according to claim 1, wherein
R2 is phenyl having only 1 substituent selected from the group consisting of —F, —Cl, —Br, —I, —CN, —OH, —NO$_2$, —SO$_2$CH$_3$, C1-C4 alkyl optionally being substituted with 1 to 3 F atoms, C1-C4 alkoxy optionally being substituted with 1 to 3 F atoms, C1-C4 alkylamino, and C1-C4 dialkylamino.

19. A compound according to claim 1, wherein
R2 is phenyl having only 1 substituent CF$_3$.

\* \* \* \* \*